US006217882B1

(12) United States Patent
Moyer et al.

(10) Patent No.: US 6,217,882 B1
(45) Date of Patent: *Apr. 17, 2001

(54) USE OF RECOMBINANT SWINE POXVIRUS AS A LIVE VACCINE VECTOR

(75) Inventors: Richard W. Moyer, Gainesville, FL (US); Eladio Viñuela, Madrid (ES); E. P. J. Gibbs, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/299,268

(22) Filed: Apr. 26, 1999

Related U.S. Application Data

(60) Continuation of application No. 08/901,127, filed on Jul. 28, 1997, now abandoned, which is a division of application No. 08/307,499, filed on Sep. 14, 1994, now Pat. No. 5,651,972, which is a continuation of application No. 07/908,241, filed on Jul. 2, 1992, now abandoned, which is a continuation-in-part of application No. 07/908,630, filed on Jun. 29, 1992, now abandoned, which is a continuation of application No. 07/342,212, filed on Apr. 21, 1989, now abandoned.

(51) Int. Cl.[7] .................... A61K 39/275; A61K 39/245; C12N 7/01; C12N 15/80
(52) U.S. Cl. .................... 424/199.1; 435/235.1; 435/320.1; 424/93.2; 424/229.1; 424/232.1
(58) Field of Search ............. 424/199.1, 93.2, 424/229.1, 232.1; 435/235.1, 320.1, 456

(56) References Cited

U.S. PATENT DOCUMENTS

| | | |
|---|---|---|
| 4,722,848 | 2/1988 | Paoletti et al. . |
| 5,069,901 | 12/1991 | Jones et al. . |
| 5,242,829 | 9/1993 | Panicali et al. . |
| 5,273,876 | 12/1993 | Hock et al. . |
| 5,310,668 | 5/1994 | Ellis et al. . |
| 5,382,425 | 1/1995 | Cochran et al. . |
| 5,387,519 | 2/1995 | Yanagida et al. . |
| 5,651,972 | 7/1997 | Moyer et al. . |

FOREIGN PATENT DOCUMENTS

| | | |
|---|---|---|
| 0447303 | 9/1991 | (EP) . |
| 9214489 | 9/1992 | (WO) . |

OTHER PUBLICATIONS

Robinson, A.J., D.J. Lyttle (1992) "Recombinant Parapoxviruses (D) Insertion of Foreign Genes" in *Recombinant Poxviruses*, pp. 310, 323, 324.

Van Der Leek, M.L. et al. (1994) "Evaluation of swinepox virus as a vaccine vector in pigs using an Aujeszky's disease (pseudorabies) virus gene insert coding for glycoproteins gp50 and gp63" *The Veterinary Record*—Jan. 1, 1994, pp. 13–18.

Bello, L.J. et al. (1987) "Map Location of the Thymidine Kinase Gene of Bovine Herpesvirus 1" *J. of Virology* 61(12):4023–4025.

Paoletti, Enzo, Bernard R. Lipinskas, Carol Samsonoff, Susan Mercer, and Dennis Panicali (1984) "Construction of Live Vaccines Using Genetically Engineered Poxviruses: Biological Activity of Vaccinia Virus Recombinants Expressing the Hepatitis B Virus Surface Antigen and the Herpes Simplex Virus Glycoprotein D" *Proc. Natl. Acad. Sci. USA* 81:193–197.

Panicali, Dennis, Stephen W. Davis, Randall L. Weinberg, Enzo Paoletti (1983) "Construction of Live Vaccines by Using Genetically Engineered Poxviruses: Biological Activity of Recombinant Vaccinia Virus Expressing Influenza Virus Hemagglutinin" *Proc. Natl. Acad. Sci. USA* 80:5364–5368.

Mackett, Michael, Geoffrey L. Smith, Bernard Moss (1985) "The Construction and Characterization of Vaccinia Virus Recombinants Expressing Foreign Genes" *DNA Cloning* 2:191–211.

Yuen, Leonard, Julie Dionne, Basil Arif, Christopher Richardson (1990) "Identification and Sequencing of the Spheroidin Gene of *Choristoneura biennis* Entomopoxvirus" *Virology* 175:427–433.

Feller, J.A., R.F. Massung, P.C. Turner, E.P.J. Gibbs, E.O. Backamp, A. Beloso, A. Talavera, E. Viñuela, R.W. Moyer (1991) "Isolation and Molecular Characterization of the Swinepox Virus Thymidine Kinase Gene" *Virology* 183–578–585.

Piccini, Antonia, Enzo Paoletti (1986) "The Use of Vaccinia Virus for the Construction of Recombinant Vaccines" *BioEssays* 5(6):248–252.

Kasza, Louis, E. H. Bohl, D. O. Jones (1960) "Isolation and Cultivation of Swine Pox Virus in Primary Cell Cultures of Swine Origin" *Am. J. Vet. Res.* pp. 269–273.

Gustafson, D.P. (1986) "Pseudorabies" in *Diseases of Swine* pp. 274–289.

Boyle, D.B. et al. (1987) *Virology* 156:355–365.
Garg, S.K. et al. (1972) *Applied Microbiology* 23:180–182.
Marchioli, C.C. et al. (1987) *J. of Virology* 61:3977–3982.
Schnitzlein, W.M. et al. (1988) *Journal of Virological Methods* 20:341–352.
Schnitzlein, W.M. et al. (1991) *Virology* 181:727–732.

*Primary Examiner*—Mary E. Mosher
(74) *Attorney, Agent, or Firm*—Saliwanchik, Lloyd & Saliwanchik

(57) ABSTRACT

The present invention provides a recombinant swinepox virus vector containing a heterologous nucleotide sequence encoding a protein from a selected pathogen inserted into, or replacing, all or a portion of a swinepox virus gene, which gene is not essential to replication of the virus in a host cell. Also provided is a recombinant SPV vector into which a pseudorabies antigen is inserted within the TK gene, which is useful in diagnostic, therapeutic, and prophylactic compositions.

17 Claims, 50 Drawing Sheets

```
AAGCTTTAAT CCTCCTCATC CTCCAAGTCA TTCCTTCTAT CTCCCTGGTA TTGTAAAACA      60
GGCTCAGGTC CCGAGCAGTT TACACATCTA TATATGCTTG GTTCTAACGT ACTATGAAAT     120
CCAACACATG CTATTCTATT AGACATGATA GTTGGTACCA TAACCCTAGG TGATGATGTA     180
AATAAATATT TATCACCTAA TCTCCTAGTT ATAGTCGGAT ATCCTGGTTC ACCCGGTAGA     240
TAGTCCGTAT CAGGAAGCAA TTCATTTACG TACGGATCAT AACGATAGTC CGGAGCAAAG     300
TCCTCGATGT TATACCATTT AACAGCGACC GACGACGGAT AATGATTATC AAATGTGCAT     360
ATCAATGTAG TATTATCTCC TCTTTCAATT CCTGTAACTG TAACAGTAGG CTTAACTGGC     420
TTATCTATAT ATCCCTTAGA AATTTTATAA TAATCATCCG CTGTAAACGG ACATGTTAAT     480
GTTACCATTG ATCCAAGATG TTCCATAACA CGTTCCCAGT GTTGTGATTT AACAGTTAAC     540
ATTCCTACCT TTGGAAATGT ACGTGATCTA ACTTTACTAA AGCGTTTATT CTTGGGGTCG     600
AATCGTGTCC ATATATTACC ACCTACAGTA ACATAACCGA AATTTACTTG AAGTTGTCTT     660
AGATCAGTAC ATCCAATTGT CAAGGACATA GTCTTGTAAG GATTACTCGT TTCTGGAAGT     720
TTATTTATCT CATCTAGCGT TTCACTCATT CTATTTAGCC AGAACATAAA ATTATAATTA     780
TTTTTCGGAT AATATCTAAT CTTAGTCTCA TTAAACCATG TTGGTGGTTC ATTTCTTAAT     840
TCTGGTCTTC CTGTCTCGCT ATTTAGTTTT AAACGTTTTA TTAGTATATC ATTAAAATAA     900
TCGGTGACTT CGAAGTCATA TCGATGATTA TCATCTTGTA AGTATATGT ATAATTGTAT     960
ACTAAGAATG CGGAAGCATC TACATATGCT GTAATAATAG ACAATATCAC AATCGCTTTA    1020
GTAATCATTA TGATTTATTT TTGGAATATT ATTTCAATTA TAAAAGAGAT TATCCGAACC    1080
AACCAGAAAA GAAACCTTCT TTTTCTTTG TTTCCTCTTT TCTAAACGGA TTTAGACTAG    1140
ATAGAAAAGA CTCCCTACGC TTTTCCTTTT TAAAGGGATT TATACTATCC AGCGACAGCC    1200
AACCTCTGTT AGATATCAGA GAGTATGGAT TCACCGCACG AAGTAAAAAA ATCATTATTT    1260
TCATAAGTAT ATATGTAAGC AGCTTAGATA CATTTCCTAA TATAAAGTAT ACAATACTTA    1320
GCAAAGGATT AATAATATAC GATAGCATGA TTACGTAATG ATTATTTATA ACTTGTGTTT    1380
TGTAAGAAAA TAACAACTAA ATAATATTGC TACTGCTAGA AGATTTTCGT GAAAAGAGTT    1440
TTTTCCTAAT CCTATTGTCT CTATATATAC ACGAACATAT GCTAGATATA CGAGATCGAA    1500
CATGTTCACC TATCAGTGTA TATATTATTG GATTTATACA ACAACGCGCT AACGAGATAG    1560
TCTCCGAAAA GGTGATCGCA TAGGCCAGGT TTAGATAGAG GCACAGATGT CTAAATATAT    1620
TAGATGTATA TAAGCTAACA ATCGTCGCTA TCATTAGAAC GATATAGAGC GGAATCCAAC    1680
ATATTAGAGA ACATACAACA ATCATTAATA CAATTTTTAT AGATTTATAC TTTCGTCTAT    1740
TTCTTAATCT AACCACTGTA GAAAAAATTC TATAATAGCA ATATACGAAT ATGATTATAG    1800
GTATCAGGAA TCCCAATATA GTGATCTCTA TTTGCATCAG TCTTTTTATG AATGCGATTA    1860
```

Fig. 2A

```
TGGAGTCATT CTCGTTCGTC AGAGTACATT GGTATATATC TTTAGACATA TGAGGAATAT   1920
TCTCGTATAG TTTAGATACG GGACTAGATA ATATCAAGGA TAATAACCAA GCGGAACAGC   1980
ACATAAGGAT ACCTATACGT TTCGTCCTAT ACGGTTGTCG CTTTATAGGA TGAACGATCG   2040
CAAAATATCT ATCTATACTC ATAAGTGTTA TTATAAACAT ATTACTAAAG AATCCTACGT   2100
AGTATAATAC GGACATTATT TTACATAGTA TATTCCCAAA AATCCATTGA TCGAGTTTAC   2160
TATACACAAT GAACGGAATC TGAAATACGA ATATACAATC TGACATAGAT AGATTAAGAA   2220
TATAGATGTC TGTTATGGAT TTGTTTCTTT TGAACGCTAT AAGGGATACT ACAAATATAT   2280
TGCCGATGCT TCATTAACAC ATTCTTCAAA CTTAGGAATA TCGTTTAAAC GCTTCCATGT   2340
ATTTTTTAAT TTATTGTACT TTCTACACT GTTTGTATTA TATCCACCTA TTATATATAA    2400
TTCATTATTA AAAACACACG ATAGACAAAA TGATCTTTTT ACATTGTAT TTGATAAATA    2460
TTTCCAACAA TCATCTCTTG AAGAATATAT ATAAACATCG TTAGTGTGTT CTATACTTAT   2520
ATGTGGTGTA TCTATACGAC CACCTATACA GTATATAAAA TCGTTATATA CTATGGATGA   2580
TATACCACTC TTTGCTATGG GAAATTGTTT TAACTTCATC CATGAATGAT CGGTCAGTTT   2640
CTCTACGGCA TCGTCTGATA CAATCATTTC TATATTAAAT TCATCCGTTA TTGATGTTTT   2700
TAATCCACCT ATTGTATATA CTTCATTATT ATAGTCTACC AACGACATAT AACATCTAGG   2760
ATAACACAAA TGTTGACCAT CATACCATGA TTTCCATTCA GGTTTCCAAA ATTCTACGAT   2820
GTTTGTCATA TATCCATTTG TATCTTTTCC ACCAATTGAA TATATCATCC CATTTGATAC   2880
ACATACAGAT GTATCGTATC TAAAATAATT TAATTCTGGT TCGTAACACC ATAATTGTT    2940
TTTTATATTA TATGACAACA CCTCTTTAGT GAAATATCCT CGTTTCTTTC CACCGATAAT   3000
ATATAGTATA CTATTTAAGT ATACAACACT AAAATGAGTT TTACAACCAA ACATATCATC   3060
GTATCTGTCT ATAATATGTT TTTTATTCGA TAACGGATTG AATGCGGTTA TATTAAATAT   3120
CTTTTTTCCT CCTACCATTA TTATAAAGTT ATGTGATATA TCTACATCGT GTTCTTTGTT   3180
ATCATATATT CGTTCCCGTA TATTATTGTA CAATTCAATA TCCGATAAGG ATGTATAATG   3240
GTCTTGATCA TTGATATGTT TCATTAATTT TTTAGTATAA ATAATTCGTT CATCTTTATG   3300
AACGATCCAA TTTAATATTA TTTTTTTAAC TATATATTCA CATGCAATGT ATTTAATTTC   3360
TTTTATAATT AATATCATAT CATCTATATC TAATTCTACT ACCAGTTTGT TATTATTTAT   3420
TATTTTTGGT AAATACCATT TTGACATTTC ACGTAATCGT TGTAGATTGT AAGTATCTGA   3480
AAAGTTTAAG AGATGTATAC AATTTGTTTC ATCTATTATA CCGCATATAT ATTCTTCACA   3540
TATTTTTATT AAAGAATCTA TACATAGATA ATCACAGACT TGTATTACTA ATTCTATATT   3600
ATCCTTTGTT AGTACTATAT TACCGGTGTA CATAAATTCC AATATAAATAT ACAATATATC  3660
ATAATCGGCG CATATATAGA TTTCATCATT ATTTTTATCA ATAAAATCTG AATTAAATAT   3720
```

Fig. 2B

| | |
|---|---|
| ATTATAAAAG TACTTAGAGT ACATAGATAA TATTAACCTA TGTGCGCTAA TGGTTTTATT | 3780 |
| ATTCTCTATG GATACTATTT TTATATCACA CATAATTCCA TGTTTAAAAA AATCATGTAA | 3840 |

```
TCGTAATAAT A ATG AAT TCA TGT TAT GAT AGA TTT AGG ATT ATT TTT CAA    3890
           Met Asn Ser Cys Tyr Asp Arg Phe Arg Ile Ile Phe Gln
             1               5                  10
           C27> [SEQ ID NO: 2]

AAA AAA AAC AAT TAT TAT TGT AAG TAT AAT GAT TGT ATG AGA TAT TTT    3938
Lys Lys Asn Asn Tyr Tyr Cys Lys Tyr Asn Asp Cys Met Arg Tyr Phe
    15              20              25

TTG AAT ATT AGT CTA TAT CTT ATA CTT ATT TGT GAA AAG AAT ATA ACA    3986
Leu Asn Ile Ser Leu Tyr Leu Ile Leu Ile Cys Glu Lys Asn Ile Thr
 30              35              40                   45

TCA AAA TCT ACG TCG ATT ATT TTC GAT GAT AAT ATA GCA AAC ATA CCT    4034
Ser Lys Ser Thr Ser Ile Ile Phe Asp Asp Asn Ile Ala Asn Ile Pro
         50              55                      60

ATA GAA GAC TTA CAA TGT TTA ATT ATA TCA TCT TTA CAT TTT AAA CGT    4082
Ile Glu Asp Leu Gln Cys Leu Ile Ile Ser Ser Leu His Phe Lys Arg
             65              70              75

ATG TTA ATG GAT ATA GTA TCT CCC TCT TTG TAT GTA TTT ATA ATA TCA    4130
Met Leu Met Asp Ile Val Ser Pro Ser Leu Tyr Val Phe Ile Ile Ser
         80              85              90

TTA TAT ATA TAT TTT GTA GCT AAT ATA TCA TAT TTC ATG AGT TCC TTA    4178
Leu Tyr Ile Tyr Phe Val Ala Asn Ile Ser Tyr Phe Met Ser Ser Leu
     95              100             105

AAT AAC TTA CCA CAT GCG CAT GTG TTG TTA TAT TTT TTT CTC CAA TGAAGATACA 4233
Asn Asn Leu Pro His Ala His Val Leu Leu Tyr Phe Phe Leu Gln
110             115             120
```

| | |
|---|---|
| TAAATATAAT ATCATCTATA CTATGATATT TATTAATCTT ATCTAATATA GTATAATTTA | 4293 |
| TCTTCTTATT TTTATAATTT GATTTTTTTA AAAGATATTC GTATTCGCTA TAAATAATAG | 4353 |
| ATGCCACATT CATATGATTA GGTACAACGG TCATGATATC ATAAAATAGT CTAAGATCAC | 4413 |
| AAAAATTGAA TTCCTCATCT ATTATTCTTA TTACTTCTTT TCTAGATGGA TTTTTATCAT | 4473 |
| CTTGAGAAAA ATCTACATTT AATCTAAATA CAGCACAAAA ATGCTTATAC TCATCCTTAT | 4533 |

```
TTAATTTTCT TATGTATTTT CTTATAATTC TTCCAGATCT ATAATCACGT A ATG AAT    4590
                                                       Met Asn
                                                         1
                                                       C26>

TTT TTA TTA CAA TAT ACG AAT TCA TTC CTT TAT CTT TAT AAA CGT ATT    4638
Phe Leu Leu Gln Tyr Thr Asn Ser Phe Leu Tyr Leu Tyr Lys Arg Ile
     5               10                  15
[SEQ ID NO: 3]

TAC TGT TCA GTA TTT ACC ATA AGT TCT TGC AAT ATT AGT TTA AAC GAA    4686
Tyr Cys Ser Val Phe Thr Ile Ser Ser Cys Asn Ile Ser Leu Asn Glu
     20              25              30
```

Fig. 2C

| | | | | | | | | | | | | | | |
|---|---|---|---|---|---|---|---|---|---|---|---|---|---|---|
| GAT | AAT | ATA | TTA | TTA | TAT | AAG | TGC | ATA | AAC | TTT | GAC | GAT | ATA | TTG | GAT | 4734 |
| Asp | Asn | Ile | Leu | Leu | Tyr | Lys | Cys | Ile | Asn | Phe | Asp | Asp | Ile | Leu | Asp |
| 35 | | | | 40 | | | | | 45 | | | | | 50 |

| TCA | TAT | TTA | TCA | CTT | ACA | ACT | CTA | TAT | AAT | CTG | TTA | TTA | ACT | CTA | TCT | 4782 |
|---|---|---|---|---|---|---|---|---|---|---|---|---|---|---|---|---|
| Ser | Tyr | Leu | Ser | Leu | Thr | Thr | Leu | Tyr | Asn | Leu | Leu | Leu | Thr | Leu | Ser |
| | | | 55 | | | | | 60 | | | | | 65 |

| ATA | TCA | TCG | AAA | TCT | TTA | ATA | AAA | TAT | GTA | TCG | ATT | TTT | CTT | GGA | ATT | 4830 |
|---|---|---|---|---|---|---|---|---|---|---|---|---|---|---|---|---|
| Ile | Ser | Ser | Lys | Ser | Leu | Ile | Lys | Tyr | Val | Ser | Ile | Phe | Leu | Gly | Ile |
| | | | 70 | | | | 75 | | | | | 80 |

| AAT | CCA | TCT | ACA | CAC | ACT | CTA | GTA | CTA | TTA | TCT | GTT | TTT | TTT | GGA | CCA | 4878 |
|---|---|---|---|---|---|---|---|---|---|---|---|---|---|---|---|---|
| Asn | Pro | Ser | Thr | His | Thr | Leu | Val | Leu | Leu | Ser | Val | Phe | Phe | Gly | Pro |
| | | 85 | | | | | 90 | | | | | 95 |

AAT TCA TAATATTGTT CCATACCCAT TACATACACA CAAACGGGTT CTTGTGATAT     4934
Asn Ser
    100

AAAGTAAAAT AAACAATGAA CATCATCACA ATATTGATTG TCTATACTAT ATGGTATAAT     4994

TGTATCATTA ATAATAAATG TAGCTTCGTA AATAAATTCA AATCCACATA ATGTTATATT     5054

ATTATATATA TAATACTGAT TATCGTATGT CATTGGATGA TGTATATCTA ATAGTATAAT     5114

| TGAACCATCT | CTTGTC | ATG | TTA | ACA | ATA | GGT | GAA | GTT | ATT | TGT | ACA | ATC | 5163 |
|---|---|---|---|---|---|---|---|---|---|---|---|---|---|
| | | Met | Leu | Thr | Ile | Gly | Glu | Val | Ile | Cys | Thr | Ile |
| | | 1 | | 5 | | | | | | | | 10 |
| | | C25> [SEQ ID NO: 4] |

| TCA | CAT | ACT | CTG | CCA | ATA | TTA | TGT | TCA | TTA | GAT | GTC | TTA | TTT | TCA | TAT | 5211 |
|---|---|---|---|---|---|---|---|---|---|---|---|---|---|---|---|---|
| Ser | His | Thr | Leu | Pro | Ile | Leu | Cys | Ser | Leu | Asp | Val | Leu | Phe | Ser | Tyr |
| | | | 15 | | | | 20 | | | | | 25 |

| TTA | AAC | CTC | ACC | CAT | GTT | TCA | TCA | TCA | TTG | TCG | ATA | TCA | GAA | TTT | GTT | 5259 |
|---|---|---|---|---|---|---|---|---|---|---|---|---|---|---|---|---|
| Leu | Asn | Leu | Thr | His | Val | Ser | Ser | Ser | Leu | Ser | Ile | Ser | Glu | Phe | Val |
| | | 30 | | | | | 35 | | | | | 40 |

| AAA | TTA | CAG | TAT | CCT | AAA | GAA | TTA | GTA | CAA | ACG | GTT | CTC | CAT | TCG | TCA | 5307 |
|---|---|---|---|---|---|---|---|---|---|---|---|---|---|---|---|---|
| Lys | Leu | Gln | Tyr | Pro | Lys | Glu | Leu | Val | Gln | Thr | Val | Leu | His | Ser | Ser |
| 45 | | | | | 50 | | | | | 55 |

TGACTGTACT GCATTAATTC TACATCGTAT GATATTACAT TATTATCCCA TTTAATTATT     5367

GTATCAAAAT CATTAGATGA TAAAGTAACC GAGGATGGAA ATACATCGGC ATTTACTACA     5427

AATGATAGTG ATAATATAAT GAATATGAAA TGCATGTTTT ATTATAAAAA TAGATTAAAT     5487

TTTCACTTTA AAGTTCATAA ATCGTATCGT ATGTGTTGTT TTTAGCGGAA ATCTTACAAT     5547

ATTTATATAG ATAAACTATC AGCGTTATGA ACGATATACA AGTTATGACA AATGGTAATA     5607

AGTAGAATAT CATCGTAACC AGCTTAAATG AAACATCATT TTTTGATGTA TCTATTATTT     5667

TTGTTATATT AATTCTAGTT AAAACAAGCG ATATAATAAA CGTACATAAG AATAGAGTAG     5727

| CGTACAAAAT | TGCTGACTTT | TTGCAATCTT | TA | ATG | GAG | AAT | ACC | CAC | TGT | GAG | 5780 |
|---|---|---|---|---|---|---|---|---|---|---|---|
| | | | | Met | Glu | Asn | Thr | His | Cys | Glu |
| | | | | 1 | | | | | | 5 |
| | | | | C24> [SEQ ID NO: 5] |

Fig. 2D

```
AAT GGT TTT CTA ACA CTA ATG ATG TTA TAT TCT TTA TTA CAT AAT TTA      5828
Asn Gly Phe Leu Thr Leu Met Met Leu Tyr Ser Leu Leu His Asn Leu
        10                  15                  20

CAA GAT CGT TCC CTT GAG TAT TGT ATC CAC TTT TTC ATA CAT TCA TCG      5876
Gln Asp Arg Ser Leu Glu Tyr Cys Ile His Phe Phe Ile His Ser Ser
        25                  30                  35

TGT ACA ACT TTA TAC TCG TTT TTA CAG TTA CAA TAATTCTTTT CAATACTGTA    5929
Cys Thr Thr Leu Tyr Ser Phe Leu Gln Leu Gln
 40              45              50

GTCATCTTTA CATATCCAAC AAACAGGATC CATTTTATAT GGTACAAAAT ATCTTCTAAG    5989

GTCTAGATTA TACTTCAGTT TTGATAAAAA AATTATACAA TTGAAACATC TATATATCCT    6049

TTTAATACAT CAACTCTAAT AACTCTCACG CTAATAGTTT TTCCAACTAA TGATTTCTTT    6109

AGATCTTCTA TTTTATCGGC TCTAATATTT ATATAATTCA ATATACACGC TTCCATTGCA    6169

TAATCTGTTA AATATGAGTA AAATATGTTA TTTCTAACAA AAATTATACC TTGCGTGATA    6229

TCATTTATGT TAGGTAATCC ATAACAAAAT GCCAACGTAT TCATAGTTGA CATTATTGTT    6289

ATTTATTTGA ATACTTTATA TTTCATATTT CATACTTGTG TAGTATTTAA ACAACTCCAT    6349

AAATTATTTA ATATTATAGA TGCCTTGATA GGTGTGTATA TATCTGATAA TACACATGTT    6409

AGTTTTGTCA TCTCCATTTC TGACGTAATA TTATATATAA TAAGATCGGT ACGTAACTTA    6469

TACATATGCT CATTTTTTTC AGTACTATTG TATTCTTCT CTTTATAATG ATCGCTATTT     6529

AGTTGTTCTA CGAATGTATT GTTGTTACCT ACCATCCAAT ATAAGATACT ATACGTAGAA    6589

TTAGTATATC CGTTACATTT TACTATAACC TTATTTGTTT TCTTATGTGG TGGATATAAC    6649

AATACATCTC GTCCGTTACA TATATAAATC ATATATAATA CACACGATAA CACTATCCAC    6709

ATATTACGGT TCATTTTTAA AAAAAAAGAT TTATTTTTAT ATTTTTAATA CATACCGTAA    6769

ACAGTAGTAA GTTACA ATG CTC GCT ATC ATC ATA CTT AAT CCA CGG CGC       6818
               Met Leu Ala Ile Ile Ile Leu Asn Pro Arg Arg
                1               5                   10
         C23> [SEQ ID NO: 6]

CTA CAT CGG GTA TCG GTA TAT TTA TCA AAT TCA TCT AAA AAT AAT ATA     6866
Leu His Arg Val Ser Val Tyr Leu Ser Asn Ser Ser Lys Asn Asn Ile
            15                  20                  25

ATA TAT ATA CCG TCT TCT GAT ATA ATA TTT ATT ATA TCA TCA ATT ATA     6914
Ile Tyr Ile Pro Ser Ser Asp Ile Ile Phe Ile Ile Ser Ser Ile Ile
        30                  35                  40

TAT TTA GCT ATA CGA ATA TTT CTA CAT ATT AGT TTA TCT ATT ATT ATA     6962
Tyr Leu Ala Ile Arg Ile Phe Leu His Ile Ser Leu Ser Ile Ile Ile
        45                  50                  55

GAT AAT AAC GAA ATA GCA GCT AAT TTG ATA CTA GGT CGC GAA TCT GAT     7010
Asp Asn Asn Glu Ile Ala Ala Asn Leu Ile Leu Gly Arg Glu Ser Asp
 60              65                  70                  75
```

Fig. 2E

```
AAC AAT ATA CTA ATA ACT TCT TTA TGC ACG TTA TCT ATA TAC TTA TTT    7058
Asn Asn Ile Leu Ile Thr Ser Leu Cys Thr Leu Ser Ile Tyr Leu Phe
             80                      85                  90

TCA TCG TAT TCT AAA ATA CAT GTA ACA GAA TTA AAA TCA TTA CAA TAT    7106
Ser Ser Tyr Ser Lys Ile His Val Thr Glu Leu Lys Ser Leu Gln Tyr
             95                     100                 105

CTG TAT TTT ATC GCT TCA CAT TGATTTTTA TCTTTGTGTA TATCATCCGT        7157
Leu Tyr Phe Ile Ala Ser His
            110
```

| | | | | |
|---|---|---|---|---|
| TCATATCTAC | TAAGTTTATT | TATAGTATTA | TATTTTAGAT | ATACATATAA TACATTCCTA | 7217 |
| ATGCATACGT | TAGAGTTATA | TTTCTTGTAC | ATATTGATAA | TAATGGATAT AATACAGATG | 7277 |
| AATTATTTTT | TCATTTATTA | TACTTTACAT | ACCACTTGAC | CCAAAACCAC TATTTCCACG | 7337 |
| TTCTGTATCT | TCCAAACATT | TTACTTCTTC | CATTATAGGA | TATTCTACTC TTTCAAATAT | 7397 |
| TATTTGTGCT | ATCCTATCAC | CTACCTTTAT | GTTAAAATCA | CTACATCCAT TATTTATAAA | 7457 |
| CACGATACCT | ATTTCCCCTC | TGTAATCACT | ATCAATAACG | CCTCCTCCTA TATCTATATT | 7517 |
| ATAATTTAAC | GATAATCCCG | ATCTAGGCGA | TATGCGTCCA | TAACATTTAT CTGGTATCAT | 7577 |
| TAAACAAATA | TCTGTTCTAA | CTAAAATTCT | ATTATACGGC | TTAACTGTAT AACTATATGC | 7637 |
| ACTATACAGA | TCATATCCAG | CGGATCCGCT | CATTGATCTA | TTTGGTATAA TAGCATTATT | 7697 |
| AGATAACTTA | ACACATTTAA | CATATAGTGA | CATGTCTAGA | AAATATTATT TTTTTTTTAA | 7757 |
| TTTTATAATA | TTACTCACTA | ACTAAAAAAG | TTTTCTACGC | ATTTTACTAC CCATAGCTTT | 7817 |
| AAGGATTTCC | GTATCTCTAA | ATCTATGTCT | GCGTCTTTTT | GAATTATCAC AATACGTATA | 7877 |
| TGATGATGTT | GTAGGTGTTA | TATTCTGTAT | AGATCTTTGT | AGTGTTCCAC TTATATATTC | 7937 |
| TGTATTATGT | ATTCGTAATA | TGACTTTATA | GAGAAAATAA | ATTGCTCTAT AATTATTATA | 7997 |
| TTTATTCATT | ATTTTAATAG | CTAGATCGAC | TCTATCTAAT | ACATTAATAT CATCGTTAGA | 8057 |
| TATATTAATG | TCATCCTGTA | TCAAGAATAA | TAACGTTTTA | AACTGATACG GTGTCAACCT | 8117 |
| TTCAAGCACA | GACAGATATG | ATCGTATAAC | GTAGTTCCAT | TGTCGTAACA AGAAAAAATG | 8177 |
| TAGATTATTT | TTTCATTTCT | TGAAAGAATG | ACTCTATATC | GATAGACCCT ACAATACCCC | 8237 |
| ATTCATCTAG | CTCCGTTATA | TATTTCTATT | TGACTAATAT | ATTTGTTAAT AATATATCCA | 8297 |
| GCCTATTATA | GCGATAGAGT | CTTCTATAAT | ACAAAGCGAT | GAATTAAATC GAGGAAAGGG | 8357 |
| TAGAGACTTT | TCTACAGTCC | ATTTATTCGA | ATGAGGGTTA | TACTTCTCAA CCATAGTAAA | 8417 |
| TACATGAATA | TTATCTATAA | AAGATAAACC | ACCAATCATA | TATATATAAC CATGGTGATA | 8477 |
| TGCTATACAT | CCACCAAAAT | GTGAATAATT | CATCGCATTA | CCAATAGACC AAGTGTTTTC | 8537 |
| TTCATAAGAA | TAGATTTCAA | TAGTTTTATC | ATCTTCAGAA | ATACCACCAA CAACATATAA | 8597 |
| ATCATTATCT | GTTCCAATTA | TGCAAGGATT | AAATCTGGGT | TGTAATAATG GTACTTCTTC | 8657 |

Fig. 2F

| | |
|---|---|
| TCTCCATTGT TGTTCTCCAG GTGACCAACT TTCTACTGTT TTTAATGGTC CATCGTATCC | 8717 |
| TATACCACCT ACCACATAAA TTCTATTTTT AAAAATAGCA ACACCCGGAC ACTTTCTAGG | 8777 |
| ATGTAATAAT GGTGGTGTAT GCAACTCTAT AAATGATCTA GTGTCTACGC TAGTTATATC | 8837 |
| ACTAACAGGA TCCAATGATT TATTTATACC ACCTATAAGA TATAATATAT CATTCATAAG | 8897 |
| TACAGATCCA CAGTAAGGAT TATGATTCTC AGCTATACTA TTGATTATAC TAAGTTCATT | 8957 |
| CTTAACAGAT ACATTACCTA GCATATTTAT ACTAAATGAA GATGGTGTAA CCATCGTATA | 9017 |
| TCTTCTGTTT GTAAATCTAT GTTGATAACT TATTCTAGGT AATTCATTTT CATTTAACTC | 9077 |
| TACATTATTA TTTTTTCCGA ATCGTGCCAA CCATTTGTT AATTTATACT TACCATATAT | 9137 |
| GGATAGATAA TTATATCTTA GTACCTCTGT TACTAGTGTA AACGATTTTC GTCTGTTGGA | 9197 |
| TTTTTTATGT CTAGACCATT TTATTATAAA TAATAATACA TCATCTTCTG ATGATACATC | 9257 |
| TAATTCTCCA CTTTTTAGAA TTATTCTCAA ATCAAATAAG GATAACGATA GTAATATATC | 9317 |
| TGTTTCTATT TTTGTGAATC TTTTCCTTAT ATATGCTATA GCATCATTAT ATACCGCAAA | 9377 |
| ACATCCATTC GAGAAACCTA TTTTGTAAAT CTTAACACAT GTAGAATCCG TTATATGTTT | 9437 |
| TGACATAAAA TCAATACATG AATTTTTTAA AAAATCTATG GCTTTACTAC AAGATATGGA | 9497 |
| AAAAATATTT TCTACATTGT CTAAATCGAT AGTAACGATT CCAGTTTCTA TATATTTTAT | 9557 |
| TATATCAAGA AAAGATTCAT ACTGGAATGA AACCGTTATT TCATTACTCT GATTCTTTGT | 9617 |
| AATAAGTTTA AAGTAATTAG ATACAGATAC AAGTAATTCT TTTTTTACTT TAACAACACC | 9677 |
| ACCAACGGTC ATAATAAATA CTATCTCTTC ATCATAACTT CTGTTTAGAT TCACAGCATT | 9737 |
| TAACCTTTCT ATATAGTTAT AATCAATGTA AGTTTCTTGT TTAGACATTT TTCACTATCT | 9797 |
| ATTTGCAAAC CAAAGCAAAT TACTATTATT AAATTATTTA TTCAACTTTA TAAAAATTAT | 9857 |
| TAATTAAAAA TCTATATCCG TAGAAAATAT ATTCTCTTCT TTATTTGTAA ACACCCCCAT | 9917 |
| CTTTTGATAT TCACTAACTC GTCGTTCGAA AAAATTAGTC TTACCTTCTA GTGATATATA | 9977 |
| CTCCATAAAG CTAAAAGGAT TATATACATT GAGACTTTTC ACAACCTAAC TCTGTTAATA | 10037 |
| ATCTATCTGC GACGAATTCT ATATACTGAG ACATTAAACA ACAATTCATA CCTATAAGAT | 10097 |
| CCACCGGAAT AGCAACTGTC AAAAACTCCT TTCTATATT AACCGCATCA ATG ATT<br>                                                                                             Met Ile<br>                                                                                                   1<br>                                                                                                C22> | 10153 |
| ATC GAC GTT ATA ACT TCC TTA GAT GGT GGA TGT AAT AAA TGT TTA AAC<br>Ile Asp Val Ile Thr Ser Leu Asp Gly Gly Cys Asn Lys Cys Leu Asn<br>        5                                10                          15<br>[SEQ ID NO: 7] | 10201 |
| ATT AAA CAC GCA AAA TCA CAA TGT AAA CCT TCG TCT CTA CTT ATT AGT<br>Ile Lys His Ala Lys Ser Gln Cys Lys Pro Ser Ser Leu Leu Ile Ser<br>   20                          25                            30 | 10249 |

Fig. 2G

```
TCA TTA GAA AAT GTT AAT CCG GGC ATC AAT CCT CGT TTT TTT ATC CAA      10297
Ser Leu Glu Asn Val Asn Pro Gly Ile Asn Pro Arg Phe Phe Ile Gln
 35              40              45              50

AAT ATA GCA GCA AAT GAA CCA GAA AAG AAT ATT CCC TCC ACA GCT GCA      10345
Asn Ile Ala Ala Asn Glu Pro Glu Lys Asn Ile Pro Ser Thr Ala Ala
                 55              60              65

AAT GCT ACT ACT CTT TCT CCA TAT ACC TTG TTG CTA GAT ATC CAT TTT      10393
Asn Ala Thr Thr Leu Ser Pro Tyr Thr Leu Leu Leu Asp Ile His Phe
             70              75              80

CTG GCC CAA TCA GCT TTC TTT TTT ACG CAT TCC ATT GTT TCT ATA GCG      10441
Leu Ala Gln Ser Ala Phe Phe Phe Thr His Ser Ile Val Ser Ile Ala
         85              90              95

TTA AAT AAA TGC ATT TTT TCT ATA TTA TCT CTT ACA TAT GTA TCT ATT      10489
Leu Asn Lys Cys Ile Phe Ser Ile Leu Ser Leu Thr Tyr Val Ser Ile
     100             105             110

AAT AAA CTA TAC ATT TCT GAA TGAATATTTT CCATAGCTAT TTGAAATCCA         10540
Asn Lys Leu Tyr Ile Ser Glu
 115             120

TAGAAACATC GTGCCTCTGA ACACTGTACA TCCACATAAA ATCTTTCCGC TAAATTCTCA    10600
TTTACAATAC CATCACTAGA TGCAAAAAAT GCTAGTATAT GTTTTATAAA GTATTTTTCG    10660
TCTTTAGTTA ATTTATCCCA ATCATCTAAA TCTTTTGATA AATCTACTTC TTCAACGGTC    10720
CAAAAACTTG CCACTGATTG TTTATACATT TTCCAGATAT CATGATACTT AATAGGGAAA    10780
ATAACGAACC TAGAATCAGA CTCTTGAAGA ATAGGCTCCA TTCGTGTATA AAAATCATTT    10840
TTCAATTTAT TCGGTATTAA CACCAACGCT GCTATCGTTC GTATAATACA TATTATCTAA    10900
TTGTAAAAAT TCTCTTCTCG ATGTCCATTG TAAACATCTA GTTCTTATTT GTCTAAATAT    10960
ATCTACTATA AACGACCATC TTACTAATTG TAGTAGTAAA TAACACGTTA TCACGATAGT    11020
AACTAAACAT AATGTAATTA CCATTATTGT TCCAACTTCA TTAGACATAT CATTATCTAT    11080
AATTATTTGT GAAGTTGTTG TATTCATTGT CTGAATGTTT AATTATTATT TTTTTGTTT     11140
TTTTTACTAA ATAAAAACAT CATCATCGCT ACTACTACAA CGTTTCCTTA TAACTTTTAC    11200
TTTATAAGGT ATTTTGATGT TATTTTTATG TATCAACTTT TCATTCTCCT GGTAATAGTC    11260
GGTATTAGAT TTTATCCTAT AAGTTGATTT CTTTCTTAAA AATGTAGTAA ATTTCTTTCG    11320
TAAATATGAC ATAAAACCAT TATTTATTGA ATACTTACGA TTATTCATTA TTATTTATTT    11380
AGAAATATAC TGATTTAATA CTATATGTGG AATATCTCGA TTCTAGACTA TATGTAGAAT    11440
ATCTCGATTC TAGTGTACTA CTACAACTAT TTTTCTTCT TACATATATT GGCTTATTTT     11500
TTATATTATA ATAATATTCA TCGTCTATAG AAGATATTGA CACTGTATCC ATACTTATAC    11560
TTATTGATTT TACAGATACA CAACTGCCCA TAGTTCGTAT ATATTGGCTT TGTATGTTGC    11620
AATATTTTTT CAATATAAAA AAAATAACAA AAAGACGAGT ATAATAAAAT ACATAAAGTA    11680
```

Fig. 2H

```
AAAACAAACA TATTATTATT TACTTCATTT TTAAGGTGCA TGCATTTTCC TTTTGAAATG   11740
AAATGAAATG AAATGAAATG TAGTGCTCTA AAACAAACTT AACCTTACTT ATAAATATCC   11800
TCCATATTTA CCCATTATAA TAGAATTGTG TGGACCTAGT AGTTATAATC ATAGGATAAT   11860
CATTATGTAA ATACGATTCT CTTTTTATAT GTTGATTAGG TTTAATATTT AGACAATATC   11920
CATATTTATT TATTTCATCA TTAGTGGGTG GTGTAGACTG TGTATGTTGT ACAGACTTGC   11980
CGGTTAAAAC AATTTTATTT ACTTTTTTCG GTTCCGCTC ATGGTTATTT AGTAGGCGAT    12040
TATTTATGTT ATTAGCTATG ATTTATGTTT CATTTTAAC CCGGTTTAGA CATATAAAAA    12100
TGTACCATAT TTGTATTTAA TTCCTATTCG TCTTTTTATA GAACATATTC CTATAACAAA   12160
TATGATAGCA ATAATAATGA TGCTAAATAT AAACCATGGT CTATTGTTA AATTCAAATA    12220
ATTATATATA TTAGCATTGT CAATATATCT TCTATTCATA GAATTCATGA TAGAATTCAT   12280
CACACAGTTT GCTTCTGCAG TACCAGAATT AACAATCTGT AATAGAATCT GTTTATCGTA   12340
CGGAGCTATG CATTTTCCAA CATCTAATGT TTGAATATCA ATAATATTTG TTACATCTGC   12400
GGATGATGAA CAGTTTCGTA TTATTTCTGG TACATATTTA GGGTCATTGT TTAATATATC   12460
AATTCCAATT TCTTTAGATA ATTCCTCTTT CTCTTTCTGA GATAACGTAC TAGTTACATC   12520
TTTAAGCGTC TTTATAAGAA TATTGAAACT TAGTTCTTTA TCGTTTATAC ACATATTGAG   12580
TATTTCAAA AAACATCTTT TGAACGTTCC TTTGATTTCT CCTATATGTA TACCACATGT    12640
TGAATTAATA GGTATAGAAT ATATTGATAA GTTCTCTATA TATCTTTCTA CGAATACGTT   12700
ATATAATGTA TTTATTCTAA CAGGATTCTC CATTTATCCA ATTTGAGAAA ATGTTTTTTG   12760
TAATCAAATT TTCTAAAAAT GATATAGGAT GCAGTATGGA TACTTTTAAT CTAAATTTCT   12820
CACATGTATT TTTTGTACAA CACATTATAA AATCCTCTAA AGAATCGCTG AATTCTTTAT   12880
CAGATTCTAT TTCTGGATAA GTTCGTAGAA GTGTATGTAT AAAAAAATGA AAATCATAAT   12940
ACCAATTGTG TTCTATTTTT AAACTATTTT TAATTTTCTT ATTTAATATA TTAGCCACCT   13000
GTGAAAAATC GAAATCGTTA AGACACGCTT TAATCGGTTC ATTAAATACG TATGTATATT   13060
TCTTAAATTT AATAGTTATA GGACAATCAG AATTAAATAT TAAAATATTA TCGGGTTTTA   13120
AATCAACGTG TAAAAAATTA TCACAACAAG GAAGTTCGTA TATTTTTATA TATAACAATG   13180
ATATTTGTAA AAAAATAAAC TTAACATATT GAACTATAGA TTTAAAACCA AGTTCTATCG   13240
CCATCTGTTC CGTCACTTTA TCTGATGAAA ATCTTGCTAA TGGGAATATA ATTATATTTC   13300
CTCTATCGTA TAAATAATTA GCTCTTTTTT CATGTTCGAA AAAATGAAAC ATATGTGTAA   13360
AATAATTTAT TACATTTATA TTACTTTGAA CAACAATAGG ATAAAAATAT GATAATAATT   13420
TTACAAATTT TATATCGCTC TTTTTTTCAT TGAACGACTT AAGAAAATAC TTATGAGAAA   13480
AATGATGAAT ATTTAATCGT TGATTATCTA TCGTTTGAAT AATAAGTAAT AACATATATA   13540
```

Fig. 2I

```
ATACTCTTTT ATATAATCTA TGTAGAAATG TTAATTTATA ATTTAAACCC ATTGCCCATG   13600
CACAAACGAT AAGTTTTTTC TCATCTCCCT TAAGATTATT ATATAAAAAT TTAGGTATTG   13660
TATACTCGGC AGTTGTATCA ATGGGACTAT ACTGTTTATT TGGTTCATAA ACAAATTTAA   13720
CAACGTATTT ATCCATTTTA AATACGATAC CATAACCTCC TGTTGATATA TGATAGAAAT   13780
CATCATTAAG TGGATAAAAT CGTTTATCTC TTTGTTGGAA AAAAGATGGG TTAATATATT   13840
CCGTATCTGA TATTTATCA AATGATTCTT TGTTAAACTT CCTAAAATAT CTTATTAGTC   13900
TGATATCAGG AGACCAATTT TGATGTATAT CTAACTGAGA AATTATATAA TCAAAATATA   13960
TATCATCACC GAGAATAGTT GTATCATTAT TATCATCGAT AGACTCCCAC TGACATTCTA   14020
ACGAATTAAT TTCTTTCATT TATTGTATAA AAAGCTACTT TATTGTATAC GAAATCCAAT   14080
ATTTGATAAT GCGAATAAAT TATTAACTAT TTCTTCTTTT AAAGAATAAG ATTCTCCCAT   14140
TGATAGTTTG TATATTACAT ATGAATCAAT AAGCTT                            14176
```

Fig. 2J

```
AAGCTTATTG ATTCATATGT AATATACAAA CTATCAATGG GAGAATCTTA TTCTTTAAAA      60

GAAGAAATAG TTAATAATTT ATTCGCATTA TCAAATATTG GATTTCGTAT ACAATAAAGT     120

AGCTTTTTAT ACAATAAATG AAAGAAATTA ATTCGTTAGA ATGTCAGTGG GAGTCTATCG     180

ATGATAATAA TGATACAACT ATTCTCGGTG ATGATATATA TTTTGATTAT ATAATTTCTC     240

AGTTAGATAT ACATCAAAAT TGGTCTCCTG ATATCAGACT AATAAGATAT TTTAGGAAGT     300

TTAACAAAGA ATCATTTGAT AAAATATCAG ATACGGAATA TATTAACCCA TCTTTTTTCC     360

AACAAAGAGA TAAACGATTT TATCCACTTA ATG ATG ATT TCT ATC ATA TAT CAA     414
                                  Met Met Ile Ser Ile Ile Tyr Gln
                                   1                 5
                                  C2> [SEQ ID NO: 33]

CAG GAG GTT ATG GTA TCG TAT TTA AAA TGG ATA AAT ACG TTG TTA AAT      462
Gln Glu Val Met Val Ser Tyr Leu Lys Trp Ile Asn Thr Leu Leu Asn
         10              15                  20

TTG TTT ATG AAC CAA ATA AAC AGT ATA GTC CCA TTG ATA CAA CTG CCG      510
Leu Phe Met Asn Gln Ile Asn Ser Ile Val Pro Leu Ile Gln Leu Pro
 25              30                  35                  40

AGT ATA CAA TAC CTA AAT TTT TAT ATA ATA ATC TTA AGG GAG ATG AGA      558
Ser Ile Gln Tyr Leu Asn Phe Tyr Ile Ile Ile Leu Arg Glu Met Arg
             45                  50                  55

AAA AAC TTA TCG TTT GTG CAT GGG CAA TGG GTT TAAATTATAA ATTAACATTT    611
Lys Asn Leu Ser Phe Val His Gly Gln Trp Val
             60                  65
Seq. ID. 14 (cont'd)

CTACATAGAT TATATAAAAG AGTATTATAT ATGTTATTAC TTATTATTCA AACGATAGAT    671

AATCAACGAT TAAATATTCA TCATTTTTCT CATAAGTATT TTCTTAAGTC GTTCAATGAA    731

AAAAAGAGCG ATATAAAATT TGTAAAATTA TTATCATATT TTTATCCTAT TGTTGTTCAA    791

AGTAATATAA ATGTAATAAA TTATTTTACA CATATGTTTC ATTTTTTCGA ACATGAAAAA    851

AGAGCTAATT ATTTATACGA TAGAGGAAAT ATAATTATAT TCCCATTAGC AAGATTTTCA    911

TCAGATAAAG TGACGGAACA GATGGCGATA GAACTTGGTT TTAAATCTAT AGTTCAATAT    971

GTTAAGTTTA TTTTTTTACA AATATCATTG TTATATATAA AAATATACGA ACTTCCTTGT   1031

TGTGATAATT TTTTACACGT TGATTTAAAA CCCGATAATA TTTTAATATT TAATTCTGAT   1091

TGTCCTATAA CTATTAAATT TAAGAAATAT ACATACGTAT TTAATGAACC GATTAAAGCG   1151

TGTCTTAACG ATTTCGATTT TTCACAGGTG GCTAATATAT TAAATAAGAA AATTAAAAAT   1211

AGTTTAAAAA TAGAACACAA TTGGTATTAT GATTTTCATT TTTTTATACA TACACTTCTA   1271

CGAACTTATC CAGAAATAGA ATCTGATAAA GAATTCAGCG ATTCTTTAGA GGATTTTATA   1331

ATGTGTTGTA CAAAAAATAC ATGTGAGAAA TTTAGATTAA AAGTATCCAT ACTGCATCCT   1391
```

Fig. 3A

```
ATATCATTTT TAGAAAATTT GATTACAAAA AACATTTTCT CAAATTGGAT AA ATG                1446
                                                           Met
                                                           1
                                                           C3>

GAG AAT CCT GTT AGA ATA AAT ACA TTA TAT AAC GTA TTC GTA GAA AGA              1494
Glu Asn Pro Val Arg Ile Asn Thr Leu Tyr Asn Val Phe Val Glu Arg
            5                   10                  15
[SEQ ID NO: 34]
TAT ATA GAG AAC TTA TCA ATA TAT TCT ATA CCT ATT AAT TCA ACA TGT              1542
Tyr Ile Glu Asn Leu Ser Ile Tyr Ser Ile Pro Ile Asn Ser Thr Cys
        20                  25                  30

GGT ATA CAT ATA GGA GAA ATC AAA GGA ACG TTC AAA AGA TGT TTT TTG              1590
Gly Ile His Ile Gly Glu Ile Lys Gly Thr Phe Lys Arg Cys Phe Leu
    35                  40                  45

AAA ATA CTC AAT ATG TGT ATA AAC GAT AAA GAA CTA AGT TTC AAT ATT              1638
Lys Ile Leu Asn Met Cys Ile Asn Asp Lys Glu Leu Ser Phe Asn Ile
50                  55                  60                  65

CTT ATA AAG ACG CTT AAA GAT GTA ACT AGT ACG TTA TCT CAG AAA GAG              1686
Leu Ile Lys Thr Leu Lys Asp Val Thr Ser Thr Leu Ser Gln Lys Glu
            70                  75                  80

AAA GAG GAA TTA TCT AAA GAA ATT GGA ATT GAT ATA TTA AAC AAT GAC              1734
Lys Glu Glu Leu Ser Lys Glu Ile Gly Ile Asp Ile Leu Asn Asn Asp
        85                  90                  95

CCT AAA TAT GTA CCA GAA ATA ATA CGA AAC TGT TCA TCA TCC GCA GAT              1782
Pro Lys Tyr Val Pro Glu Ile Ile Arg Asn Cys Ser Ser Ser Ala Asp
    100                 105                 110

GTA ACA AAT ATT ATT GAT ATT CAA ACA TTA GAT GTT GGA AAA TGC ATA              1830
Val Thr Asn Ile Ile Asp Ile Gln Thr Leu Asp Val Gly Lys Cys Ile
    115                 120                 125

GCT CCG TAC GAT AAA CAG ATT CTA TTA CAG ATT GTT AAT TCT GGT ACT              1878
Ala Pro Tyr Asp Lys Gln Ile Leu Leu Gln Ile Val Asn Ser Gly Thr
130                 135                 140                 145

GCA GAA GCA AAC TGT GTG ATG AAT TCT ATC ATG AAT TCT ATG AAT AGA              1926
Ala Glu Ala Asn Cys Val Met Asn Ser Ile Met Asn Ser Met Asn Arg
                150                 155                 160

AGA TAT ATT GAC AAT GCT AAT ATA TAT AAT TAT TTG AAT TTA ACA AAT              1974
Arg Tyr Ile Asp Asn Ala Asn Ile Tyr Asn Tyr Leu Asn Leu Thr Asn
            165                 170                 175

AGA CCA TGG TTT ATA TTT AGC ATC ATT ATT ATT GCT ATC ATA TTT GTT              2022
Arg Pro Trp Phe Ile Phe Ser Ile Ile Ile Ile Ala Ile Ile Phe Val
        180                 185                 190

ATA GGA ATA TGT TCT ATA AAA AGA CGA ATA GGA ATT AAA TAC AAA TAT              2070
Ile Gly Ile Cys Ser Ile Lys Arg Arg Ile Gly Ile Lys Tyr Lys Tyr
    195                 200                 205

GGT ACA TTT TTA TAT GTC TAAACCGGGT TAAAAATGAA ACATAAATCA                    2118
Gly Thr Phe Leu Tyr Val
210             215
```

Fig. 3B

```
TAGCTAATAA CATAAATAAT CGCCTACTAA ATAACCATGA GCGGAAACCG AAAAAAGTAA    2178

ATAAAATTGT TTTAACCGGC AAGTCTGTAC AACATACACA GTCTACACCA CCCACTAATG    2238

ATGAAATAAA TAAATATGGA TATTGTCTAA ATATTAAACC TAATCAACAT ATAAAAGAG     2298

AATCGTATTT ACATAATGAT TATCCTATGA TTATAACTAC TAGGTCCACA CAATTCTATT    2358

ATAATGGGTA AATATGGAGG ATATTTATAA GTAAGGTTAA GTTTGTTTTA GAGCACTACA    2418

TTTCATTTCA TTTCATTTCA TTTCAAAAGG AAAATGCATG CACCTTAAAA ATGAAGTAAA    2478

TAATAATATG TTTGTTTTA CTTTATGTAT TTTATTATAC TCGTCTTTTT GTTATTTTTT     2538

TTATATTGAA AAAATATTGC AACATACAAA GCCAATATAT ACGAACTATG GGCAGTTGTG    2598

TATCTGTAAA ATCAATAAGT ATAAGTATGG ATACAGTGTC AATATCTTCT ATAGACGATG    2658

AATATTATTA TAATATAAAA AATAAGCCAA TATATGTAAG AAGAAAAAAT AGTTGTAGTA    2718

GTACACTAGA ATCGAGATAT TCTACATATA GTCTAGAATC GAGATATTCC ACATATAGTA   2778

TTAAATCAGT ATATTTCTAA ATAAATAATA ATG AAT AAT CGT AAG TAT TCA ATA    2832
                                  Met Asn Asn Arg Lys Tyr Ser Ile
                                   1                   5
                                  C6> [SEQ ID NO: 17]

AAT AAT GGT TTT ATG TCA TAT TTA CGA AAG AAA TTT ACT ACA TTT TTA    2880
Asn Asn Gly Phe Met Ser Tyr Leu Arg Lys Lys Phe Thr Thr Phe Leu
     10              15                  20

AGA AAG AAA TCA ACT TAT AGG ATA AAA TCT AAT ACC GAC TAT TAC CAG    2928
Arg Lys Lys Ser Thr Tyr Arg Ile Lys Ser Asn Thr Asp Tyr Tyr Gln
 25              30              35                  40

GAG AAT GAA AAG TTG ATA CAT AAA AAT AAC ATC AAA ATA CCT TAT AAA    2976
Glu Asn Glu Lys Leu Ile His Lys Asn Asn Ile Lys Ile Pro Tyr Lys
                 45              50                  55

GTA AAA GTT ATA AGG AAA CGT TGT AGT AGT AGC GAT GAT GAT GTT TTT    3024
Val Lys Val Ile Arg Lys Arg Cys Ser Ser Ser Asp Asp Asp Val Phe
         60              65              70

ATT TAGTAAAAAA AACAAAAAAA ATAATAATTA AACATTCAGA CA ATG AAT ACA     3078
Ile                                                   Met Asn Thr
                                                       1
                                                      C7> [SEQ ID NO: 18]

ACA ACT TCA CAA ATA ATT ATA GAT AAT GAT ATG TCT AAT GAA GTT GGA    3126
Thr Thr Ser Gln Ile Ile Ile Asp Asn Asp Met Ser Asn Glu Val Gly
         5               10                  15

ACA ATA ATG GTA ATT ACA TTA TGT TTA GTT ACT ATC GTG ATA ACG TGT    3174
Thr Ile Met Val Ile Thr Leu Cys Leu Val Thr Ile Val Ile Thr Cys
 20              25                  30                  35

TAT TTA CTA CTA CAA TTA GTA AGA TGG TCG TTT ATA GTA GAT ATA TTT    3222
Tyr Leu Leu Leu Gln Leu Val Arg Trp Ser Phe Ile Val Asp Ile Phe
                 40                  45                  50

AGA CAA ATA AGA ACT AGA TGT TTA CAA TGG ACA TCG AGA AGA GAA TTT    3270
Arg Gln Ile Arg Thr Arg Cys Leu Gln Trp Thr Ser Arg Arg Glu Phe
         55                  60                  65
```

Fig. 3C

| | |
|---|---|
| TTA CAA TTA GAT AAT ATG TAT TAT ACG AAC GAT AGC AGC GTT GGT GTT<br>Leu Gln Leu Asp Asn Met Tyr Tyr Thr Asn Asp Ser Ser Val Gly Val<br>70                       75                     80 | 3318 |
| AAT ACC GAA TAAATTGAAA AATGATTTTT ATACACGAAT GGAGCCTATT<br>Asn Thr Glu<br>85 | 3367 |
| CTTCAAGAGT CTGATTCTAG GTTCGTTATT TTCCCTATTA AGTATCATGA TATCTGGAAA | 3427 |
| ATGTATAAAC AATCAGTGGC AAGTTTTTGG ACCGTTGAAG AAGTAGATTT ATCAAAAGAT | 3487 |
| TTAGATGATT GGGATAAATT AACTAAAGAC GAAAAATACT TTATAAAACA TATACTAGCA | 3547 |
| TTTTTTGCAT CTAGTGATGG TATTGTAAAT GAGAATTTAG CGGAAAGATT TTATGTGGAT | 3607 |
| GTACAGTGTT CAGAGGCACG ATGTTTCTAT GGATTTCAAA TAGCTATGGA AAATATTCAT | 3667 |
| TCAGAAATGT ATAGTTTATT AATAGATACA TATGTAAGAG ATAATATAGA AAAAATGCAT | 3727 |
| TTATTTAACG CTATAGAAAC AATGGAATGC GTAAAAAGA AAGCTGATTG GGCCAGAAAA | 3787 |
| TGGATATCTA GCAACAAGGT ATATGGAGAA AGAGTAGTAG CATTTGCAGC TGTGGAGGGA | 3847 |
| ATATTCTTTT CTGGTTCATT TGCTGCTATA TTTTGGATAA AAAAACGAGG ATTGATGCCC | 3907 |
| GGATTAACAT TTTCTAATGA ACTAATAAGT AGAGACGAAG GTTTACATTG TGATTTTGCG | 3967 |
| TGTTTAATGT TTAAACATTT ATTACATCCA CCATCTAAGG AAGTTATAAC GTCGATAATC | 4027 |
| ATTGATGCGG TTAATATAGA AAAGGAGTTT TTGACAGTTG CTATTCCGGT GGATCTTATA | 4087 |
| GGTATGAATT GTTGTTTAAT GTCTCAGTAT ATAGAATTCG TCGCAGATAG ATTATTAACA | 4147 |
| GAGTTAGGTT GTGAAAAGTC TCAATGTATA TAATCCTTTT AGCTTTATGG AGTATATATC | 4207 |
| ACTAGAAGGT AAGACTAATT TTTTCGAACG ACGAGTTAGT GAATATCAAA AGATGGGGGT | 4267 |
| GTTTACAAAT AAAGAAGAGA ATATATTTTC TACGGATATA GATTTTTAAT TAATAATTTT | 4327 |
| TATAAAGTTG AATAAATAAT TTAATAATAG TAATTTGCTT TGGTTTGCAA ATAGATAGTG | 4387 |
| AAAAATGTCT AAACAAGAAA CTTACATTGA TTATAACTAT ATAGAAAGGT TAAATGCTGT | 4447 |
| GAATCTAAAC AGAAGTTATG ATGAAGAGAT AGTATTTATT ATGACCGTTG GTGGTGTTGT | 4507 |
| TAAAGTAAAA AAAGAATTAC TTGTATCTGT ATCTAATTAC TTTAAACTTA TTACAAAGAA | 4567 |
| TCAGAGTAAT GAAATAACGG TTTCATTCCA GTATGAATCT TTTCTTGATA TAATAAAATA | 4627 |
| TATAGAAACT GGAATCGTTA CTATCGATTT AGACAATGTA GAAAATATTT TTTCCATATC | 4687 |
| TTGTAGTAAA GCCATAGATT TTTTAAAAAA TTCATGTATT GATTTATGT CAAAACATAT | 4747 |
| AACGGATTCT ACATGTGTTA AGATTTACAA AATAGGTTTC TCGAATGGAT GTTTTGCGGT | 4807 |
| ATATAATGAT GCTATAGCAT ATATAAGGAA AAGATTCACA AAAATAGAAA CAGATATATT | 4867 |
| ACTATCGTTA TCCTTATTTG ATTTGAGAAT AATTCTAAAA AGTGGAGAAT TAGATGTATC | 4927 |
| ATCAGAAGAT GATGTATTAT TATTTATAAT AAAATGGTCT AGACATAAAA AATCCAACAG | 4987 |

Fig. 3D

```
ACGAAAATCG TTTACACTAG TAACAGAGGT ACTAAGATAT AATTATCTAT CCATATATGG   5047
TAAGTATAAA TTAACAAAAT GGTTGGCACG ATTCGGAAAA AATAATAATG TAGAGTTAAA   5107
TGAAAATGAA TTACCTAGAA TAAGTTATCA ACATAGATTT ACAAACAGAA GATATACGAT   5167
GGTTACACCA TCTTCATTTA GTATAAATAT GCTAGGTAAT GTATCTGTTA AGAATGAACT   5227
TAGTATAATC AATAGTATAG CTGAGAATCA TAATCCTTAC TGTGGATCTG TACTTATGAA   5287
TGATATATTA TATCTTATAG GTGGTATAAA TAAATCATTG GATCCTGTTA GTGATATAAC   5347
TAGCGTAGAC ACTAGATCAT TTATAGAGTT GCATACACCA CCATTATTAC ATCCTAGAAA   5407
GTGTCCGGGT GTTGCTATTT TTAAAAATAG AATTTATGTG GTAGGTGGTA TAGGATACGA   5467
TGGACCATTA AAAACAGTAG AAAGTTGGTC ACCTGGAGAA CAACAATGGA GAGAAGAAGT   5527
ACCATTATTA CAACCCAGAT TTAATCCTTG CATAATTGGA ACAGATAATG ATTTATATGT   5587
TGTTGGTGGT ATTTCTGAAG ATGATAAAAC TATTGAAATC TATTCTTATG AAGAAAACAC   5647
TTGGTCTATT GGTAATGCGA TGAATTATTC ACATTTGGT GGATGTATAG CATATCACCA   5707
TGGTTATATA TATATGATTG GTGGTTTATC TTTTATAGAT AATATTCATG TATTTACTAT   5767
GGTTGAGAAG TATAACCCTC ATTCGAATAA ATGGACTGTA GAAAAGTCTC TACCCTTTCC   5827
TCGATTTAAT TCATCGCTTT GTATTATAGA AGACTCTATC GCTATAATAG GCTGGATATA   5887
TTATTAACAA ATATATTAGT CAAATAGAAA TATATAACGG AGCTAGATGA ATGGGGTATT   5947
GTAGGGTCTA TCGATATAGA GTCATTCTTT CAAGAAATGA AAAAATAATC TACATTTTTT   6007
CTTGTTACGA CAATGGAACT ACGTTATACG ATCATATCTG TCTGTGCTTG AAAGGTTGAC   6067
ACCGTATCAG TTTAAAACGT TATTATTCTT GATACAGGAT GACATTAATA TATCTAACGA   6127
TGATATTAAT GTATTAGATA GAGTCGATCT AGCTATTAAA ATAATGAATA AATATAATAA   6187
TTATAGAGCA ATTTATTTTC TCTATAAAGT CATATTACGA ATACATAATA CAGAATATAT   6247
AAGTGGAACA CTACAAAGAT CTATACAGAA TATAACACCT ACAACATCAT CATATACGTA   6307
TTGTGATAAT TCAAAAGAC GCAGACATAG ATTTAGAGAT ACGGAAATCC TTAAAGCTAT   6367
GGGTAGTAAA ATGCGTAGAA AACTTTTTTA GTTAGTGAGT AATATTATAA AATTAAAAAA   6427
AAAATAATAT TTTCTAGACA TGTCACTATA TGTTAAATGT GTTAAGTTAT CTAATAATGC   6487
TATTATACCA AATAGATCAA TGAGCGGATC CGCTGGATAT GATCTGTATA GTGCATATAG   6547
TTATACAGTT AAGCCGTATA ATAGAATTTT AGTTAGAACA GATATTTGTT TAATGATACC   6607
AGATAAATGT TATGGACGCA TATCGCCTAG ATCGGGATTA TCGTTAAATT ATAATATAGA   6667
TATAGGAGGA GGCGTTATTG ATAGTGATTA CAGAGGGGAA ATAGGTATCG TGTTTATAAA   6727
TAATGGATGT AGTGATTTTA ACATAAAGGT AGGTGATAGG ATAGCACAAA TAATATTTGA   6787
AAGAGTAGAA TATCCTATAA TGGAAGAAGT AAAATGTTTG GAAGATACAG AACGTGGAAA   6847
```

Fig. 3E

```
TAGTGGTTTT GGGTCAAGTG GTATGTAAAG TATAATAAAT GAAAAAATAA TTCATCTGTA         6907

TTATATCCAT TATTATCAAT ATG TAC AAG AAA TAT AAC TCT AAC GTA TGC             6957
                     Met Tyr Lys Lys Tyr Asn Ser Asn Val Cys
                      1           5                      10
              C12> [SEQ ID NO: 23]

ATT AGG AAT GTA TTA TAT GTA TAT CTA AAA TAT AAT ACT ATA AAT AAA           7005
Ile Arg Asn Val Leu Tyr Val Tyr Leu Lys Tyr Asn Thr Ile Asn Lys
            15              20                  25

CTT AGT AGA TAT GAA CGG ATG ATA TAC ACA AAG ATA AAA AAT CAA TGT           7053
Leu Ser Arg Tyr Glu Arg Met Ile Tyr Thr Lys Ile Lys Asn Gln Cys
        30              35                  40

GAA GCG ATA AAA TAC AGA TAT TGT AAT GAT TTT AAT TCT GTT ACA TGT           7101
Glu Ala Ile Lys Tyr Arg Tyr Cys Asn Asp Phe Asn Ser Val Thr Cys
            45              50                  55

ATT TTA GAA TAC GAT GAA AAT AAG TAT ATA GAT AAC GTG CAT AAA GAA           7149
Ile Leu Glu Tyr Asp Glu Asn Lys Tyr Ile Asp Asn Val His Lys Glu
        60              65                  70

GTT ATT AGT ATA TTG TTA TCA GAT TCG CGA CCT AGT ATC AAA TTA GCT           7197
Val Ile Ser Ile Leu Leu Ser Asp Ser Arg Pro Ser Ile Lys Leu Ala
 75             80                  85                      90

GCT ATT TCG TTA TTA TCT ATA ATA ATA GAT AAA CTA ATA TGT AGA AAT           7245
Ala Ile Ser Leu Leu Ser Ile Ile Ile Asp Lys Leu Ile Cys Arg Asn
                95                 100                 105

ATT CGT ATA GCT AAA TAT ATA ATT GAT GAT ATA ATA AAT ATT ATA TCA           7293
Ile Arg Ile Ala Lys Tyr Ile Ile Asp Asp Ile Ile Asn Ile Ile Ser
            110                 115                 120

GAA GAC GGT ATA TAT ATT ATA TTA TTT TTA GAT GAA TTT GAT AAA TAT           7341
Glu Asp Gly Ile Tyr Ile Ile Leu Phe Leu Asp Glu Phe Asp Lys Tyr
        125                 130                 135

ACC GAT ACC CGA TGT AGG CGC CGT GGA TTA AGT ATG ATG ATA GCG AGC           7389
Thr Asp Thr Arg Cys Arg Arg Arg Gly Leu Ser Met Met Ile Ala Ser
    140                 145                 150

ATT GTA ACT TAC TAC TGT TTA CGG TAT GTA TTA AAA ATA TAAAAATAAA            7438
Ile Val Thr Tyr Tyr Cys Leu Arg Tyr Val Leu Lys Ile
155                 160                 165

TCTTTTTTTT TAAAAATGAA CCGTAATATG TGGATAGTGT TATCGTGTGT ATTATATATG         7498

ATTTATATAT GTAACGGACG AGATGTATTG TTATATCCAC CACATAAGAA AACAAATAAG         7558

GTTATAGTAA AATGTAACGG ATATACTAAT TCTACGTATA GTATCTTATA TTGGATGGTA         7618

GGTAACAACA ATACATTCGT AGAACAACTA AATAGCGATC ATTATAAAGA GAAGAAATAC         7678

AATAGTACTG AAAAAAATGA GCATATGTAT AAGTTACGTA CCGATCTTAT TATATATAAT         7738

ATTACGTCAG AAATGGAGAT GACAAAACTA ACATGTGTAT TATCAGATAT ATACACACCT         7798

ATCAAGGCAT CTATAATATT AAATAATTTA TGGAGTTGTT TAAATACTAC ACAAGTATGA         7858

AATATGAAAT ATAAAGTATT CAAATAAATA ACAATAATGT CAACTATGAA TACGTTGGCA         7918
```

Fig. 3F

```
TTTTGTTATG GATTACCTAA CATAAATGAT ATCACGCAAG GTATAATTTT TGTTAGAAAT     7978

AACATATTTT ACTCATATTT AACAGATTAT GCAATGGAAG CGTGTATATT GAATTATATA     8038

AATATTAGAG CCGATAAAAT AGAAGATCTA AAGAAATCAT TAGTTGGAAA AACTATTAGC     8098

GTGAGAGTTA TTAGAGTTGA TGTATTAAAA GGATATATAG ATGTTTCAAT TGTATAATTT     8158

TTTTATCAAA ACTGAAGTAT AATCTAGACC TTAGAAGATA TTTTGTACCA TATAAA         8214
```

```
ATG GAT CCT GTT TGT TGG ATA TGT AAA GAT GAC TAC AGT ATT GAA AAG                8262
Met Asp Pro Val Cys Trp Ile Cys Lys Asp Asp Tyr Ser Ile Glu Lys
 1               5                  10                  15
C15> [SEQ ID NO: 26]

AAT TAT TGT AAC TGT AAA AAC GAG TAT AAA GTT GTA CAC GAT GAA TGT                8310
Asn Tyr Cys Asn Cys Lys Asn Glu Tyr Lys Val Val His Asp Glu Cys
             20                  25                  30

ATG AAA AAG TGG ATA CAA TAC TCA AGG GAA CGA TCT TGT AAA TTA TGT                8358
Met Lys Lys Trp Ile Gln Tyr Ser Arg Glu Arg Ser Cys Lys Leu Cys
         35                  40                  45

AAT AAA GAA TAT AAC ATC ATT AGT GTT AGA AAA CCA TTC TCA CAG TGG                8406
Asn Lys Glu Tyr Asn Ile Ile Ser Val Arg Lys Pro Phe Ser Gln Trp
     50                  55                  60

GTA TTC TCC ATT AAA GAT TGC AAA AAG TCA GCA ATT TTG TAC GCT ACT                8454
Val Phe Ser Ile Lys Asp Cys Lys Lys Ser Ala Ile Leu Tyr Ala Thr
 65                  70                  75                  80

CTA TTC TTA TGT ACG TTT ATT ATA TCG CTT GTT TTA ACT AGA ATT AAT                8502
Leu Phe Leu Cys Thr Phe Ile Ile Ser Leu Val Leu Thr Arg Ile Asn
                 85                  90                  95

ATA ACA AAA ATA ATA GAT ACA TCA AAA AAT GAT GTT TCA TTT AAG CTG                8550
Ile Thr Lys Ile Ile Asp Thr Ser Lys Asn Asp Val Ser Phe Lys Leu
             100                 105                 110

GTT ACG ATA TTC TAC TTA TTA CCA TTT GTC ATA ACT TGT ATA TCG                    8598
Val Thr Met Ile Phe Tyr Leu Leu Pro Phe Val Ile Thr Cys Ile Ser
         115                 120                 125

TTC ATA ACG CTG ATA GTT TAT CTA TAT AAA TAT TGT AAG ATT TCC GCT                8646
Phe Ile Thr Leu Ile Val Tyr Leu Tyr Lys Tyr Cys Lys Ile Ser Ala
     130                 135                 140

AAA AAC AAC ACA TAC GAT ACG ATT TAT GAA CTT TAAAGTGAAA ATTTAATCTA              8699
Lys Asn Asn Thr Tyr Asp Thr Ile Tyr Glu Leu
145                 150                 155
```

```
TTTTTATAAT AAAACATGCA TTTCATATTC ATTATATTAT CACTATCATT TGTAGTAAAT    8759

GCCGATGTAT TTCCATCGTC GGTTACTTTA TCATCTAATG ATTTGATAC AATAATTAAA     8819

TGGGATAATA ATGTAATATC ATACGATGTA GAATTAATGC AGTACAGTCA TGACGAATGG    8879

AGAACCGTTT GTACTAATTC TTTAGGATAC TGTAATTTAA CAAATTCTGA TATCGACAAT    8939

GATGATGAAA CATGGGTGAG GTTTAAATAT GAAAATAAGA CATCTAATGA ACATAATATT    8999
```

Fig. 3G

```
GGCAGAGTAT GTGAGATTGT ACAAATAACT TCACCTATTG TTAACATGAC AAGAGATGGT    9059

TCAATTATAC TATTAGATAT ACATCATCCA ATGACATACG ATAATCAGTA TTATATATAT    9119

AATAATATAA CATTATGTGG ATTTGAATTT ATTTACGAAG CTACATTTAT TATTAATGAT    9179

ACAATTATAC CATATAGTAT AGACAATCAA TATTGTGATG ATGTTCATTG TTTATTTTAC    9239

TTTATATCAC AAGAACCCGT TTGTGTGTAT GTAATGGGTA TGGAACAATA TTATGAATTT    9299

GGTCCAAAAA AAACAGATAA TAGTACTAGA GTGTGTGTAG ATGGATTAAT TCCAAGAAAA    9359

ATCGATACAT ATTTTATTAA AGATTTCGAT GATATAGATA GAGTTAATAA CAGATTATAT    9419

AGAGTTGTAA GTGATAAATA TGAATCCAAT ATATCGTCAA AGTTTATGCA CTTATATAAT    9479

AATATATTAT CTTCGTTTAA ACTAATATTG CAAGAACTTA TGGTAAATAC TGAACAGTAA    9539

ATACGTTTAT AAAGATAAAG GA ATG AAT TCG TAT ATT GTA ATA AAA AAT TCA    9591
                         Met Asn Ser Tyr Ile Val Ile Lys Asn Ser
                          1               5                   10
                        C17> [SEQ ID NO: 28]

TTA CGT GAT TAT AGA TCT GGA AGA ATT ATA AGA AAA TAC ATA AGA AAA     9639
Leu Arg Asp Tyr Arg Ser Gly Arg Ile Ile Arg Lys Tyr Ile Arg Lys
                15                  20                  25

TTA AAT AAG GAT GAG TAT AAG CAT TTT TGT GCT GTA TTT AGA TTA AAT     9687
Leu Asn Lys Asp Glu Tyr Lys His Phe Cys Ala Val Phe Arg Leu Asn
            30                  35                  40

GTA GAT TTT TCT CAA GAT GAT AAA AAT CCA TCT AGA AAA GAA GTA ATA     9735
Val Asp Phe Ser Gln Asp Asp Lys Asn Pro Ser Arg Lys Glu Val Ile
        45                  50                  55

AGA ATA ATA GAT GAG GAA TTC AAT TTT TGT GAT CTT AGA CTA TTT TAT     9783
Arg Ile Ile Asp Glu Glu Phe Asn Phe Cys Asp Leu Arg Leu Phe Tyr
    60                  65                  70

GAT ATC ATG ACC GTT GTA CCT AAT CAT ATG AAT GTG GCA TCT ATT ATT     9831
Asp Ile Met Thr Val Val Pro Asn His Met Asn Val Ala Ser Ile Ile
75                  80                  85                  90

TAT AGC GAA TAC GAA TAT CTT TTA AAA AAA TCA AAT TAT AAA AAT AAG     9879
Tyr Ser Glu Tyr Glu Tyr Leu Leu Lys Lys Ser Asn Tyr Lys Asn Lys
                95                  100                 105

AAG ATA AAT TAT ACT ATA TTA GAT AAG ATT AAT AAA TAT CAT AGT ATA     9927
Lys Ile Asn Tyr Thr Ile Leu Asp Lys Ile Asn Lys Tyr His Ser Ile
            110                 115                 120

GAT GAT ATT ATA TTT ATG TAT CTT CAT TGG AGA AAA AAA TAT AAC AAC     9975
Asp Asp Ile Ile Phe Met Tyr Leu His Trp Arg Lys Lys Tyr Asn Asn
        125                 130                 135

ACA TGC GCA TGT GGT AAG TTA TTT AAG GAA CTC ATG AAA TAT GAT ATA    10023
Thr Cys Ala Cys Gly Lys Leu Phe Lys Glu Leu Met Lys Tyr Asp Ile
    140                 145                 150

TTA GCT ACA AAA TAT ATA TAT AAT GAT ATT ATA AAT ACA TAC AAA GAG    10071
Leu Ala Thr Lys Tyr Ile Tyr Asn Asp Ile Ile Asn Thr Tyr Lys Glu
155                 160                 165                 170
```

Fig. 3H

```
GGA GAT ACT ATA TCC ATT AAC ATA CGT TTA AAA TGT AAA GAT GAT ATA        10119
Gly Asp Thr Ile Ser Ile Asn Ile Arg Leu Lys Cys Lys Asp Asp Ile
            175             180                     185

ATT AAA CAT TGT AAG TCT TCT ATA GGT ATG TTT GCT ATA TTA TCA TCG        10167
Ile Lys His Cys Lys Ser Ser Ile Gly Met Phe Ala Ile Leu Ser Ser
            190             195                     200

AAA ATA ATC GAC GTA GAT TTT GAT GTT ATA TTC TTT TCA CAA ATA AGT        10215
Lys Ile Ile Asp Val Asp Phe Asp Val Ile Phe Phe Ser Gln Ile Ser
            205             210                     215

ATA AGA TAT AGA CTA ATA TTC AAA AAA TAT CTC ATA CAA TCA TTA TAC        10263
Ile Arg Tyr Arg Leu Ile Phe Lys Lys Tyr Leu Ile Gln Ser Leu Tyr
            220             225                     230

TTA CAA TAATAATTGT TTTTTTTTG AAAAATAATC CTAAATCTAT CATAACATGA          10319
Leu Gln
235

ATTCATTATT ATTACGATTA CATGATTTTT TTAAACATGG AATTATGTGT GATATAAAAA      10379

TAGTATCCAT AGAGAATAAT AAAACCATTA GCGCACATAG GTTAATATTA TCTATGTACT      10439

CTAAGTACTT TTATAATATA TTTAATTCAG ATTTTATTGA TAAAAATAAT GATGAAATCT      10499

ATATATGCGC CGATTATGAT ATATTGTATA TTATATTGGA ATTTATGTAC ACCGGTAATA      10559

TAGTACTAAC AAAGGATAAT ATAGAATTAG TAATACAAGT CTGTGATTAT CTATGTATAG      10619

ATTCTTTAAT AAAAATATGT GAAGAATATA TATGCGGTAT AATAGATGAA ACAAATTGTA      10679

TACATCTCTT AAACTTTTCA GATACTTACA ATCTACAACG ATTACGTGAA ATGTCAAAAT      10739

GGTATTTACC AAAAATAATA AATAATAACA AACTGGTAGT AGAATTAGAT ATAGATGATA      10799

TGATATTAAT TATAAAAGAA ATTAAATACA TTGCATGTGA ATATATAGTT AAAAAAATAA      10859

TATTAAATTG GATCGTTCAT AAAGATGAAC GAATTATTTA TACTAAAAAA TTAATGAAAC      10919

ATATCAATGA TCAAGACCAT TATACATCCT TATCGGATAT TGAATTGTAC AATAATATAC      10979

GGGAACGAAT ATATGATAAC AAAGAACACG ATGTAGATAT ATCACATAAC TTTATAATAA      11039

TGGTAGGAGG AAAAAAGATA TTTAATATAA CCGCATTCAA TCCGTTATCG AATAAAAAAC      11099

ATATTATAGA CAGATACGAT GATATGTTTG GTTGTAAAAC TCATTTAGT GTTGTATACT       11159

TAAATAGTAT ACTATATATT ATCGGTGGAA AGAAACGAGG ATATTTCACT AAAGAGGTGT      11219

TGTCATATAA TATAAAAAAC AAATTATGGT GTTACGAACC AGAATTAAAT TATTTTAGAT      11279

ACGATACATC TGTATGTGTA TCAAATGGGA TGATATATTC AATTGGTGGA AAAGATACAA      11339

ATGGATATAT GACAAACATC GTAGAATTTT GGAAACCTGA ATGGAAATCA TGGTATGATG      11399

GTCAACATTT GTGTTATCCT AGATGTTATA TGTCGTTGGT AGACTATAAT AATGAAGTAT      11459

ATACAATAGG TGGATTAAAA ACATCAATAA CGGATGAATT TAATATAGAA ATGATTGTAT      11519

CAGACGATGC CGTAGAGAAA CTGACCGATC ATTCATGGAT GAAGTTAAAA CAATTTCCCA      11579

TAGCAAAGAG TGGTATATCA TCCATAGTAT ATAACGATTT TATATACTGT ATAGGTGGTC      11639
```

Fig. 3I

```
GTATAGATAC ACCACATATA AGTATAGAAC ACACTAACGA TGTTTATATA TATTCTTCAA    11699

GAGATGATTG TTGGAAATAT TTATCAAATA CAAATGTAAA AAGATCATTT TGTCTATCGT    11759

GTGTTTTTAA TAATGAATTA TATATAATAG GTGGATATAA TACAAACAGT GTAGAAAAGT    11819

ACAATAAATT AAAAAATACA TGGAAGCGTT TAAACGATAT TCCTAAGTTT GAAGAATGTG    11879

TTAATGAAGC ATCGGCAATA TATTTGTAGT ATCCCTTATA GCGTTCAAAA GAAACAAATC    11939

CATAACAGAC ATCTATATTC TTAATCTATC T ATG TCA GAT TGT ATA TTC GTA      11991
                                   Met Ser Asp Cys Ile Phe Val
                                    1               5
                                   C19> [SEQ ID NO: 30]
```

| | | | | | | | | |
|---|---|---|---|---|---|---|---|---|
| TTT CAG ATT CCG TTC ATT GTG TAT AGT AAA CTC GAT CAA TGG ATT TTT | | | | | | | | 12039 |
| Phe Gln Ile Pro Phe Ile Val Tyr Ser Lys Leu Asp Gln Trp Ile Phe | | | | | | | | |
| 10 15 20 | | | | | | | | |

```
TTT CAG ATT CCG TTC ATT GTG TAT AGT AAA CTC GAT CAA TGG ATT TTT    12039
Phe Gln Ile Pro Phe Ile Val Tyr Ser Lys Leu Asp Gln Trp Ile Phe
        10              15              20

GGG AAT ATA CTA TGT AAA ATA ATG TCC GTA TTA TAC TAC GTA GGA TTC    12087
Gly Asn Ile Leu Cys Lys Ile Met Ser Val Leu Tyr Tyr Val Gly Phe
    25              30              35

TTT AGT AAT ATG TTT ATA ATA ACA CTT ATG AGT ATA GAT AGA TAT TTT    12135
Phe Ser Asn Met Phe Ile Ile Thr Leu Met Ser Ile Asp Arg Tyr Phe
40              45              50              55

GCG ATC GTT CAT CCT ATA AAG CGA CAA CCG TAT AGG ACG AAA CGT ATA    12183
Ala Ile Val His Pro Ile Lys Arg Gln Pro Tyr Arg Thr Lys Arg Ile
            60              65              70

GGT ATC CTT ATG TGC TGT TCC GCT TGG TTA TTA TCC TTG ATA TTA TCT    12231
Gly Ile Leu Met Cys Cys Ser Ala Trp Leu Leu Ser Leu Ile Leu Ser
        75              80              85

AGT CCC GTA TCT AAA CTA TAC GAG AAT ATT CCT CAT ATG TCT AAA GAT    12279
Ser Pro Val Ser Lys Leu Tyr Glu Asn Ile Pro His Met Ser Lys Asp
    90              95              100

ATA TAC CAA TGT ACT CTG ACG AAC GAG AAT GAC TCC ATA ATC GCA TTC    12327
Ile Tyr Gln Cys Thr Leu Thr Asn Glu Asn Asp Ser Ile Ile Ala Phe
105             110             115

ATA AAA AGA CTG ATG CAA ATA GAG ATC ACT ATA TTG GGA TTC CTG ATA    12375
Ile Lys Arg Leu Met Gln Ile Glu Ile Thr Ile Leu Gly Phe Leu Ile
120             125             130             135

CCT ATA ATC ATA TTC GTA TAT TGC TAT TAT AGA ATT TTT TCT ACA GTG    12423
Pro Ile Ile Ile Phe Val Tyr Cys Tyr Tyr Arg Ile Phe Ser Thr Val
            140             145             150

GTT AGA TTA AGA AAT AGA CGA AAG TAT AAA TCT ATA AAA ATT GTA TTA    12471
Val Arg Leu Arg Asn Arg Arg Lys Tyr Lys Ser Ile Lys Ile Val Leu
        155             160             165

ATG ATT GTT GTA TGT TCT CTA ATA TGT TGG ATT CCG CTC TAT ATC GTT    12519
Met Ile Val Val Cys Ser Leu Ile Cys Trp Ile Pro Leu Tyr Ile Val
            170             175             180

CTA ATG ATA GCG ACG ATT GTT AGC TTA TAT ACA TCT AAT ATA TTT AGA    12567
Leu Met Ile Ala Thr Ile Val Ser Leu Tyr Thr Ser Asn Ile Phe Arg
185             190             195
```

Fig. 3J

| | |
|---|---|
| CAT CTG TGC CTC TAT CTA AAC CTG GCC TAT GCG ATC ACC TTT TCG GAG<br>His Leu Cys Leu Tyr Leu Asn Leu Ala Tyr Ala Ile Thr Phe Ser Glu<br>200           205             210             215 | 12615 |
| ACT ATC TCG TTA GCG CGT TGT TGT ATA AAT CCA ATA ATA TAT ACA CTG<br>Thr Ile Ser Leu Ala Arg Cys Cys Ile Asn Pro Ile Ile Tyr Thr Leu<br>          220             225             230 | 12663 |
| ATA GGT GAA CAT GTT CGA TCT CGT ATA TCT AGC ATA TGT TCG TGT ATA<br>Ile Gly Glu His Val Arg Ser Arg Ile Ser Ser Ile Cys Ser Cys Ile<br>          235             240             245 | 12711 |
| TAT AGA GAC AAT AGG ATT AGG AAA AAA CTC TTT TCA CGA AAA TCT TCT<br>Tyr Arg Asp Asn Arg Ile Arg Lys Lys Leu Phe Ser Arg Lys Ser Ser<br>          250             255             260 | 12759 |
| AGC AGT AGC AAT ATT ATT TAGTTGTTAT TTTCTTACAA AACACAAGTT<br>Ser Ser Ser Asn Ile Ile<br>          265 | 12807 |
| ATAAATAATC ATTACGTAAT C ATG CTA TCG TAT ATT ATT AAT CCT TTG CTA<br>                    Met Leu Ser Tyr Ile Ile Asn Pro Leu Leu<br>                     1           5            10<br>                    C20> [SEQ ID NO: 31] | 12858 |
| AGT ATT GTA TAC TTT ATA TTA GGA AAT GTA TCT AAG CTG CTT ACA TAT<br>Ser Ile Val Tyr Phe Ile Leu Gly Asn Val Ser Lys Leu Leu Thr Tyr<br>          15              20              25 | 12906 |
| ATA CTT ATG AAA ATA ATG ATT TTT TTA CTT CGT GCG GTG AAT CCA TAC<br>Ile Leu Met Lys Ile Met Ile Phe Leu Leu Arg Ala Val Asn Pro Tyr<br>          30              35              40 | 12954 |
| TCT CTG ATA TCT AAC AGA GGT TGG CTG TCG CTG GAT AGT ATA AAT CCC<br>Ser Leu Ile Ser Asn Arg Gly Trp Leu Ser Leu Asp Ser Ile Asn Pro<br>          45              50              55 | 13002 |
| TTT AAA AAG GAA AAG CGT AGG GAG TCT TTT CTA TCT AGT CTA AAT CCG<br>Phe Lys Lys Glu Lys Arg Arg Glu Ser Phe Leu Ser Ser Leu Asn Pro<br>          60              65              70 | 13050 |
| TTT AGA AAA GAG GAA ACA AAG AAA AAA GAA GGT TTC TTT TCT GGT TGG<br>Phe Arg Lys Glu Glu Thr Lys Lys Lys Glu Gly Phe Phe Ser Gly Trp<br>75            80              85              90 | 13098 |
| TTC GGA TAATCTCTTT TATAATTGAA ATAATATTCC AAAAATAAAT CATAATGATT<br>Phe Gly | 13154 |
| ACTAAAGCGA TTGTGATATT GTCTATTATT ACAGCATATG TAGATGCTTC CGCATTCTTA | 13214 |
| GTATACAATT ATACATATAC TTTACAAGAT GATAATCATC GATATGACTT CGAAGTCACC | 13274 |
| GATTATTTTA ATGATATACT AATAAAACGT TTAAAACTAA ATAGCGAGAC AGGAAGACCA | 13334 |
| GAATTAAGAA ATGAACCACC AACATGGTTT AATGAGACTA AGATTAGATA TTATCCGAAA | 13394 |
| AATAATTATA ATTTTATGTT CTGGCTAAAT AGAATGAGTG AAACGCTAGA TGAGATAAAT | 13454 |
| AAACTTCCAG AAACGAGTAA TCCTTACAAG ACTATGTCCT TGACAATTGG ATGTACTGAT | 13514 |
| CTAAGACAAC TTCAAGTAAA TTTCGGTTAT GTTACTGTAG GTGGTAATAT ATGGACACGA | 13574 |

Fig. 3K

```
TTCGACCCCA AGAATAAACG CTTTAGTAAA GTTAGATCAC GTACATTTCC AAAGGTAGGA    13634
ATGTTAACTG TTAAATCACA ACACTGGGAA CGTGTTATGG AACATCTTGG ATCAATGGTA    13694
ACATTAACAT GTCCGTTTAC AGCGGATGAT TATTATAAAA TTTCTAAGGG ATATATAGAT    13754
AAGCCAGTTA AGCCTACTGT TACAGTTACA GGAATTGAAA GAGGAGATAA TACTACATTG    13814
ATATGCACAT TTGATAATCA TTATCCGTCG TCGGTCGCTG TTAAATGGTA TAACATCGAG    13874
GACTTTGCTC CGGACTATCG TTATGATCCG TACGTAAATG AATTGCTTCC TGATACGGAC    13934
TATCTACCGG GTGAACCAGG ATATCCGACT ATAACTAGGA GATTAGGTGA TAAATATTTA    13994
TTTACATCAT CACCTAGGGT TATGGTACCA ACTATCATGT CTAATAGAAT AGCATGTGTT    14054
GGATTTCATA GTACGTTAGA ACCAAGCATA TATAGATGTG TAAACTGCTC GGGACCTGAG    14114
CCTGTTTTAC AATACCAGGG AGATAGAAGG AATGACTTGG AGGATGAGGA GGATTAAAGC    14174
TT                                                                    14176
```

Fig. 3L

```
AAGCTTATTG ATTCATATGT AATATACAAA CTATCAATGG GAGAATCTTA TTCTTTAAAA        60

GAAGAAATAG TTAATAATTT ATTCGCATTA TCAAATATTG GATTTCGTAT ACAATAAAGT       120

AGCTTTTTAT ACAATAA ATG AAA GAA ATT AAT TCG TTA GAA TGT CAG TGG         170
                   Met Lys Glu Ile Asn Ser Leu Glu Cys Gln Trp
                     1           5                      10
              C4>  [SEQ ID NO: 15]

GAG TCT ATC GAT GAT AAT AAT GAT ACA ACT ATT CTC GGT GAT GAT ATA        218
Glu Ser Ile Asp Asp Asn Asn Asp Thr Thr Ile Leu Gly Asp Asp Ile
            15                  20                  25

TAT TTT GAT TAT ATA ATT TCT CAG TTA GAT ATA CAT CAA AAT TGG TCT        266
Tyr Phe Asp Tyr Ile Ile Ser Gln Leu Asp Ile His Gln Asn Trp Ser
        30                  35                  40

CCT GAT ATC AGA CTA ATA AGA TAT TTT AGG AAG TTT AAC AAA GAA TCA        314
Pro Asp Ile Arg Leu Ile Arg Tyr Phe Arg Lys Phe Asn Lys Glu Ser
    45                  50                  55

TTT GAT AAA ATA TCA GAT ACG GAA TAT ATT AAC CCA TCT TTT TTC CAA        362
Phe Asp Lys Ile Ser Asp Thr Glu Tyr Ile Asn Pro Ser Phe Phe Gln
 60              65                  70                  75

CAA AGA GAT AAA CGA TTT TAT CCA CTT AAT GAT GAT TTC TAT CAT ATA        410
Gln Arg Asp Lys Arg Phe Tyr Pro Leu Asn Asp Asp Phe Tyr His Ile
                 80                  85                  90

TCA ACA GGA GGT TAT GGT ATC GTA TTT AAA ATG GAT AAA TAC GTT GTT        458
Ser Thr Gly Gly Tyr Gly Ile Val Phe Lys Met Asp Lys Tyr Val Val
             95                 100                 105

AAA TTT GTT TAT GAA CCA AAT AAA CAG TAT AGT CCC ATT GAT ACA ACT        506
Lys Phe Val Tyr Glu Pro Asn Lys Gln Tyr Ser Pro Ile Asp Thr Thr
        110                 115                 120

GCC GAG TAT ACA ATA CCT AAA TTT TTA TAT AAT AAT CTT AAG GGA GAT        554
Ala Glu Tyr Thr Ile Pro Lys Phe Leu Tyr Asn Asn Leu Lys Gly Asp
    125                 130                 135

GAG AAA AAA CTT ATC GTT TGT GCA TGG GCA ATG GGT TTA AAT TAT AAA        602
Glu Lys Lys Leu Ile Val Cys Ala Trp Ala Met Gly Leu Asn Tyr Lys
140                 145                 150                 155

TTA ACA TTT CTA CAT AGA TTA TAT AAA AGA GTA TTA TAT ATG TTA TTA        650
Leu Thr Phe Leu His Arg Leu Tyr Lys Arg Val Leu Tyr Met Leu Leu
                160                 165                 170

CTT ATT ATT CAA ACG ATA GAT AAT CAA CGA TTA AAT ATT CAT CAT TTT        698
Leu Ile Ile Gln Thr Ile Asp Asn Gln Arg Leu Asn Ile His His Phe
            175                 180                 185

TCT CAT AAG TAT TTT CTT AAG TCG TTC AAT GAA AAA AAG AGC GAT ATA        746
Ser His Lys Tyr Phe Leu Lys Ser Phe Asn Glu Lys Lys Ser Asp Ile
        190                 195                 200

AAA TTT GTA AAA TTA TTA TCA TAT TTT TAT CCT ATT GTT GTT CAA AGT        794
Lys Phe Val Lys Leu Leu Ser Tyr Phe Tyr Pro Ile Val Val Gln Ser
205                 210                 215
```

Fig. 4A

```
AAT ATA AAT GTA ATA AAT TAT TTT ACA CAT ATG TTT CAT TTT TTC GAA      842
Asn Ile Asn Val Ile Asn Tyr Phe Thr His Met Phe His Phe Phe Glu
220             225             230             235

CAT GAA AAA AGA GCT AAT TAT TTA TAC GAT AGA GGA AAT ATA ATT ATA      890
His Glu Lys Arg Ala Asn Tyr Leu Tyr Asp Arg Gly Asn Ile Ile Ile
                240             245             250

TTC CCA TTA GCA AGA TTT TCA TCA GAT AAA GTG ACG GAA CAG ATG GCG      938
Phe Pro Leu Ala Arg Phe Ser Ser Asp Lys Val Thr Glu Gln Met Ala
            255             260             265

ATA GAA CTT GGT TTT AAA TCT ATA GTT CAA TAT GTT AAG TTT ATT TTT      986
Ile Glu Leu Gly Phe Lys Ser Ile Val Gln Tyr Val Lys Phe Ile Phe
        270             275             280

TTA CAA ATA TCA TTG TTA TAT ATA AAA ATA TAC GAA CTT CCT TGT TGT     1034
Leu Gln Ile Ser Leu Leu Tyr Ile Lys Ile Tyr Glu Leu Pro Cys Cys
    285             290             295

GAT AAT TTT TTA CAC GTT GAT TTA AAA CCC GAT AAT ATT TTA ATA TTT     1082
Asp Asn Phe Leu His Val Asp Leu Lys Pro Asp Asn Ile Leu Ile Phe
300             305             310             315

AAT TCT GAT TGT CCT ATA ACT ATT AAA TTT AAG AAA TAT ACA TAC GTA     1130
Asn Ser Asp Cys Pro Ile Thr Ile Lys Phe Lys Lys Tyr Thr Tyr Val
                320             325             330

TTT AAT GAA CCG ATT AAA GCG TGT CTT AAC GAT TTC GAT TTT TCA CAG     1178
Phe Asn Glu Pro Ile Lys Ala Cys Leu Asn Asp Phe Asp Phe Ser Gln
            335             340             345

GTG GCT AAT ATA TTA AAT AAG AAA ATT AAA AAT AGT TTA AAA ATA GAA     1226
Val Ala Asn Ile Leu Asn Lys Lys Ile Lys Asn Ser Leu Lys Ile Glu
        350             355             360

CAC AAT TGG TAT TAT GAT TTT CAT TTT TTT ATA CAT ACA CTT CTA CGA     1274
His Asn Trp Tyr Tyr Asp Phe His Phe Phe Ile His Thr Leu Leu Arg
    365             370             375

ACT TAT CCA GAA ATA GAA TCT GAT AAA GAA TTC AGC GAT TCT TTA GAG     1322
Thr Tyr Pro Glu Ile Glu Ser Asp Lys Glu Phe Ser Asp Ser Leu Glu
380             385             390             395

GAT TTT ATA ATG TGT TGT ACA AAA AAT ACA TGT GAG AAA TTT AGA TTA     1370
Asp Phe Ile Met Cys Cys Thr Lys Asn Thr Cys Glu Lys Phe Arg Leu
                400             405             410

AAA GTA TCC ATA CTG CAT CCT ATA TCA TTT TTA GAA AAT TTG ATT ACA     1418
Lys Val Ser Ile Leu His Pro Ile Ser Phe Leu Glu Asn Leu Ile Thr
            415             420             425

AAA AAC ATT TTC TCA AAT TGG ATA AAT GGA GAA TCC TGT TAGAATAAAT      1467
Lys Asn Ile Phe Ser Asn Trp Ile Asn Gly Glu Ser Cys
        430             435             440

ACATTATATA ACGTATTCGT AGAAAGATAT ATAGAGAACT TATCAATATA TTCTATACCT   1527

ATTAATTCAA CATGTGGTAT ACATATAGGA GAAATCAAAG GAACGTTCAA AAGATGTTTT   1587
```

Fig. 4B

```
TTGAAAATAC TCAATATGTG TATAAACGAT AAAGAACTAA GTTTCAATAT TCTTATAAAG    1647

ACGCTTAAAG ATGTAACTAG TACGTTATCT CAGAAAGAGA AAGAGGAATT ATCTAAAGAA    1707

ATTGGAATTG ATATATTAAA CAATGACCCT AAATATGTAC CAGAAATAAT ACGAAACTGT    1767

TCATCATCCG CAGATGTAAC AAATATTATT GATATTCAAA CATTAGATGT TGGAAAATGC    1827

ATAGCTCCGT ACGATAAACA GATTCTATTA CAGATTGTTA ATTCTGGTAC TGCAGAAGCA    1887

AACTGTGTGA TGAATTCTAT CATGAATTCT ATGAATAGAA GATATATTGA CAATGCTAAT    1947

ATATATAATT ATTTGAATTT AACAAATAGA CCATGGTTTA TATTTAGCAT CATTATTATT    2007

GCTATCATAT TTGTTATAGG AATATGTTCT ATAAAAGAC  GAATAGGAAT TAAATACAAA    2067

TATGGTACAT TTTTATATGT CTAAACCGGG TTAAAAATGA AACATAAATC ATAGCTAATA    2127

ACATAAATAA TCGCCTACTA AATAACCATG AGCGGAAACC GAAAAAGTA  AATAAAATTG    2187

TTTTAACCGG CAAGTCTGTA CAACATACAC AGTCTACACC ACCCACTAAT GATGAAATAA    2247

ATAAATATGG ATATTGTCTA AATATTAAAC CTAATCAACA TATAAAAAGA GAATCGTATT    2307

TACATAATGA TTATCCTATG ATTATAACTA CTAGGTCCAC ACAATTCTAT TATAATGGGT    2367

AAATATGGAG GATATTTATA AGTAAGGTTA AGTTTGTTTT AGAGCACTAC ATTTCATTTC    2427

ATTTCATTTC ATTTCAAAAG GAAATGCAT  GCACCTTAAA AATGAAGTAA ATAATAATAT    2487

GTTTGTTTTT ACTTATGTA  TTTTATTATA CTCGTCTTTT TGTTATTTTT TTTATATTGA    2547

AAAAATATTG CAACATACAA AGCCAATATA TACGAACT ATG GGC AGT TGT GTA        2600
                                          Met Gly Ser Cys Val
                                          1                 5
                                          C5> [SEQ ID NO: 35]

TCT GTA AAA TCA ATA AGT ATA AGT ATG GAT ACA GTG TCA ATA TCT TCT      2648
Ser Val Lys Ser Ile Ser Ile Ser Met Asp Thr Val Ser Ile Ser Ser
             10              15                  20

ATA GAC GAT GAA TAT TAT TAT AAT ATA AAA AAT AAG CCA ATA TAT GTA      2696
Ile Asp Asp Glu Tyr Tyr Tyr Asn Ile Lys Asn Lys Pro Ile Tyr Val
             25              30              35

AGA AGA AAA AAT AGT TGT AGT AGT ACA CTA GAA TCG AGA TAT TCT ACA      2744
Arg Arg Lys Asn Ser Cys Ser Ser Thr Leu Glu Ser Arg Tyr Ser Thr
         40              45              50

TAT AGT CTA GAA TCG AGA TAT TCC ACA TAT AGT ATT AAA TCA GTA TAT      2792
Tyr Ser Leu Glu Ser Arg Tyr Ser Thr Tyr Ser Ile Lys Ser Val Tyr
     55              60              65

TTC TAAATAAATA ATAATGAATA ATCGTAAGTA TTCAATAAAT AATGGTTTTA           2845
Phe
70

TGTCATATTT ACGAAAGAAA TTTACTACAT TTTTAAGAAA GAAATCAACT TATAGGATAA    2905
```

Fig. 4C

```
AATCTAATAC CGACTATTAC CAGGAGAATG AAAAGTTGAT ACATAAAAAT AACATCAAAA    2965
TACCTTATAA AGTAAAAGTT ATAAGGAAAC GTTGTAGTAG TAGCGATGAT GATGTTTTTA    3025
TTTAGTAAAA AAAACAAAAA AAATAATAAT TAAACATTCA GACAATGAAT ACAACAACTT    3085
CACAAATAAT TATAGATAAT GATATGTCTA ATGAAGTTGG AACAATAATG GTAATTACAT    3145
TATGTTTAGT TACTATCGTG ATAACGTGTT ATTTACTACT ACAATTAGTA AGATGGTCGT    3205
TTATAGTAGA TATATTTAGA CAAATAAGAA CTAGATGTTT ACAATGGACA TCGAGAAGAG    3265
AATTTTTACA ATTAGATAAT ATGTATTATA CGAACGATAG CAGCGTTGGT GTTAATACCG    3325
AATAAATTGA AAAATGATTT TTATACACGA ATGGAGCCTA TTCTTCAAGA GTCTGATTCT    3385
AGGTTCGTTA TTTTCCCTAT TAAGTATCAT GATATCTGGA AAATGTATAA ACAATCAGTG    3445
GCAAGTTTTT GGACCGTTGA AGAAGTAGAT TTATCAAAAG ATTTAGATGA TTGGGATAAA    3505
TTAACTAAAG ACGAAAAATA CTTTATAAAA CATATACTAG CATTTTTTGC ATCTAGTGAT    3565
GGTATTGTAA ATGAGAATTT AGCGGAAAGA TTTTATGTGG ATGTACAGTG TTCAGAGGCA    3625
CGATGTTTCT ATGGATTTCA AATAGCTATG GAAAATATTC ATTCAGAAAT GTATAGTTTA    3685
TTAATAGATA CATATGTAAG AGATAATATA GAAAAAATGC ATTTATTTAA CGCTATAGAA    3745
ACAATGGAAT GCGTAAAAAA GAAAGCTGAT TGGGCCAGAA AATGGATATC TAGCAACAAG    3805
GTATATGGAG AAAGAGTAGT AGCATTTGCA GCTGTGGAGG AATATTCTT TTCTGGTTCA    3865
TTTGCTGCTA TATTTTGGAT AAAAAAACGA GGATTGATGC CCGGATTAAC ATTTTCTAAT    3925
GAACTAATAA GTAGAGACGA AGGTTTACAT TGTGATTTTG CGTGTTTAAT GTTTAAACAT    3985
TTATTACATC CACCATCTAA GGAAGTTATA ACGTCGATAA TCATTGATGC GGTTAATATA    4045
GAAAAGGAGT TTTTGACAGT TGCTATTCCG GTGGATCTTA TAGGTATGAA TTGTTGTTTA    4105
ATGTCTCAGT ATATAGAATT CGTCGCAGAT AGATTATTAA CAGAGTTAGG TTGTGAAAAG    4165
TCTCAATGTA TATAATCCTT TTAGCTTTAT GGAGTATATA TCACTAGAAG GTAAGACTAA    4225
TTTTTTCGAA CGACGAGTTA GTGAATATCA AAAGATGGGG GTGTTTACAA ATAAAGAAGA    4285
GAATATATTT TCTACGGATA TAGATTTTTA ATTAATAATT TTATAAAGT TGAATAAATA    4345
ATTTAATAAT AGTAATTTGC TTTGGTTTGC AAATAGATAG TGAAAA ATG TCT AAA       4400
                                                   Met Ser Lys
                                                    1
                                                   C9> [SEQ ID NO: 20]
CAA GAA ACT TAC ATT GAT TAT AAC TAT ATA GAA AGG TTA AAT GCT GTG     4448
Gln Glu Thr Tyr Ile Asp Tyr Asn Tyr Ile Glu Arg Leu Asn Ala Val
         5               10                  15
AAT CTA AAC AGA AGT TAT GAT GAA GAG ATA GTA TTT ATT ATG ACC GTT     4496
Asn Leu Asn Arg Ser Tyr Asp Glu Glu Ile Val Phe Ile Met Thr Val
 20              25                  30                  35
```

Fig. 4D

```
GGT GGT GTT GTT AAA GTA AAA AAA GAA TTA CTT GTA TCT GTA TCT AAT      4544
Gly Gly Val Val Lys Val Lys Lys Glu Leu Leu Val Ser Val Ser Asn
                40                      45                  50

TAC TTT AAA CTT ATT ACA AAG AAT CAG AGT AAT GAA ATA ACG GTT TCA      4592
Tyr Phe Lys Leu Ile Thr Lys Asn Gln Ser Asn Glu Ile Thr Val Ser
            55                      60                  65

TTC CAG TAT GAA TCT TTT CTT GAT ATA ATA AAA TAT ATA GAA ACT GGA      4640
Phe Gln Tyr Glu Ser Phe Leu Asp Ile Ile Lys Tyr Ile Glu Thr Gly
        70                      75                  80

ATC GTT ACT ATC GAT TTA GAC AAT GTA GAA AAT ATT TTT TCC ATA TCT      4688
Ile Val Thr Ile Asp Leu Asp Asn Val Glu Asn Ile Phe Ser Ile Ser
    85                      90                  95

TGT AGT AAA GCC ATA GAT TTT TTA AAA AAT TCA TGT ATT GAT TTT ATG      4736
Cys Ser Lys Ala Ile Asp Phe Leu Lys Asn Ser Cys Ile Asp Phe Met
100                 105                 110                 115

TCA AAA CAT ATA ACG GAT TCT ACA TGT GTT AAG ATT TAC AAA ATA GGT      4784
Ser Lys His Ile Thr Asp Ser Thr Cys Val Lys Ile Tyr Lys Ile Gly
            120                 125                 130

TTC TCG AAT GGA TGT TTT GCG GTA TAT AAT GAT GCT ATA GCA TAT ATA      4832
Phe Ser Asn Gly Cys Phe Ala Val Tyr Asn Asp Ala Ile Ala Tyr Ile
        135                 140                 145

AGG AAA AGA TTC ACA AAA ATA GAA ACA GAT ATA TTA CTA TCG TTA TCC      4880
Arg Lys Arg Phe Thr Lys Ile Glu Thr Asp Ile Leu Leu Ser Leu Ser
    150                 155                 160

TTA TTT GAT TTG AGA ATA ATT CTA AAA AGT GGA GAA TTA GAT GTA TCA      4928
Leu Phe Asp Leu Arg Ile Ile Leu Lys Ser Gly Glu Leu Asp Val Ser
165                 170                 175

TCA GAA GAT GAT GTA TTA TTA TTT ATA ATA AAA TGG TCT AGA CAT AAA      4976
Ser Glu Asp Asp Val Leu Leu Phe Ile Ile Lys Trp Ser Arg His Lys
180                 185                 190                 195

AAA TCC AAC AGA CGA AAA TCG TTT ACA CTA GTA ACA GAG GTA CTA AGA      5024
Lys Ser Asn Arg Arg Lys Ser Phe Thr Leu Val Thr Glu Val Leu Arg
            200                 205                 210

TAT AAT TAT CTA TCC ATA TAT GGT AAG TAT AAA TTA ACA AAA TGG TTG      5072
Tyr Asn Tyr Leu Ser Ile Tyr Gly Lys Tyr Lys Leu Thr Lys Trp Leu
        215                 220                 225

GCA CGA TTC GGA AAA AAT AAT AAT GTA GAG TTA AAT GAA AAT GAA TTA      5120
Ala Arg Phe Gly Lys Asn Asn Asn Val Glu Leu Asn Glu Asn Glu Leu
    230                 235                 240

CCT AGA ATA AGT TAT CAA CAT AGA TTT ACA AAC AGA AGA TAT ACG ATG      5168
Pro Arg Ile Ser Tyr Gln His Arg Phe Thr Asn Arg Arg Tyr Thr Met
245                 250                 255

GTT ACA CCA TCT TCA TTT AGT ATA AAT ATG CTA GGT AAT GTA TCT GTT      5216
Val Thr Pro Ser Ser Phe Ser Ile Asn Met Leu Gly Asn Val Ser Val
260                 265                 270                 275
```

Fig. 4E

| | |
|---|---|
| AAG AAT GAA CTT AGT ATA ATC AAT AGT ATA GCT GAG AAT CAT AAT CCT<br>Lys Asn Glu Leu Ser Ile Ile Asn Ser Ile Ala Glu Asn His Asn Pro<br>              280                         285                        290 | 5264 |
| TAC TGT GGA TCT GTA CTT ATG AAT GAT ATA TTA TAT CTT ATA GGT GGT<br>Tyr Cys Gly Ser Val Leu Met Asn Asp Ile Leu Tyr Leu Ile Gly Gly<br>             295                         300                        305 | 5312 |
| ATA AAT AAA TCA TTG GAT CCT GTT AGT GAT ATA ACT AGC GTA GAC ACT<br>Ile Asn Lys Ser Leu Asp Pro Val Ser Asp Ile Thr Ser Val Asp Thr<br>        310                        315                        320 | 5360 |
| AGA TCA TTT ATA GAG TTG CAT ACA CCA CCA TTA TTA CAT CCT AGA AAG<br>Arg Ser Phe Ile Glu Leu His Thr Pro Pro Leu Leu His Pro Arg Lys<br>    325                         330                        335 | 5408 |
| TGT CCG GGT GTT GCT ATT TTT AAA AAT AGA ATT TAT GTG GTA GGT GGT<br>Cys Pro Gly Val Ala Ile Phe Lys Asn Arg Ile Tyr Val Val Gly Gly<br>340                       345                        350                        355 | 5456 |
| ATA GGA TAC GAT GGA CCA TTA AAA ACA GTA GAA AGT TGG TCA CCT GGA<br>Ile Gly Tyr Asp Gly Pro Leu Lys Thr Val Glu Ser Trp Ser Pro Gly<br>              360                         365                        370 | 5504 |
| GAA CAA CAA TGG AGA GAA GAA GTA CCA TTA TTA CAA CCC AGA TTT AAT<br>Glu Gln Gln Trp Arg Glu Glu Val Pro Leu Leu Gln Pro Arg Phe Asn<br>        375                        380                        385 | 5552 |
| CCT TGC ATA ATT GGA ACA GAT AAT GAT TTA TAT GTT GTT GGT GGT ATT<br>Pro Cys Ile Ile Gly Thr Asp Asn Asp Leu Tyr Val Val Gly Gly Ile<br>            390                        395                        400 | 5600 |
| TCT GAA GAT GAT AAA ACT ATT GAA ATC TAT TCT TAT GAA GAA AAC ACT<br>Ser Glu Asp Asp Lys Thr Ile Glu Ile Tyr Ser Tyr Glu Glu Asn Thr<br>405                       410                        415 | 5648 |
| TGG TCT ATT GGT AAT GCG ATG AAT TAT TCA CAT TTT GGT GGA TGT ATA<br>Trp Ser Ile Gly Asn Ala Met Asn Tyr Ser His Phe Gly Gly Cys Ile<br>420                    425                        430                        435 | 5696 |
| GCA TAT CAC CAT GGT TAT ATA TAT ATG ATT GGT GGT TTA TCT TTT ATA<br>Ala Tyr His His Gly Tyr Ile Tyr Met Ile Gly Gly Leu Ser Phe Ile<br>              440                         445                        450 | 5744 |
| GAT AAT ATT CAT GTA TTT ACT ATG GTT GAG AAG TAT AAC CCT CAT TCG<br>Asp Asn Ile His Val Phe Thr Met Val Glu Lys Tyr Asn Pro His Ser<br>            455                        460                        465 | 5792 |
| AAT AAA TGG ACT GTA GAA AAG TCT CTA CCC TTT CCT CGA TTT AAT TCA<br>Asn Lys Trp Thr Val Glu Lys Ser Leu Pro Phe Pro Arg Phe Asn Ser<br>        470                        475                        480 | 5840 |
| TCG CTT TGT ATT ATA GAA GAC TCT ATC GCT ATA ATA GGC TGG ATA TAT<br>Ser Leu Cys Ile Ile Glu Asp Ser Ile Ala Ile Ile Gly Trp Ile Tyr<br>    485                         490                        495 | 5888 |
| TAT TAACAAATAT ATTAGTCAAA TAGAAATATA TAACGGAGCT AGATGAATGG<br>Tyr<br>500 | 5941 |
| GGTATTGTAG GGTCTATCGA TATAGAGTCA TTCTTTCAAG AAATGAAAAA ATAATCTACA | 6001 |

Fig. 4F

```
TTTTTTCTTG TTACGACAAT GGAACTACGT TATACGATCA TATCTGTCTG TGCTTGAAAG      6061

GTTGACACCG TATCAGTTTA AAACGTTATT ATTCTTGATA CAGGATGACA TTAATATATC      6121

TAACGATGAT ATTAATGTAT TAGATAGAGT CGATCTAGCT ATTAAAATA ATG AAT          6176
                                                     Met Asn
                                                      1
                                                     C10>
```

```
AAA TAT AAT AAT TAT AGA GCA ATT TAT TTT CTC TAT AAA GTC ATA TTA        6224
Lys Tyr Asn Asn Tyr Arg Ala Ile Tyr Phe Leu Tyr Lys Val Ile Leu
         5                   10                  15
[SEQ ID NO: 21]

CGA ATA CAT AAT ACA GAA TAT ATA AGT GGA ACA CTA CAA AGA TCT ATA        6272
Arg Ile His Asn Thr Glu Tyr Ile Ser Gly Thr Leu Gln Arg Ser Ile
         20                  25                  30

CAG AAT ATA ACA CCT ACA ACA TCA TCA TAT ACG TAT TGT GAT AAT TCA        6320
Gln Asn Ile Thr Pro Thr Thr Ser Ser Tyr Thr Tyr Cys Asp Asn Ser
 35              40                  45                  50

AAA AGA CGC AGA CAT AGA TTT AGA GAT ACG GAA ATC CTT AAA GCT ATG        6368
Lys Arg Arg Arg His Arg Phe Arg Asp Thr Glu Ile Leu Lys Ala Met
                 55                  60                  65

GGT AGT AAA ATG CGT AGA AAA CTT TTT TAGTTAGTGA GTAATATTAT              6415
Gly Ser Lys Met Arg Arg Lys Leu Phe
             70              75

AAAATTAAAA AAAAAATAAT ATTTTCTAGA C ATG TCA CTA TAT GTT AAA TGT         6467
                                 Met Ser Leu Tyr Val Lys Cys
                                  1               5
                                 C11> [SEQ ID NO: 22]

GTT AAG TTA TCT AAT AAT GCT ATT ATA CCA AAT AGA TCA ATG AGC GGA        6515
Val Lys Leu Ser Asn Asn Ala Ile Ile Pro Asn Arg Ser Met Ser Gly
         10                  15                  20

TCC GCT GGA TAT GAT CTG TAT AGT GCA TAT AGT TAT ACA GTT AAG CCG        6563
Ser Ala Gly Tyr Asp Leu Tyr Ser Ala Tyr Ser Tyr Thr Val Lys Pro
         25                  30                  35

TAT AAT AGA ATT TTA GTT AGA ACA GAT ATT TGT TTA ATG ATA CCA GAT        6611
Tyr Asn Arg Ile Leu Val Arg Thr Asp Ile Cys Leu Met Ile Pro Asp
 40              45                  50                  55

AAA TGT TAT GGA CGC ATA TCG CCT AGA TCG GGA TTA TCG TTA AAT TAT        6659
Lys Cys Tyr Gly Arg Ile Ser Pro Arg Ser Gly Leu Ser Leu Asn Tyr
                 60                  65                  70

AAT ATA GAT ATA GGA GGA GGC GTT ATT GAT AGT GAT TAC AGA GGG GAA        6707
Asn Ile Asp Ile Gly Gly Gly Val Ile Asp Ser Asp Tyr Arg Gly Glu
         75                  80                  85

ATA GGT ATC GTG TTT ATA AAT AAT GGA TGT AGT GAT TTT AAC ATA AAG        6755
Ile Gly Ile Val Phe Ile Asn Asn Gly Cys Ser Asp Phe Asn Ile Lys
         90                  95                 100
```

Fig. 4G

```
GTA GGT GAT AGG ATA GCA CAA ATA ATA TTT GAA AGA GTA GAA TAT CCT        6803
Val Gly Asp Arg Ile Ala Gln Ile Ile Phe Glu Arg Val Glu Tyr Pro
    105             110                 115
ATA ATG GAA GAA GTA AAA TGT TTG GAA GAT ACA GAA CGT GGA AAT AGT        6851
Ile Met Glu Glu Val Lys Cys Leu Glu Asp Thr Glu Arg Gly Asn Ser
120             125                 130                 135
GGT TTT GGG TCA AGT GGT ATG TAAAGTATAA TAAATGAAAA AATAATTCAT           6902
Gly Phe Gly Ser Ser Gly Met
                140
CTGTATTATA TCCATTATTA TCAATATGTA CAAGAAATAT AACTCTAACG TATGCATTAG      6962
GAATGTATTA TATGTATATC TAAAATATAA TACTATAAAT AAACTTAGTA GATATGAACG      7022
GATGATATAC ACAAAGATAA AAAATCAATG TGAAGCGATA AAATACAGAT ATTGTAATGA      7082
TTTTAATTCT GTTACATGTA TTTTAGAATA CGATGAAAAT AAGTATATAG ATAACGTGCA      7142
TAAAGAAGTT ATTAGTATAT TGTTATCAGA TTCGCGACCT AGTATCAAAT TAGCTGCTAT      7202
TTCGTTATTA TCTATAATAA TAGATAAACT AATATGTAGA AATATTCGTA TAGCTAAATA      7262
TATAATTGAT GATATAATAA ATATTATATC AGAAGACGGT ATATATATTA TATTATTTTT     7322
AGATGAATTT GATAAATATA CCGATACCCG ATGTAGGCGC CGTGGATTAA GTATGATGAT      7382
AGCGAGCATT GTAACTTACT ACTGTTTACG GTATGTATTA AAAATATAAA AATAAATCTT      7442
TTTTTTTAAA AATGAACCGT AATATGTGGA TAGTGTTATC GTGTGTATTA TATATGATTT      7502
ATATATGTAA CGGACGAGAT GTATTGTTAT ATCCACCACA TAAGAAAACA AATAAGGTTA      7562
TAGTAAAATG TAACGGATAT ACTAATTCTA CGTATAGTAT CTTATATTGG ATGGTAGGTA      7622
ACAACAATAC ATTCGTAGAA CAACTAAATA GCGATCATTA TAAAGAGAAG AAATACAATA      7682
GTACTGAAAA AAATGAGCAT ATGTATAAGT TACGTACCGA TCTTATTATA TATAATATTA      7742
CGTCAGAAAT GGAGATGACA AAACTAACAT GTGTATTATC AGATATATAC ACACCTATCA      7802
AGGCATCTAT AATATTAAAT AATTTATGGA GTTGTTTAAA TACTACACAA GTATGAAATA      7862
TGAAATATAA AGTATTCAAA TAAATAACAA TAATGTCAAC TATGAATACG TTGGCATTTT      7922
GTTATGGATT ACCTAACATA AATGATATCA CGCAAGGTAT AATTTTTGTT AGAAATAACA      7982
TATTTTACTC ATATTTAACA GATTATGCAA TGGAAGCGTG TATATTGAAT TATATAAATA      8042
TTAGAGCCGA TAAAATAGAA GATCTAAAGA AATCATTAGT TGGAAAAACT ATTAGCGTGA      8102
GAGTTATTAG AGTTGATGTA TTAAAAGGAT ATATAGATGT TTCAATTGTA TAATTTTTTT     8162
ATCAAAACTG AAGTATAATC TAGACCTTAG AAGATATTTT GTACCATATA AAATGGATCC      8222
TGTTTGTTGG ATATGTAAAG ATGACTACAG TATTGAAAAG AATTATTGTA ACTGTAAAAA      8282
CGAGTATAAA GTTGTACACG ATGAATGTAT GAAAAGTGG ATACAATACT CAAGGGAACG      8342
```

Fig. 4H

```
ATCTTGTAAA TTATGTAATA AAGAATATAA CATCATTAGT GTTAGAAAAC CATTCTCACA    8402
GTGGGTATTC TCCATTAAAG ATTGCAAAAA GTCAGCAATT TTGTACGCTA CTCTATTCTT    8462
ATGTACGTTT ATTATATCGC TTGTTTTAAC TAGAATTAAT ATAACAAAAA TAATAGATAC    8522
ATCAAAAAAT GATGTTTCAT TTAAGCTGGT TACGATGATA TTCTACTTAT TACCATTTGT    8582
CATAACTTGT ATATCGTTCA TAACGCTGAT AGTTTATCTA TATAAATATT GTAAGATTTC    8642
CGCTAAAAAC AACACATACG ATACGATTTA TGAACTTTAA AGTGAAAATT TAATCTATTT    8702
TTATAATAAA AC ATG CAT TTC ATA TTC ATT ATA TTA TCA CTA TCA TTT       8750
              Met His Phe Ile Phe Ile Ile Leu Ser Leu Ser Phe
              1                 5                      10
              C16> [SEQ ID NO: 27]

GTA GTA AAT GCC GAT GTA TTT CCA TCG TCG GTT ACT TTA TCA TCT AAT      8798
Val Val Asn Ala Asp Val Phe Pro Ser Ser Val Thr Leu Ser Ser Asn
            15              20                      25

GAT TTT GAT ACA ATA ATT AAA TGG GAT AAT AAT GTA ATA TCA TAC GAT      8846
Asp Phe Asp Thr Ile Ile Lys Trp Asp Asn Asn Val Ile Ser Tyr Asp
        30              35                      40

GTA GAA TTA ATG CAG TAC AGT CAT GAC GAA TGG AGA ACC GTT TGT ACT      8894
Val Glu Leu Met Gln Tyr Ser His Asp Glu Trp Arg Thr Val Cys Thr
45              50                      55                      60

AAT TCT TTA GGA TAC TGT AAT TTA ACA AAT TCT GAT ATC GAC AAT GAT      8942
Asn Ser Leu Gly Tyr Cys Asn Leu Thr Asn Ser Asp Ile Asp Asn Asp
                65                      70                      75

GAT GAA ACA TGG GTG AGG TTT AAA TAT GAA AAT AAG ACA TCT AAT GAA      8990
Asp Glu Thr Trp Val Arg Phe Lys Tyr Glu Asn Lys Thr Ser Asn Glu
            80                      85                      90

CAT AAT ATT GGC AGA GTA TGT GAG ATT GTA CAA ATA ACT TCA CCT ATT      9038
His Asn Ile Gly Arg Val Cys Glu Ile Val Gln Ile Thr Ser Pro Ile
                95                     100                     105

GTT AAC ATG ACA AGA GAT GGT TCA ATT ATA CTA TTA GAT ATA CAT CAT      9086
Val Asn Met Thr Arg Asp Gly Ser Ile Ile Leu Leu Asp Ile His His
        110                     115                     120

CCA ATG ACA TAC GAT AAT CAG TAT TAT ATA TAT AAT AAT ATA ACA TTA      9134
Pro Met Thr Tyr Asp Asn Gln Tyr Tyr Ile Tyr Asn Asn Ile Thr Leu
125                     130                     135                 140

TGT GGA TTT GAA TTT ATT TAC GAA GCT ACA TTT ATT ATT AAT GAT ACA      9182
Cys Gly Phe Glu Phe Ile Tyr Glu Ala Thr Phe Ile Ile Asn Asp Thr
                145                     150                     155

ATT ATA CCA TAT AGT ATA GAC AAT CAA TAT TGT GAT GAT GTT CAT TGT      9230
Ile Ile Pro Tyr Ser Ile Asp Asn Gln Tyr Cys Asp Asp Val His Cys
        160                     165                     170

TTA TTT TAC TTT ATA TCA CAA GAA CCC GTT TGT GTG TAT GTA ATG GGT      9278
Leu Phe Tyr Phe Ile Ser Gln Glu Pro Val Cys Val Tyr Val Met Gly
    175                     180                     185
```

Fig. 4I

```
ATG GAA CAA TAT TAT GAA TTT GGT CCA AAA AAA ACA GAT AAT AGT ACT      9326
Met Glu Gln Tyr Tyr Glu Phe Gly Pro Lys Lys Thr Asp Asn Ser Thr
    190                 195                 200

AGA GTG TGT GTA GAT GGA TTA ATT CCA AGA AAA ATC GAT ACA TAT TTT      9374
Arg Val Cys Val Asp Gly Leu Ile Pro Arg Lys Ile Asp Thr Tyr Phe
205                 210                 215                 220

ATT AAA GAT TTC GAT GAT ATA GAT AGA GTT AAT AAC AGA TTA TAT AGA      9422
Ile Lys Asp Phe Asp Asp Ile Asp Arg Val Asn Asn Arg Leu Tyr Arg
                225                 230                 235

GTT GTA AGT GAT AAA TAT GAA TCC AAT ATA TCG TCA AAG TTT ATG CAC      9470
Val Val Ser Asp Lys Tyr Glu Ser Asn Ile Ser Ser Lys Phe Met His
            240                 245                 250

TTA TAT AAT AAT ATA TTA TCT TCG TTT AAA CTA ATA TTG CAA GAA CTT      9518
Leu Tyr Asn Asn Ile Leu Ser Ser Phe Lys Leu Ile Leu Gln Glu Leu
        255                 260                 265

ATG GTA AAT ACT GAA CAG TAAATACGTT TATAAAGATA AAGGAATGAA             9566
Met Val Asn Thr Glu Gln
    270

TTCGTATATT GTAATAAAAA ATTCATTACG TGATTATAGA TCTGGAAGAA TTATAAGAAA    9626

ATACATAAGA AAATTAAATA AGGATGAGTA TAAGCATTTT TGTGCTGTAT TTAGATTAAA    9686

TGTAGATTTT TCTCAAGATG ATAAAAATCC ATCTAGAAAA GAAGTAATAA GAATAATAGA    9746

TGAGGAATTC AATTTTTGTG ATCTTAGACT ATTTTATGAT ATCATGACCG TTGTACCTAA    9806

TCATATGAAT GTGGCATCTA TTATTTATAG CGAATACGAA TATCTTTTAA AAAAATCAAA    9866

TTATAAAAAT AAGAAGATAA ATTATACTAT ATTAGATAAG ATTAATAAAT ATCATAGTAT    9926

AGATGATATT ATATTTATGT ATCTTCATTG GAGAAAAAAA TATAACAACA CATGCGCATG    9986

TGGTAAGTTA TTTAAGGAAC TCATGAAATA TGATATATTA GCTACAAAAT ATATATATAA   10046

TGATATTATA AATACATACA AAGAGGGAGA TACTATATCC ATTAACATAC GTTTAAAATG   10106

TAAAGATGAT ATAATTAAAC ATTGTAAGTC TTCTATAGGT ATGTTTGCTA TATTATCATC   10166

GAAAATAATC GACGTAGATT TTGATGTTAT ATTCTTTTCA CAAATAAGTA TAAGATATAG   10226

ACTAATATTC AAAAAATATC TCATACAATC ATTATACTTA CAATAATAAT TGTTTTTTTT   10286

TTGAAAAATA ATCCTAAATC TATCATAACA TGAATTCATT ATTATTACGA TTACATGATT   10346

TTTTTAAACA TGGAATTATG TGTGATATAA AAATAGTATC CATAGAGAAT AATAAAACCA   10406

TTAGCGCACA TAGGTTAATA TTATCTATGT ACTCTAAGTA CTTTTATAAT ATATTTAATT   10466

CAGATTTTAT TGATAAAAAT AATGATGAAA TCTATATATG CGCCGATTAT GATATATTGT   10526

ATATTATATT GGAATTTATG TACACCGGTA ATATAGTACT AACAAAGGAT AATATAGAAT   10586

TAGTAATACA AGTCTGTGAT TATCTATGTA TAGATTCTTT AATAAAAATA TGTGAAGAAT   10646
```

Fig. 4J

| | | | | | |
|---|---|---|---|---|---|
| ATATATGCGG | TATAATAGAT | GAAACAAATT | GTATACATCT | CTTAAACTTT | TCAGATACTT | 10706 |
| ACAATCTACA | ACGATTACGT | GAAATGTCAA | AATGGTATTT | ACCAAAAATA | ATAAATAATA | 10766 |
| ACAAACTGGT | AGTAGAATTA | GATATAGATG | ATATGATATT | AATTATAAAA | GAAATTAAAT | 10826 |
| ACATTGCATG | TGAATATATA | GTTAAAAAAA | TAATATTAAA | TTGGATCGTT | CATAAAGATG | 10886 |
| AACGAATTAT | TTATACTAAA | AAATTAATGA | AACATATCAA | TGATCAAGAC | CATTATACAT | 10946 |
| CCTTATCGGA | TATTGAATTG | TACAATAATA | TACGGGAACG | AATATATGAT | AACAAAGAAC | 11006 |
| ACGATGTAGA | TATATCACAT | AACTTTATAA | TAATGGTAGG | AGGAAAAAAG | ATATTTAATA | 11066 |
| TAACCGCATT | CAATCCGTTA | TCGAATAAAA | AACATATTAT | AGACAGATAC | GATGATATGT | 11126 |
| TTGGTTGTAA | AACTCATTTT | AGTGTTGTAT | ACTTAAATAG | TATACTATAT | ATTATCGGTG | 11186 |
| GAAAGAAACG | AGGATATTTC | ACTAAGAGG | TGTTGTCATA | TAATATAAAA | AACAAATTAT | 11246 |
| GGTGTTACGA | ACCAGAATTA | AATTATTTTA | GATACGATAC | ATCTGTATGT | GTATCAAATG | 11306 |
| GGATGATATA | TTCAATTGGT | GGAAAAGATA | CAAATGGATA | TATGACAAAC | ATCGTAGAAT | 11366 |
| TTTGGAAACC | TGAATGGAAA | TCATGGTATG | ATGGTCAACA | TTTGTGTTAT | CCTAGATGTT | 11426 |
| ATATGTCGTT | GGTAGACTAT | AATAATGAAG | TATATACAAT | AGGTGGATTA | AAAACATCAA | 11486 |
| TAACGGATGA | ATTTAATATA | GAAATGATTG | TATCAGACGA | TGCCGTAGAG | AAACTGACCG | 11546 |
| ATCATTCATG | GATGAAGTTA | AAACAATTTC | CCATAGCAAA | GAGTGGTATA | TCATCCATAG | 11606 |
| TATATAACGA | TTTTATATAC | TGTATAGGTG | GTCGTATAGA | TACACCACAT | ATAAGTATAG | 11666 |
| AACACACTAA | CGATGTTTAT | ATATATTCTT | CAAGAGATGA | TTGTTGGAAA | TATTTATCAA | 11726 |
| ATACAAATGT | AAAAGATCA | TTTTGTCTAT | CGTGTGTTTT | TAATAATGAA | TTATATATAA | 11786 |
| TAGGTGGATA | TAATACAAAC | AGTGTAGAAA | AGTACAATAA | ATTAAAAAAT | ACATGGAAGC | 11846 |
| GTTTAAACGA | TATTCCTAAG | TTTGAAGAAT | GTGTTAATGA | AGCATCGGCA | ATATATTTGT | 11906 |
| AGTATCCCTT | ATAGCGTTCA | AAAGAAACAA | ATCCATAACA | GACATCTATA | TTCTTAATCT | 11966 |
| ATCTATGTCA | GATTGTATAT | TCGTATTTCA | GATTCCGTTC | ATTGTGTATA | GTAAACTCGA | 12026 |
| TCAATGGATT | TTTGGGAATA | TACTATGTAA | AATAATGTCC | GTATTATACT | ACGTAGGATT | 12086 |
| CTTTAGTAAT | ATGTTTATAA | TAACACTTAT | GAGTATAGAT | AGATATTTTG | CGATCGTTCA | 12146 |
| TCCTATAAAG | CGACAACCGT | ATAGGACGAA | ACGTATAGGT | ATCCTTATGT | GCTGTTCCGC | 12206 |
| TTGGTTATTA | TCCTTGATAT | TATCTAGTCC | CGTATCTAAA | CTATACGAGA | ATATTCCTCA | 12266 |
| TATGTCTAAA | GATATATACC | AATGTACTCT | GACGAACGAG | AATGACTCCA | TAATCGCATT | 12326 |
| CATAAAAAGA | CTGATGCAAA | TAGAGATCAC | TATATTGGGA | TTCCTGATAC | CTATAATCAT | 12386 |
| ATTCGTATAT | TGCTATTATA | GAATTTTTTC | TACAGTGGTT | AGATTAAGAA | ATAGACGAAA | 12446 |
| GTATAAATCT | ATAAAAATTG | TATTAATGAT | TGTTGTATGT | TCTCTAATAT | GTTGGATTCC | 12506 |

Fig. 4K

```
GCTCTATATC GTTCTAATGA TAGCGACGAT TGTTAGCTTA TATACATCTA ATATATTTAG    12566

ACATCTGTGC CTCTATCTAA ACCTGGCCTA TGCGATCACC TTTTCGGAGA CTATCTCGTT    12626

AGCGCGTTGT TGTATAAATC CAATAATATA TACACTGATA GGTGAACATG TTCGATCTCG    12686

TATATCTAGC ATATGTTCGT GTATATATAG AGACAATAGG ATTAGGAAAA AACTCTTTTC    12746

ACGAAAATCT TCTAGCAGTA GCAATATTAT TTAGTTGTTA TTTTCTTACA AAACACAAGT    12806

TATAAATAAT CATTACGTAA TCATGCTATC GTATATTATT AATCCTTTGC TAAGTATTGT    12866

ATACTTTATA TTAGGAAATG TATCTAAGCT GCTTACATAT ATACTTATGA AAATAATGAT    12926

TTTTTTACTT CGTGCGGTGA ATCCATACTC TCTGATATCT AACAGAGGTT GGCTGTCGCT    12986

GGATAGTATA AATCCCTTTA AAAGGAAAA GCGTAGGGAG TCTTTTCTAT CTAGTCTAAA     13046

TCCGTTTAGA AAAGAGGAAA CAAAGAAAAA AGAAGGTTTC TTTTCTGGTT GGTTCGGATA    13106

ATCTCTTTTA TAATTGAAAT AATATTCCAA AAATAAATCA TA ATG ATT ACT AAA       13160
                                              Met Ile Thr Lys
                                               1
                                              C21> [SEQ ID NO: 32]

GCG ATT GTG ATA TTG TCT ATT ATT ACA GCA TAT GTA GAT GCT TCC GCA      13208
Ala Ile Val Ile Leu Ser Ile Ile Thr Ala Tyr Val Asp Ala Ser Ala
 5              10                  15                  20

TTC TTA GTA TAC AAT TAT ACA TAT ACT TTA CAA GAT GAT AAT CAT CGA      13256
Phe Leu Val Tyr Asn Tyr Thr Tyr Thr Leu Gln Asp Asp Asn His Arg
                25                  30                  35

TAT GAC TTC GAA GTC ACC GAT TAT TTT AAT GAT ATA CTA ATA AAA CGT      13304
Tyr Asp Phe Glu Val Thr Asp Tyr Phe Asn Asp Ile Leu Ile Lys Arg
            40                  45                  50

TTA AAA CTA AAT AGC GAG ACA GGA AGA CCA GAA TTA AGA AAT GAA CCA      13352
Leu Lys Leu Asn Ser Glu Thr Gly Arg Pro Glu Leu Arg Asn Glu Pro
        55                  60                  65

CCA ACA TGG TTT AAT GAG ACT AAG ATT AGA TAT TAT CCG AAA AAT AAT      13400
Pro Thr Trp Phe Asn Glu Thr Lys Ile Arg Tyr Tyr Pro Lys Asn Asn
    70                  75                  80

TAT AAT TTT ATG TTC TGG CTA AAT AGA ATG AGT GAA ACG CTA GAT GAG      13448
Tyr Asn Phe Met Phe Trp Leu Asn Arg Met Ser Glu Thr Leu Asp Glu
85                  90                  95                  100

ATA AAT AAA CTT CCA GAA ACG AGT AAT CCT TAC AAG ACT ATG TCC TTG      13496
Ile Asn Lys Leu Pro Glu Thr Ser Asn Pro Tyr Lys Thr Met Ser Leu
                105                 110                 115

ACA ATT GGA TGT ACT GAT CTA AGA CAA CTT CAA GTA AAT TTC GGT TAT      13544
Thr Ile Gly Cys Thr Asp Leu Arg Gln Leu Gln Val Asn Phe Gly Tyr
            120                 125                 130

GTT ACT GTA GGT GGT AAT ATA TGG ACA CGA TTC GAC CCC AAG AAT AAA      13592
Val Thr Val Gly Gly Asn Ile Trp Thr Arg Phe Asp Pro Lys Asn Lys
        135                 140                 145
```

Fig. 4L

```
CGC TTT AGT AAA GTT AGA TCA CGT ACA TTT CCA AAG GTA GGA ATG TTA    13640
Arg Phe Ser Lys Val Arg Ser Arg Thr Phe Pro Lys Val Gly Met Leu
    150             155             160

ACT GTT AAA TCA CAA CAC TGG GAA CGT GTT ATG GAA CAT CTT GGA TCA    13688
Thr Val Lys Ser Gln His Trp Glu Arg Val Met Glu His Leu Gly Ser
165             170             175             180

ATG GTA ACA TTA ACA TGT CCG TTT ACA GCG GAT GAT TAT TAT AAA ATT    13736
Met Val Thr Leu Thr Cys Pro Phe Thr Ala Asp Asp Tyr Tyr Lys Ile
                185             190             195

TCT AAG GGA TAT ATA GAT AAG CCA GTT AAG CCT ACT GTT ACA GTT ACA    13784
Ser Lys Gly Tyr Ile Asp Lys Pro Val Lys Pro Thr Val Thr Val Thr
        200             205             210

GGA ATT GAA AGA GGA GAT AAT ACT ACA TTG ATA TGC ACA TTT GAT AAT    13832
Gly Ile Glu Arg Gly Asp Asn Thr Thr Leu Ile Cys Thr Phe Asp Asn
            215             220             225

CAT TAT CCG TCG TCG GTC GCT GTT AAA TGG TAT AAC ATC GAG GAC TTT    13880
His Tyr Pro Ser Ser Val Ala Val Lys Trp Tyr Asn Ile Glu Asp Phe
        230             235             240

GCT CCG GAC TAT CGT TAT GAT CCG TAC GTA AAT GAA TTG CTT CCT GAT    13928
Ala Pro Asp Tyr Arg Tyr Asp Pro Tyr Val Asn Glu Leu Leu Pro Asp
245             250             255             260

ACG GAC TAT CTA CCG GGT GAA CCA GGA TAT CCG ACT ATA ACT AGG AGA    13976
Thr Asp Tyr Leu Pro Gly Glu Pro Gly Tyr Pro Thr Ile Thr Arg Arg
                265             270             275

TTA GGT GAT AAA TAT TTA TTT ACA TCA TCA CCT AGG GTT ATG GTA CCA    14024
Leu Gly Asp Lys Tyr Leu Phe Thr Ser Ser Pro Arg Val Met Val Pro
        280             285             290

ACT ATC ATG TCT AAT AGA ATA GCA TGT GTT GGA TTT CAT AGT ACG TTA    14072
Thr Ile Met Ser Asn Arg Ile Ala Cys Val Gly Phe His Ser Thr Leu
            295             300             305

GAA CCA AGC ATA TAT AGA TGT GTA AAC TGC TCG GGA CCT GAG CCT GTT    14120
Glu Pro Ser Ile Tyr Arg Cys Val Asn Cys Ser Gly Pro Glu Pro Val
310             315             320

TTA CAA TAC CAG GGA GAT AGA AGG AAT GAC TTG GAG GAT GAG GAG GAT    14168
Leu Gln Tyr Gln Gly Asp Arg Arg Asn Asp Leu Glu Asp Glu Glu Asp
325             330             335             340

TAAAGCTT                                                          14176
```

Fig. 4M

```
AAGCTTATTG ATTCATATGT AATATACAAA CTATCAATGG GAGAATCTTA TTCTTTAAAA      60
GAAGAAATAG TTAATAATTT ATTCGCATTA TCAAATATTG GATTTCGTAT ACAATAAAGT     120
AGCTTTTTAT ACAATAAATG AAAGAAATTA ATTCGTTAGA ATGTCAGTGG GAGTCTATCG     180
ATGATAATAA TGATACAACT ATTCTCGGTG ATGATATATA TTTTGATTAT ATAATTTCTC     240
AGTTAGATAT ACATCAAAAT TGGTCTCCTG ATATCAGACT AATAAGATAT TTTAGGAAGT     300
TTAACAAAGA ATCATTTGAT AAAATATCAG ATACGGAATA TATTAACCCA TCTTTTTTCC     360
AACAAAGAGA TAAACGATTT TATCCACTTA ATGATGATTT CTATCATATA TCAACAGGAG     420
GTTATGGTAT CGTATTTAAA ATGGATAAAT ACGTTGTTAA ATTGTTTAT GAACCAAATA      480
AACAGTATAG TCCCATTGAT ACAACTGCCG AGTATACAAT ACCTAAATTT TTATATAATA     540
ATCTTAAGGG AGATGAGAAA AAACTTATCG TTTGTGCATG GGCAATGGGT TTAAATTATA     600
AATTAACATT TCTACATAGA TTATATAAAA GAGTATTATA TATGTTATTA CTTATTATTC     660
AAACGATAGA TAATCAACGA TTAAATATTC ATCATTTTC TCATAAGTAT TTTCTTAAGT      720
CGTTCAATGA AAAAAAGAGC GATATAAAAT TTGTAAAATT ATTATCATAT TTTTATCCTA     780
TTGTTGTTCA AAGTAATATA AATGTAATAA ATTATTTTAC ACATATGTTT CATTTTTCG      840
AACATGAAAA AAGAGCTAAT TATTTATACG ATAGAGGAAA TATAATTATA TTCCCATTAG     900
CAAGATTTTC ATCAGATAAA GTGACGGAAC AGATGGCGAT AGAACTTGGT TTAAATCTA      960
TAGTTCAATA TGTTAAGTTT ATTTTTTTAC AAATATCATT GTTATATATA AAAATATACG    1020
AACTTCCTTG TTGTGATAAT TTTTTACACG TTGATTTAAA ACCCGATAAT ATTTTAATAT    1080
TTAATTCTGA TTGTCCTATA ACTATTAAAT TTAAGAAATA TACATACGTA TTTAATGAAC    1140
CGATTAAAGC GTGTCTTAAC GATTCGATT TTTCACAGGT GGCTAATATA TTAAATAAGA     1200
AAATTAAAAA TAGTTTAAAA ATAGAACACA ATTGGTATTA TGATTTTCAT TTTTTTATAC    1260
ATACACTTCT ACGAACTTAT CCAGAAATAG AATCTGATAA AGAATTCAGC GATTCTTTAG    1320
AGGATTTTAT AATGTGTTGT ACAAAAAATA CATGTGAGAA ATTTAGATTA AAAGTATCCA    1380
TACTGCATCC TATATCATTT TTAGAAAATT TGATTACAAA AACATTTTC TCAAATTGGA     1440
TAAATGGAGA ATCCTGTTAG AATAAATACA TTATATAACG TATTCGTAGA AAGATATATA    1500
GAGAACTTAT CAATATATTC TATACCTATT AATTCAACAT GTGGTATACA TATAGGAGAA    1560
ATCAAAGGAA CGTTCAAAAG ATGTTTTTTG AAAATACTCA ATATGTGTAT AAACGATAAA    1620
GAACTAAGTT TCAATATTCT TATAAAGACG CTTAAAGATG TAACTAGTAC GTTATCTCAG    1680
AAAGAGAAAG AGGAATTATC TAAAGAAATT GGAATTGATA TATTAAACAA TGACCCTAAA    1740
TATGTACCAG AAATAATACG AAACTGTTCA TCATCCGCAG ATGTAACAAA TATTATTGAT    1800
```

Fig. 5A

```
ATTCAAACAT TAGATGTTGG AAAATGCATA GCTCCGTACG ATAAACAGAT TCTATTACAG      1860

ATTGTTAATT CTGGTACTGC AGAAGCAAAC TGTGTGATGA ATTCTATCAT GAATTCTATG      1920

AATAGAAGAT ATATTGACAA TGCTAATATA TATAATTATT TGAATTTAAC AAATAGACCA      1980

TGGTTTATAT TTAGCATCAT TATTATTGCT ATCATATTTG TTATAGGAAT ATGTTCTATA      2040

AAAAGACGAA TAGGAATTAA ATACAAATAT GGTACATTTT TATATGTCTA AACCGGGTTA      2100

AAAATGAAAC ATAAATCATA GCTAATAACA TAAATAATCG CCTACTAAAT AACCATGAGC      2160

GGAAACCGAA AAAAGTAAAT AAAATTGTTT TAACCGGCAA GTCTGTACAA CATACACAGT      2220

CTACACCACC CACTAATGAT GAAATAAATA AATATGGATA TTGTCTAAAT ATTAAACCTA      2280

ATCAACATAT AAAAAGAGAA TCGTATTTAC ATAATGATTA TCCTATGATT ATAACTACTA      2340

GGTCCACACA ATTCTATTAT AATGGGTAAA TATGGAGGAT ATTTATAAGT AAGGTTAAGT      2400

TTGTTTTAGA GCACTACATT TCATTTCATT TCATTTCATT TCAAAAGGAA AATGC ATG      2458
                                                               Met
                                                                1
                                                               C4>
```

```
CAC CTT AAA AAT GAA GTA AAT AAT AAT ATG TTT GTT TTT ACT TTA TGT      2506
His Leu Lys Asn Glu Val Asn Asn Asn Met Phe Val Phe Thr Leu Cys
         5                   10                  15
[SEQ ID NO: 16]

ATT TTA TTA TAC TCG TCT TTT TGT TAT TTT TTT TAT ATT GAA AAA ATA      2554
Ile Leu Leu Tyr Ser Ser Phe Cys Tyr Phe Phe Tyr Ile Glu Lys Ile
         20                  25                  30

TTG CAA CAT ACA AAG CCA ATA TAT ACG AAC TAT GGG CAG TTG TGT ATC      2602
Leu Gln His Thr Lys Pro Ile Tyr Thr Asn Tyr Gly Gln Leu Cys Ile
         35                  40                  45

TGT AAA ATC AAT AAG TAT AAG TAT GGA TAC AGT GTC AAT ATC TTC TAT      2650
Cys Lys Ile Asn Lys Tyr Lys Tyr Gly Tyr Ser Val Asn Ile Phe Tyr
 50              55                  60                      65

AGA CGA TGAATATTAT TATAATATAA AAAATAAGCC AATATATGTA AGAAGAAAAA       2706
Arg Arg
```

```
ATAGTTGTAG TAGTACACTA GAATCGAGAT ATTCTACATA TAGTCTAGAA TCGAGATATT      2766

CCACATATAG TATTAAATCA GTATATTTCT AAATAAATAA TAATGAATAA TCGTAAGTAT      2826

TCAATAAATA ATGGTTTTAT GTCATATTTA CGAAAGAAAT TTACTACATT TTTAAGAAAG      2886

AAATCAACTT ATAGGATAAA ATCTAATACC GACTATTACC AGGAGAATGA AAAGTTGATA      2946

CATAAAAATA ACATCAAAAT ACCTTATAAA GTAAAGTTA  TAAGGAAACG TTGTAGTAGT      3006

AGCGATGATG ATGTTTTTAT TTAGTAAAAA AAACAAAAAA AATAATAATT AAACATTCAG      3066

ACAATGAATA CAACAACTTC ACAAATAATT ATAGATAATG ATATGTCTAA TGAAGTTGGA      3126

ACAATAATGG TAATTACATT ATGTTTAGTT ACTATCGTGA TAACGTGTTA TTTACTACTA      3186
```

Fig. 5B

```
CAATTAGTAA GATGGTCGTT TATAGTAGAT ATATTTAGAC AAATAAGAAC TAGATGTTTA      3246

CAATGGACAT CGAGAAGAGA ATTTTTACAA TTAGATAATA TGTATTATAC GAACGATAGC      3306

AGCGTTGGTG TTAATACCGA ATAAATTGAA AAATGATTTT TATACACGA ATG GAG         3361
                                                       Met Glu
                                                        1
                                                        C8>
```

| | | | | | | | | | | | | | | | | |
|---|---|---|---|---|---|---|---|---|---|---|---|---|---|---|---|---|
| CCT | ATT | CTT | CAA | GAG | TCT | GAT | TCT | AGG | TTC | GTT | ATT | TTC | CCT | ATT | AAG | 3409 |
| Pro | Ile | Leu | Gln | Glu | Ser | Asp | Ser | Arg | Phe | Val | Ile | Phe | Pro | Ile | Lys | |
| | | 5 | | | | | 10 | | | | | 15 | | | | |

[SEQ ID NO: 19]

| | | | | | | | | | | | | | | | | |
|---|---|---|---|---|---|---|---|---|---|---|---|---|---|---|---|---|
| TAT | CAT | GAT | ATC | TGG | AAA | ATG | TAT | AAA | CAA | TCA | GTG | GCA | AGT | TTT | TGG | 3457 |
| Tyr | His | Asp | Ile | Trp | Lys | Met | Tyr | Lys | Gln | Ser | Val | Ala | Ser | Phe | Trp | |
| | | 20 | | | | 25 | | | | | 30 | | | | | |
| ACC | GTT | GAA | GAA | GTA | GAT | TTA | TCA | AAA | GAT | TTA | GAT | GAT | TGG | GAT | AAA | 3505 |
| Thr | Val | Glu | Glu | Val | Asp | Leu | Ser | Lys | Asp | Leu | Asp | Asp | Trp | Asp | Lys | |
| 35 | | | | | 40 | | | | | 45 | | | | | 50 | |
| TTA | ACT | AAA | GAC | GAA | AAA | TAC | TTT | ATA | AAA | CAT | ATA | CTA | GCA | TTT | TTT | 3553 |
| Leu | Thr | Lys | Asp | Glu | Lys | Tyr | Phe | Ile | Lys | His | Ile | Leu | Ala | Phe | Phe | |
| | | | | 55 | | | | | 60 | | | | | 65 | | |
| GCA | TCT | AGT | GAT | GGT | ATT | GTA | AAT | GAG | AAT | TTA | GCG | GAA | AGA | TTT | TAT | 3601 |
| Ala | Ser | Ser | Asp | Gly | Ile | Val | Asn | Glu | Asn | Leu | Ala | Glu | Arg | Phe | Tyr | |
| | | | 70 | | | | | 75 | | | | | 80 | | | |
| GTG | GAT | GTA | CAG | TGT | TCA | GAG | GCA | CGA | TGT | TTC | TAT | GGA | TTT | CAA | ATA | 3649 |
| Val | Asp | Val | Gln | Cys | Ser | Glu | Ala | Arg | Cys | Phe | Tyr | Gly | Phe | Gln | Ile | |
| | | 85 | | | | | 90 | | | | | 95 | | | | |
| GCT | ATG | GAA | AAT | ATT | CAT | TCA | GAA | ATG | TAT | AGT | TTA | TTA | ATA | GAT | ACA | 3697 |
| Ala | Met | Glu | Asn | Ile | His | Ser | Glu | Met | Tyr | Ser | Leu | Leu | Ile | Asp | Thr | |
| | 100 | | | | | 105 | | | | | 110 | | | | | |
| TAT | GTA | AGA | GAT | AAT | ATA | GAA | AAA | ATG | CAT | TTA | TTT | AAC | GCT | ATA | GAA | 3745 |
| Tyr | Val | Arg | Asp | Asn | Ile | Glu | Lys | Met | His | Leu | Phe | Asn | Ala | Ile | Glu | |
| 115 | | | | | 120 | | | | | 125 | | | | | 130 | |
| ACA | ATG | GAA | TGC | GTA | AAA | AAG | AAA | GCT | GAT | TGG | GCC | AGA | AAA | TGG | ATA | 3793 |
| Thr | Met | Glu | Cys | Val | Lys | Lys | Lys | Ala | Asp | Trp | Ala | Arg | Lys | Trp | Ile | |
| | | | | 135 | | | | | 140 | | | | | 145 | | |
| TCT | AGC | AAC | AAG | GTA | TAT | GGA | GAA | AGA | GTA | GTA | GCA | TTT | GCA | GCT | GTG | 3841 |
| Ser | Ser | Asn | Lys | Val | Tyr | Gly | Glu | Arg | Val | Val | Ala | Phe | Ala | Ala | Val | |
| | | | 150 | | | | | 155 | | | | | 160 | | | |
| GAG | GGA | ATA | TTC | TTT | TCT | GGT | TCA | TTT | GCT | GCT | ATA | TTT | TGG | ATA | AAA | 3889 |
| Glu | Gly | Ile | Phe | Phe | Ser | Gly | Ser | Phe | Ala | Ala | Ile | Phe | Trp | Ile | Lys | |
| | | 165 | | | | | 170 | | | | | 175 | | | | |
| AAA | CGA | GGA | TTG | ATG | CCC | GGA | TTA | ACA | TTT | TCT | AAT | GAA | CTA | ATA | AGT | 3937 |
| Lys | Arg | Gly | Leu | Met | Pro | Gly | Leu | Thr | Phe | Ser | Asn | Glu | Leu | Ile | Ser | |
| | 180 | | | | | 185 | | | | | 190 | | | | | |

Fig. 5C

```
AGA GAC GAA GGT TTA CAT TGT GAT TTT GCG TGT TTA ATG TTT AAA CAT        3985
Arg Asp Glu Gly Leu His Cys Asp Phe Ala Cys Leu Met Phe Lys His
195                 200                 205                 210

TTA TTA CAT CCA CCA TCT AAG GAA GTT ATA ACG TCG ATA ATC ATT GAT        4033
Leu Leu His Pro Pro Ser Lys Glu Val Ile Thr Ser Ile Ile Ile Asp
                215                 220                 225

GCG GTT AAT ATA GAA AAG GAG TTT TTG ACA GTT GCT ATT CCG GTG GAT        4081
Ala Val Asn Ile Glu Lys Glu Phe Leu Thr Val Ala Ile Pro Val Asp
            230                 235                 240

CTT ATA GGT ATG AAT TGT TGT TTA ATG TCT CAG TAT ATA GAA TTC GTC        4129
Leu Ile Gly Met Asn Cys Cys Leu Met Ser Gln Tyr Ile Glu Phe Val
        245                 250                 255

GCA GAT AGA TTA TTA ACA GAG TTA GGT TGT GAA AAG TCT CAA TGT ATA        4177
Ala Asp Arg Leu Leu Thr Glu Leu Gly Cys Glu Lys Ser Gln Cys Ile
    260                 265                 270

TAATCCTTTT AGCTTTATGG AGTATATATC ACTAGAAGGT AAGACTAATT TTTTCGAACG      4237

ACGAGTTAGT GAATATCAAA AGATGGGGGT GTTTACAAAT AAAGAAGAGA ATATATTTTC      4297

TACGGATATA GATTTTTAAT TAATAATTTT TATAAAGTTG AATAAATAAT TTAATAATAG      4357

TAATTTGCTT TGGTTTGCAA ATAGATAGTG AAAAATGTCT AAACAAGAAA CTTACATTGA      4417

TTATAACTAT ATAGAAAGGT TAAATGCTGT GAATCTAAAC AGAAGTTATG ATGAAGAGAT      4477

AGTATTTATT ATGACCGTTG GTGGTGTTGT TAAAGTAAAA AAAGAATTAC TTGTATCTGT      4537

ATCTAATTAC TTTAAACTTA TTACAAAGAA TCAGAGTAAT GAAATAACGG TTTCATTCCA      4597

GTATGAATCT TTTCTTGATA TAATAAAATA TATAGAAACT GGAATCGTTA CTATCGATTT      4657

AGACAATGTA GAAAATATTT TTTCCATATC TTGTAGTAAA GCCATAGATT TTTTAAAAAA      4717

TTCATGTATT GATTTTATGT CAAAACATAT AACGGATTCT ACATGTGTTA AGATTTACAA      4777

AATAGGTTTC TCGAATGGAT GTTTTGCGGT ATATAATGAT GCTATAGCAT ATATAAGGAA      4837

AAGATTCACA AAAATAGAAA CAGATATATT ACTATCGTTA TCCTTATTTG ATTTGAGAAT      4897

AATTCTAAAA AGTGGAGAAT TAGATGTATC ATCAGAAGAT GATGTATTAT TATTTATAAT      4957

AAAATGGTCT AGACATAAAA AATCCAACAG ACGAAAATCG TTTACACTAG TAACAGAGGT      5017

ACTAAGATAT AATTATCTAT CCATATATGG TAAGTATAAA TTAACAAAAT GGTTGGCACG      5077

ATTCGGAAAA AATAATAATG TAGAGTTAAA TGAAAATGAA TTACCTAGAA TAAGTTATCA      5137

ACATAGATTT ACAAACAGAA GATATACGAT GGTTACACCA TCTTCATTTA GTATAAATAT      5197

GCTAGGTAAT GTATCTGTTA AGAATGAACT TAGTATAATC AATAGTATAG CTGAGAATCA      5257

TAATCCTTAC TGTGGATCTG TACTTATGAA TGATATATTA TATCTTATAG GTGGTATAAA      5317

TAAATCATTG GATCCTGTTA GTGATATAAC TAGCGTAGAC ACTAGATCAT TTATAGAGTT      5377
```

Fig. 5D

```
GCATACACCA CCATTATTAC ATCCTAGAAA GTGTCCGGGT GTTGCTATTT TTAAAAATAG    5437
AATTTATGTG GTAGGTGGTA TAGGATACGA TGGACCATTA AAAACAGTAG AAAGTTGGTC    5497
ACCTGGAGAA CAACAATGGA GAGAAGAAGT ACCATTATTA CAACCCAGAT TTAATCCTTG    5557
CATAATTGGA ACAGATAATG ATTTATATGT TGTTGGTGGT ATTTCTGAAG ATGATAAAAC    5617
TATTGAAATC TATTCTTATG AAGAAACAC TTGGTCTATT GGTAATGCGA TGAATTATTC     5677
ACATTTTGGT GGATGTATAG CATATCACCA TGGTTATATA TATATGATTG GTGGTTTATC    5737
TTTTATAGAT AATATTCATG TATTTACTAT GGTTGAGAAG TATAACCCTC ATTCGAATAA    5797
ATGGACTGTA GAAAAGTCTC TACCCTTTCC TCGATTTAAT TCATCGCTTT GTATTATAGA    5857
AGACTCTATC GCTATAATAG GCTGGATATA TTATTAACAA ATATATTAGT CAAATAGAAA    5917
TATATAACGG AGCTAGATGA ATGGGGTATT GTAGGGTCTA TCGATATAGA GTCATTCTTT    5977
CAAGAAATGA AAAAATAAATC TACATTTTTT CTTGTTACGA CAATGGAACT ACGTTATACG    6037
ATCATATCTG TCTGTGCTTG AAAGGTTGAC ACCGTATCAG TTTAAAACGT TATTATTCTT    6097
GATACAGGAT GACATTAATA TATCTAACGA TGATATTAAT GTATTAGATA GAGTCGATCT    6157
AGCTATTAAA ATAATGAATA AATATAATAA TTATAGAGCA ATTTATTTTC TCTATAAAGT    6217
CATATTACGA ATACATAATA CAGAATATAT AAGTGGAACA CTACAAAGAT CTATACAGAA    6277
TATAACACCT ACAACATCAT CATATACGTA TTGTGATAAT TCAAAAGAC GCAGACATAG     6337
ATTTAGAGAT ACGGAAATCC TTAAAGCTAT GGGTAGTAAA ATGCGTAGAA AACTTTTTTA    6397
GTTAGTGAGT AATATTATAA AATTAAAAAA AAAATAATAT TTTCTAGACA TGTCACTATA    6457
TGTTAAATGT GTTAAGTTAT CTAATAATGC TATTATACCA AATAGATCAA TGAGCGGATC    6517
CGCTGGATAT GATCTGTATA GTGCATATAG TTATACAGTT AAGCCGTATA ATAGAATTTT    6577
AGTTAGAACA GATATTTGTT TAATGATACC AGATAAATGT TATGGACGCA TATCGCCTAG    6637
ATCGGGATTA TCGTTAAATT ATAATATAGA TATAGGAGGA GGCGTTATTG ATAGTGATTA    6697
CAGAGGGGAA ATAGGTATCG TGTTTATAAA TAATGGATGT AGTGATTTTA ACATAAAGGT    6757
AGGTGATAGG ATAGCACAAA TAATATTTGA AAGAGTAGAA TATCCTATAA TGGAAGAAGT    6817
AAAATGTTTG GAAGATACAG AACGTGGAAA TAGTGGTTTT GGGTCAAGTG GTATGTAAAG    6877
TATAATAAAT GAAAAAATAA TTCATCTGTA TTATATCCAT TATTATCAAT ATGTACAAGA    6937
AATATAACTC TAACGTATGC ATTAGGAATG TATTATATGT ATATCTAAAA TATAATACTA    6997
TAAATAAACT TAGTAGATAT GAACGGATGA TATACACAAA GATAAAAAAT CAATGTGAAG    7057
CGATAAAATA CAGATATTGT AATGATTTTA ATTCTGTTAC ATGTATTTTA GAATACGATG    7117
AAAATAAGTA TATAGATAAC GTGCATAAAG AAGTTATTAG TATATTGTTA TCAGATTCGC    7177
```

Fig. 5E

```
GACCTAGTAT CAAATTAGCT GCTATTTCGT TATTATCTAT AATAATAGAT AAACTAATAT    7237

GTAGAAATAT TCGTATAGCT AAATATATAA TTGATGATAT AATAAATATT ATATCAGAAG    7297

ACGGTATATA TATTATATTA TTTTTAGATG AATTTGATAA ATATACCGAT ACCCGATGTA    7357

GGCGCCGTGG ATTAAGTATG ATGATAGCGA GCATTGTAAC TTACTACTGT TTACGGTATG    7417

TATTAAAAAT ATAAAAATAA ATCTTTTTTT TTAAAA ATG AAC CGT AAT ATG TGG      7471
                                         Met Asn Arg Asn Met Trp
                                          1                   5
                                        C13> [SEQ ID NO: 24]

ATA GTG TTA TCG TGT GTA TTA TAT ATG ATT TAT ATA TGT AAC GGA CGA      7519
Ile Val Leu Ser Cys Val Leu Tyr Met Ile Tyr Ile Cys Asn Gly Arg
            10                  15                  20

GAT GTA TTG TTA TAT CCA CCA CAT AAG AAA ACA AAT AAG GTT ATA GTA      7567
Asp Val Leu Leu Tyr Pro Pro His Lys Lys Thr Asn Lys Val Ile Val
        25                  30                  35

AAA TGT AAC GGA TAT ACT AAT TCT ACG TAT AGT ATC TTA TAT TGG ATG      7615
Lys Cys Asn Gly Tyr Thr Asn Ser Thr Tyr Ser Ile Leu Tyr Trp Met
40                  45                  50

GTA GGT AAC AAC AAT ACA TTC GTA GAA CAA CTA AAT AGC GAT CAT TAT      7663
Val Gly Asn Asn Asn Thr Phe Val Glu Gln Leu Asn Ser Asp His Tyr
55                  60                  65                  70

AAA GAG AAG AAA TAC AAT AGT ACT GAA AAA AAT GAG CAT ATG TAT AAG      7711
Lys Glu Lys Lys Tyr Asn Ser Thr Glu Lys Asn Glu His Met Tyr Lys
                75                  80                  85

TTA CGT ACC GAT CTT ATT ATA TAT AAT ATT ACG TCA GAA ATG GAG ATG      7759
Leu Arg Thr Asp Leu Ile Ile Tyr Asn Ile Thr Ser Glu Met Glu Met
            90                  95                 100

ACA AAA CTA ACA TGT GTA TTA TCA GAT ATA TAC ACA CCT ATC AAG GCA      7807
Thr Lys Leu Thr Cys Val Leu Ser Asp Ile Tyr Thr Pro Ile Lys Ala
        105                 110                 115

TCT ATA ATA TTA AAT AAT TTA TGG AGT TGT TTA AAT ACT ACA CAA GTA      7855
Ser Ile Ile Leu Asn Asn Leu Trp Ser Cys Leu Asn Thr Thr Gln Val
120                 125                 130

TGAAATATGA AATATAAAGT ATTCAAATAA ATAACAATA ATG TCA ACT ATG AAT       7909
                                           Met Ser Thr Met Asn
                                            1               5
                                          C14> [SEQ ID NO: 25]

ACG TTG GCA TTT TGT TAT GGA TTA CCT AAC ATA AAT GAT ATC ACG CAA      7957
Thr Leu Ala Phe Cys Tyr Gly Leu Pro Asn Ile Asn Asp Ile Thr Gln
                10                  15                  20

GGT ATA ATT TTT GTT AGA AAT AAC ATA TTT TAC TCA TAT TTA ACA GAT      8005
Gly Ile Ile Phe Val Arg Asn Asn Ile Phe Tyr Ser Tyr Leu Thr Asp
            25                  30                  35

TAT GCA ATG GAA GCG TGT ATA TTG AAT TAT ATA AAT ATT AGA GCC GAT      8053
Tyr Ala Met Glu Ala Cys Ile Leu Asn Tyr Ile Asn Ile Arg Ala Asp
        40                  45                  50
```

Fig. 5F

```
AAA ATA GAA GAT CTA AAG AAA TCA TTA GTT GGA AAA ACT ATT AGC GTG    8101
Lys Ile Glu Asp Leu Lys Lys Ser Leu Val Gly Lys Thr Ile Ser Val
         55                  60                  65

AGA GTT ATT AGA GTT GAT GTA TTA AAA GGA TAT ATA GAT GTT TCA ATT    8149
Arg Val Ile Arg Val Asp Val Leu Lys Gly Tyr Ile Asp Val Ser Ile
 70                  75                  80                  85

GTA TAATTTTTTT ATCAAAACTG AAGTATAATC TAGACCTTAG AAGATATTTT         8202
Val

GTACCATATA AAATGGATCC TGTTTGTTGG ATATGTAAAG ATGACTACAG TATTGAAAAG  8262

AATTATTGTA ACTGTAAAAA CGAGTATAAA GTTGTACACG ATGAATGTAT GAAAAAGTGG  8322

ATACAATACT CAAGGGAACG ATCTTGTAAA TTATGTAATA AAGAATATAA CATCATTAGT  8382

GTTAGAAAAC CATTCTCACA GTGGGTATTC TCCATTAAAG ATTGCAAAAA GTCAGCAATT  8442

TTGTACGCTA CTCTATTCTT ATGTACGTTT ATTATATCGC TTGTTTTAAC TAGAATTAAT  8502

ATAACAAAAA TAATAGATAC ATCAAAAAAT GATGTTTCAT TTAAGCTGGT TACGATGATA  8562

TTCTACTTAT TACCATTTGT CATAACTTGT ATATCGTTCA TAACGCTGAT AGTTTATCTA  8622

TATAAATATT GTAAGATTTC CGCTAAAAAC AACACATACG ATACGATTTA TGAACTTTAA  8682

AGTGAAAATT TAATCTATTT TTATAATAAA ACATGCATTT CATATTCATT ATATTATCAC  8742

TATCATTTGT AGTAAATGCC GATGTATTTC CATCGTCGGT TACTTTATCA TCTAATGATT  8802

TTGATACAAT AATTAAATGG GATAATAATG TAATATCATA CGATGTAGAA TTAATGCAGT  8862

ACAGTCATGA CGAATGGAGA ACCGTTTGTA CTAATTCTTT AGGATACTGT AATTTAACAA  8922

ATTCTGATAT CGACAATGAT GATGAAACAT GGGTGAGGTT TAAATATGAA AATAAGACAT  8982

CTAATGAACA TAATATTGGC AGAGTATGTG AGATTGTACA AATAACTTCA CCTATTGTTA  9042

ACATGACAAG AGATGGTTCA ATTATACTAT TAGATATACA TCATCCAATG ACATACGATA  9102

ATCAGTATTA TATATATAAT AATATAACAT TATGTGGATT TGAATTTATT TACGAAGCTA  9162

CATTTATTAT TAATGATACA ATTATACCAT ATAGTATAGA CAATCAATAT TGTGATGATG  9222

TTCATTGTTT ATTTTACTTT ATATCACAAG AACCCGTTTG TGTGTATGTA ATGGGTATGG  9282

AACAATATTA TGAATTTGGT CCAAAAAAAA CAGATAATAG TACTAGAGTG TGTGTAGATG  9342

GATTAATTCC AAGAAAAATC GATACATATT TTATTAAAGA TTTCGATGAT ATAGATAGAG  9402

TTAATAACAG ATTATATAGA GTTGTAAGTG ATAAATATGA ATCCAATATA TCGTCAAAGT  9462

TTATGCACTT ATATAATAAT ATATTATCTT CGTTTAAACT AATATTGCAA GAACTTATGG  9522

TAAATACTGA ACAGTAAATA CGTTTATAAA GATAAAGGAA TGAATTCGTA TATTGTAATA  9582

AAAAATTCAT TACGTGATTA TAGATCTGGA AGAATTATAA GAAAATACAT AAGAAAATTA  9642

AATAAGGATG AGTATAAGCA TTTTTGTGCT GTATTTAGAT TAAATGTAGA TTTTTCTCAA  9702
```

Fig. 5G

```
GATGATAAAA ATCCATCTAG AAAAGAAGTA ATAAGAATAA TAGATGAGGA ATTCAATTTT    9762

TGTGATCTTA GACTATTTTA TGATATCATG ACCGTTGTAC CTAATCATAT GAATGTGGCA    9822

TCTATTATTT ATAGCGAATA CGAATATCTT TTAAAAAAAT CAAATTATAA AATAAGAAG     9882

ATAAATTATA CTATATTAGA TAAGATTAAT AAATATCATA GTATAGATGA TATTATATTT    9942

ATGTATCTTC ATTGGAGAAA AAAATATAAC AACACATGCG CATGTGGTAA GTTATTTAAG   10002

GAACTCATGA AATATGATAT ATTAGCTACA AAATATATAT ATAATGATAT TATAAATACA   10062

TACAAAGAGG GAGATACTAT ATCCATTAAC ATACGTTTAA AATGTAAAGA TGATATAATT   10122

AAACATTGTA AGTCTTCTAT AGGTATGTTT GCTATATTAT CATCGAAAAT AATCGACGTA   10182

GATTTTGATG TTATATTCTT TTCACAAATA AGTATAAGAT ATAGACTAAT ATTCAAAAAA   10242

TATCTCATAC AATCATTATA CTTACAATAA TAATTGTTTT TTTTTTGAAA AATAATCCTA   10302
```

```
AATCTATCAT AAC ATG AAT TCA TTA TTA TTA CGA TTA CAT GAT TTT TTT     10351
        Met Asn Ser Leu Leu Leu Arg Leu His Asp Phe Phe
         1            5                    10
        C18> [SEQ ID NO: 29]

AAA CAT GGA ATT ATG TGT GAT ATA AAA ATA GTA TCC ATA GAG AAT AAT    10399
Lys His Gly Ile Met Cys Asp Ile Lys Ile Val Ser Ile Glu Asn Asn
         15              20              25

AAA ACC ATT AGC GCA CAT AGG TTA ATA TTA TCT ATG TAC TCT AAG TAC    10447
Lys Thr Ile Ser Ala His Arg Leu Ile Leu Ser Met Tyr Ser Lys Tyr
     30              35              40

TTT TAT AAT ATA TTT AAT TCA GAT TTT ATT GAT AAA AAT AAT GAT GAA    10495
Phe Tyr Asn Ile Phe Asn Ser Asp Phe Ile Asp Lys Asn Asn Asp Glu
 45              50              55              60

ATC TAT ATA TGC GCC GAT TAT GAT ATA TTG TAT ATT ATA TTG GAA TTT    10543
Ile Tyr Ile Cys Ala Asp Tyr Asp Ile Leu Tyr Ile Ile Leu Glu Phe
         65              70              75

ATG TAC ACC GGT AAT ATA GTA CTA ACA AAG GAT AAT ATA GAA TTA GTA    10591
Met Tyr Thr Gly Asn Ile Val Leu Thr Lys Asp Asn Ile Glu Leu Val
             80              85              90

ATA CAA GTC TGT GAT TAT CTA TGT ATA GAT TCT TTA ATA AAA ATA TGT    10639
Ile Gln Val Cys Asp Tyr Leu Cys Ile Asp Ser Leu Ile Lys Ile Cys
             95             100             105

GAA GAA TAT ATA TGC GGT ATA ATA GAT GAA ACA AAT TGT ATA CAT CTC    10687
Glu Glu Tyr Ile Cys Gly Ile Ile Asp Glu Thr Asn Cys Ile His Leu
         110             115             120

TTA AAC TTT TCA GAT ACT TAC AAT CTA CAA CGA TTA CGT GAA ATG TCA    10735
Leu Asn Phe Ser Asp Thr Tyr Asn Leu Gln Arg Leu Arg Glu Met Ser
 125             130             135             140
```

Fig. 5H

```
AAA TGG TAT TTA CCA AAA ATA ATA AAT AAT AAC AAA CTG GTA GTA GAA    10783
Lys Trp Tyr Leu Pro Lys Ile Ile Asn Asn Asn Lys Leu Val Val Glu
            145                 150                 155

TTA GAT ATA GAT GAT ATG ATA TTA ATT ATA AAA GAA ATT AAA TAC ATT    10831
Leu Asp Ile Asp Asp Met Ile Leu Ile Ile Lys Glu Ile Lys Tyr Ile
            160                 165                 170

GCA TGT GAA TAT ATA GTT AAA AAA ATA ATA TTA AAT TGG ATC GTT CAT    10879
Ala Cys Glu Tyr Ile Val Lys Lys Ile Ile Leu Asn Trp Ile Val His
            175                 180                 185

AAA GAT GAA CGA ATT ATT TAT ACT AAA AAA TTA ATG AAA CAT ATC AAT    10927
Lys Asp Glu Arg Ile Ile Tyr Thr Lys Lys Leu Met Lys His Ile Asn
            190                 195                 200

GAT CAA GAC CAT TAT ACA TCC TTA TCG GAT ATT GAA TTG TAC AAT AAT    10975
Asp Gln Asp His Tyr Thr Ser Leu Ser Asp Ile Glu Leu Tyr Asn Asn
205                 210                 215                 220

ATA CGG GAA CGA ATA TAT GAT AAC AAA GAA CAC GAT GTA GAT ATA TCA    11023
Ile Arg Glu Arg Ile Tyr Asp Asn Lys Glu His Asp Val Asp Ile Ser
            225                 230                 235

CAT AAC TTT ATA ATA ATG GTA GGA GGA AAA AAG ATA TTT AAT ATA ACC    11071
His Asn Phe Ile Ile Met Val Gly Gly Lys Lys Ile Phe Asn Ile Thr
            240                 245                 250

GCA TTC AAT CCG TTA TCG AAT AAA AAA CAT ATT ATA GAC AGA TAC GAT    11119
Ala Phe Asn Pro Leu Ser Asn Lys Lys His Ile Ile Asp Arg Tyr Asp
            255                 260                 265

GAT ATG TTT GGT TGT AAA ACT CAT TTT AGT GTT GTA TAC TTA AAT AGT    11167
Asp Met Phe Gly Cys Lys Thr His Phe Ser Val Val Tyr Leu Asn Ser
            270                 275                 280

ATA CTA TAT ATT ATC GGT GGA AAG AAA CGA GGA TAT TTC ACT AAA GAG    11215
Ile Leu Tyr Ile Ile Gly Gly Lys Lys Arg Gly Tyr Phe Thr Lys Glu
285                 290                 295                 300

GTG TTG TCA TAT AAT ATA AAA AAC AAA TTA TGG TGT TAC GAA CCA GAA    11263
Val Leu Ser Tyr Asn Ile Lys Asn Lys Leu Trp Cys Tyr Glu Pro Glu
            305                 310                 315

TTA AAT TAT TTT AGA TAC GAT ACA TCT GTA TGT GTA TCA AAT GGG ATG    11311
Leu Asn Tyr Phe Arg Tyr Asp Thr Ser Val Cys Val Ser Asn Gly Met
            320                 325                 330

ATA TAT TCA ATT GGT GGA AAA GAT ACA AAT GGA TAT ATG ACA AAC ATC    11359
Ile Tyr Ser Ile Gly Gly Lys Asp Thr Asn Gly Tyr Met Thr Asn Ile
            335                 340                 345

GTA GAA TTT TGG AAA CCT GAA TGG AAA TCA TGG TAT GAT GGT CAA CAT    11407
Val Glu Phe Trp Lys Pro Glu Trp Lys Ser Trp Tyr Asp Gly Gln His
            350                 355                 360

TTG TGT TAT CCT AGA TGT TAT ATG TCG TTG GTA GAC TAT AAT AAT GAA    11455
Leu Cys Tyr Pro Arg Cys Tyr Met Ser Leu Val Asp Tyr Asn Asn Glu
365                 370                 375                 380
```

Fig. 5I

```
GTA TAT ACA ATA GGT GGA TTA AAA ACA TCA ATA ACG GAT GAA TTT AAT      11503
Val Tyr Thr Ile Gly Gly Leu Lys Thr Ser Ile Thr Asp Glu Phe Asn
                385             390             395

ATA GAA ATG ATT GTA TCA GAC GAT GCC GTA GAG AAA CTG ACC GAT CAT      11551
Ile Glu Met Ile Val Ser Asp Asp Ala Val Glu Lys Leu Thr Asp His
            400             405             410

TCA TGG ATG AAG TTA AAA CAA TTT CCC ATA GCA AAG AGT GGT ATA TCA      11599
Ser Trp Met Lys Leu Lys Gln Phe Pro Ile Ala Lys Ser Gly Ile Ser
        415             420             425

TCC ATA GTA TAT AAC GAT TTT ATA TAC TGT ATA GGT GGT CGT ATA GAT      11647
Ser Ile Val Tyr Asn Asp Phe Ile Tyr Cys Ile Gly Gly Arg Ile Asp
    430             435             440

ACA CCA CAT ATA AGT ATA GAA CAC ACT AAC GAT GTT TAT ATA TAT TCT      11695
Thr Pro His Ile Ser Ile Glu His Thr Asn Asp Val Tyr Ile Tyr Ser
445             450             455             460

TCA AGA GAT GAT TGT TGG AAA TAT TTA TCA AAT ACA AAT GTA AAA AGA      11743
Ser Arg Asp Asp Cys Trp Lys Tyr Leu Ser Asn Thr Asn Val Lys Arg
                465             470             475

TCA TTT TGT CTA TCG TGT GTT TTT AAT AAT GAA TTA TAT ATA ATA GGT      11791
Ser Phe Cys Leu Ser Cys Val Phe Asn Asn Glu Leu Tyr Ile Ile Gly
            480             485             490

GGA TAT AAT ACA AAC AGT GTA GAA AAG TAC AAT AAA TTA AAA AAT ACA      11839
Gly Tyr Asn Thr Asn Ser Val Glu Lys Tyr Asn Lys Leu Lys Asn Thr
        495             500             505

TGG AAG CGT TTA AAC GAT ATT CCT AAG TTT GAA GAA TGT GTT AAT GAA      11887
Trp Lys Arg Leu Asn Asp Ile Pro Lys Phe Glu Glu Cys Val Asn Glu
    510             515             520

GCA TCG GCA ATA TAT TTG TAGTATCCCT TATAGCGTTC AAAAGAAACA             11935
Ala Ser Ala Ile Tyr Leu
525             530

AATCCATAAC AGACATCTAT ATTCTTAATC TATCTATGTC AGATTGTATA TTCGTATTTC    11995

AGATTCCGTT CATTGTGTAT AGTAAACTCG ATCAATGGAT TTTTGGGAAT ATACTATGTA    12055

AAATAATGTC CGTATTATAC TACGTAGGAT TCTTTAGTAA TATGTTTATA ATAACACTTA    12115

TGAGTATAGA TAGATATTTT GCGATCGTTC ATCCTATAAA GCGACAACCG TATAGGACGA    12175

AACGTATAGG TATCCTTATG TGCTGTTCCG CTTGGTTATT ATCCTTGATA TTATCTAGTC    12235

CCGTATCTAA ACTATACGAG AATATTCCTC ATATGTCTAA AGATATATAC CAATGTACTC    12295

TGACGAACGA GAATGACTCC ATAATCGCAT TCATAAAAAG ACTGATGCAA ATAGAGATCA    12355

CTATATTGGG ATTCCTGATA CCTATAATCA TATTCGTATA TTGCTATTAT AGAATTTTTT    12415

CTACAGTGGT TAGATTAAGA AATAGACGAA AGTATAAATC TATAAAAATT GTATTAATGA    12475

TTGTTGTATG TTCTCTAATA TGTTGGATTC CGCTCTATAT CGTTCTAATG ATAGCGACGA    12535
```

Fig. 5J

```
TTGTTAGCTT ATATACATCT AATATATTTA GACATCTGTG CCTCTATCTA AACCTGGCCT    12595
ATGCGATCAC CTTTTCGGAG ACTATCTCGT TAGCGCGTTG TTGTATAAAT CCAATAATAT    12655
ATACACTGAT AGGTGAACAT GTTCGATCTC GTATATCTAG CATATGTTCG TGTATATATA    12715
GAGACAATAG GATTAGGAAA AAACTCTTTT CACGAAAATC TTCTAGCAGT AGCAATATTA    12775
TTTAGTTGTT ATTTTCTTAC AAAACACAAG TTATAAATAA TCATTACGTA ATCATGCTAT    12835
CGTATATTAT TAATCCTTTG CTAAGTATTG TATACTTTAT ATTAGGAAAT GTATCTAAGC    12895
TGCTTACATA TATACTTATG AAAATAATGA TTTTTTTACT TCGTGCGGTG AATCCATACT    12955
CTCTGATATC TAACAGAGGT TGGCTGTCGC TGGATAGTAT AAATCCCTTT AAAAAGGAAA    13015
AGCGTAGGGA GTCTTTTCTA TCTAGTCTAA ATCCGTTTAG AAAAGAGGAA ACAAAGAAAA    13075
AAGAAGGTTT CTTTTCTGGT TGGTTCGGAT AATCTCTTTT ATAATTGAAA TAATATTCCA    13135
AAAATAAATC ATAATGATTA CTAAAGCGAT TGTGATATTG TCTATTATTA CAGCATATGT    13195
AGATGCTTCC GCATTCTTAG TATACAATTA TACATATACT TTACAAGATG ATAATCATCG    13255
ATATGACTTC GAAGTCACCG ATTATTTTAA TGATATACTA ATAAAACGTT TAAAACTAAA    13315
TAGCGAGACA GGAAGACCAG AATTAAGAAA TGAACCACCA ACATGGTTTA ATGAGACTAA    13375
GATTAGATAT TATCCGAAAA ATAATTATAA TTTTATGTTC TGGCTAAATA GAATGAGTGA    13435
AACGCTAGAT GAGATAAATA AACTTCCAGA AACGAGTAAT CCTTACAAGA CTATGTCCTT    13495
GACAATTGGA TGTACTGATC TAAGACAACT TCAAGTAAAT TTCGGTTATG TTACTGTAGG    13555
TGGTAATATA TGGACACGAT TCGACCCCAA GAATAAACGC TTTAGTAAAG TTAGATCACG    13615
TACATTTCCA AAGGTAGGAA TGTTAACTGT TAAATCACAA CACTGGGAAC GTGTTATGGA    13675
ACATCTTGGA TCAATGGTAA CATTAACATG TCCGTTTACA GCGGATGATT ATTATAAAAT    13735
TTCTAAGGGA TATATAGATA AGCCAGTTAA GCCTACTGTT ACAGTTACAG GAATTGAAAG    13795
AGGAGATAAT ACTACATTGA TATGCACATT TGATAATCAT TATCCGTCGT CGGTCGCTGT    13855
TAAATGGTAT AACATCGAGG ACTTTGCTCC GGACTATCGT TATGATCCGT ACGTAAATGA    13915
ATTGCTTCCT GATACGGACT ATCTACCGGG TGAACCAGGA TATCCGACTA TAACTAGGAG    13975
ATTAGGTGAT AAATATTTAT TTACATCATC ACCTAGGGTT ATGGTACCAA CTATCATGTC    14035
TAATAGAATA GCATGTGTTG GATTTCATAG TACGTTAGAA CCAAGCATAT ATAGATGTGT    14095
AAACTGCTCG GGACCTGAGC CTGTTTTACA ATACCAGGGA GATAGAAGGA ATGACTTGGA    14155
GGATGAGGAG GATTAAAGCT T                                              14176
```

Fig. 5K nucleotide sequence [SEQ ID NO: 57]
amino acid sequence [SEQ ID NO: 58]

```
CTATTGGTTATTTATACGAACCATTATCCGAGGAGTATAGACGTGTTATCGACTTTAGTG    60

ACATGAAGAATTTACGATCTATGTTTAACAAAATAACGATCACGTATCTGATAAATGCAT   120

ACAAGTTAATAAAGGATATTTATCAGATTTTGTAACATCATTAATACGATTAAGCGATGT   180

GATATAAATACCTATGATTCGTTTGATATTACTTATATAGATCCAAGAAGACATATAACT   240
                                                    M  Y  I  I  M
TGGAATAATATTTTATCCATATTGAAGAAAAATAAATAAACACTTTATGTATATAATAAT   300
 S  C  G  F  I  H  L  I  L  G  P  M  F  S  G  K  S  T  E  L
GTCATGTGGATTTATTCATCTTATATTAGGACCTATGTTCTCTGGAAAGAGTACAGAATT   360
 I  R  L  V  N  R  Y  Q  I  A  T  Y  N  C  R  V  I  K  Y  S
AATTAGGTTAGTAAACCGGTATCAAATAGCCACGTATAATTGTAGAGTTATAAAATATTC   420
 K  D  N  R  Y  G  N  D  A  V  Y  T  H  D  K  C  Y  I  S  A
TAAAGATAATAGATATGGAAATGATGCGGTATATACACACGATAAATGTTATATATCGGC   480
 V  S  T  D  S  L  F  D  I  K  D  T  L  D  D  V  D  I  V  G
TGTATCTACGGATTCCTTATTTGATATAAAAGATACACTAGATGATGTAGATATTGTTGG   540
 I  D  E  G  Q  F  F  N  D  I  V  E  F  C  E  Y  I  A  N  K
AATAGACGAAGGACAATTCTTTAATGATATTGTAGAGTTTTGTGAATATATAGCAAATAA   600
 G  K  I  V  I  V  A  A  L  D  G  T  Y  E  R  K  P  F  G  N
AGGAAAAATTGTTATCGTTGCTGCATTAGATGGAACATATGAACGTAAACCATTTGGTAA   660
 I  L  N  L  I  P  L  S  E  K  V  T  K  L  N  A  I  C  M  I
TATTCTTAATCTTATACCATTATCGGAAAAAGTTACTAAATTAAATGCTATATGCATGAT   720
 C  H  R  D  A  S  F  S  K  R  L  S  D  E  K  E  I  E  L  I
ATGTCATCGTGATGCATCTTTTTCAAAGAGATTAAGCGACGAGAAAGAAATAGAATTGAT   780
 G  G  K  E  K  Y  L  S  V  C  R  S  C  Y  L  T  *
AGGAGGAAAAGAAAAGTATTTATCGGTATGTCGTTCATGTTACTTAACCTGAAATATTGA   840

AAATATAATTAATATCTTAGAGCTATTTAATTTATAGTTATTTACCATGGGTATTACACA   900

TGAATTAGATATCTTTCTGGTTAGTGAAGACATTGCTATGAAACATGTCGAACTTCATAA   960

AGGTAATAGTTATGGTTGTGTATTAAACATTAAATCATCTTGTAGGAAACAAATGAAATA  1020

ATATTTGTGTTAAAGCCTGATGGACCGAAATAGATGCATTAAACCATATCAAATGGAAGC  1080

AGATCGAATATATATAGACGTGAC                                     1104
```

Fig. 7

```
                             SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
          (A) LENGTH: 14176 base pairs
          (B) TYPE: nucleic acid
          (C) STRANDEDNESS: double
          (D) TOPOLOGY: unknown (ii) MOLECULE TYPE: DNA (genomic)

(ix) FEATURE:
          (A) NAME/KEY: CDS
          (B) LOCATION: 3852..4226

(ix) FEATURE:
          (A) NAME/KEY: CDS
          (B) LOCATION: 4585..4887

(ix) FEATURE:
          (A) NAME/KEY: CDS
          (B) LOCATION: 5131..5310

(ix) FEATURE:
          (A) NAME/KEY: CDS
          (B) LOCATION: 5760..5912

(ix) FEATURE:
          (A) NAME/KEY: CDS
          (B) LOCATION: 6786..7130

(ix) FEATURE:
          (A) NAME/KEY: CDS
          (B) LOCATION: 10148..10513

(xi) SEQUENCE DESCRIPTION: SEQ ID NO:1:

AAGCTTTAAT CCTCCTCATC CTCCAAGTCA TTCCTTCTAT CTCCCTGGTA TTGTAAAACA      60

GGCTCAGGTC CCGAGCAGTT TACACATCTA TATATGCTTG GTTCTAACGT ACTATGAAAT     120

CCAACACATG CTATTCTATT AGACATGATA GTTGGTACCA TAACCCTAGG TGATGATGTA     180

AATAAATATT TATCACCTAA TCTCCTAGTT ATAGTCGGAT ATCCTGGTTC ACCCGGTAGA     240

TAGTCCGTAT CAGGAAGCAA TTCATTTACG TACGGATCAT AACGATAGTC CGGAGCAAAG     300

TCCTCGATGT TATACCATTT AACAGCGACC GACGACGGAT AATGATTATC AAATGTGCAT     360

ATCAATGTAG TATTATCTCC TCTTTCAATT CCTGTAACTG TAACAGTAGG CTTAACTGGC     420

TTATCTATAT ATCCCTTAGA AATTTTATAA TAATCATCCG CTGTAAACGG ACATGTTAAT     480

GTTACCATTG ATCCAAGATG TTCCATAACA CGTTCCCAGT GTTGTGATTT AACAGTTAAC     540

ATTCCTACCT TTGGAAATGT ACGTGATCTA ACTTTACTAA AGCGTTTATT CTTGGGGTCG     600

AATCGTGTCC ATATATTACC ACCTACAGTA ACATAACCGA AATTTACTTG AAGTTGTCTT     660

AGATCAGTAC ATCCAATTGT CAAGGACATA GTCTTGTAAG GATTACTCGT TTCTGGAAGT     720

TTATTTATCT CATCTAGCGT TTCACTCATT CTATTTAGCC AGAACATAAA ATTATAATTA     780

TTTTTCGGAT AAATATCTAAT CTTAGTCTCA TTAAACCATG TTGGTGGTTC ATTTCTTAAT     840

TCTGGTCTTC CTGTCTCGCT ATTTAGTTTT AAACGTTTTA TTAGTATATC ATTAAAATAA     900
```

```
TCGGTGACTT CGAAGTCATA TCGATGATTA TCATCTTGTA AAGTATATGT ATAATTGTAT    960

ACTAAGAATG CGGAAGCATC TACATATGCT GTAATAATAG ACAATATCAC AATCGCTTTA   1020

GTAATCATTA TGATTTATTT TTGGAATATT ATTTCAATTA TAAAAGAGAT TATCCGAACC   1080

AACCAGAAAA GAAACCTTCT TTTTTCTTTG TTTCCTCTTT TCTAAACGGA TTTAGACTAG   1140

ATAGAAAAGA CTCCCTACGC TTTTCCTTTT TAAAGGGATT TATACTATCC AGCGACAGCC   1200

AACCTCTGTT AGATATCAGA GAGTATGGAT TCACCGCACG AAGTAAAAAA ATCATTATTT   1260

TCATAAGTAT ATATGTAAGC AGCTTAGATA CATTTCCTAA TATAAAGTAT ACAATACTTA   1320

GCAAAGGATT AATAATATAC GATAGCATGA TTACGTAATG ATTATTTATA ACTTGTGTTT   1380

TGTAAGAAAA TAACAACTAA ATAATATTGC TACTGCTAGA AGATTTTCGT GAAAAGAGTT   1440

TTTTCCTAAT CCTATTGTCT CTATATATAC ACGAACATAT GCTAGATATA CGAGATCGAA   1500

CATGTTCACC TATCAGTGTA TATATTATTG GATTTATACA ACAACGCGCT AACGAGATAG   1560

TCTCCGAAAA GGTGATCGCA TAGGCCAGGT TTAGATAGAG GCACAGATGT CTAAATATAT   1620

TAGATGTATA TAAGCTAACA ATCGTCGCTA TCATTAGAAC GATATAGAGC GGAATCCAAC   1680

ATATTAGAGA ACATACAACA ATCATTAATA CAATTTTTAT AGATTTATAC TTTCGTCTAT   1740

TTCTTAATCT AACCACTGTA GAAAAAATTC TATAATAGCA ATATACGAAT ATGATTATAG   1800

GTATCAGGAA TCCCAATATA GTGATCTCTA TTTGCATCAG TCTTTTTATG AATGCGATTA   1860

TGGAGTCATT CTCGTTCGTC AGAGTACATT GGTATATATC TTTAGACATA TGAGGAATAT   1920

TCTCGTATAG TTTAGATACG GGACTAGATA ATATCAAGGA TAATAACCAA GCGGAACAGC   1980

ACATAAGGAT ACCTATACGT TTCGTCCTAT ACGGTTGTCG CTTTATAGGA TGAACGATCG   2040

CAAAATATCT ATCTATACTC ATAAGTGTTA TTATAAACAT ATTACTAAAG AATCCTACGT   2100

AGTATAATAC GGACATTATT TTACATAGTA TATTCCCAAA AATCCATTGA TCGAGTTTAC   2160

TATACACAAT GAACGGAATC TGAAATACGA ATATACAATC TGACATAGAT AGATTAAGAA   2220

TATAGATGTC TGTTATGGAT TTGTTTCTTT TGAACGCTAT AAGGGATACT ACAAATATAT   2280

TGCCGATGCT TCATTAACAC ATTCTTCAAA CTTAGGAATA TCGTTTAAAC GCTTCCATGT   2340

ATTTTTTAAT TTATTGTACT TTTCTACACT GTTTGTATTA TATCCACCTA TTATATATAA   2400

TTCATTATTA AAAACACACG ATAGACAAAA TGATCTTTTT ACATTTGTAT TTGATAAATA   2460

TTTCCAACAA TCATCTCTTG AAGAATATAT ATAAACATCG TTAGTGTGTT CTATACTTAT   2520

ATGTGGTGTA TCTATACGAC CACCTATACA GTATATAAAA TCGTTATATA CTATGGATGA   2580

TATACCACTC TTTGCTATGG GAAATTGTTT TAACTTCATC CATGAATGAT CGGTCAGTTT   2640

CTCTACGGCA TCGTCTGATA CAATCATTTC TATATTAAAT TCATCCGTTA TTGATGTTTT   2700

TAATCCACCT ATTGTATATA CTTCATTATT ATAGTCTACC AACGACATAT AACATCTAGG   2760

ATAACACAAA TGTTGACCAT CATACCATGA TTTCCATTCA GGTTTCCAAA ATTCTACGAT   2820

GTTTGTCATA TATCCATTTG TATCTTTTCC ACCAATTGAA TATATCATCC CATTTGATAC   2880

ACATACAGAT GTATCGTATC TAAAATAATT TAATTCTGGT TCGTAACACC ATAATTTGTT   2940

TTTTATATTA TATGACAACA CCTCTTTAGT GAAATATCCT CGTTTCTTTC CACCGATAAT   3000

ATATAGTATA CTATTTAAGT ATACAACACT AAAATGAGTT TTACAACCAA ACATATCATC   3060

GTATCTGTCT ATAATATGTT TTTTATTCGA TAACGGATTG AATGCGGTTA TATTAAATAT   3120

CTTTTTTCCT CCTACCATTA TTATAAAGTT ATGTGATATA TCTACATCGT GTTCTTTGTT   3180

ATCATATATT CGTTCCCGTA TATTATTGTA CAATTCAATA TCCGATAAGG ATGTATAATG   3240

GTCTTGATCA TTGATATGTT TCATTAATTT TTTAGTATAA ATAATTCGTT CATCTTTATG   3300
```

```
AACGATCCAA TTTAATATTA TTTTTTTAAC TATATATTCA CATGCAATGT ATTTAATTTC    3360

TTTTATAATT AATATCATAT CATCTATATC TAATTCTACT ACCAGTTTGT TATTATTTAT    3420

TATTTTTGGT AAATACCATT TTGACATTTC ACGTAATCGT TGTAGATTGT AAGTATCTGA    3480

AAAGTTTAAG AGATGTATAC AATTTGTTTC ATCTATTATA CCGCATATAT ATTCTTCACA    3540

TATTTTTATT AAAGAATCTA TACATAGATA ATCACAGACT TGTATTACTA ATTCTATATT    3600

ATCCTTTGTT AGTACTATAT TACCGGTGTA CATAAATTCC AATATAATAT ACAATATATC    3660

ATAATCGGCG CATATATAGA TTTCATCATT ATTTTTATCA ATAAAATCTG AATTAAATAT    3720

ATTATAAAAG TACTTAGAGT ACATAGATAA TATTAACCTA TGTGCGCTAA TGGTTTTATT    3780

ATTCTCTATG GATACTATTT TTATATCACA CATAATTCCA TGTTTAAAAA AATCATGTAA    3840

TCGTAATAAT A ATG AAT TCA TGT TAT GAT AGA TTT AGG ATT ATT TTT CAA     3890
             Met Asn Ser Cys Tyr Asp Arg Phe Arg Ile Ile Phe Gln
              1               5                  10

AAA AAA AAC AAT TAT TAT TGT AAG TAT AAT GAT TGT ATG AGA TAT TTT      3938
Lys Lys Asn Asn Tyr Tyr Cys Lys Tyr Asn Asp Cys Met Arg Tyr Phe
         15              20              25

TTG AAT ATT AGT CTA TAT CTT ATA CTT ATT TGT GAA AAG AAT ATA ACA      3986
Leu Asn Ile Ser Leu Tyr Leu Ile Leu Ile Cys Glu Lys Asn Ile Thr
 30              35              40                  45

TCA AAA TCT ACG TCG ATT ATT TTC GAT GAT AAT ATA GCA AAC ATA CCT      4034
Ser Lys Ser Thr Ser Ile Ile Phe Asp Asp Asn Ile Ala Asn Ile Pro
             50              55                  60

ATA GAA GAC TTA CAA TGT TTA ATT ATA TCA TCT TTA CAT TTT AAA CGT      4082
Ile Glu Asp Leu Gln Cys Leu Ile Ile Ser Ser Leu His Phe Lys Arg
         65              70              75

ATG TTA ATG GAT ATA GTA TCT CCC TCT TTG TAT GTA TTT ATA ATA TCA      4130
Met Leu Met Asp Ile Val Ser Pro Ser Leu Tyr Val Phe Ile Ile Ser
 80              85                  90

TTA TAT ATA TAT TTT GTA GCT AAT ATA TCA TAT TTC ATG AGT TCC TTA AAT  4181
Leu Tyr Ile Tyr Phe Val Ala Asn Ile Ser Tyr Phe Met Ser Ser Leu Asn
         95              100             105                 110

AAC TTA CCA CAT GCG CAT GTG TTG TTA TAT TTT TTT CTC CAA TGAAGATACA  4233
Asn Leu Pro His Ala His Val Leu Leu Tyr Phe Phe Leu Gln
                 115             120             125

TAAATATAAT ATCATCTATA CTATGATATT TATTAATCTT ATCTAATATA GTATAATTTA    4293

TCTTCTTATT TTTATAATTT GATTTTTTTA AAAGATATTC GTATTCGCTA TAAATAATAG    4353

ATGCCACATT CATATGATTA GGTACAACGG TCATGATATC ATAAAAATAGT CTAAGATCAC   4413

AAAAATTGAA TTCCTCATCT ATTATTCTTA TTACTTCTTT TCTAGATGGA TTTTTATCAT    4473

CTTGAGAAAA ATCTACATTT AATCTAAATA CAGCACAAAA ATGCTTATAC TCATCCTTAT    4533

TTAATTTTCT TATGTATTTT CTTATAATTC TTCCAGATCT ATAATCACGT A ATG AAT    4590
                                                         Met Asn
                                                          1

TTT TTA TTA CAA TAT ACG AAT TCA TTC CTT TAT CTT TAT AAA CGT ATT      4638
Phe Leu Leu Gln Tyr Thr Asn Ser Phe Leu Tyr Leu Tyr Lys Arg Ile
             5               10              15

TAC TGT TCA GTA TTT ACC ATA AGT TCT TGC AAT ATT AGT TTA AAC GAA      4686
Tyr Cys Ser Val Phe Thr Ile Ser Ser Cys Asn Ile Ser Leu Asn Glu
         20              25              30

GAT AAT ATA TTA TTA TAT AAG TGC ATA AAC TTT GAC GAT ATA TTG GAT      4734
Asp Asn Ile Leu Leu Tyr Lys Cys Ile Asn Phe Asp Asp Ile Leu Asp
 35              40              45                  50

TCA TAT TTA TCA CTT ACA ACT CTA TAT AAT CTG TTA TTA ACT CTA TCT      4782
Ser Tyr Leu Ser Leu Thr Thr Leu Tyr Asn Leu Leu Leu Thr Leu Ser
```

|  |  |
|---|---:|
| ATA TCA TCG AAA TCT TTA ATA AAA TAT GTA TCG ATT TTT CTT GGA ATT<br>Ile Ser Ser Lys Ser Leu Ile Lys Tyr Val Ser Ile Phe Leu Gly Ile<br>            70                     75                  80 | 4830 |
| AAT CCA TCT ACA CAC ACT CTA GTA CTA TTA TCT GTT TTT TTT GGA CCA<br>Asn Pro Ser Thr His Thr Leu Val Leu Leu Ser Val Phe Phe Gly Pro<br>            85                     90                  95 | 4878 |
| AAT TCA TAATATTGTT CCATACCCAT TACATACACA CAAACGGGTT CTTGTGATAT<br>Asn Ser<br>100 | 4934 |
| AAAGTAAAAT AAACAATGAA CATCATCACA ATATTGATTG TCTATACTAT ATGGTATAAT | 4994 |
| TGTATCATTA ATAATAAATG TAGCTTCGTA AATAAATTCA AATCCACATA ATGTTATATT | 5054 |
| ATTATATATA TAATACTGAT TATCGTATGT CATTGGATGA TGTATATCTA ATAGTATAAT | 5114 |
| TGAACCATCT CTTGTC ATG TTA ACA ATA GGT GAA GTT ATT TGT ACA ATC<br>                           Met Leu Thr Ile Gly Glu Val Ile Cys Thr Ile<br>                             1                 5                     10 | 5163 |
| TCA CAT ACT CTG CCA ATA TTA TGT TCA TTA GAT GTC TTA TTT TCA TAT<br>Ser His Thr Leu Pro Ile Leu Cys Ser Leu Asp Val Leu Phe Ser Tyr<br>            15                     20                  25 | 5211 |
| TTA AAC CTC ACC CAT GTT TCA TCA TCA TTG TCG ATA TCA GAA TTT GTT<br>Leu Asn Leu Thr His Val Ser Ser Ser Leu Ser Ile Ser Glu Phe Val<br>            30                     35                  40 | 5259 |
| AAA TTA CAG TAT CCT AAA GAA TTA GTA CAA ACG GTT CTC CAT TCG TCA<br>Lys Leu Gln Tyr Pro Lys Glu Leu Val Gln Thr Val Leu His Ser Ser<br>            45                     50                  55 | 5307 |
| TGACTGTACT GCATTAATTC TACATCGTAT GATATTACAT TATTATCCCA TTTAATTATT | 5367 |
| GTATCAAAAT CATTAGATGA TAAAGTAACC GACGATGGAA ATACATCGGC ATTTACTACA | 5427 |
| AATGATAGTG ATAATATAAT GAATATGAAA TGCATGTTTT ATTATAAAAA TAGATTAAAT | 5487 |
| TTTCACTTTA AAGTTCATAA ATCGTATCGT ATGTGTTGTT TTTAGCGGAA ATCTTACAAT | 5547 |
| ATTTATATAG ATAAACTATC AGCGTTATGA ACGATATACA AGTTATGACA ATGGTAATA | 5607 |
| AGTAGAATAT CATCGTAACC AGCTTAAATG AAACATCATT TTTTGATGTA TCTATTATTT | 5667 |
| TTGTTATATT AATTCTAGTT AAAACAAGCG ATATAATAAA CGTACATAAG AATAGAGTAG | 5727 |
| CGTACAAAAT TGCTGACTTT TTGCAATCTT TA ATG GAG AAT ACC CAC TGT GAG<br>                                                         Met Glu Asn Thr His Cys Glu<br>                                                         1                 5 | 5780 |
| AAT GGT TTT CTA ACA CTA ATG ATG TTA TAT TCT TTA TTA CAT AAT TTA<br>Asn Gly Phe Leu Thr Leu Met Met Leu Tyr Ser Leu Leu His Asn Leu<br>            10                     15                  20 | 5828 |
| CAA GAT CGT TCC CTT GAG TAT TGT ATC CAC TTT TTC ATA CAT TCA TCG<br>Gln Asp Arg Ser Leu Glu Tyr Cys Ile His Phe Phe Ile His Ser Ser<br>            25                     30                  35 | 5876 |
| TGT ACA ACT TTA TAC TCG TTT TTA CAG TTA CAA TAATTCTTTT CAATACTGTA<br>Cys Thr Thr Leu Tyr Ser Phe Leu Gln Leu Gln<br>40                       45                     50 | 5929 |
| GTCATCTTTA CATATCCAAC AAACAGGATC CATTTTATAT GGTACAAAAT ATCTTCTAAG | 5989 |
| GTCTAGATTA TACTTCAGTT TTGATAAAAA AATTATACAA TTGAAACATC TATATATCCT | 6049 |
| TTTAATACAT CAACTCTAAT AACTCTCACG CTAAATAGTTT TTCCAACTAA TGATTTCTTT | 6109 |
| AGATCTTCTA TTTTATCGGC TCTAATATTT ATATAATTCA ATATACACGC TTCCATTGCA | 6169 |
| TAATCTGTTA AATATGAGTA AAATATGTTA TTTCTAACAA AAATTATACC TTGCGTGATA | 6229 |
| TCATTTATGT TAGGTAATCC ATAACAAAAT GCCAACGTAT TCATAGTTGA CATTATTGTT | 6289 |
| ATTTATTTGA ATACTTTATA TTTCATATTT CATACTTGTG TAGTATTTAA ACAACTCCAT | 6349 |

```
AAATTATTTA ATATTATAGA TGCCTTGATA GGTGTGTATA TATCTGATAA TACACATGTT    6409

AGTTTTGTCA TCTCCATTTC TGACGTAATA TTATATATAA TAAGATCGGT ACGTAACTTA    6469

TACATATGCT CATTTTTTTC AGTACTATTG TATTTCTTCT CTTTATAATG ATCGCTATTT    6529

AGTTGTTCTA CGAATGTATT GTTGTTACCT ACCATCCAAT ATAAGATACT ATACGTAGAA    6589

TTAGTATATC CGTTACATTT TACTATAACC TTATTTGTTT TCTTATGTGG TGGATATAAC    6649

AATACATCTC GTCCGTTACA TATATAAATC ATATATAATA CACACGATAA CACTATCCAC    6709

ATATTACGGT TCATTTTTAA AAAAAAAGAT TTATTTTTAT ATTTTTAATA CATACCGTAA    6769

ACAGTAGTAA GTTACA ATG CTC GCT ATC ATC ATA CTT AAT CCA CGG CGC        6818
              Met Leu Ala Ile Ile Ile Leu Asn Pro Arg Arg
                1               5                   10

CTA CAT CGG GTA TCG GTA TAT TTA TCA AAT TCA TCT AAA AAT AAT ATA      6866
Leu His Arg Val Ser Val Tyr Leu Ser Asn Ser Ser Lys Asn Asn Ile
            15                  20                  25

ATA TAT ATA CCG TCT TCT GAT ATA ATA TTT ATT ATA TCA TCA ATT ATA      6914
Ile Tyr Ile Pro Ser Ser Asp Ile Ile Phe Ile Ile Ser Ser Ile Ile
        30                  35                  40

TAT TTA GCT ATA CGA ATA TTT CTA CAT ATT AGT TTA TCT ATT ATT ATA      6962
Tyr Leu Ala Ile Arg Ile Phe Leu His Ile Ser Leu Ser Ile Ile Ile
    45                  50                  55

GAT AAT AAC GAA ATA GCA GCT AAT TTG ATA CTA GGT CGC GAA TCT GAT      7010
Asp Asn Asn Glu Ile Ala Ala Asn Leu Ile Leu Gly Arg Glu Ser Asp
60                  65                  70                  75

AAC AAT ATA CTA ATA ACT TCT TTA TGC ACG TTA TCT ATA TAC TTA TTT      7058
Asn Asn Ile Leu Ile Thr Ser Leu Cys Thr Leu Ser Ile Tyr Leu Phe
                80                  85                  90

TCA TCG TAT TCT AAA ATA CAT GTA ACA GAA TTA AAA TCA TTA CAA TAT      7106
Ser Ser Tyr Ser Lys Ile His Val Thr Glu Leu Lys Ser Leu Gln Tyr
            95                  100                 105

CTG TAT TTT ATC GCT TCA CAT TGATTTTTTA TCTTTGTGTA TATCATCCGT         7157
Leu Tyr Phe Ile Ala Ser His
        110                 115

TCATATCTAC TAAGTTTATT TATAGTATTA TATTTTAGAT ATACATATAA TACATTCCTA    7217

ATGCATACGT TAGAGTTATA TTTCTTGTAC ATATTGATAA TAATGGATAT AATACAGATG    7277

AATTATTTTT TCATTTATTA TACTTTACAT ACCACTTGAC CCAAAACCAC TATTTCCACG    7337

TTCTGTATCT TCCAAACATT TTACTTCTTC CATTATAGGA TATTCTACTC TTTCAAATAT    7397

TATTTGTGCT ATCCTATCAC CTACCTTTAT GTTAAAATCA CTACATCCAT TATTTATAAA    7457

CACGATACCT ATTTCCCCTC TGTAATCACT ATCAATAACG CCTCCTCCTA TATCTATATT    7517

ATAATTTAAC GATAATCCCG ATCTAGGCGA TATGCGTCCA TAACATTTAT CTGGTATCAT    7577

TAAACAAATA TCTGTTCTAA CTAAAATTCT ATTATACGGC TTAACTGTAT AACTATATGC    7637

ACTATACAGA TCATATCCAG CGGATCCGCT CATTGATCTA TTTGGTATAA TAGCATTATT    7697

AGATAACTTA ACACATTTAA CATATAGTGA CATGTCTAGA AAATATTATT TTTTTTTTAA    7757

TTTTATAATA TTACTCACTA ACTAAAAAAG TTTTCTACGC ATTTTACTAC CCATAGCTTT    7817

AAGGATTTCC GTATCTCTAA ATCTATGTCT GCGTCTTTTT GAATTATCAC AATACGTATA    7877

TGATGATGTT GTAGGTGTTA TATTCTGTAT AGATCTTTGT AGTGTTCCAC TTATATATTC    7937

TGTATTATGT ATTCGTAATA TGACTTTATA GAGAAAATAA ATTGCTCTAT AATTATTATA    7997

TTTATTCATT ATTTTAATAG CTAGATCGAC TCTATCTAAT ACATTAATAT CATCGTTAGA    8057

TATATTAATG TCATCCTGTA TCAAGAATAA TAACGTTTTA AACTGATACG GTGTCAACCT    8117
```

```
TTCAAGCACA GACAGATATG ATCGTATAAC GTAGTTCCAT TGTCGTAACA AGAAAAAATG      8177

TAGATTATTT TTTCATTTCT TGAAAGAATG ACTCTATATC GATAGACCCT ACAATACCCC      8237

ATTCATCTAG CTCCGTTATA TATTTCTATT TGACTAATAT ATTTGTTAAT AATATATCCA      8297

GCCTATTATA GCGATAGAGT CTTCTATAAT ACAAAGCGAT GAATTAAATC GAGGAAAGGG      8357

TAGAGACTTT TCTACAGTCC ATTTATTCGA ATGAGGGTTA TACTTCTCAA CCATAGTAAA      8417

TACATGAATA TTATCTATAA AAGATAAACC ACCAATCATA TATATATAAC CATGGTGATA      8477

TGCTATACAT CCACCAAAAT GTGAATAATT CATCGCATTA CCAATAGACC AAGTGTTTTC      8537

TTCATAAGAA TAGATTTCAA TAGTTTTATC ATCTTCAGAA ATACCACCAA CAACATATAA      8597

ATCATTATCT GTTCCAATTA TGCAAGGATT AAATCTGGGT TGTAATAATG GTACTTCTTC      8657

TCTCCATTGT TGTTCTCCAG GTGACCAACT TTCTACTGTT TTTAATGGTC CATCGTATCC      8717

TATACCACCT ACCACATAAA TTCTATTTTT AAAAATAGCA ACACCCGGAC ACTTTCTAGG      8777

ATGTAATAAT GGTGGTGTAT GCAACTCTAT AAATGATCTA GTGTCTACGC TAGTTATATC      8837

ACTAACAGGA TCCAATGATT TATTTATACC ACCTATAAGA TATAATATAT CATTCATAAG      8897

TACAGATCCA CAGTAAGGAT TATGATTCTC AGCTATACTA TTGATTATAC TAAGTTCATT      8957

CTTAACAGAT ACATTACCTA GCATATTTAT ACTAAATGAA GATGGTGTAA CCATCGTATA      9017

TCTTCTGTTT GTAAATCTAT GTTGATAACT TATTCTAGGT AATTCATTTT CATTTAACTC      9077

TACATTATTA TTTTTTCCGA ATCGTGCCAA CCATTTTGTT AATTTATACT TACCATATAT      9137

GGATAGATAA TTATATCTTA GTACCTCTGT TACTAGTGTA AACGATTTTC GTCTGTTGGA      9197

TTTTTTATGT CTAGACCATT TTATTATAAA TAATAATACA TCATCTTCTG ATGATACATC      9257

TAATTCTCCA CTTTTTAGAA TTATTCTCAA ATCAAATAAG GATAACGATA GTAATATATC      9317

TGTTTCTATT TTTGTGAATC TTTTCCTTAT ATATGCTATA GCATCATTAT ATACCGCAAA      9377

ACATCCATTC GAGAAACCTA TTTTGTAAAT CTTAACACAT GTAGAATCCG TTATATGTTT      9437

TGACATAAAA TCAATACATG AATTTTTTAA AAAATCTATG GCTTTACTAC AAGATATGGA      9497

AAAAATATTT TCTACATTGT CTAAATCGAT AGTAACGATT CCAGTTTCTA TATATTTTAT      9557

TATATCAAGA AAGATTCAT ACTGGAATGA AACCGTTATT TCATTACTCT GATTCTTTGT      9617

AATAAGTTTA AAGTAATTAG ATACAGATAC AAGTAATTCT TTTTTTACTT TAACAACACC      9677

ACCAACGGTC ATAATAAATA CTATCTCTTC ATCATAACTT CTGTTTAGAT TCACAGCATT      9737

TAACCTTTCT ATATAGTTAT AATCAATGTA AGTTTCTTGT TTAGACATTT TTCACTATCT      9797

ATTTGCAAAC CAAAGCAAAT TACTATTATT AAATTATTTA TTCAACTTTA TAAAAATTAT      9857

TAATTAAAAA TCTATATCCG TAGAAAATAT ATTCTCTTCT TTATTTGTAA ACACCCCCAT      9917

CTTTTGATAT TCACTAACTC GTCGTTCGAA AAAATTAGTC TTACCTTCTA GTGATATATA      9977

CTCCATAAAG CTAAAAGGAT TATATACATT GAGACTTTTC ACAACCTAAC TCTGTTAATA     10037

ATCTATCTGC GACGAATTCT ATATACTGAG ACATTAAACA ACAATTCATA CCTATAAGAT     10097

CCACCGGAAT AGCAACTGTC AAAAACTCCT TTCTATATT AACCGCATCA ATG ATT        10153
                                                          Met Ile
                                                            1

ATC GAC GTT ATA ACT TCC TTA GAT GGT GGA TGT AAT AAA TGT TTA AAC      10201
Ile Asp Val Ile Thr Ser Leu Asp Gly Gly Cys Asn Lys Cys Leu Asn
            5                  10                  15

ATT AAA CAC GCA AAA TCA CAA TGT AAA CCT TCG TCT CTA CTT ATT AGT      10249
Ile Lys His Ala Lys Ser Gln Cys Lys Pro Ser Ser Leu Leu Ile Ser
        20                  25                  30

TCA TTA GAA AAT GTT AAT CCG GGC ATC AAT CCT CGT TTT TTT ATC CAA      10297
```

```
Ser Leu Glu Asn Val Asn Pro Gly Ile Asn Pro Arg Phe Phe Ile Gln
 35              40                  45                  50

AAT ATA GCA GCA AAT GAA CCA GAA AAG AAT ATT CCC TCC ACA GCT GCA       10345
Asn Ile Ala Ala Asn Glu Pro Glu Lys Asn Ile Pro Ser Thr Ala Ala
                 55                  60                  65

AAT GCT ACT ACT CTT TCT CCA TAT ACC TTG TTG CTA GAT ATC CAT TTT       10393
Asn Ala Thr Thr Leu Ser Pro Tyr Thr Leu Leu Leu Asp Ile His Phe
             70                  75                  80

CTG GCC CAA TCA GCT TTC TTT TTT ACG CAT TCC ATT GTT TCT ATA GCG       10441
Leu Ala Gln Ser Ala Phe Phe Phe Thr His Ser Ile Val Ser Ile Ala
         85                  90                  95

TTA AAT AAA TGC ATT TTT TCT ATA TTA TCT CTT ACA TAT GTA TCT ATT       10489
Leu Asn Lys Cys Ile Phe Ser Ile Leu Ser Leu Thr Tyr Val Ser Ile
    100                 105                 110

AAT AAA CTA TAC ATT TCT GAA TGAATATTTT CCATAGCTAT TTGAAATCCA          10540
Asn Lys Leu Tyr Ile Ser Glu
115             120

TAGAAACATC GTGCCTCTGA ACACTGTACA TCCACATAAA ATCTTTCCGC TAAATTCTCA     10600

TTTACAATAC CATCACTAGA TGCAAAAAAT GCTAGTATAT GTTTTATAAA GTATTTTTCG     10660

TCTTTAGTTA ATTTATCCCA ATCATCTAAA TCTTTTGATA AATCTACTTC TTCAACGGTC     10720

CAAAAACTTG CCACTGATTG TTTATACATT TTCCAGATAT CATGATACTT AATAGGGAAA     10780

ATAACGAACC TAGAATCAGA CTCTTGAAGA ATAGGCTCCA TTCGTGTATA AAAATCATTT     10840

TTCAATTTAT TCGGTATTAA CACCAACGCT GCTATCGTTC GTATAATACA TATTATCTAA     10900

TTGTAAAAAT TCTCTTCTCG ATGTCCATTG TAAACATCTA GTTCTTATTT GTCTAAATAT     10960

ATCTACTATA AACGACCATC TTACTAATTG TAGTAGTAAA TAACACGTTA TCACGATAGT     11020

AACTAAACAT AATGTAATTA CCATTATTGT TCCAACTTCA TTAGACATAT CATTATCTAT     11080

AATTATTTGT GAAGTTGTTG TATTCATTGT CTGAATGTTT AATTATTATT TTTTTTGTTT     11140

TTTTTACTAA ATAAAAACAT CATCATCGCT ACTACTACAA CGTTTCCTTA TAACTTTTAC     11200

TTTATAAGGT ATTTTGATGT TATTTTTATG TATCAACTTT TCATTCTCCT GGTAATAGTC     11260

GGTATTAGAT TTTATCCTAT AAGTTGATTT CTTTCTTAAA AATGTAGTAA ATTTCTTTCG     11320

TAAATATGAC ATAAAACCAT TATTTATTGA ATACTTACGA TTATTCATTA TTATTTATTT     11380

AGAAATATAC TGATTTAATA CTATATGTGG AATATCTCGA TTCTAGACTA TATGTAGAAT     11440

ATCTCGATTC TAGTGTACTA CTACAACTAT TTTTTCTTCT TACATATATT GGCTTATTTT     11500

TTATATTATA ATAATATTCA TCGTCTATAG AAGATATTGA CACTGTATCC ATACTTATAC     11560

TTATTGATTT TACAGATACA CAACTGCCCA TAGTTCGTAT ATATTGGCTT TGTATGTTGC     11620

AATATTTTTT CAATATAAAA AAAATAACAA AAAGACGAGT ATAATAAAAT ACATAAAGTA     11680

AAAACAAACA TATTATTATT TACTTCATTT TTAAGGTGCA TGCATTTTCC TTTTGAAATG     11740

AAATGAAATG AAATGAAATG TAGTGCTCTA AAACAAACTT AACCTTACTT ATAAATATCC     11800

TCCATATTTA CCCATTATAA TAGAATTGTG TGGACCTAGT AGTTATAATC ATAGGATAAT     11860

CATTATGTAA ATACGATTCT CTTTTTATAT GTTGATTAGG TTTAATATTT AGACAATATC     11920

CATATTTATT TATTTCATCA TTAGTGGGTG GTGTAGACTG TGTATGTTGT ACAGACTTGC     11980

CGGTAAAAC AATTTTATTT ACTTTTTTCG GTTTCCGCTC ATGGTTATTT AGTAGGCGAT      12040

TATTTATGTT ATTAGCTATG ATTTATGTTT CATTTTTAAC CCGGTTTAGA CATATAAAAA     12100

TGTACCTATAT TTGTATTTAA TTCCTATTCG TCTTTTTATA GAACATATTC CTATAACAAA   12160

TATGATAGCA ATAATAATGA TGCTAAATAT AAACCATGGT CTATTTGTTA AATTCAAATA    12220
```

-continued

```
ATTATATATA TTAGCATTGT CAATATATCT TCTATTCATA GAATTCATGA TAGAATTCAT   12280

CACACAGTTT GCTTCTGCAG TACCAGAATT AACAATCTGT AATAGAATCT GTTTATCGTA   12340

CGGAGCTATG CATTTTCCAA CATCTAATGT TTGAATATCA ATAATATTTG TTACATCTGC   12400

GGATGATGAA CAGTTTCGTA TTATTTCTGG TACATATTTA GGGTCATTGT TTAATATATC   12460

AATTCCAATT TCTTTAGATA ATTCCTCTTT CTCTTTCTGA GATAACGTAC TAGTTACATC   12520

TTTAAGCGTC TTTATAAGAA TATTGAAACT TAGTTCTTTA TCGTTATAC ACATATTGAG    12580

TATTTTCAAA AAACATCTTT TGAACGTTCC TTTGATTTCT CCTATATGTA TACCACATGT   12640

TGAATTAATA GGTATAGAAT ATATTGATAA GTTCTCTATA TATCTTTCTA CGAATACGTT   12700

ATATAATGTA TTTATTCTAA CAGGATTCTC CATTTATCCA ATTTGAGAAA ATGTTTTTG    12760

TAATCAAATT TTCTAAAAAT GATATAGGAT GCAGTATGGA TACTTTTAAT CTAAATTTCT   12820

CACATGTATT TTTTGTACAA CACATTATAA AATCCTCTAA AGAATCGCTG AATTCTTTAT   12880

CAGATTCTAT TTCTGGATAA GTTCGTAGAA GTGTATGTAT AAAAAAATGA AAATCATAAT   12940

ACCAATTGTG TTCTATTTTT AAACTATTTT TAATTTTCTT ATTTAATATA TTAGCCACCT   13000

GTGAAAAATC GAAATCGTTA AGACACGCTT TAATCGGTTC ATTAAATACG TATGTATATT   13060

TCTTAAATTT AATAGTTATA GGACAATCAG AATTAAAATAT TAAAATATTA TCGGGTTTTA   13120

AATCAACGTG TAAAAAATTA TCACAACAAG GAAGTTCGTA TATTTTTATA TATAACAATG   13180

ATATTTGTAA AAAAATAAAC TTAACATATT GAACTATAGA TTTAAAACCA AGTTCTATCG   13240

CCATCTGTTC CGTCACTTTA TCTGATGAAA ATCTTGCTAA TGGGAATATA ATTATATTTC   13300

CTCTATCGTA TAAATAATTA GCTCTTTTTT CATGTTCGAA AAAATGAAAC ATATGTGTAA   13360

AATAATTTAT TACATTTATA TTACTTTGAA CAACAATAGG ATAAAAATAT GATAATAATT   13420

TTACAAATTT TATATCGCTC TTTTTTTCAT TGAACGACTT AAGAAAATAC TTATGAGAAA   13480

AATGATGAAT ATTTAATCGT TGATTATCTA TCGTTTGAAT AATAAGTAAT AACATATATA   13540

ATACTCTTTT ATATAATCTA TGTAGAAATG TTAATTTATA ATTTAAACCC ATTGCCCATG   13600

CACAAACGAT AAGTTTTTTC TCATCTCCCT TAAGATTATT ATATAAAAAT TTAGGTATTG   13660

TATACTCGGC AGTTGTATCA ATGGGACTAT ACTGTTTATT TGGTTCATAA ACAAATTTAA   13720

CAACGTATTT ATCCATTTTA AATACGATAC CATAACCTCC TGTTGATATA TGATAGAAAT   13780

CATCATTAAG TGGATAAAAT CGTTTATCTC TTTGTTGGAA AAAAGATGGG TTAATATATT   13840

CCGTATCTGA TATTTTATCA AATGATTCTT TGTTAAACTT CCTAAAATAT CTTATTAGTC   13900

TGATATCAGG AGACCAATTT TGATGTATAT CTAACTGAGA AATTATATAA TCAAAATATA   13960

TATCATCACC GAGAATAGTT GTATCATTAT TATCATCGAT AGACTCCCAC TGACATTCTA   14020

ACGAATTAAT TTCTTTCATT TATTGTATAA AAAGCTACTT TATTGTATAC GAAATCCAAT   14080

ATTTGATAAT GCGAATAAAT TATTAACTAT TTCTTCTTTT AAAGAATAAG ATTCTCCCAT   14140

TGATAGTTTG TATATTACAT ATGAATCAAT AAGCTT                             14176
```

(2) INFORMATION FOR SEQ ID NO:2:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Ser Cys Tyr Asp Arg Phe Arg Ile Ile Phe Gln Lys Lys Asn

```
            1               5                  10                 15
Asn Tyr Tyr Cys Lys Tyr Asn Asp Cys Met Arg Tyr Phe Leu Asn Ile
                20                  25                  30

Ser Leu Tyr Leu Ile Leu Ile Cys Glu Lys Asn Ile Thr Ser Lys Ser
                35                  40                  45

Thr Ser Ile Ile Phe Asp Asp Asn Ile Ala Asn Ile Pro Ile Glu Asp
                50                  55                  60

Leu Gln Cys Leu Ile Ile Ser Ser Leu His Phe Lys Arg Met Leu Met
 65                     70                  75                  80

Asp Ile Val Ser Pro Ser Leu Tyr Val Phe Ile Ile Ser Leu Tyr Ile
                85                  90                  95

Tyr Phe Val Ala Asn Ile Ser Tyr Phe Met Ser Ser Leu Asn Asn Leu
               100                 105                 110

Pro His Ala His Val Leu Leu Tyr Phe Phe Leu Gln
               115                 120
```

(2) INFORMATION FOR SEQ ID NO:3:

(i) SEQUENCE CHARACTERISTICS:
        (A) LENGTH: 100 amino acids
        (B) TYPE: amino acid
        (D) TOPOLOGY: linear (ii) MOLECULE TYPE: protein (xi) SEQUENCE DESCRIPTION: SEQ ID NO:3:

```
Met Asn Phe Leu Leu Gln Tyr Thr Asn Ser Phe Leu Tyr Leu Tyr Lys
 1               5                  10                  15

Arg Ile Tyr Cys Ser Val Phe Thr Ile Ser Ser Cys Asn Ile Ser Leu
                20                  25                  30

Asn Glu Asp Asn Ile Leu Leu Tyr Lys Cys Ile Asn Phe Asp Asp Ile
                35                  40                  45

Leu Asp Ser Tyr Leu Ser Leu Thr Thr Leu Tyr Asn Leu Leu Leu Thr
 50                     55                  60

Leu Ser Ile Ser Ser Lys Ser Leu Ile Lys Tyr Val Ser Ile Phe Leu
 65                     70                  75                  80

Gly Ile Asn Pro Ser Thr His Thr Leu Val Leu Leu Ser Val Phe Phe
                85                  90                  95

Gly Pro Asn Ser
               100
```

(2) INFORMATION FOR SEQ ID NO:4:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:4:

```
Met Leu Thr Ile Gly Glu Val Ile Cys Thr Ile Ser His Thr Leu Pro
 1               5                  10                  15

Ile Leu Cys Ser Leu Asp Val Leu Phe Ser Tyr Leu Asn Leu Thr His
                20                  25                  30

Val Ser Ser Ser Leu Ser Ile Ser Glu Phe Val Lys Leu Gln Tyr Pro
                35                  40                  45

Lys Glu Leu Val Gln Thr Val Leu His Ser Ser
 50                     55
```

(2) INFORMATION FOR SEQ ID NO:5:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO:5:

```
Met Glu Asn Thr His Cys Glu Asn Gly Phe Leu Thr Leu Met Met Leu
 1               5                  10                  15

Tyr Ser Leu Leu His Asn Leu Gln Asp Arg Ser Leu Glu Tyr Cys Ile
                20                  25                  30

His Phe Phe Ile His Ser Ser Cys Thr Thr Leu Tyr Ser Phe Leu Gln
                35                  40                  45

Leu Gln
    50
```

(2) INFORMATION FOR SEQ ID NO:6:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Ala Ile Ile Ile Leu Asn Pro Arg Arg Leu His Arg Val Ser
 1               5                  10                  15

Val Tyr Leu Ser Asn Ser Ser Lys Asn Asn Ile Ile Tyr Ile Pro Ser
                20                  25                  30

Ser Asp Ile Ile Phe Ile Ile Ser Ile Ile Tyr Leu Ala Ile Arg
                35                  40                  45

Ile Phe Leu His Ile Ser Leu Ser Ile Ile Ile Asp Asn Asn Glu Ile
    50                  55                  60

Ala Ala Asn Leu Ile Leu Gly Arg Glu Ser Asp Asn Asn Ile Leu Ile
65                  70                  75                  80

Thr Ser Leu Cys Thr Leu Ser Ile Tyr Leu Phe Ser Ser Tyr Ser Lys
                85                  90                  95

Ile His Val Thr Glu Leu Lys Ser Leu Gln Tyr Leu Tyr Phe Ile Ala
                100                 105                 110

Ser His
```

(2) INFORMATION FOR SEQ ID NO:7:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ile Ile Asp Val Ile Thr Ser Leu Asp Gly Gly Cys Asn Lys Cys
 1               5                  10                  15

Leu Asn Ile Lys His Ala Lys Ser Gln Cys Lys Pro Ser Ser Leu Leu
                20                  25                  30

Ile Ser Ser Leu Glu Asn Val Asn Pro Gly Ile Asn Pro Arg Phe Phe
```

```
              35                  40                  45
Ile Gln Asn Ile Ala Ala Asn Glu Pro Glu Lys Asn Ile Pro Ser Thr
             50                  55                  60

Ala Ala Asn Ala Thr Thr Leu Ser Pro Tyr Thr Leu Leu Leu Asp Ile
 65                  70                  75                  80

His Phe Leu Ala Gln Ser Ala Phe Phe Phe Thr His Ser Ile Val Ser
                 85                  90                  95

Ile Ala Leu Asn Lys Cys Ile Phe Ser Ile Leu Ser Leu Thr Tyr Val
                100                 105                 110

Ser Ile Asn Lys Leu Tyr Ile Ser Glu
            115                 120
```

(2) INFORMATION FOR SEQ ID NO:8:

(i) SEQUENCE CHARACTERISTICS:
        (A) LENGTH: 375 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:8:

```
ATGAATTCAT GTTATGATAG ATTTAGGATT ATTTTTCAAA AAAAAAACAA TTATTATTGT      60

AAGTATAATG ATTGTATGAG ATATTTTTTG AATATTAGTC TATATCTTAT ACTTATTTGT     120

GAAAAGAATA TAACATCAAA ATCTACGTCG ATTATTTTCG ATGATAATAT AGCAAACATA     180

CCTATAGAAG ACTTACAATG TTTAATTATA TCATCTTTAC ATTTTAAACG TATGTTAATG     240

GATATAGTAT CTCCCTCTTT GTATGTATTT ATAATATCAT TATATATATA TTTTGTAGCT     300

AATATATCAT ATTTCATGAG TTCCTTAAAT AACTTACCAC ATGCGCATGT GTTGTTATAT     360

TTTTTTCTCC AATGA                                                     375
```

(2) INFORMATION FOR SEQ ID NO:9:

(i) SEQUENCE CHARACTERISTICS:
        (A) LENGTH: 303 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:9:

```
ATGAATTTTT TATTACAATA TACGAATTCA TTCCTTTATC TTTATAAACG TATTTACTGT      60

TCAGTATTTA CCATAAGTTC TTGCAATATT AGTTTAAACG AAGATAATAT ATTATTATAT     120

AAGTGCATAA ACTTTGACGA TATATTGGAT TCATATTTAT CACTTACAAC TCTATATAAT     180

CTGTTATTAA CTCTATCTAT ATCATCGAAA TCTTTAATAA AATATGTATC GATTTTTCTT     240

GGAATTAATC CATCTACACA CACTCTAGTA CTATTATCTG TTTTTTTTGG ACCAAATTCA     300

TAA                                                                   303
```

(2) INFORMATION FOR SEQ ID NO:10:

(i) SEQUENCE CHARACTERISTICS:
        (A) LENGTH: 180 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:10:

```
ATGTTAACAA TAGGTGAAGT TATTTGTACA ATCTCACATA CTCTGCCAAT ATTATGTTCA      60

TTAGATGTCT TATTTTCATA TTTAAACCTC ACCCATGTTT CATCATCATT GTCGATATCA     120

GAATTTGTTA AATTACAGTA TCCTAAAGAA TTAGTACAAA CGGTTCTCCA TTCGTCATGA     180
```

(2) INFORMATION FOR SEQ ID NO:11:

(i) SEQUENCE CHARACTERISTICS:
        (A) LENGTH: 153 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:11:

```
ATGGAGAATA CCCACTGTGA GAATGGTTTT CTAACACTAA TGATGTTATA TTCTTTATTA      60

CATAATTTAC AAGATCGTTC CCTTGAGTAT TGTATCCACT TTTTCATACA TTCATCGTGT     120

ACAACTTTAT ACTCGTTTTT ACAGTTACAA TAA                                  153
```

(2) INFORMATION FOR SEQ ID NO:12:

(i) SEQUENCE CHARACTERISTICS:
        (A) LENGTH: 345 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:12:

```
ATGCTCGCTA TCATCATACT TAATCCACGG CGCCTACATC GGGTATCGGT ATATTTATCA      60

AATTCATCTA AAAATAATAT AATATATATA CCGTCTTCTG ATATAATATT TATTATATCA     120

TCAATTATAT ATTTAGCTAT ACGAATATTT CTACATATTA GTTTATCTAT TATTATAGAT     180

AATAACGAAA TAGCAGCTAA TTTGATACTA GGTCGCGAAT CTGATAACAA TATACTAATA     240

ACTTCTTTAT GCACGTTATC TATATACTTA TTTTCATCGT ATTCTAAAAT ACATGTAACA     300

GAATTAAAAT CATTACAATA TCTGTATTTT ATCGCTTCAC ATTGA                     345
```

(2) INFORMATION FOR SEQ ID NO:13:

(i) SEQUENCE CHARACTERISTICS:
        (A) LENGTH: 366 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:13:

```
ATGATTATCG ACGTTATAAC TTCCTTAGAT GGTGGATGTA ATAAATGTTT AAACATTAAA      60

CACGCAAAAT CACAATGTAA ACCTTCGTCT CTACTTATTA GTTCATTAGA AAATGTTAAT     120

CCGGGCATCA ATCCTCGTTT TTTTATCCAA AATATAGCAG CAAATGAACC AGAAAAGAAT     180

ATTCCCTCCA CAGCTGCAAA TGCTACTACT CTTTCTCCAT ATACCTTGTT GCTAGATATC     240

CATTTTCTGG CCCAATCAGC TTTCTTTTTT ACGCATTCCA TTGTTTCTAT AGCGTTAAAT     300

AAATGCATTT TTTCTATATT ATCTCTTACA TATGTATCTA TTAATAAACT ATACATTTCT     360

GAATGA                                                                366
```

(2) INFORMATION FOR SEQ ID NO:14:

(i) SEQUENCE CHARACTERISTICS:
        (A) LENGTH: 14176 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 138..1460

(ix) FEATURE:
        (A) NAME/KEY: CDS
        (B) LOCATION: 2456..2659

(ix) FEATURE:
        (A) NAME/KEY: CDS
        (B) LOCATION: 2809..3030

(ix) FEATURE:
        (A) NAME/KEY: CDS
        (B) LOCATION: 3070..3330

(ix) FEATURE:
        (A) NAME/KEY: CDS
        (B) LOCATION: 3356..4180

(ix) FEATURE:
        (A) NAME/KEY: CDS
        (B) LOCATION: 4392..5894

(ix) FEATURE:
        (A) NAME/KEY: CDS
        (B) LOCATION: 6171..6398

(ix) FEATURE:
        (A) NAME/KEY: CDS
        (B) LOCATION: 6447..6875

(ix) FEATURE:
        (A) NAME/KEY: CDS
        (B) LOCATION: 6928..7431

(ix) FEATURE:
        (A) NAME/KEY: CDS
        (B) LOCATION: 7454..7858

(ix) FEATURE:
        (A) NAME/KEY: CDS
        (B) LOCATION: 7895..8155

(ix) FEATURE:
        (A) NAME/KEY: CDS
        (B) LOCATION: 8215..8682

(ix) FEATURE:
        (A) NAME/KEY: CDS
        (B) LOCATION: 8715..9539

(ix) FEATURE:
        (A) NAME/KEY: CDS
        (B) LOCATION: 9562..10272

(ix) FEATURE:
        (A) NAME/KEY: CDS
        (B) LOCATION: 10316..11908

(ix) FEATURE:
        (A) NAME/KEY: CDS
        (B) LOCATION: 11971..12780

(ix) FEATURE:
        (A) NAME/KEY: CDS
        (B) LOCATION: 12829..13107

(ix) FEATURE:
    (A) NAME/KEY: CDS
    (B) LOCATION: 13149..14171

(xi) SEQUENCE DESCRIPTION: SEQ ID NO:14:

```
AAGCTTATTG ATTCATATGT AAATATACAAA CTATCAATGG GAGAATCTTA TTCTTTAAAA        60

GAAGAAATAG TTAATAATTT ATTCGCATTA TCAAATATTG GATTTCGTAT ACAATAAAGT       120

AGCTTTTTAT ACAATAA ATG AAA GAA ATT AAT TCG TTA GAA TGT CAG TGG         170
                Met Lys Glu Ile Asn Ser Leu Glu Cys Gln Trp
                  1               5                  10

GAG TCT ATC GAT GAT AAT AAT GAT ACA ACT ATT CTC GGT GAT GAT ATA         218
Glu Ser Ile Asp Asp Asn Asn Asp Thr Thr Ile Leu Gly Asp Asp Ile
             15                  20                  25

TAT TTT GAT TAT ATA ATT TCT CAG TTA GAT ATA CAT CAA AAT TGG TCT         266
Tyr Phe Asp Tyr Ile Ile Ser Gln Leu Asp Ile His Gln Asn Trp Ser
         30                  35                  40

CCT GAT ATC AGA CTA ATA AGA TAT TTT AGG AAG TTT AAC AAA GAA TCA         314
Pro Asp Ile Arg Leu Ile Arg Tyr Phe Arg Lys Phe Asn Lys Glu Ser
     45                  50                  55

TTT GAT AAA ATA TCA GAT ACG GAA TAT ATT AAC CCA TCT TTT TTC CAA         362
Phe Asp Lys Ile Ser Asp Thr Glu Tyr Ile Asn Pro Ser Phe Phe Gln
 60                  65                  70                  75

CAA AGA GAT AAA CGA TTT TAT CCA CTT AAT GAT GAT TTC TAT CAT ATA         410
Gln Arg Asp Lys Arg Phe Tyr Pro Leu Asn Asp Asp Phe Tyr His Ile
                 80                  85                  90

TCA ACA GGA GGT TAT GGT ATC GTA TTT AAA ATG GAT AAA TAC GTT GTT         458
Ser Thr Gly Gly Tyr Gly Ile Val Phe Lys Met Asp Lys Tyr Val Val
             95                 100                 105

AAA TTT GTT TAT GAA CCA AAT AAA CAG TAT AGT CCC ATT GAT ACA ACT         506
Lys Phe Val Tyr Glu Pro Asn Lys Gln Tyr Ser Pro Ile Asp Thr Thr
        110                 115                 120

GCC GAG TAT ACA ATA CCT AAA TTT TTA TAT AAT AAT CTT AAG GGA GAT         554
Ala Glu Tyr Thr Ile Pro Lys Phe Leu Tyr Asn Asn Leu Lys Gly Asp
    125                 130                 135

GAG AAA AAA CTT ATC GTT TGT GCA TGG GCA ATG GGT TTA AAT TAT AAA         602
Glu Lys Lys Leu Ile Val Cys Ala Trp Ala Met Gly Leu Asn Tyr Lys
140                 145                 150                 155

TTA ACA TTT CTA CAT AGA TTA TAT AAA AGA GTA TTA TAT ATG TTA TTA         650
Leu Thr Phe Leu His Arg Leu Tyr Lys Arg Val Leu Tyr Met Leu Leu
                160                 165                 170

CTT ATT ATT CAA ACG ATA GAT AAT CAA CGA TTA AAT ATT CAT CAT TTT         698
Leu Ile Ile Gln Thr Ile Asp Asn Gln Arg Leu Asn Ile His His Phe
            175                 180                 185

TCT CAT AAG TAT TTT CTT AAG TCG TTC AAT GAA AAA AAG AGC GAT ATA         746
Ser His Lys Tyr Phe Leu Lys Ser Phe Asn Glu Lys Lys Ser Asp Ile
        190                 195                 200

AAA TTT GTA AAA TTA TTA TCA TAT TTT TAT CCT ATT GTT GTT CAA AGT         794
Lys Phe Val Lys Leu Leu Ser Tyr Phe Tyr Pro Ile Val Val Gln Ser
    205                 210                 215

AAT ATA AAT GTA ATA AAT TAT TTT ACA CAT ATG TTT CAT TTT TTC GAA         842
Asn Ile Asn Val Ile Asn Tyr Phe Thr His Met Phe His Phe Phe Glu
220                 225                 230                 235

CAT GAA AAA AGA GCT AAT TAT TTA TAC GAT AGA GGA AAT ATA ATT ATA         890
His Glu Lys Arg Ala Asn Tyr Leu Tyr Asp Arg Gly Asn Ile Ile Ile
                240                 245                 250

TTC CCA TTA GCA AGA TTT TCA TCA GAT AAA GTG ACG GAA CAG ATG GCG         938
Phe Pro Leu Ala Arg Phe Ser Ser Asp Lys Val Thr Glu Gln Met Ala
            255                 260                 265
```

```
ATA GAA CTT GGT TTT AAA TCT ATA GTT CAA TAT GTT AAG TTT ATT TTT        986
Ile Glu Leu Gly Phe Lys Ser Ile Val Gln Tyr Val Lys Phe Ile Phe
            270                 275                 280

TTA CAA ATA TCA TTG TTA TAT ATA AAA ATA TAC GAA CTT CCT TGT TGT       1034
Leu Gln Ile Ser Leu Leu Tyr Ile Lys Ile Tyr Glu Leu Pro Cys Cys
        285                 290                 295

GAT AAT TTT TTA CAC GTT GAT TTA AAA CCC GAT AAT ATT TTA ATA TTT       1082
Asp Asn Phe Leu His Val Asp Leu Lys Pro Asp Asn Ile Leu Ile Phe
300                 305                 310                 315

AAT TCT GAT TGT CCT ATA ACT ATT AAA TTT AAG AAA TAT ACA TAC GTA       1130
Asn Ser Asp Cys Pro Ile Thr Ile Lys Phe Lys Lys Tyr Thr Tyr Val
                320                 325                 330

TTT AAT GAA CCG ATT AAA GCG TGT CTT AAC GAT TTC GAT TTT TCA CAG       1178
Phe Asn Glu Pro Ile Lys Ala Cys Leu Asn Asp Phe Asp Phe Ser Gln
            335                 340                 345

GTG GCT AAT ATA TTA AAT AAG AAA ATT AAA AAT AGT TTA AAA ATA GAA       1226
Val Ala Asn Ile Leu Asn Lys Lys Ile Lys Asn Ser Leu Lys Ile Glu
        350                 355                 360

CAC AAT TGG TAT TAT GAT TTT CAT TTT TTT ATA CAT ACA CTT CTA CGA       1274
His Asn Trp Tyr Tyr Asp Phe His Phe Phe Ile His Thr Leu Leu Arg
    365                 370                 375

ACT TAT CCA GAA ATA GAA TCT GAT AAA GAA TTC AGC GAT TCT TTA GAG       1322
Thr Tyr Pro Glu Ile Glu Ser Asp Lys Glu Phe Ser Asp Ser Leu Glu
380                 385                 390                 395

GAT TTT ATA ATG TGT TGT ACA AAA AAT ACA TGT GAG AAA TTT AGA TTA       1370
Asp Phe Ile Met Cys Cys Thr Lys Asn Thr Cys Glu Lys Phe Arg Leu
                400                 405                 410

AAA GTA TCC ATA CTG CAT CCT ATA TCA TTT TTA GAA AAT TTG ATT ACA       1418
Lys Val Ser Ile Leu His Pro Ile Ser Phe Leu Glu Asn Leu Ile Thr
            415                 420                 425

AAA AAC ATT TTC TCA AAT TGG ATA AAT GGA GAA TCC TGT TAGAATAAAT        1467
Lys Asn Ile Phe Ser Asn Trp Ile Asn Gly Glu Ser Cys
        430                 435                 440

ACATTATATA ACGTATTCGT AGAAAGATAT ATAGAGAACT TATCAATATA TTCTATACCT     1527

ATTAATTCAA CATGTGGTAT ACATATAGGA GAAATCAAAG GAACGTTCAA AGATGTTTT      1587

TTGAAAATAC TCAATATGTG TATAAACGAT AAAGAACTAA GTTTCAATAT TCTTATAAAG    1647

ACGCTTAAAG ATGTAACTAG TACGTTATCT CAGAAAGAGA AAGAGGAATT ATCTAAAGAA     1707

ATTGGAATTG ATATATTAAA CAATGACCCT AAATATGTAC CAGAAATAAT ACGAAACTGT    1767

TCATCATCCG CAGATGTAAC AAATATTATT GATATTCAAA CATTAGATGT TGGAAAATGC    1827

ATAGCTCCGT ACGATAAACA GATTCTATTA CAGATTGTTA ATTCTGGTAC TGCAGAAGCA    1887

AACTGTGTGA TGAATTCTAT CATGAATTCT ATGAATAGAA GATATATTGA CAATGCTAAT    1947

ATATATAATT ATTTGAATTT AACAAATAGA CCATGGTTTA TATTTAGCAT CATTATTATT    2007

GCTATCATAT TTGTTATAGG AATATGTTCT ATAAAAAGAC GAATAGGAAT TAAATACAAA    2067

TATGGTACAT TTTTATATGT CTAAACCGGG TTAAAAATGA ACATAAATC ATAGCTAATA     2127

ACATAAATAA TCGCCTACTA ATAACCATG AGCGGAAACC GAAAAAAGTA AATAAAATTG     2187

TTTTAACCGG CAAGTCTGTA CAACATACAC AGTCTACACC ACCCACTAAT GATGAAATAA    2247

ATAAATATGG ATATTGTCTA AATATTAAAC CTAATCAACA TATAAAAAGA GAATCGTATT    2307

TACATAATGA TTATCCTATG ATTATAACTA CTAGGTCCAC ACAATTCTAT TATAATGGGT    2367

AAATATGGAG GATATTTATA AGTAAGGTTA AGTTTGTTTT AGAGCACTAC ATTTCATTTC    2427

ATTTCATTTC ATTTCAAAAG GAAAATGC ATG CAC CTT AAA AAT GAA GTA AAT       2479
                                Met His Leu Lys Asn Glu Val Asn
                                 1                   5
```

-continued

```
AAT AAT ATG TTT GTT TTT ACT TTA TGT ATT TTA TTA TAC TCG TCT TTT          2527
Asn Asn Met Phe Val Phe Thr Leu Cys Ile Leu Leu Tyr Ser Ser Phe
         10                  15                  20

TGT TAT TTT TTT TAT ATT GAA AAA ATA TTG CAA CAT ACA AAG CCA ATA          2575
Cys Tyr Phe Phe Tyr Ile Glu Lys Ile Leu Gln His Thr Lys Pro Ile
 25                  30                  35                  40

TAT ACG AAC TAT GGG CAG TTG TGT ATC TGT AAA ATC AAT AAG TAT AAG          2623
Tyr Thr Asn Tyr Gly Gln Leu Cys Ile Cys Lys Ile Asn Lys Tyr Lys
                 45                  50                  55

TAT GGA TAC AGT GTC AAT ATC TTC TAT AGA CGA TGAATATTAT TATAATATAA        2676
Tyr Gly Tyr Ser Val Asn Ile Phe Tyr Arg Arg
 60                  65

AAAATAAGCC AATATATGTA AGAAGAAAAA ATAGTTGTAG TAGTACACTA GAATCGAGAT        2736

ATTCTACATA TAGTCTAGAA TCGAGATATT CCACATATAG TATTAAATCA GTATATTTCT        2796

AAATAAATAA TA ATG AAT AAT CGT AAG TAT TCA ATA AAT AAT GGT TTT           2844
              Met Asn Asn Arg Lys Tyr Ser Ile Asn Asn Gly Phe
               1               5                  10

ATG TCA TAT TTA CGA AAG AAA TTT ACT ACA TTT TTA AGA AAG AAA TCA          2892
Met Ser Tyr Leu Arg Lys Lys Phe Thr Thr Phe Leu Arg Lys Lys Ser
             15                  20                  25

ACT TAT AGG ATA AAA TCT AAT ACC GAC TAT TAC CAG GAG AAT GAA AAG          2940
Thr Tyr Arg Ile Lys Ser Asn Thr Asp Tyr Tyr Gln Glu Asn Glu Lys
 30                  35                  40

TTG ATA CAT AAA AAT AAC ATC AAA ATA CCT TAT AAA GTA AAA GTT ATA          2988
Leu Ile His Lys Asn Asn Ile Lys Ile Pro Tyr Lys Val Lys Val Ile
 45                  50                  55                  60

AGG AAA CGT TGT AGT AGT AGC GAT GAT GAT GTT TTT ATT TAGTAAAAAA          3037
Arg Lys Arg Cys Ser Ser Ser Asp Asp Asp Val Phe Ile
                 65                  70

AACAAAAAAA ATAATAATTA AACATTCAGA CA ATG AAT ACA ACA ACT TCA CAA         3090
                                  Met Asn Thr Thr Thr Ser Gln
                                   1               5

ATA ATT ATA GAT AAT GAT ATG TCT AAT GAA GTT GGA ACA ATA ATG GTA          3138
Ile Ile Ile Asp Asn Asp Met Ser Asn Glu Val Gly Thr Ile Met Val
         10                  15                  20

ATT ACA TTA TGT TTA GTT ACT ATC GTG ATA ACG TGT TAT TTA CTA CTA          3186
Ile Thr Leu Cys Leu Val Thr Ile Val Ile Thr Cys Tyr Leu Leu Leu
 25                  30                  35

CAA TTA GTA AGA TGG TCG TTT ATA GTA GAT ATA TTT AGA CAA ATA AGA          3234
Gln Leu Val Arg Trp Ser Phe Ile Val Asp Ile Phe Arg Gln Ile Arg
 40                  45                  50                  55

ACT AGA TGT TTA CAA TGG ACA TCG AGA AGA GAA TTT TTA CAA TTA GAT AAT     3285
Thr Arg Cys Leu Gln Trp Thr Ser Arg Arg Glu Phe Leu Gln Leu Asp Asn
                 60                  65                  70

ATG TAT TAT ACG AAC GAT AGC AGC GTT GGT GTT AAT ACC GAA TAAATTGAAA      3337
Met Tyr Tyr Thr Asn Asp Ser Ser Val Gly Val Asn Thr Glu
 75                  80                  85

AATGATTTTT ATACACGA ATG GAG CCT ATT CTT CAA GAG TCT GAT TCT AGG         3388
                   Met Glu Pro Ile Leu Gln Glu Ser Asp Ser Arg
                    1               5                  10

TTC GTT ATT TTC CCT ATT AAG TAT CAT GAT ATC TGG AAA ATG TAT AAA          3436
Phe Val Ile Phe Pro Ile Lys Tyr His Asp Ile Trp Lys Met Tyr Lys
             15                  20                  25

CAA TCA GTG GCA AGT TTT TGG ACC GTT GAA GAA GTA GAT TTA TCA AAA          3484
Gln Ser Val Ala Ser Phe Trp Thr Val Glu Glu Val Asp Leu Ser Lys
 30                  35                  40

GAT TTA GAT GAT TGG GAT AAA TTA ACT AAA GAC GAA AAA TAC TTT ATA          3532
Asp Leu Asp Asp Trp Asp Lys Leu Thr Lys Asp Glu Lys Tyr Phe Ile
```

```
                    45                  50                  55
AAA CAT ATA CTA GCA TTT TTT GCA TCT AGT GAT GGT ATT GTA AAT GAG    3580
Lys His Ile Leu Ala Phe Phe Ala Ser Ser Asp Gly Ile Val Asn Glu
 60                  65                  70                  75

AAT TTA GCG GAA AGA TTT TAT GTG GAT GTA CAG TGT TCA GAG GCA CGA    3628
Asn Leu Ala Glu Arg Phe Tyr Val Asp Val Gln Cys Ser Glu Ala Arg
                 80                  85                  90

TGT TTC TAT GGA TTT CAA ATA GCT ATG GAA AAT ATT CAT TCA GAA ATG    3676
Cys Phe Tyr Gly Phe Gln Ile Ala Met Glu Asn Ile His Ser Glu Met
             95                 100                 105

TAT AGT TTA TTA ATA GAT ACA TAT GTA AGA GAT AAT ATA GAA AAA ATG    3724
Tyr Ser Leu Leu Ile Asp Thr Tyr Val Arg Asp Asn Ile Glu Lys Met
        110                 115                 120

CAT TTA TTT AAC GCT ATA GAA ACA ATG GAA TGC GTA AAA AAG AAA GCT    3772
His Leu Phe Asn Ala Ile Glu Thr Met Glu Cys Val Lys Lys Lys Ala
    125                 130                 135

GAT TGG GCC AGA AAA TGG ATA TCT AGC AAC AAG GTA TAT GGA GAA AGA    3820
Asp Trp Ala Arg Lys Trp Ile Ser Ser Asn Lys Val Tyr Gly Glu Arg
140                 145                 150                 155

GTA GTA GCA TTT GCA GCT GTG GAG GGA ATA TTC TTT TCT GGT TCA TTT    3868
Val Val Ala Phe Ala Ala Val Glu Gly Ile Phe Phe Ser Gly Ser Phe
                160                 165                 170

GCT GCT ATA TTT TGG ATA AAA AAA CGA GGA TTG ATG CCC GGA TTA ACA    3916
Ala Ala Ile Phe Trp Ile Lys Lys Arg Gly Leu Met Pro Gly Leu Thr
            175                 180                 185

TTT TCT AAT GAA CTA ATA AGT AGA GAC GAA GGT TTA CAT TGT GAT TTT    3964
Phe Ser Asn Glu Leu Ile Ser Arg Asp Glu Gly Leu His Cys Asp Phe
        190                 195                 200

GCG TGT TTA ATG TTT AAA CAT TTA TTA CAT CCA CCA TCT AAG GAA GTT    4012
Ala Cys Leu Met Phe Lys His Leu Leu His Pro Pro Ser Lys Glu Val
    205                 210                 215

ATA ACG TCG ATA ATC ATT GAT GCG GTT AAT ATA GAA AAG GAG TTT TTG    4060
Ile Thr Ser Ile Ile Ile Asp Ala Val Asn Ile Glu Lys Glu Phe Leu
220                 225                 230                 235

ACA GTT GCT ATT CCG GTG GAT CTT ATA GGT ATG AAT TGT TGT TTA ATG    4108
Thr Val Ala Ile Pro Val Asp Leu Ile Gly Met Asn Cys Cys Leu Met
                240                 245                 250

TCT CAG TAT ATA GAA TTC GTC GCA GAT AGA TTA TTA ACA GAG TTA GGT    4156
Ser Gln Tyr Ile Glu Phe Val Ala Asp Arg Leu Leu Thr Glu Leu Gly
            255                 260                 265

TGT GAA AAG TCT CAA TGT ATA TAATCCTTTT AGCTTTATGG AGTATATATC       4207
Cys Glu Lys Ser Gln Cys Ile
        270                 275

ACTAGAAGGT AAGACTAATT TTTTCGAACG ACGAGTTAGT GAATATCAAA AGATGGGGGT  4267

GTTTACAAAT AAAGAAGAGA ATATATTTTC TACGGATATA GATTTTTAAT TAATAATTTT  4327

TATAAAGTTG AATAAATAAT TTAATAATAG TAATTTGCTT TGGTTTGCAA ATAGATAGTG  4387

AAAA ATG TCT AAA CAA GAA ACT TAC ATT GAT TAT AAC TAT ATA GAA AGG   4436
     Met Ser Lys Gln Glu Thr Tyr Ile Asp Tyr Asn Tyr Ile Glu Arg
      1               5                  10                  15

TTA AAT GCT GTG AAT CTA AAC AGA AGT TAT GAT GAA GAG ATA GTA TTT   4484
Leu Asn Ala Val Asn Leu Asn Arg Ser Tyr Asp Glu Glu Ile Val Phe
                 20                  25                  30

ATT ATG ACC GTT GGT GGT GTT GTT AAA GTA AAA AAA GAA TTA CTT GTA   4532
Ile Met Thr Val Gly Gly Val Val Lys Val Lys Lys Glu Leu Leu Val
             35                  40                  45

TCT GTA TCT AAT TAC TTT AAA CTT ATT ACA AAG AAT CAG AGT AAT GAA   4580
Ser Val Ser Asn Tyr Phe Lys Leu Ile Thr Lys Asn Gln Ser Asn Glu
        50                  55                  60
```

```
ATA ACG GTT TCA TTC CAG TAT GAA TCT TTT CTT GAT ATA ATA AAA TAT        4628
Ile Thr Val Ser Phe Gln Tyr Glu Ser Phe Leu Asp Ile Ile Lys Tyr
    65                  70                  75

ATA GAA ACT GGA ATC GTT ACT ATC GAT TTA GAC AAT GTA GAA AAT ATT        4676
Ile Glu Thr Gly Ile Val Thr Ile Asp Leu Asp Asn Val Glu Asn Ile
80                  85                  90                  95

TTT TCC ATA TCT TGT AGT AAA GCC ATA GAT TTT TTA AAA AAT TCA TGT        4724
Phe Ser Ile Ser Cys Ser Lys Ala Ile Asp Phe Leu Lys Asn Ser Cys
                100                 105                 110

ATT GAT TTT ATG TCA AAA CAT ATA ACG GAT TCT ACA TGT GTT AAG ATT        4772
Ile Asp Phe Met Ser Lys His Ile Thr Asp Ser Thr Cys Val Lys Ile
            115                 120                 125

TAC AAA ATA GGT TTC TCG AAT GGA TGT TTT GCG GTA TAT AAT GAT GCT        4820
Tyr Lys Ile Gly Phe Ser Asn Gly Cys Phe Ala Val Tyr Asn Asp Ala
        130                 135                 140

ATA GCA TAT ATA AGG AAA AGA TTC ACA AAA ATA GAA ACA GAT ATA TTA        4868
Ile Ala Tyr Ile Arg Lys Arg Phe Thr Lys Ile Glu Thr Asp Ile Leu
    145                 150                 155

CTA TCG TTA TCC TTA TTT GAT TTG AGA ATA ATT CTA AAA AGT GGA GAA        4916
Leu Ser Leu Ser Leu Phe Asp Leu Arg Ile Ile Leu Lys Ser Gly Glu
160                 165                 170                 175

TTA GAT GTA TCA TCA GAA GAT GAT GTA TTA TTA TTT ATA ATA AAA TGG        4964
Leu Asp Val Ser Ser Glu Asp Asp Val Leu Leu Phe Ile Ile Lys Trp
                180                 185                 190

TCT AGA CAT AAA AAA TCC AAC AGA CGA AAA TCG TTT ACA CTA GTA ACA        5012
Ser Arg His Lys Lys Ser Asn Arg Arg Lys Ser Phe Thr Leu Val Thr
            195                 200                 205

GAG GTA CTA AGA TAT AAT TAT CTA TCC ATA TAT GGT AAG TAT AAA TTA        5060
Glu Val Leu Arg Tyr Asn Tyr Leu Ser Ile Tyr Gly Lys Tyr Lys Leu
        210                 215                 220

ACA AAA TGG TTG GCA CGA TTC GGA AAA AAT AAT AAT GTA GAG TTA AAT        5108
Thr Lys Trp Leu Ala Arg Phe Gly Lys Asn Asn Asn Val Glu Leu Asn
    225                 230                 235

GAA AAT GAA TTA CCT AGA ATA AGT TAT CAA CAT AGA TTT ACA AAC AGA        5156
Glu Asn Glu Leu Pro Arg Ile Ser Tyr Gln His Arg Phe Thr Asn Arg
240                 245                 250                 255

AGA TAT ACG ATG GTT ACA CCA TCT TCA TTT AGT ATA AAT ATG CTA GGT        5204
Arg Tyr Thr Met Val Thr Pro Ser Ser Phe Ser Ile Asn Met Leu Gly
                260                 265                 270

AAT GTA TCT GTT AAG AAT GAA CTT AGT ATA ATC AAT AGT ATA GCT GAG        5252
Asn Val Ser Val Lys Asn Glu Leu Ser Ile Ile Asn Ser Ile Ala Glu
            275                 280                 285

AAT CAT AAT CCT TAC TGT GGA TCT GTA CTT ATG AAT GAT ATA TTA TAT        5300
Asn His Asn Pro Tyr Cys Gly Ser Val Leu Met Asn Asp Ile Leu Tyr
        290                 295                 300

CTT ATA GGT GGT ATA AAT AAA TCA TTG GAT CCT GTT AGT GAT ATA ACT        5348
Leu Ile Gly Gly Ile Asn Lys Ser Leu Asp Pro Val Ser Asp Ile Thr
    305                 310                 315

AGC GTA GAC ACT AGA TCA TTT ATA GAG TTG CAT ACA CCA CCA TTA TTA        5396
Ser Val Asp Thr Arg Ser Phe Ile Glu Leu His Thr Pro Pro Leu Leu
320                 325                 330                 335

CAT CCT AGA AAG TGT CCG GGT GTT GCT ATT TTT AAA AAT AGA ATT TAT        5444
His Pro Arg Lys Cys Pro Gly Val Ala Ile Phe Lys Asn Arg Ile Tyr
                340                 345                 350

GTG GTA GGT GGT ATA GGA TAC GAT GGA CCA TTA AAA ACA GTA GAA AGT        5492
Val Val Gly Gly Ile Gly Tyr Asp Gly Pro Leu Lys Thr Val Glu Ser
            355                 360                 365

TGG TCA CCT GGA GAA CAA CAA TGG AGA GAA GAA GTA CCA TTA TTA CAA        5540
Trp Ser Pro Gly Glu Gln Gln Trp Arg Glu Glu Val Pro Leu Leu Gln
```

```
                    370                375               380
CCC AGA TTT AAT CCT TGC ATA ATT GGA ACA GAT AAT GAT TTA TAT GTT         5588
Pro Arg Phe Asn Pro Cys Ile Ile Gly Thr Asp Asn Asp Leu Tyr Val
    385                 390               395

GTT GGT GGT ATT TCT GAA GAT GAT AAA ACT ATT GAA ATC TAT TCT TAT         5636
Val Gly Gly Ile Ser Glu Asp Asp Lys Thr Ile Glu Ile Tyr Ser Tyr
400                 405                 410                 415

GAA GAA AAC ACT TGG TCT ATT GGT AAT GCG ATG AAT TAT TCA CAT TTT         5684
Glu Glu Asn Thr Trp Ser Ile Gly Asn Ala Met Asn Tyr Ser His Phe
                420                 425                 430

GGT GGA TGT ATA GCA TAT CAC CAT GGT TAT ATA TAT ATG ATT GGT GGT         5732
Gly Gly Cys Ile Ala Tyr His His Gly Tyr Ile Tyr Met Ile Gly Gly
            435                 440                 445

TTA TCT TTT ATA GAT AAT ATT CAT GTA TTT ACT ATG GTT GAG AAG TAT         5780
Leu Ser Phe Ile Asp Asn Ile His Val Phe Thr Met Val Glu Lys Tyr
        450                 455                 460

AAC CCT CAT TCG AAT AAA TGG ACT GTA GAA AAG TCT CTA CCC TTT CCT         5828
Asn Pro His Ser Asn Lys Trp Thr Val Glu Lys Ser Leu Pro Phe Pro
    465                 470                 475

CGA TTT AAT TCA TCG CTT TGT ATT ATA GAA GAC TCT ATC GCT ATA ATA         5876
Arg Phe Asn Ser Ser Leu Cys Ile Ile Glu Asp Ser Ile Ala Ile Ile
480                 485                 490                 495

GGC TGG ATA TAT TAT TAACAAATAT ATTAGTCAAA TAGAAATATA TAACGGAGCT         5931
Gly Trp Ile Tyr Tyr
                500

AGATGAATGG GGTATTGTAG GGTCTATCGA TATAGAGTCA TTCTTTCAAG AAATGAAAAA      5991

ATAATCTACA TTTTTTCTTG TTACGACAAT GGAACTACGT TATACGATCA TATCTGTCTG      6051

TGCTTGAAAG GTTGACACCG TATCAGTTTA AAACGTTATT ATTCTTGATA CAGGATGACA      6111

TTAATATATC TAACGATGAT ATTAATGTAT TAGATAGAGT CGATCTAGCT ATTAAAATA       6170

ATG AAT AAA TAT AAT AAT TAT AGA GCA ATT TAT TTT CTC TAT AAA GTC         6218
Met Asn Lys Tyr Asn Asn Tyr Arg Ala Ile Tyr Phe Leu Tyr Lys Val
 1               5                  10                  15

ATA TTA CGA ATA CAT AAT ACA GAA TAT ATA AGT GGA ACA CTA CAA AGA         6266
Ile Leu Arg Ile His Asn Thr Glu Tyr Ile Ser Gly Thr Leu Gln Arg
                20                  25                  30

TCT ATA CAG AAT ATA ACA CCT ACA ACA TCA TCA TAT ACG TAT TGT GAT         6314
Ser Ile Gln Asn Ile Thr Pro Thr Thr Ser Ser Tyr Thr Tyr Cys Asp
            35                  40                  45

AAT TCA AAA AGA CGC AGA CAT AGA TTT AGA GAT ACG GAA ATC CTT AAA         6362
Asn Ser Lys Arg Arg Arg His Arg Phe Arg Asp Thr Glu Ile Leu Lys
        50                  55                  60

GCT ATG GGT AGT AAA ATG CGT AGA AAA CTT TTT TAGTTAGTGA GTAATATTAT      6415
Ala Met Gly Ser Lys Met Arg Arg Lys Leu Phe
 65                  70                  75

AAAATTAAAA AAAAAATAAT ATTTTCTAGA C ATG TCA CTA TAT GTT AAA TGT         6467
                                 Met Ser Leu Tyr Val Lys Cys
                                  1               5

GTT AAG TTA TCT AAT AAT GCT ATT ATA CCA AAT AGA TCA ATG AGC GGA         6515
Val Lys Leu Ser Asn Asn Ala Ile Ile Pro Asn Arg Ser Met Ser Gly
            10                  15                  20

TCC GCT GGA TAT GAT CTG TAT AGT GCA TAT AGT TAT ACA GTT AAG CCG         6563
Ser Ala Gly Tyr Asp Leu Tyr Ser Ala Tyr Ser Tyr Thr Val Lys Pro
        25                  30                  35

TAT AAT AGA ATT TTA GTT AGA ACA GAT ATT TGT TTA ATG ATA CCA GAT         6611
Tyr Asn Arg Ile Leu Val Arg Thr Asp Ile Cys Leu Met Ile Pro Asp
 40                  45                  50                  55

AAA TGT TAT GGA CGC ATA TCG CCT AGA TCG GGA TTA TCG TTA AAT TAT         6659
```

```
                Lys Cys Tyr Gly Arg Ile Ser Pro Arg Ser Gly Leu Ser Leu Asn Tyr
                                    60                  65                  70

AAT ATA GAT ATA GGA GGA GGC GTT ATT GAT AGT GAT TAC AGA GGG GAA              6707
Asn Ile Asp Ile Gly Gly Gly Val Ile Asp Ser Asp Tyr Arg Gly Glu
                75                  80                  85

ATA GGT ATC GTG TTT ATA AAT AAT GGA TGT AGT GAT TTT AAC ATA AAG              6755
Ile Gly Ile Val Phe Ile Asn Asn Gly Cys Ser Asp Phe Asn Ile Lys
            90                  95                 100

GTA GGT GAT AGG ATA GCA CAA ATA ATA TTT GAA AGA GTA GAA TAT CCT              6803
Val Gly Asp Arg Ile Ala Gln Ile Ile Phe Glu Arg Val Glu Tyr Pro
       105                 110                 115

ATA ATG GAA GAA GTA AAA TGT TTG GAA GAT ACA GAA CGT GGA AAT AGT              6851
Ile Met Glu Glu Val Lys Cys Leu Glu Asp Thr Glu Arg Gly Asn Ser
120                 125                 130                 135

GGT TTT GGG TCA AGT GGT ATG TAAAGTATAA TAAATGAAAA AATAATTCAT                 6902
Gly Phe Gly Ser Ser Gly Met
                140

CTGTATTATA TCCATTATTA TCAAT ATG TAC AAG AAA TAT AAC TCT AAC GTA              6954
                           Met Tyr Lys Lys Tyr Asn Ser Asn Val
                            1               5

TGC ATT AGG AAT GTA TTA TAT GTA TAT CTA AAA TAT AAT ACT ATA AAT              7002
Cys Ile Arg Asn Val Leu Tyr Val Tyr Leu Lys Tyr Asn Thr Ile Asn
 10                  15                  20                  25

AAA CTT AGT AGA TAT GAA CGG ATG ATA TAC ACA AAG ATA AAA AAT CAA              7050
Lys Leu Ser Arg Tyr Glu Arg Met Ile Tyr Thr Lys Ile Lys Asn Gln
                 30                  35                  40

TGT GAA GCG ATA AAA TAC AGA TAT TGT AAT GAT TTT AAT TCT GTT ACA              7098
Cys Glu Ala Ile Lys Tyr Arg Tyr Cys Asn Asp Phe Asn Ser Val Thr
            45                  50                  55

TGT ATT TTA GAA TAC GAT GAA AAT AAG TAT ATA GAT AAC GTG CAT AAA              7146
Cys Ile Leu Glu Tyr Asp Glu Asn Lys Tyr Ile Asp Asn Val His Lys
        60                  65                  70

GAA GTT ATT AGT ATA TTG TTA TCA GAT TCG CGA CCT AGT ATC AAA TTA              7194
Glu Val Ile Ser Ile Leu Leu Ser Asp Ser Arg Pro Ser Ile Lys Leu
 75                  80                  85

GCT GCT ATT TCG TTA TTA TCT ATA ATA ATA GAT AAA CTA ATA TGT AGA              7242
Ala Ala Ile Ser Leu Leu Ser Ile Ile Ile Asp Lys Leu Ile Cys Arg
 90                  95                 100                 105

AAT ATT CGT ATA GCT AAA TAT ATA ATT GAT GAT ATA ATA AAT ATT ATA              7290
Asn Ile Arg Ile Ala Lys Tyr Ile Ile Asp Asp Ile Ile Asn Ile Ile
                110                 115                 120

TCA GAA GAC GGT ATA TAT ATT ATA TTA TTT TTA GAT GAA TTT GAT AAA              7338
Ser Glu Asp Gly Ile Tyr Ile Ile Leu Phe Leu Asp Glu Phe Asp Lys
            125                 130                 135

TAT ACC GAT ACC CGA TGT AGG CGC CGT GGA TTA AGT ATG ATG ATA GCG              7386
Tyr Thr Asp Thr Arg Cys Arg Arg Arg Gly Leu Ser Met Met Ile Ala
        140                 145                 150

AGC ATT GTA ACT TAC TAC TGT TTA CGG TAT GTA TTA AAA ATA TAAAAATAAA           7438
Ser Ile Val Thr Tyr Tyr Cys Leu Arg Tyr Val Leu Lys Ile
155                 160                 165

TCTTTTTTTT TAAAA ATG AAC CGT AAT ATG TGG ATA GTG TTA TCG TGT GTA             7489
              Met Asn Arg Asn Met Trp Ile Val Leu Ser Cys Val
               1               5                  10

TTA TAT ATG ATT TAT ATA TGT AAC GGA CGA GAT GTA TTG TTA TAT CCA              7537
Leu Tyr Met Ile Tyr Ile Cys Asn Gly Arg Asp Val Leu Leu Tyr Pro
         15                  20                  25

CCA CAT AAG AAA ACA AAT AAG GTT ATA GTA AAA TGT AAC GGA TAT ACT              7585
Pro His Lys Lys Thr Asn Lys Val Ile Val Lys Cys Asn Gly Tyr Thr
     30                  35                  40
```

```
AAT TCT ACG TAT AGT ATC TTA TAT TGG ATG GTA GGT AAC AAC AAT ACA      7633
Asn Ser Thr Tyr Ser Ile Leu Tyr Trp Met Val Gly Asn Asn Asn Thr
 45                  50                  55                  60

TTC GTA GAA CAA CTA AAT AGC GAT CAT TAT AAA GAG AAG AAA TAC AAT      7681
Phe Val Glu Gln Leu Asn Ser Asp His Tyr Lys Glu Lys Lys Tyr Asn
                 65                  70                  75

AGT ACT GAA AAA AAT GAG CAT ATG TAT AAG TTA CGT ACC GAT CTT ATT      7729
Ser Thr Glu Lys Asn Glu His Met Tyr Lys Leu Arg Thr Asp Leu Ile
             80                  85                  90

ATA TAT AAT ATT ACG TCA GAA ATG GAG ATG ACA AAA CTA ACA TGT GTA      7777
Ile Tyr Asn Ile Thr Ser Glu Met Glu Met Thr Lys Leu Thr Cys Val
                 95                 100                 105

TTA TCA GAT ATA TAC ACA CCT ATC AAG GCA TCT ATA ATA TTA AAT AAT      7825
Leu Ser Asp Ile Tyr Thr Pro Ile Lys Ala Ser Ile Ile Leu Asn Asn
            110                 115                 120

TTA TGG AGT TGT TTA AAT ACT ACA CAA GTA TGAAATATGA AATATAAAGT        7875
Leu Trp Ser Cys Leu Asn Thr Thr Gln Val
125                 130                 135

ATTCAAATAA ATAACAATA ATG TCA ACT ATG AAT ACG TTG GCA TTT TGT TAT     7927
                    Met Ser Thr Met Asn Thr Leu Ala Phe Cys Tyr
                     1               5                  10

GGA TTA CCT AAC ATA AAT GAT ATC ACG CAA GGT ATA ATT TTT GTT AGA      7975
Gly Leu Pro Asn Ile Asn Asp Ile Thr Gln Gly Ile Ile Phe Val Arg
             15                  20                  25

AAT AAC ATA TTT TAC TCA TAT TTA ACA GAT TAT GCA ATG GAA GCG TGT      8023
Asn Asn Ile Phe Tyr Ser Tyr Leu Thr Asp Tyr Ala Met Glu Ala Cys
         30                  35                  40

ATA TTG AAT TAT ATA AAT ATT AGA GCC GAT AAA ATA GAA GAT CTA AAG      8071
Ile Leu Asn Tyr Ile Asn Ile Arg Ala Asp Lys Ile Glu Asp Leu Lys
     45                  50                  55

AAA TCA TTA GTT GGA AAA ACT ATT AGC GTG AGA GTT ATT AGA GTT GAT      8119
Lys Ser Leu Val Gly Lys Thr Ile Ser Val Arg Val Ile Arg Val Asp
 60                  65                  70                  75

GTA TTA AAA GGA TAT ATA GAT GTT TCA ATT GTA TAATTTTTTT ATCAAAACTG    8172
Val Leu Lys Gly Tyr Ile Asp Val Ser Ile Val
                 80                  85

AAGTATAATC TAGACCTTAG AAGATATTTT GTACCATATA AA ATG GAT CCT GTT       8226
                                              Met Asp Pro Val
                                               1

TGT TGG ATA TGT AAA GAT GAC TAC AGT ATT GAA AAG AAT TAT TGT AAC      8274
Cys Trp Ile Cys Lys Asp Asp Tyr Ser Ile Glu Lys Asn Tyr Cys Asn
  5                  10                  15                  20

TGT AAA AAC GAG TAT AAA GTT GTA CAC GAT GAA TGT ATG AAA AAG TGG      8322
Cys Lys Asn Glu Tyr Lys Val Val His Asp Glu Cys Met Lys Lys Trp
             25                  30                  35

ATA CAA TAC TCA AGG GAA CGA TCT TGT AAA TTA TGT AAT AAA GAA TAT      8370
Ile Gln Tyr Ser Arg Glu Arg Ser Cys Lys Leu Cys Asn Lys Glu Tyr
         40                  45                  50

AAC ATC ATT AGT GTT AGA AAA CCA TTC TCA CAG TGG GTA TTC TCC ATT      8418
Asn Ile Ile Ser Val Arg Lys Pro Phe Ser Gln Trp Val Phe Ser Ile
     55                  60                  65

AAA GAT TGC AAA AAG TCA GCA ATT TTG TAC GCT ACT CTA TTC TTA TGT      8466
Lys Asp Cys Lys Lys Ser Ala Ile Leu Tyr Ala Thr Leu Phe Leu Cys
 70                  75                  80

ACG TTT ATT ATA TCG CTT GTT TTA ACT AGA ATT AAT ATA ACA AAA ATA      8514
Thr Phe Ile Ile Ser Leu Val Leu Thr Arg Ile Asn Ile Thr Lys Ile
             85                  90                  95                 100

ATA GAT ACA TCA AAA AAT GAT GTT TCA TTT AAG CTG GTT ACG ATG ATA      8562
Ile Asp Thr Ser Lys Asn Asp Val Ser Phe Lys Leu Val Thr Met Ile
            105                 110                 115
```

```
TTC TAC TTA TTA CCA TTT GTC ATA ACT TGT ATA TCG TTC ATA ACG CTG        8610
Phe Tyr Leu Leu Pro Phe Val Ile Thr Cys Ile Ser Phe Ile Thr Leu
            120                 125                 130

ATA GTT TAT CTA TAT AAA TAT TGT AAG ATT TCC GCT AAA AAC AAC ACA        8658
Ile Val Tyr Leu Tyr Lys Tyr Cys Lys Ile Ser Ala Lys Asn Asn Thr
            135                 140                 145

TAC GAT ACG ATT TAT GAA CTT TAAAGTGAAA ATTTAATCTA TTTTTATAAT           8709
Tyr Asp Thr Ile Tyr Glu Leu
            150             155

AAAAC ATG CAT TTC ATA TTC ATT ATA TTA TCA CTA TCA TTT GTA GTA          8756
      Met His Phe Ile Phe Ile Ile Leu Ser Leu Ser Phe Val Val
      1                   5                   10

AAT GCC GAT GTA TTT CCA TCG TCG GTT ACT TTA TCA TCT AAT GAT TTT        8804
Asn Ala Asp Val Phe Pro Ser Ser Val Thr Leu Ser Ser Asn Asp Phe
 15                  20                  25                  30

GAT ACA ATA ATT AAA TGG GAT AAT AAT GTA ATA TCA TAC GAT GTA GAA        8852
Asp Thr Ile Ile Lys Trp Asp Asn Asn Val Ile Ser Tyr Asp Val Glu
                35                  40                  45

TTA ATG CAG TAC AGT CAT GAC GAA TGG AGA ACC GTT TGT ACT AAT TCT        8900
Leu Met Gln Tyr Ser His Asp Glu Trp Arg Thr Val Cys Thr Asn Ser
            50                  55                  60

TTA GGA TAC TGT AAT TTA ACA AAT TCT GAT ATC GAC AAT GAT GAT GAA        8948
Leu Gly Tyr Cys Asn Leu Thr Asn Ser Asp Ile Asp Asn Asp Asp Glu
            65                  70                  75

ACA TGG GTG AGG TTT AAA TAT GAA AAT AAG ACA TCT AAT GAA CAT AAT        8996
Thr Trp Val Arg Phe Lys Tyr Glu Asn Lys Thr Ser Asn Glu His Asn
 80                  85                  90

ATT GGC AGA GTA TGT GAG ATT GTA CAA ATA ACT TCA CCT ATT GTT AAC        9044
Ile Gly Arg Val Cys Glu Ile Val Gln Ile Thr Ser Pro Ile Val Asn
 95                  100                 105                 110

ATG ACA AGA GAT GGT TCA ATT ATA CTA TTA GAT ATA CAT CAT CCA ATG        9092
Met Thr Arg Asp Gly Ser Ile Ile Leu Leu Asp Ile His His Pro Met
                115                 120                 125

ACA TAC GAT AAT CAG TAT TAT ATA TAT AAT AAT ATA ACA TTA TGT GGA        9140
Thr Tyr Asp Asn Gln Tyr Tyr Ile Tyr Asn Asn Ile Thr Leu Cys Gly
            130                 135                 140

TTT GAA TTT ATT TAC GAA GCT ACA TTT ATT ATT AAT GAT ACA ATT ATA        9188
Phe Glu Phe Ile Tyr Glu Ala Thr Phe Ile Ile Asn Asp Thr Ile Ile
            145                 150                 155

CCA TAT AGT ATA GAC AAT CAA TAT TGT GAT GAT GTT CAT TGT TTA TTT        9236
Pro Tyr Ser Ile Asp Asn Gln Tyr Cys Asp Asp Val His Cys Leu Phe
160                 165                 170

TAC TTT ATA TCA CAA GAA CCC GTT TGT GTG TAT GTA ATG GGT ATG GAA        9284
Tyr Phe Ile Ser Gln Glu Pro Val Cys Val Tyr Val Met Gly Met Glu
175                 180                 185                 190

CAA TAT TAT GAA TTT GGT CCA AAA AAA ACA GAT AAT AGT ACT AGA GTG        9332
Gln Tyr Tyr Glu Phe Gly Pro Lys Lys Thr Asp Asn Ser Thr Arg Val
            195                 200                 205

TGT GTA GAT GGA TTA ATT CCA AGA AAA ATC GAT ACA TAT TTT ATT AAA        9380
Cys Val Asp Gly Leu Ile Pro Arg Lys Ile Asp Thr Tyr Phe Ile Lys
            210                 215                 220

GAT TTC GAT GAT ATA GAT AGA GTT AAT AAC AGA TTA TAT AGA GTT GTA        9428
Asp Phe Asp Asp Ile Asp Arg Val Asn Asn Arg Leu Tyr Arg Val Val
            225                 230                 235

AGT GAT AAA TAT GAA TCC AAT ATA TCG TCA AAG TTT ATG CAC TTA TAT        9476
Ser Asp Lys Tyr Glu Ser Asn Ile Ser Ser Lys Phe Met His Leu Tyr
240                 245                 250

AAT AAT ATA TTA TCT TCG TTT AAA CTA ATA TTG CAA GAA CTT ATG GTA        9524
Asn Asn Ile Leu Ser Ser Phe Lys Leu Ile Leu Gln Glu Leu Met Val
```

-continued

```
255                 260                 265                 270
AAT ACT GAA CAG TAAATACGTT TATAAAGATA AAGGA ATG AAT TCG TAT ATT     9576
Asn Thr Glu Gln                               Met Asn Ser Tyr Ile
            275                                 1               5

GTA ATA AAA AAT TCA TTA CGT GAT TAT AGA TCT GGA AGA ATT ATA AGA    9624
Val Ile Lys Asn Ser Leu Arg Asp Tyr Arg Ser Gly Arg Ile Ile Arg
                10                  15                  20

AAA TAC ATA AGA AAA TTA AAT AAG GAT GAG TAT AAG CAT TTT TGT GCT    9672
Lys Tyr Ile Arg Lys Leu Asn Lys Asp Glu Tyr Lys His Phe Cys Ala
                25                  30                  35

GTA TTT AGA TTA AAT GTA GAT TTT TCT CAA GAT GAT AAA AAT CCA TCT    9720
Val Phe Arg Leu Asn Val Asp Phe Ser Gln Asp Asp Lys Asn Pro Ser
            40                  45                  50

AGA AAA GAA GTA ATA AGA ATA ATA GAT GAG GAA TTC AAT TTT TGT GAT    9768
Arg Lys Glu Val Ile Arg Ile Ile Asp Glu Glu Phe Asn Phe Cys Asp
        55                  60                  65

CTT AGA CTA TTT TAT GAT ATC ATG ACC GTT GTA CCT AAT CAT ATG AAT    9816
Leu Arg Leu Phe Tyr Asp Ile Met Thr Val Val Pro Asn His Met Asn
70                  75                  80                  85

GTG GCA TCT ATT ATT TAT AGC GAA TAC GAA TAT CTT TTA AAA AAA TCA    9864
Val Ala Ser Ile Ile Tyr Ser Glu Tyr Glu Tyr Leu Leu Lys Lys Ser
                90                  95                 100

AAT TAT AAA AAT AAG AAG ATA AAT TAT ACT ATA TTA GAT AAG ATT AAT    9912
Asn Tyr Lys Asn Lys Lys Ile Asn Tyr Thr Ile Leu Asp Lys Ile Asn
                105                 110                 115

AAA TAT CAT AGT ATA GAT GAT ATT ATA TTT ATG TAT CTT CAT TGG AGA    9960
Lys Tyr His Ser Ile Asp Asp Ile Ile Phe Met Tyr Leu His Trp Arg
            120                 125                 130

AAA AAA TAT AAC AAC ACA TGC GCA TGT GGT AAG TTA TTT AAG GAA CTC    10008
Lys Lys Tyr Asn Asn Thr Cys Ala Cys Gly Lys Leu Phe Lys Glu Leu
135                 140                 145

ATG AAA TAT GAT ATA TTA GCT ACA AAA TAT ATA TAT AAT GAT ATT ATA    10056
Met Lys Tyr Asp Ile Leu Ala Thr Lys Tyr Ile Tyr Asn Asp Ile Ile
150                 155                 160                 165

AAT ACA TAC AAA GAG GGA GAT ACT ATA TCC ATT AAC ATA CGT TTA AAA    10104
Asn Thr Tyr Lys Glu Gly Asp Thr Ile Ser Ile Asn Ile Arg Leu Lys
                170                 175                 180

TGT AAA GAT GAT ATA ATT AAA CAT TGT AAG TCT TCT ATA GGT ATG TTT    10152
Cys Lys Asp Asp Ile Ile Lys His Cys Lys Ser Ser Ile Gly Met Phe
            185                 190                 195

GCT ATA TTA TCA TCG AAA ATA ATC GAC GTA GAT TTT GAT GTT ATA TTC    10200
Ala Ile Leu Ser Ser Lys Ile Ile Asp Val Asp Phe Asp Val Ile Phe
            200                 205                 210

TTT TCA CAA ATA AGT ATA AGA TAT AGA CTA ATA TTC AAA AAA TAT CTC    10248
Phe Ser Gln Ile Ser Ile Arg Tyr Arg Leu Ile Phe Lys Lys Tyr Leu
        215                 220                 225

ATA CAA TCA TTA TAC TTA CAA TAATAATTGT TTTTTTTTG AAAAATAATC        10299
Ile Gln Ser Leu Tyr Leu Gln
230                 235

CTAAATCTAT CATAAC ATG AAT TCA TTA TTA TTA CGA TTA CAT GAT TTT      10348
                  Met Asn Ser Leu Leu Leu Arg Leu His Asp Phe
                    1               5                   10

TTT AAA CAT GGA ATT ATG TGT GAT ATA AAA ATA GTA TCC ATA GAG AAT    10396
Phe Lys His Gly Ile Met Cys Asp Ile Lys Ile Val Ser Ile Glu Asn
                15                  20                  25

AAT AAA ACC ATT AGC GCA CAT AGG TTA ATA TTA TCT ATG TAC TCT AAG    10444
Asn Lys Thr Ile Ser Ala His Arg Leu Ile Leu Ser Met Tyr Ser Lys
            30                  35                  40

TAC TTT TAT AAT ATA TTT AAT TCA GAT TTT ATT GAT AAA AAT AAT GAT    10492
```

```
Tyr Phe Tyr Asn Ile Phe Asn Ser Asp Phe Ile Asp Lys Asn Asn Asp
     45                  50                  55

GAA ATC TAT ATA TGC GCC GAT TAT GAT ATA TTG TAT ATT ATA TTG GAA         10540
Glu Ile Tyr Ile Cys Ala Asp Tyr Asp Ile Leu Tyr Ile Ile Leu Glu
 60                  65                  70                  75

TTT ATG TAC ACC GGT AAT ATA GTA CTA ACA AAG GAT AAT ATA GAA TTA         10588
Phe Met Tyr Thr Gly Asn Ile Val Leu Thr Lys Asp Asn Ile Glu Leu
                 80                  85                  90

GTA ATA CAA GTC TGT GAT TAT CTA TGT ATA GAT TCT TTA ATA AAA ATA         10636
Val Ile Gln Val Cys Asp Tyr Leu Cys Ile Asp Ser Leu Ile Lys Ile
             95                 100                 105

TGT GAA GAA TAT ATA TGC GGT ATA ATA GAT GAA ACA AAT TGT ATA CAT         10684
Cys Glu Glu Tyr Ile Cys Gly Ile Ile Asp Glu Thr Asn Cys Ile His
        110                 115                 120

CTC TTA AAC TTT TCA GAT ACT TAC AAT CTA CAA CGA TTA CGT GAA ATG         10732
Leu Leu Asn Phe Ser Asp Thr Tyr Asn Leu Gln Arg Leu Arg Glu Met
125                 130                 135

TCA AAA TGG TAT TTA CCA AAA ATA ATA AAT AAT AAC AAA CTG GTA GTA         10780
Ser Lys Trp Tyr Leu Pro Lys Ile Ile Asn Asn Asn Lys Leu Val Val
140                 145                 150                 155

GAA TTA GAT ATA GAT GAT ATG ATA TTA ATT ATA AAA GAA ATT AAA TAC         10828
Glu Leu Asp Ile Asp Asp Met Ile Leu Ile Ile Lys Glu Ile Lys Tyr
                160                 165                 170

ATT GCA TGT GAA TAT ATA GTT AAA AAA ATA ATA TTA AAT TGG ATC GTT         10876
Ile Ala Cys Glu Tyr Ile Val Lys Lys Ile Ile Leu Asn Trp Ile Val
            175                 180                 185

CAT AAA GAT GAA CGA ATT ATT TAT ACT AAA AAA TTA ATG AAA CAT ATC         10924
His Lys Asp Glu Arg Ile Ile Tyr Thr Lys Lys Leu Met Lys His Ile
        190                 195                 200

AAT GAT CAA GAC CAT TAT ACA TCC TTA TCG GAT ATT GAA TTG TAC AAT         10972
Asn Asp Gln Asp His Tyr Thr Ser Leu Ser Asp Ile Glu Leu Tyr Asn
205                 210                 215

AAT ATA CGG GAA CGA ATA TAT GAT AAC AAA GAA CAC GAT GTA GAT ATA         11020
Asn Ile Arg Glu Arg Ile Tyr Asp Asn Lys Glu His Asp Val Asp Ile
220                 225                 230                 235

TCA CAT AAC TTT ATA ATA ATG GTA GGA GGA AAA AAG ATA TTT AAT ATA         11068
Ser His Asn Phe Ile Ile Met Val Gly Gly Lys Lys Ile Phe Asn Ile
                240                 245                 250

ACC GCA TTC AAT CCG TTA TCG AAT AAA AAA CAT ATT ATA GAC AGA TAC         11116
Thr Ala Phe Asn Pro Leu Ser Asn Lys Lys His Ile Ile Asp Arg Tyr
            255                 260                 265

GAT GAT ATG TTT GGT TGT AAA ACT CAT TTT AGT GTT GTA TAC TTA AAT         11164
Asp Asp Met Phe Gly Cys Lys Thr His Phe Ser Val Val Tyr Leu Asn
        270                 275                 280

AGT ATA CTA TAT ATT ATC GGT GGA AAG AAA CGA GGA TAT TTC ACT AAA         11212
Ser Ile Leu Tyr Ile Ile Gly Gly Lys Lys Arg Gly Tyr Phe Thr Lys
285                 290                 295

GAG GTG TTG TCA TAT AAT ATA AAA AAC AAA TTA TGG TGT TAC GAA CCA         11260
Glu Val Leu Ser Tyr Asn Ile Lys Asn Lys Leu Trp Cys Tyr Glu Pro
300                 305                 310                 315

GAA TTA AAT TAT TTT AGA TAC GAT ACA TCT GTA TGT GTA TCA AAT GGG         11308
Glu Leu Asn Tyr Phe Arg Tyr Asp Thr Ser Val Cys Val Ser Asn Gly
                320                 325                 330

ATG ATA TAT TCA ATT GGT GGA AAA GAT ACA AAT GGA TAT ATG ACA AAC         11356
Met Ile Tyr Ser Ile Gly Gly Lys Asp Thr Asn Gly Tyr Met Thr Asn
            335                 340                 345

ATC GTA GAA TTT TGG AAA CCT GAA TGG AAA TCA TGG TAT GAT GGT CAA         11404
Ile Val Glu Phe Trp Lys Pro Glu Trp Lys Ser Trp Tyr Asp Gly Gln
        350                 355                 360
```

| | | |
|---|---|---|
| CAT TTG TGT TAT CCT AGA TGT TAT ATG TCG TTG GTA GAC TAT AAT AAT<br>His Leu Cys Tyr Pro Arg Cys Tyr Met Ser Leu Val Asp Tyr Asn Asn<br>365                          370                         375 | 11452 |
| GAA GTA TAT ACA ATA GGT GGA TTA AAA ACA TCA ATA ACG GAT GAA TTT<br>Glu Val Tyr Thr Ile Gly Gly Leu Lys Thr Ser Ile Thr Asp Glu Phe<br>380                          385                       390                       395 | 11500 |
| AAT ATA GAA ATG ATT GTA TCA GAC GAT GCC GTA GAG AAA CTG ACC GAT<br>Asn Ile Glu Met Ile Val Ser Asp Asp Ala Val Glu Lys Leu Thr Asp<br>                        400                         405                       410 | 11548 |
| CAT TCA TGG ATG AAG TTA AAA CAA TTT CCC ATA GCA AAG AGT GGT ATA<br>His Ser Trp Met Lys Leu Lys Gln Phe Pro Ile Ala Lys Ser Gly Ile<br>              415                       420                       425 | 11596 |
| TCA TCC ATA GTA TAT AAC GAT TTT ATA TAC TGT ATA GGT GGT CGT ATA<br>Ser Ser Ile Val Tyr Asn Asp Phe Ile Tyr Cys Ile Gly Gly Arg Ile<br>                430                       435                       440 | 11644 |
| GAT ACA CCA CAT ATA AGT ATA GAA CAC ACT AAC GAT GTT TAT ATA TAT<br>Asp Thr Pro His Ile Ser Ile Glu His Thr Asn Asp Val Tyr Ile Tyr<br>              445                       450                       455 | 11692 |
| TCT TCA AGA GAT GAT TGT TGG AAA TAT TTA TCA AAT ACA AAT GTA AAA<br>Ser Ser Arg Asp Asp Cys Trp Lys Tyr Leu Ser Asn Thr Asn Val Lys<br>460                          465                       470                       475 | 11740 |
| AGA TCA TTT TGT CTA TCG TGT GTT TTT AAT AAT GAA TTA TAT ATA ATA<br>Arg Ser Phe Cys Leu Ser Cys Val Phe Asn Asn Glu Leu Tyr Ile Ile<br>                        480                         485                       490 | 11788 |
| GGT GGA TAT AAT ACA AAC AGT GTA GAA AAG TAC AAT AAA TTA AAA AAT<br>Gly Gly Tyr Asn Thr Asn Ser Val Glu Lys Tyr Asn Lys Leu Lys Asn<br>                495                       500                       505 | 11836 |
| ACA TGG AAG CGT TTA AAC GAT ATT CCT AAG TTT GAA GAA TGT GTT AAT<br>Thr Trp Lys Arg Leu Asn Asp Ile Pro Lys Phe Glu Glu Cys Val Asn<br>              510                       515                       520 | 11884 |
| GAA GCA TCG GCA ATA TAT TTG TAGTATCCCT TATAGCGTTC AAAAGAAACA<br>Glu Ala Ser Ala Ile Tyr Leu<br>525                         530 | 11935 |
| AATCCATAAC AGACATCTAT ATTCTTAATC TATCT ATG TCA GAT TGT ATA TTC<br>                                                                      Met Ser Asp Cys Ile Phe<br>                                                                              1                   5 | 11988 |
| GTA TTT CAG ATT CCG TTC ATT GTG TAT AGT AAA CTC GAT CAA TGG ATT<br>Val Phe Gln Ile Pro Phe Ile Val Tyr Ser Lys Leu Asp Gln Trp Ile<br>                10                         15                       20 | 12036 |
| TTT GGG AAT ATA CTA TGT AAA ATA ATG TCC GTA TTA TAC TAC GTA GGA<br>Phe Gly Asn Ile Leu Cys Lys Ile Met Ser Val Leu Tyr Tyr Val Gly<br>                25                         30                       35 | 12084 |
| TTC TTT AGT AAT ATG TTT ATA ATA ACA CTT ATG AGT ATA GAT AGA TAT<br>Phe Phe Ser Asn Met Phe Ile Ile Thr Leu Met Ser Ile Asp Arg Tyr<br>40                          45                       50 | 12132 |
| TTT GCG ATC GTT CAT CCT ATA AAG CGA CAA CCG TAT AGG ACG AAA CGT<br>Phe Ala Ile Val His Pro Ile Lys Arg Gln Pro Tyr Arg Thr Lys Arg<br>55                          60                       65                       70 | 12180 |
| ATA GGT ATC CTT ATG TGC TGT TCC GCT TGG TTA TTA TCC TTG ATA TTA<br>Ile Gly Ile Leu Met Cys Cys Ser Ala Trp Leu Leu Ser Leu Ile Leu<br>                75                         80                       85 | 12228 |
| TCT AGT CCC GTA TCT AAA CTA TAC GAG AAT ATT CCT CAT ATG TCT AAA<br>Ser Ser Pro Val Ser Lys Leu Tyr Glu Asn Ile Pro His Met Ser Lys<br>              90                         95                       100 | 12276 |
| GAT ATA TAC CAA TGT ACT CTG ACG AAC GAG AAT GAC TCC ATA ATC GCA<br>Asp Ile Tyr Gln Cys Thr Leu Thr Asn Glu Asn Asp Ser Ile Ile Ala<br>              105                       110                       115 | 12324 |
| TTC ATA AAA AGA CTG ATG CAA ATA GAG ATC ACT ATA TTG GGA TTC CTG<br>Phe Ile Lys Arg Leu Met Gln Ile Glu Ile Thr Ile Leu Gly Phe Leu<br>120                          125                       130 | 12372 |

```
ATA CCT ATA ATC ATA TTC GTA TAT TGC TAT TAT AGA ATT TTT TCT ACA      12420
Ile Pro Ile Ile Ile Phe Val Tyr Cys Tyr Tyr Arg Ile Phe Ser Thr
135             140                 145                 150

GTG GTT AGA TTA AGA AAT AGA CGA AAG TAT AAA TCT ATA AAA ATT GTA      12468
Val Val Arg Leu Arg Asn Arg Arg Lys Tyr Lys Ser Ile Lys Ile Val
            155                 160                 165

TTA ATG ATT GTT GTA TGT TCT CTA ATA TGT TGG ATT CCG CTC TAT ATC      12516
Leu Met Ile Val Val Cys Ser Leu Ile Cys Trp Ile Pro Leu Tyr Ile
        170                 175                 180

GTT CTA ATG ATA GCG ACG ATT GTT AGC TTA TAT ACA TCT AAT ATA TTT      12564
Val Leu Met Ile Ala Thr Ile Val Ser Leu Tyr Thr Ser Asn Ile Phe
            185                 190                 195

AGA CAT CTG TGC CTC TAT CTA AAC CTG GCC TAT GCG ATC ACC TTT TCG      12612
Arg His Leu Cys Leu Tyr Leu Asn Leu Ala Tyr Ala Ile Thr Phe Ser
        200                 205                 210

GAG ACT ATC TCG TTA GCG CGT TGT TGT ATA AAT CCA ATA ATA TAT ACA      12660
Glu Thr Ile Ser Leu Ala Arg Cys Cys Ile Asn Pro Ile Ile Tyr Thr
215             220                 225                 230

CTG ATA GGT GAA CAT GTT CGA TCT CGT ATA TCT AGC ATA TGT TCG TGT      12708
Leu Ile Gly Glu His Val Arg Ser Arg Ile Ser Ser Ile Cys Ser Cys
            235                 240                 245

ATA TAT AGA GAC AAT AGG ATT AGG AAA AAA CTC TTT TCA CGA AAA TCT      12756
Ile Tyr Arg Asp Asn Arg Ile Arg Lys Lys Leu Phe Ser Arg Lys Ser
        250                 255                 260

TCT AGC AGT AGC AAT ATT ATT TAGTTGTTAT TTTCTTACAA AACACAAGTT         12807
Ser Ser Ser Ser Asn Ile Ile
            265             270

ATAAATAATC ATTACGTAAT C ATG CTA TCG TAT ATT ATT AAT CCT TTG CTA      12858
                       Met Leu Ser Tyr Ile Ile Asn Pro Leu Leu
                         1               5                  10

AGT ATT GTA TAC TTT ATA TTA GGA AAT GTA TCT AAG CTG CTT ACA TAT      12906
Ser Ile Val Tyr Phe Ile Leu Gly Asn Val Ser Lys Leu Leu Thr Tyr
                15                  20                  25

ATA CTT ATG AAA ATA ATG ATT TTT TTA CTT CGT GCG GTG AAT CCA TAC      12954
Ile Leu Met Lys Ile Met Ile Phe Leu Leu Arg Ala Val Asn Pro Tyr
            30                  35                  40

TCT CTG ATA TCT AAC AGA GGT TGG CTG TCG CTG GAT AGT ATA AAT CCC      13002
Ser Leu Ile Ser Asn Arg Gly Trp Leu Ser Leu Asp Ser Ile Asn Pro
        45                  50                  55

TTT AAA AAG GAA AAG CGT AGG GAG TCT TTT CTA TCT AGT CTA AAT CCG      13050
Phe Lys Lys Glu Lys Arg Arg Glu Ser Phe Leu Ser Ser Leu Asn Pro
    60                  65                  70

TTT AGA AAA GAG GAA ACA AAG AAA AAA GAA GGT TTC TTT TCT GGT TGG      13098
Phe Arg Lys Glu Glu Thr Lys Lys Lys Glu Gly Phe Phe Ser Gly Trp
75                  80                  85                  90

TTC GGA TAATCTCTTT TATAATTGAA ATAATATTCC AAAAATAAAT CATA ATG ATT     13154
Phe Gly                                                  Met Ile
                                                           1

ACT AAA GCG ATT GTG ATA TTG TCT ATT ATT ACA GCA TAT GTA GAT GCT      13202
Thr Lys Ala Ile Val Ile Leu Ser Ile Ile Thr Ala Tyr Val Asp Ala
        5                   10                  15

TCC GCA TTC TTA GTA TAC AAT TAT ACA TAT ACT TTA CAA GAT GAT AAT      13250
Ser Ala Phe Leu Val Tyr Asn Tyr Thr Tyr Thr Leu Gln Asp Asp Asn
            20                  25                  30

CAT CGA TAT GAC TTC GAA GTC ACC GAT TAT TTT AAT GAT ATA CTA ATA      13298
His Arg Tyr Asp Phe Glu Val Thr Asp Tyr Phe Asn Asp Ile Leu Ile
35                  40                  45                  50

AAA CGT TTA AAA CTA AAT AGC GAG ACA GGA AGA CCA GAA TTA AGA AAT      13346
Lys Arg Leu Lys Leu Asn Ser Glu Thr Gly Arg Pro Glu Leu Arg Asn
```

```
                      55                  60                  65
GAA CCA CCA ACA TGG TTT AAT GAG ACT AAG ATT AGA TAT TAT CCG AAA       13394
Glu Pro Pro Thr Trp Phe Asn Glu Thr Lys Ile Arg Tyr Tyr Pro Lys
                70                  75                  80

AAT AAT TAT AAT TTT ATG TTC TGG CTA AAT AGA ATG AGT GAA ACG CTA       13442
Asn Asn Tyr Asn Phe Met Phe Trp Leu Asn Arg Met Ser Glu Thr Leu
            85                  90                  95

GAT GAG ATA AAT AAA CTT CCA GAA ACG AGT AAT CCT TAC AAG ACT ATG       13490
Asp Glu Ile Asn Lys Leu Pro Glu Thr Ser Asn Pro Tyr Lys Thr Met
        100                 105                 110

TCC TTG ACA ATT GGA TGT ACT GAT CTA AGA CAA CTT CAA GTA AAT TTC       13538
Ser Leu Thr Ile Gly Cys Thr Asp Leu Arg Gln Leu Gln Val Asn Phe
115                 120                 125                 130

GGT TAT GTT ACT GTA GGT GGT AAT ATA TGG ACA CGA TTC GAC CCC AAG       13586
Gly Tyr Val Thr Val Gly Gly Asn Ile Trp Thr Arg Phe Asp Pro Lys
                135                 140                 145

AAT AAA CGC TTT AGT AAA GTT AGA TCA CGT ACA TTT CCA AAG GTA GGA       13634
Asn Lys Arg Phe Ser Lys Val Arg Ser Arg Thr Phe Pro Lys Val Gly
            150                 155                 160

ATG TTA ACT GTT AAA TCA CAA CAC TGG GAA CGT GTT ATG GAA CAT CTT       13682
Met Leu Thr Val Lys Ser Gln His Trp Glu Arg Val Met Glu His Leu
        165                 170                 175

GGA TCA ATG GTA ACA TTA ACA TGT CCG TTT ACA GCG GAT GAT TAT TAT       13730
Gly Ser Met Val Thr Leu Thr Cys Pro Phe Thr Ala Asp Asp Tyr Tyr
180                 185                 190

AAA ATT TCT AAG GGA TAT ATA GAT AAG CCA GTT AAG CCT ACT GTT ACA       13778
Lys Ile Ser Lys Gly Tyr Ile Asp Lys Pro Val Lys Pro Thr Val Thr
195                 200                 205                 210

GTT ACA GGA ATT GAA AGA GGA GAT AAT ACT ACA TTG ATA TGC ACA TTT       13826
Val Thr Gly Ile Glu Arg Gly Asp Asn Thr Thr Leu Ile Cys Thr Phe
                215                 220                 225

GAT AAT CAT TAT CCG TCG TCG GTC GCT GTT AAA TGG TAT AAC ATC GAG       13874
Asp Asn His Tyr Pro Ser Ser Val Ala Val Lys Trp Tyr Asn Ile Glu
            230                 235                 240

GAC TTT GCT CCG GAC TAT CGT TAT GAT CCG TAC GTA AAT GAA TTG CTT       13922
Asp Phe Ala Pro Asp Tyr Arg Tyr Asp Pro Tyr Val Asn Glu Leu Leu
        245                 250                 255

CCT GAT ACG GAC TAT CTA CCG GGT GAA CCA GGA TAT CCG ACT ATA ACT       13970
Pro Asp Thr Asp Tyr Leu Pro Gly Glu Pro Gly Tyr Pro Thr Ile Thr
260                 265                 270

AGG AGA TTA GGT GAT AAA TAT TTA TTT ACA TCA TCA CCT AGG GTT ATG       14018
Arg Arg Leu Gly Asp Lys Tyr Leu Phe Thr Ser Ser Pro Arg Val Met
275                 280                 285                 290

GTA CCA ACT ATC ATG TCT AAT AGA ATA GCA TGT GTT GGA TTT CAT AGT       14066
Val Pro Thr Ile Met Ser Asn Arg Ile Ala Cys Val Gly Phe His Ser
                295                 300                 305

ACG TTA GAA CCA AGC ATA TAT AGA TGT GTA AAC TGC TCG GGA CCT GAG       14114
Thr Leu Glu Pro Ser Ile Tyr Arg Cys Val Asn Cys Ser Gly Pro Glu
            310                 315                 320

CCT GTT TTA CAA TAC CAG GGA GAT AGA AGG AAT GAC TTG GAG GAT GAG       14162
Pro Val Leu Gln Tyr Gln Gly Asp Arg Arg Asn Asp Leu Glu Asp Glu
        325                 330                 335

GAG GAT TAAAGCTT                                                      14176
Glu Asp
    340
```

(2) INFORMATION FOR SEQ ID NO:15:

(i) SEQUENCE CHARACTERISTICS:
        (A) LENGTH: 440 amino acids (B) TYPE: amino acid
(D) TOPOLOGY: linear (ii) MOLECULE TYPE: protein (xi) SEQUENCE DESCRIPTION: SEQ ID NO:15:

```
Met Lys Glu Ile Asn Ser Leu Glu Cys Gln Trp Ser Ile Asp Asp
  1               5                  10                  15

Asn Asn Asp Thr Thr Ile Leu Gly Asp Asp Ile Tyr Phe Asp Tyr Ile
                 20                  25                  30

Ile Ser Gln Leu Asp Ile His Gln Asn Trp Ser Pro Asp Ile Arg Leu
             35                  40                  45

Ile Arg Tyr Phe Arg Lys Phe Asn Lys Glu Ser Phe Asp Lys Ile Ser
         50                  55                  60

Asp Thr Glu Tyr Ile Asn Pro Ser Phe Phe Gln Gln Arg Asp Lys Arg
 65                  70                  75                  80

Phe Tyr Pro Leu Asn Asp Asp Phe Tyr His Ile Ser Thr Gly Gly Tyr
                 85                  90                  95

Gly Ile Val Phe Lys Met Asp Lys Tyr Val Val Lys Phe Val Tyr Glu
                100                 105                 110

Pro Asn Lys Gln Tyr Ser Pro Ile Asp Thr Thr Ala Glu Tyr Thr Ile
            115                 120                 125

Pro Lys Phe Leu Tyr Asn Asn Leu Lys Gly Asp Glu Lys Lys Leu Ile
        130                 135                 140

Val Cys Ala Trp Ala Met Gly Leu Asn Tyr Lys Leu Thr Phe Leu His
145                 150                 155                 160

Arg Leu Tyr Lys Arg Val Leu Tyr Met Leu Leu Ile Ile Gln Thr
                165                 170                 175

Ile Asp Asn Gln Arg Leu Asn Ile His His Phe Ser His Lys Tyr Phe
                180                 185                 190

Leu Lys Ser Phe Asn Glu Lys Lys Ser Asp Ile Lys Phe Val Lys Leu
            195                 200                 205

Leu Ser Tyr Phe Tyr Pro Ile Val Val Gln Ser Asn Ile Asn Val Ile
        210                 215                 220

Asn Tyr Phe Thr His Met Phe His Phe Phe Glu His Glu Lys Arg Ala
225                 230                 235                 240

Asn Tyr Leu Tyr Asp Arg Gly Asn Ile Ile Phe Pro Leu Ala Arg
                245                 250                 255

Phe Ser Ser Asp Lys Val Thr Glu Gln Met Ala Ile Glu Leu Gly Phe
            260                 265                 270

Lys Ser Ile Val Gln Tyr Val Lys Phe Ile Phe Leu Gln Ile Ser Leu
        275                 280                 285

Leu Tyr Ile Lys Ile Tyr Glu Leu Pro Cys Cys Asp Asn Phe Leu His
    290                 295                 300

Val Asp Leu Lys Pro Asp Asn Ile Leu Ile Phe Asn Ser Asp Cys Pro
305                 310                 315                 320

Ile Thr Ile Lys Phe Lys Lys Tyr Thr Tyr Val Phe Asn Glu Pro Ile
                325                 330                 335

Lys Ala Cys Leu Asn Asp Phe Asp Phe Ser Gln Val Ala Asn Ile Leu
            340                 345                 350

Asn Lys Lys Ile Lys Asn Ser Leu Lys Ile Glu His Asn Trp Tyr Tyr
        355                 360                 365

Asp Phe His Phe Ile His Thr Leu Leu Arg Thr Tyr Pro Glu Ile
370                 375                 380
```

```
Glu Ser Asp Lys Glu Phe Ser Asp Ser Leu Glu Asp Phe Ile Met Cys
385                 390                 395                 400

Cys Thr Lys Asn Thr Cys Glu Lys Phe Arg Leu Lys Val Ser Ile Leu
            405                 410                 415

His Pro Ile Ser Phe Leu Glu Asn Leu Ile Thr Lys Asn Ile Phe Ser
                420                 425                 430

Asn Trp Ile Asn Gly Glu Ser Cys
            435                 440
```

(2) INFORMATION FOR SEQ ID NO:16:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO:16:

```
Met His Leu Lys Asn Glu Val Asn Asn Met Phe Val Phe Thr Leu
 1               5                  10                  15

Cys Ile Leu Leu Tyr Ser Ser Phe Cys Tyr Phe Phe Tyr Ile Glu Lys
                20                  25                  30

Ile Leu Gln His Thr Lys Pro Ile Tyr Thr Asn Tyr Gly Gln Leu Cys
                35                  40                  45

Ile Cys Lys Ile Asn Lys Tyr Lys Tyr Gly Tyr Ser Val Asn Ile Phe
            50                  55                  60

Tyr Arg Arg
 65
```

(2) INFORMATION FOR SEQ ID NO:17:

(i) SEQUENCE CHARACTERISTICS:
        (A) LENGTH: 73 amino acids
        (B) TYPE: amino acid
        (D) TOPOLOGY: linear (ii) MOLECULE TYPE: protein (xi) SEQUENCE DESCRIPTION: SEQ ID NO:17:

```
Met Asn Asn Arg Lys Tyr Ser Ile Asn Asn Gly Phe Met Ser Tyr Leu
 1               5                  10                  15

Arg Lys Lys Phe Thr Thr Phe Leu Arg Lys Lys Ser Thr Tyr Arg Ile
                20                  25                  30

Lys Ser Asn Thr Asp Tyr Tyr Gln Glu Asn Glu Lys Leu Ile His Lys
            35                  40                  45

Asn Asn Ile Lys Ile Pro Tyr Lys Val Lys Val Ile Arg Lys Arg Cys
        50                  55                  60

Ser Ser Ser Asp Asp Asp Val Phe Ile
 65                 70
```

(2) INFORMATION FOR SEQ ID NO:18:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO:18:

Met Asn Thr Thr Thr Ser Gln Ile Ile Ile Asp Asn Asp Met Ser Asn

```
  1               5                  10                 15
Glu Val Gly Thr Ile Met Val Ile Thr Leu Cys Leu Val Thr Ile Val
            20                  25                 30

Ile Thr Cys Tyr Leu Leu Gln Leu Val Arg Trp Ser Phe Ile Val
            35                  40                 45

Asp Ile Phe Arg Gln Ile Arg Thr Arg Cys Leu Gln Trp Thr Ser Arg
        50                  55                 60

Arg Glu Phe Leu Gln Leu Asp Asn Met Tyr Tyr Thr Asn Asp Ser Ser
65                  70                  75                 80

Val Gly Val Asn Thr Glu
                85
```

(2) INFORMATION FOR SEQ ID NO:19:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:19:

```
Met Glu Pro Ile Leu Gln Glu Ser Asp Ser Arg Phe Val Ile Phe Pro
1                   5                  10                 15

Ile Lys Tyr His Asp Ile Trp Lys Met Tyr Lys Gln Ser Val Ala Ser
            20                  25                 30

Phe Trp Thr Val Glu Glu Val Asp Leu Ser Lys Asp Leu Asp Asp Trp
            35                  40                 45

Asp Lys Leu Thr Lys Asp Glu Lys Tyr Phe Ile Lys His Ile Leu Ala
        50                  55                 60

Phe Phe Ala Ser Ser Asp Gly Ile Val Asn Glu Asn Leu Ala Glu Arg
65                  70                  75                 80

Phe Tyr Val Asp Val Gln Cys Ser Glu Ala Arg Cys Phe Tyr Gly Phe
                85                  90                 95

Gln Ile Ala Met Glu Asn Ile His Ser Glu Met Tyr Ser Leu Leu Ile
                100                 105                110

Asp Thr Tyr Val Arg Asp Asn Ile Glu Lys Met His Leu Phe Asn Ala
            115                 120                125

Ile Glu Thr Met Glu Cys Val Lys Lys Ala Asp Trp Ala Arg Lys
            130                 135                 140

Trp Ile Ser Ser Asn Lys Val Tyr Gly Glu Arg Val Val Ala Phe Ala
145                 150                 155                160

Ala Val Glu Gly Ile Phe Phe Ser Gly Ser Phe Ala Ala Ile Phe Trp
                165                 170                175

Ile Lys Lys Arg Gly Leu Met Pro Gly Leu Thr Phe Ser Asn Glu Leu
            180                 185                 190

Ile Ser Arg Asp Glu Gly Leu His Cys Asp Phe Ala Cys Leu Met Phe
            195                 200                 205

Lys His Leu Leu His Pro Ser Lys Glu Val Ile Thr Ser Ile Ile
            210                 215                 220

Ile Asp Ala Val Asn Ile Glu Lys Glu Phe Leu Thr Val Ala Ile Pro
225                 230                 235                240

Val Asp Leu Ile Gly Met Asn Cys Cys Leu Met Ser Gln Tyr Ile Glu
                245                 250                 255

Phe Val Ala Asp Arg Leu Leu Thr Glu Leu Gly Cys Glu Lys Ser Gln
            260                 265                 270
```

Cys Ile (2) INFORMATION FOR SEQ ID NO:20:

(i) SEQUENCE CHARACTERISTICS:
        (A) LENGTH: 500 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ser Lys Gln Glu Thr Tyr Ile Asp Tyr Asn Tyr Ile Glu Arg Leu
 1               5                  10                  15

Asn Ala Val Asn Leu Asn Arg Ser Tyr Asp Glu Glu Ile Val Phe Ile
            20                  25                  30

Met Thr Val Gly Gly Val Val Lys Val Lys Lys Glu Leu Leu Val Ser
        35                  40                  45

Val Ser Asn Tyr Phe Lys Leu Ile Thr Lys Asn Gln Ser Asn Glu Ile
    50                  55                  60

Thr Val Ser Phe Gln Tyr Glu Ser Phe Leu Asp Ile Ile Lys Tyr Ile
65                  70                  75                  80

Glu Thr Gly Ile Val Thr Ile Asp Leu Asp Asn Val Glu Asn Ile Phe
                85                  90                  95

Ser Ile Ser Cys Ser Lys Ala Ile Asp Phe Leu Lys Asn Ser Cys Ile
            100                 105                 110

Asp Phe Met Ser Lys His Ile Thr Asp Ser Thr Cys Val Lys Ile Tyr
        115                 120                 125

Lys Ile Gly Phe Ser Asn Gly Cys Phe Ala Val Tyr Asn Asp Ala Ile
    130                 135                 140

Ala Tyr Ile Arg Lys Arg Phe Thr Lys Ile Glu Thr Asp Ile Leu Leu
145                 150                 155                 160

Ser Leu Ser Leu Phe Asp Leu Arg Ile Ile Leu Lys Ser Gly Glu Leu
                165                 170                 175

Asp Val Ser Ser Glu Asp Asp Val Leu Leu Phe Ile Ile Lys Trp Ser
            180                 185                 190

Arg His Lys Lys Ser Asn Arg Arg Lys Ser Phe Thr Leu Val Thr Glu
        195                 200                 205

Val Leu Arg Tyr Asn Tyr Leu Ser Ile Tyr Gly Lys Tyr Lys Leu Thr
    210                 215                 220

Lys Trp Leu Ala Arg Phe Gly Lys Asn Asn Val Glu Leu Asn Glu
225                 230                 235                 240

Asn Glu Leu Pro Arg Ile Ser Tyr Gln His Arg Phe Thr Asn Arg Arg
                245                 250                 255

Tyr Thr Met Val Thr Pro Ser Ser Phe Ser Ile Asn Met Leu Gly Asn
            260                 265                 270

Val Ser Val Lys Asn Glu Leu Ser Ile Ile Asn Ser Ile Ala Glu Asn
        275                 280                 285

His Asn Pro Tyr Cys Gly Ser Val Leu Met Asn Asp Ile Leu Tyr Leu
    290                 295                 300

Ile Gly Gly Ile Asn Lys Ser Leu Asp Pro Val Ser Asp Ile Thr Ser
305                 310                 315                 320

Val Asp Thr Arg Ser Phe Ile Glu Leu His Thr Pro Leu Leu His
                325                 330                 335

Pro Arg Lys Cys Pro Gly Val Ala Ile Phe Lys Asn Arg Ile Tyr Val
```

```
                      340                 345                 350
Val Gly Gly Ile Gly Tyr Asp Gly Pro Leu Lys Thr Val Glu Ser Trp
                355                 360                 365

Ser Pro Gly Glu Gln Gln Trp Arg Glu Val Pro Leu Leu Gln Pro
    370                 375                 380

Arg Phe Asn Pro Cys Ile Ile Gly Thr Asp Asn Asp Leu Tyr Val Val
385                 390                 395                 400

Gly Gly Ile Ser Glu Asp Asp Lys Thr Ile Glu Ile Tyr Ser Tyr Glu
                405                 410                 415

Glu Asn Thr Trp Ser Ile Gly Asn Ala Met Asn Tyr Ser His Phe Gly
                420                 425                 430

Gly Cys Ile Ala Tyr His His Gly Tyr Ile Tyr Met Ile Gly Gly Leu
            435                 440                 445

Ser Phe Ile Asp Asn Ile His Val Phe Thr Met Val Glu Lys Tyr Asn
            450                 455                 460

Pro His Ser Asn Lys Trp Thr Val Glu Lys Ser Leu Pro Phe Pro Arg
465                 470                 475                 480

Phe Asn Ser Ser Leu Cys Ile Ile Glu Asp Ser Ile Ala Ile Ile Gly
                485                 490                 495

Trp Ile Tyr Tyr
            500

(2) INFORMATION FOR SEQ ID NO:21:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO:21:

Met Asn Lys Tyr Asn Asn Tyr Arg Ala Ile Tyr Phe Leu Tyr Lys Val
  1               5                  10                  15

Ile Leu Arg Ile His Asn Thr Glu Tyr Ile Ser Gly Thr Leu Gln Arg
                20                  25                  30

Ser Ile Gln Asn Ile Thr Pro Thr Thr Ser Ser Tyr Thr Tyr Cys Asp
            35                  40                  45

Asn Ser Lys Arg Arg Arg His Arg Phe Arg Asp Thr Glu Ile Leu Lys
     50                  55                  60

Ala Met Gly Ser Lys Met Arg Arg Lys Leu Phe
 65                  70                  75

(2) INFORMATION FOR SEQ ID NO:22:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:22:

Met Ser Leu Tyr Val Lys Cys Val Lys Leu Ser Asn Asn Ala Ile Ile
  1               5                  10                  15

Pro Asn Arg Ser Met Ser Gly Ser Ala Gly Tyr Asp Leu Tyr Ser Ala
                20                  25                  30

Tyr Ser Tyr Thr Val Lys Pro Tyr Asn Arg Ile Leu Val Arg Thr Asp
            35                  40                  45
```

Ile Cys Leu Met Ile Pro Asp Lys Cys Tyr Gly Arg Ile Ser Pro Arg
 50                  55                  60

Ser Gly Leu Ser Leu Asn Tyr Asn Ile Asp Ile Gly Gly Val Ile
 65                  70                  75                  80

Asp Ser Asp Tyr Arg Gly Glu Ile Gly Ile Val Phe Ile Asn Asn Gly
                 85                  90                  95

Cys Ser Asp Phe Asn Ile Lys Val Gly Asp Arg Ile Ala Gln Ile Ile
             100                 105                 110

Phe Glu Arg Val Glu Tyr Pro Ile Met Glu Val Lys Cys Leu Glu
         115                 120                 125

Asp Thr Glu Arg Gly Asn Ser Gly Phe Gly Ser Ser Gly Met
 130                 135                 140

(2) INFORMATION FOR SEQ ID NO:23:

(i) SEQUENCE CHARACTERISTICS:
        (A) LENGTH: 167 amino acids
        (B) TYPE: amino acid
        (D) TOPOLOGY: linear (ii) MOLECULE TYPE: protein (xi) SEQUENCE DESCRIPTION: SEQ ID NO:23:

Met Tyr Lys Lys Tyr Asn Ser Asn Val Cys Ile Arg Asn Val Leu Tyr
 1               5                  10                  15

Val Tyr Leu Lys Tyr Asn Thr Ile Asn Lys Leu Ser Arg Tyr Glu Arg
                 20                  25                  30

Met Ile Tyr Thr Lys Ile Lys Asn Gln Cys Glu Ala Ile Lys Tyr Arg
             35                  40                  45

Tyr Cys Asn Asp Phe Asn Ser Val Thr Cys Ile Leu Glu Tyr Asp Glu
 50                  55                  60

Asn Lys Tyr Ile Asp Asn Val His Lys Glu Val Ile Ser Ile Leu Leu
 65                  70                  75                  80

Ser Asp Ser Arg Pro Ser Ile Lys Leu Ala Ala Ile Ser Leu Leu Ser
                 85                  90                  95

Ile Ile Ile Asp Lys Leu Ile Cys Arg Asn Ile Arg Ile Ala Lys Tyr
             100                 105                 110

Ile Ile Asp Asp Ile Ile Asn Ile Ile Ser Glu Asp Gly Ile Tyr Ile
         115                 120                 125

Ile Leu Phe Leu Asp Glu Phe Asp Lys Tyr Thr Asp Thr Arg Cys Arg
 130                 135                 140

Arg Arg Gly Leu Ser Met Met Ile Ala Ser Ile Val Thr Tyr Tyr Cys
145                 150                 155                 160

Leu Arg Tyr Val Leu Lys Ile
                 165

(2) INFORMATION FOR SEQ ID NO:24:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:24:

Met Asn Arg Asn Met Trp Ile Val Leu Ser Cys Val Leu Tyr Met Ile
 1               5                  10                  15

-continued

```
Tyr Ile Cys Asn Gly Arg Asp Val Leu Leu Tyr Pro Pro His Lys Lys
            20                  25                  30

Thr Asn Lys Val Ile Val Lys Cys Asn Gly Tyr Thr Asn Ser Thr Tyr
        35                  40                  45

Ser Ile Leu Tyr Trp Met Val Gly Asn Asn Asn Thr Phe Val Glu Gln
    50                  55                  60

Leu Asn Ser Asp His Tyr Lys Glu Lys Tyr Asn Ser Thr Glu Lys
65                  70                  75                  80

Asn Glu His Met Tyr Lys Leu Arg Thr Asp Leu Ile Ile Tyr Asn Ile
                85                  90                  95

Thr Ser Glu Met Glu Met Thr Lys Leu Thr Cys Val Leu Ser Asp Ile
                100                 105                 110

Tyr Thr Pro Ile Lys Ala Ser Ile Ile Leu Asn Asn Leu Trp Ser Cys
            115                 120                 125

Leu Asn Thr Thr Gln Val
        130

(2) INFORMATION FOR SEQ ID NO:25:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO:25:

Met Ser Thr Met Asn Thr Leu Ala Phe Cys Tyr Gly Leu Pro Asn Ile
1               5                   10                  15

Asn Asp Ile Thr Gln Gly Ile Ile Phe Val Arg Asn Asn Ile Phe Tyr
            20                  25                  30

Ser Tyr Leu Thr Asp Tyr Ala Met Glu Ala Cys Ile Leu Asn Tyr Ile
        35                  40                  45

Asn Ile Arg Ala Asp Lys Ile Glu Asp Leu Lys Lys Ser Leu Val Gly
    50                  55                  60

Lys Thr Ile Ser Val Arg Val Ile Arg Val Asp Val Leu Lys Gly Tyr
65                  70                  75                  80

Ile Asp Val Ser Ile Val
            85

(2) INFORMATION FOR SEQ ID NO:26:

(i) SEQUENCE CHARACTERISTICS:
        (A) LENGTH: 155 amino acids
        (B) TYPE: amino acid
        (D) TOPOLOGY: linear (ii) MOLECULE TYPE: protein (xi) SEQUENCE DESCRIPTION: SEQ ID NO:26:

Met Asp Pro Val Cys Trp Ile Cys Lys Asp Asp Tyr Ser Ile Glu Lys
1               5                   10                  15

Asn Tyr Cys Asn Cys Lys Asn Glu Tyr Lys Val Val His Asp Glu Cys
            20                  25                  30

Met Lys Lys Trp Ile Gln Tyr Ser Arg Glu Arg Ser Cys Lys Leu Cys
        35                  40                  45

Asn Lys Glu Tyr Asn Ile Ile Ser Val Arg Lys Pro Phe Ser Gln Trp
    50                  55                  60

Val Phe Ser Ile Lys Asp Cys Lys Lys Ser Ala Ile Leu Tyr Ala Thr
```

```
                65                  70                  75                  80
Leu Phe Leu Cys Thr Phe Ile Ile Ser Leu Val Leu Thr Arg Ile Asn
                    85                  90                  95

Ile Thr Lys Ile Ile Asp Thr Ser Lys Asn Asp Val Ser Phe Lys Leu
                100                 105                 110

Val Thr Met Ile Phe Tyr Leu Leu Pro Phe Val Ile Thr Cys Ile Ser
                115                 120                 125

Phe Ile Thr Leu Ile Val Tyr Leu Tyr Lys Tyr Cys Lys Ile Ser Ala
                130                 135                 140

Lys Asn Asn Thr Tyr Asp Thr Ile Tyr Glu Leu
145                 150                 155
```

(2) INFORMATION FOR SEQ ID NO:27:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:27:

```
Met His Phe Ile Phe Ile Ile Leu Ser Leu Ser Phe Val Val Asn Ala
1               5                   10                  15

Asp Val Phe Pro Ser Ser Val Thr Leu Ser Ser Asn Asp Phe Asp Thr
                20                  25                  30

Ile Ile Lys Trp Asp Asn Asn Val Ile Ser Tyr Asp Val Glu Leu Met
                35                  40                  45

Gln Tyr Ser His Asp Glu Trp Arg Thr Val Cys Thr Asn Ser Leu Gly
    50                  55                  60

Tyr Cys Asn Leu Thr Asn Ser Asp Ile Asp Asn Asp Glu Thr Trp
65                  70                  75                  80

Val Arg Phe Lys Tyr Glu Asn Lys Thr Ser Asn Glu His Asn Ile Gly
                85                  90                  95

Arg Val Cys Glu Ile Val Gln Ile Thr Ser Pro Ile Val Asn Met Thr
                100                 105                 110

Arg Asp Gly Ser Ile Ile Leu Leu Asp Ile His His Pro Met Thr Tyr
                115                 120                 125

Asp Asn Gln Tyr Tyr Ile Tyr Asn Asn Ile Thr Leu Cys Gly Phe Glu
130                 135                 140

Phe Ile Tyr Glu Ala Thr Phe Ile Ile Asn Asp Thr Ile Ile Pro Tyr
145                 150                 155                 160

Ser Ile Asp Asn Gln Tyr Cys Asp Asp Val His Cys Leu Phe Tyr Phe
                165                 170                 175

Ile Ser Gln Glu Pro Val Cys Val Tyr Val Met Gly Met Glu Gln Tyr
                180                 185                 190

Tyr Glu Phe Gly Pro Lys Lys Thr Asp Asn Ser Thr Arg Val Cys Val
                195                 200                 205

Asp Gly Leu Ile Pro Arg Lys Ile Asp Thr Tyr Phe Ile Lys Asp Phe
                210                 215                 220

Asp Asp Ile Asp Arg Val Asn Asn Arg Leu Tyr Arg Val Val Ser Asp
225                 230                 235                 240

Lys Tyr Glu Ser Asn Ile Ser Ser Lys Phe Met His Leu Tyr Asn Asn
                245                 250                 255

Ile Leu Ser Ser Phe Lys Leu Ile Leu Gln Glu Leu Met Val Asn Thr
                260                 265                 270
```

Glu Gln (2) INFORMATION FOR SEQ ID NO:28:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:28:

```
Met Asn Ser Tyr Ile Val Ile Lys Asn Ser Leu Arg Asp Tyr Arg Ser
 1               5                  10                  15

Gly Arg Ile Ile Arg Lys Tyr Ile Arg Lys Leu Asn Lys Asp Glu Tyr
                20                  25                  30

Lys His Phe Cys Ala Val Phe Arg Leu Asn Val Asp Phe Ser Gln Asp
            35                  40                  45

Asp Lys Asn Pro Ser Arg Lys Glu Val Ile Arg Ile Ile Asp Glu Glu
        50                  55                  60

Phe Asn Phe Cys Asp Leu Arg Leu Phe Tyr Asp Ile Met Thr Val Val
 65                 70                  75                  80

Pro Asn His Met Asn Val Ala Ser Ile Ile Tyr Ser Glu Tyr Glu Tyr
                85                  90                  95

Leu Leu Lys Lys Ser Asn Tyr Lys Asn Lys Lys Ile Asn Tyr Thr Ile
               100                 105                 110

Leu Asp Lys Ile Asn Lys Tyr His Ser Ile Asp Asp Ile Ile Phe Met
           115                 120                 125

Tyr Leu His Trp Arg Lys Lys Tyr Asn Asn Thr Cys Ala Cys Gly Lys
130                 135                 140

Leu Phe Lys Glu Leu Met Lys Tyr Asp Ile Leu Ala Thr Lys Tyr Ile
145                 150                 155                 160

Tyr Asn Asp Ile Ile Asn Thr Tyr Lys Glu Gly Asp Thr Ile Ser Ile
                165                 170                 175

Asn Ile Arg Leu Lys Cys Lys Asp Asp Ile Ile Lys His Cys Lys Ser
            180                 185                 190

Ser Ile Gly Met Phe Ala Ile Leu Ser Ser Lys Ile Ile Asp Val Asp
        195                 200                 205

Phe Asp Val Ile Phe Phe Ser Gln Ile Ser Ile Arg Tyr Arg Leu Ile
    210                 215                 220

Phe Lys Lys Tyr Leu Ile Gln Ser Leu Tyr Leu Gln
225                 230                 235
```

(2) INFORMATION FOR SEQ ID NO:29:

(i) SEQUENCE CHARACTERISTICS:
        (A) LENGTH: 530 amino acids
        (B) TYPE: amino acid
        (D) TOPOLOGY: linear (ii) MOLECULE TYPE: protein (xi) SEQUENCE DESCRIPTION: SEQ ID NO:29:

```
Met Asn Ser Leu Leu Leu Arg Leu His Asp Phe Phe Lys His Gly Ile
 1               5                  10                  15

Met Cys Asp Ile Lys Ile Val Ser Ile Glu Asn Asn Lys Thr Ile Ser
                20                  25                  30

Ala His Arg Leu Ile Leu Ser Met Tyr Ser Lys Tyr Phe Tyr Asn Ile
```

```
                    35                  40                  45
    Phe Asn Ser Asp Phe Ile Asp Lys Asn Asn Asp Glu Ile Tyr Ile Cys
                50                  55                  60

Ala Asp Tyr Asp Ile Leu Tyr Ile Ile Leu Glu Phe Met Tyr Thr Gly
 65                  70                  75                  80

Asn Ile Val Leu Thr Lys Asp Asn Ile Glu Leu Val Ile Gln Val Cys
                    85                  90                  95

Asp Tyr Leu Cys Ile Asp Ser Leu Ile Lys Ile Cys Glu Glu Tyr Ile
                    100                 105                 110

Cys Gly Ile Ile Asp Glu Thr Asn Cys Ile His Leu Leu Asn Phe Ser
                    115                 120                 125

Asp Thr Tyr Asn Leu Gln Arg Leu Arg Glu Met Ser Lys Trp Tyr Leu
                    130                 135                 140

Pro Lys Ile Ile Asn Asn Asn Lys Leu Val Val Glu Leu Asp Ile Asp
145                 150                 155                 160

Asp Met Ile Leu Ile Ile Lys Glu Ile Lys Tyr Ile Ala Cys Glu Tyr
                    165                 170                 175

Ile Val Lys Lys Ile Ile Leu Asn Trp Ile Val His Lys Asp Glu Arg
                    180                 185                 190

Ile Ile Tyr Thr Lys Lys Leu Met Lys His Ile Asn Asp Gln Asp His
                    195                 200                 205

Tyr Thr Ser Leu Ser Asp Ile Glu Leu Tyr Asn Asn Ile Arg Glu Arg
                    210                 215                 220

Ile Tyr Asp Asn Lys Glu His Asp Val Asp Ile Ser His Asn Phe Ile
225                 230                 235                 240

Ile Met Val Gly Gly Lys Lys Ile Phe Asn Ile Thr Ala Phe Asn Pro
                    245                 250                 255

Leu Ser Asn Lys Lys His Ile Ile Asp Arg Tyr Asp Asp Met Phe Gly
                    260                 265                 270

Cys Lys Thr His Phe Ser Val Val Tyr Leu Asn Ser Ile Leu Tyr Ile
                    275                 280                 285

Ile Gly Gly Lys Lys Arg Gly Tyr Phe Thr Lys Glu Val Leu Ser Tyr
                    290                 295                 300

Asn Ile Lys Asn Lys Leu Trp Cys Tyr Glu Pro Glu Leu Asn Tyr Phe
305                 310                 315                 320

Arg Tyr Asp Thr Ser Val Cys Val Ser Asn Gly Met Ile Tyr Ser Ile
                    325                 330                 335

Gly Gly Lys Asp Thr Asn Gly Tyr Met Thr Asn Ile Val Glu Phe Trp
                    340                 345                 350

Lys Pro Glu Trp Lys Ser Trp Tyr Asp Gly Gln His Leu Cys Tyr Pro
                    355                 360                 365

Arg Cys Tyr Met Ser Leu Val Asp Tyr Asn Asn Glu Val Tyr Thr Ile
                    370                 375                 380

Gly Gly Leu Lys Thr Ser Ile Thr Asp Glu Phe Asn Ile Glu Met Ile
385                 390                 395                 400

Val Ser Asp Asp Ala Val Glu Lys Leu Thr Asp His Ser Trp Met Lys
                    405                 410                 415

Leu Lys Gln Phe Pro Ile Ala Lys Ser Gly Ile Ser Ser Ile Val Tyr
                    420                 425                 430

Asn Asp Phe Ile Tyr Cys Ile Gly Gly Arg Ile Asp Thr Pro His Ile
                    435                 440                 445

Ser Ile Glu His Thr Asn Asp Val Tyr Ile Tyr Ser Ser Arg Asp Asp
450                 455                 460
```

```
Cys Trp Lys Tyr Leu Ser Asn Thr Asn Val Lys Arg Ser Phe Cys Leu
465                 470                 475                 480

Ser Cys Val Phe Asn Asn Glu Leu Tyr Ile Ile Gly Gly Tyr Asn Thr
            485                 490                 495

Asn Ser Val Glu Lys Tyr Asn Lys Leu Lys Asn Thr Trp Lys Arg Leu
            500                 505                 510

Asn Asp Ile Pro Lys Phe Glu Glu Cys Val Asn Glu Ala Ser Ala Ile
            515                 520                 525

Tyr Leu
    530

(2) INFORMATION FOR SEQ ID NO:30:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO:30:

Met Ser Asp Cys Ile Phe Val Phe Gln Ile Pro Phe Ile Val Tyr Ser
1               5                   10                  15

Lys Leu Asp Gln Trp Ile Phe Gly Asn Ile Leu Cys Lys Ile Met Ser
            20                  25                  30

Val Leu Tyr Tyr Val Gly Phe Phe Ser Asn Met Phe Ile Ile Thr Leu
            35                  40                  45

Met Ser Ile Asp Arg Tyr Phe Ala Ile Val His Pro Ile Lys Arg Gln
    50                  55                  60

Pro Tyr Arg Thr Lys Arg Ile Gly Ile Leu Met Cys Cys Ser Ala Trp
65                  70                  75                  80

Leu Leu Ser Leu Ile Leu Ser Ser Pro Val Ser Lys Leu Tyr Glu Asn
                85                  90                  95

Ile Pro His Met Ser Lys Asp Ile Tyr Gln Cys Thr Leu Thr Asn Glu
            100                 105                 110

Asn Asp Ser Ile Ile Ala Phe Ile Lys Arg Leu Met Gln Ile Glu Ile
            115                 120                 125

Thr Ile Leu Gly Phe Leu Ile Pro Ile Ile Phe Val Tyr Cys Tyr
    130                 135                 140

Tyr Arg Ile Phe Ser Thr Val Val Arg Leu Arg Asn Arg Lys Tyr
145                 150                 155                 160

Lys Ser Ile Lys Ile Val Leu Met Ile Val Val Cys Ser Leu Ile Cys
            165                 170                 175

Trp Ile Pro Leu Tyr Ile Val Leu Met Ile Ala Thr Ile Val Ser Leu
            180                 185                 190

Tyr Thr Ser Asn Ile Phe Arg His Leu Cys Leu Tyr Leu Asn Leu Ala
        195                 200                 205

Tyr Ala Ile Thr Phe Ser Glu Thr Ile Ser Leu Ala Arg Cys Cys Ile
        210                 215                 220

Asn Pro Ile Ile Tyr Thr Leu Ile Gly Glu His Val Arg Ser Arg Ile
225                 230                 235                 240

Ser Ser Ile Cys Ser Cys Ile Tyr Arg Asp Asn Arg Ile Arg Lys Lys
            245                 250                 255

Leu Phe Ser Arg Lys Ser Ser Ser Ser Asn Ile Ile
            260                 265
```

(2) INFORMATION FOR SEQ ID NO:31:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO:31:

```
Met Leu Ser Tyr Ile Ile Asn Pro Leu Leu Ser Ile Val Tyr Phe Ile
  1               5                  10                  15

Leu Gly Asn Val Ser Lys Leu Leu Thr Tyr Ile Leu Met Lys Ile Met
                 20                  25                  30

Ile Phe Leu Leu Arg Ala Val Asn Pro Tyr Ser Leu Ile Ser Asn Arg
             35                  40                  45

Gly Trp Leu Ser Leu Asp Ser Ile Asn Pro Phe Lys Lys Glu Lys Arg
         50                  55                  60

Arg Glu Ser Phe Leu Ser Ser Leu Asn Pro Phe Arg Lys Glu Glu Thr
 65                  70                  75                  80

Lys Lys Lys Glu Gly Phe Phe Ser Gly Trp Phe Gly
                 85                  90
```

(2) INFORMATION FOR SEQ ID NO:32:

(i) SEQUENCE CHARACTERISTICS:
        (A) LENGTH: 340 amino acids
        (B) TYPE: amino acid
        (D) TOPOLOGY: linear (ii) MOLECULE TYPE: protein (xi) SEQUENCE DESCRIPTION: SEQ ID NO:32:

```
Met Ile Thr Lys Ala Ile Val Ile Leu Ser Ile Ile Thr Ala Tyr Val
  1               5                  10                  15

Asp Ala Ser Ala Phe Leu Val Tyr Asn Tyr Thr Tyr Thr Leu Gln Asp
                 20                  25                  30

Asp Asn His Arg Tyr Asp Phe Glu Val Thr Asp Tyr Phe Asn Asp Ile
             35                  40                  45

Leu Ile Lys Arg Leu Lys Leu Asn Ser Glu Thr Gly Arg Pro Glu Leu
         50                  55                  60

Arg Asn Glu Pro Pro Thr Trp Phe Asn Glu Thr Lys Ile Arg Tyr Tyr
 65                  70                  75                  80

Pro Lys Asn Asn Tyr Asn Phe Met Phe Trp Leu Asn Arg Met Ser Glu
                 85                  90                  95

Thr Leu Asp Glu Ile Asn Lys Leu Pro Glu Thr Ser Asn Pro Tyr Lys
                100                 105                 110

Thr Met Ser Leu Thr Ile Gly Cys Thr Asp Leu Arg Gln Leu Gln Val
                115                 120                 125

Asn Phe Gly Tyr Val Thr Val Gly Gly Asn Ile Trp Thr Arg Phe Asp
            130                 135                 140

Pro Lys Asn Lys Arg Phe Ser Lys Val Arg Ser Arg Thr Phe Pro Lys
145                 150                 155                 160

Val Gly Met Leu Thr Val Lys Ser Gln His Trp Glu Arg Val Met Glu
                165                 170                 175

His Leu Gly Ser Met Val Thr Leu Thr Cys Pro Phe Thr Ala Asp Asp
                180                 185                 190

Tyr Tyr Lys Ile Ser Lys Gly Tyr Ile Asp Lys Pro Val Lys Pro Thr
```

-continued

```
                     195                 200                 205
Val Thr Val Thr Gly Ile Glu Arg Gly Asp Asn Thr Thr Leu Ile Cys
    210                 215                 220

Thr Phe Asp Asn His Tyr Pro Ser Ser Val Ala Val Lys Trp Tyr Asn
225                 230                 235                 240

Ile Glu Asp Phe Ala Pro Asp Tyr Arg Tyr Asp Pro Tyr Val Asn Glu
            245                 250                 255

Leu Leu Pro Asp Thr Asp Tyr Leu Pro Gly Glu Pro Gly Tyr Pro Thr
            260                 265                 270

Ile Thr Arg Arg Leu Gly Asp Lys Tyr Leu Phe Thr Ser Ser Pro Arg
            275                 280                 285

Val Met Val Pro Thr Ile Met Ser Asn Arg Ile Ala Cys Val Gly Phe
    290                 295                 300

His Ser Thr Leu Glu Pro Ser Ile Tyr Arg Cys Val Asn Cys Ser Gly
305                 310                 315                 320

Pro Glu Pro Val Leu Gln Tyr Gln Gly Asp Arg Arg Asn Asp Leu Glu
            325                 330                 335

Asp Glu Glu Asp
            340
```

(2) INFORMATION FOR SEQ ID NO:33:

(i) SEQUENCE CHARACTERISTICS:
        (A) LENGTH: 67 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:33:

```
Met Met Ile Ser Ile Ile Tyr Gln Gln Glu Val Met Val Ser Tyr Leu
1               5                   10                  15

Lys Trp Ile Asn Thr Leu Leu Asn Leu Phe Met Asn Gln Ile Asn Ser
            20                  25                  30

Ile Val Pro Leu Ile Gln Leu Pro Ser Ile Gln Tyr Leu Asn Phe Tyr
        35                  40                  45

Ile Ile Ile Leu Arg Glu Met Arg Lys Asn Leu Ser Phe Val His Gly
    50                  55                  60

Gln Trp Val
65
```

(2) INFORMATION FOR SEQ ID NO:34:

(i) SEQUENCE CHARACTERISTICS:
        (A) LENGTH: 215 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:34:

```
Met Glu Asn Pro Val Arg Ile Asn Thr Leu Tyr Asn Val Phe Val Glu
1               5                   10                  15

Arg Tyr Ile Glu Asn Leu Ser Ile Tyr Ser Ile Pro Ile Asn Ser Thr
            20                  25                  30

Cys Gly Ile His Ile Gly Glu Ile Lys Gly Thr Phe Lys Arg Cys Phe
        35                  40                  45
```

```
Leu Lys Ile Leu Asn Met Cys Ile Asn Asp Lys Glu Leu Ser Phe Asn
 50                  55                  60

Ile Leu Ile Lys Thr Leu Lys Asp Val Thr Ser Thr Leu Ser Gln Lys
 65                  70                  75                  80

Glu Lys Glu Glu Leu Ser Lys Glu Ile Gly Ile Asp Ile Leu Asn Asn
                 85                  90                  95

Asp Pro Lys Tyr Val Pro Glu Ile Arg Asn Cys Ser Ser Ser Ala
             100                 105                 110

Asp Val Thr Asn Ile Ile Asp Ile Gln Thr Leu Asp Val Gly Lys Cys
             115                 120                 125

Ile Ala Pro Tyr Asp Lys Gln Ile Leu Leu Gln Ile Val Asn Ser Gly
             130                 135                 140

Thr Ala Glu Ala Asn Cys Val Met Asn Ser Ile Met Asn Ser Met Asn
145                 150                 155                 160

Arg Arg Tyr Ile Asp Asn Ala Asn Ile Tyr Asn Tyr Leu Asn Leu Thr
                165                 170                 175

Asn Arg Pro Trp Phe Ile Phe Ser Ile Ile Ile Ala Ile Ile Phe
             180                 185                 190

Val Ile Gly Ile Cys Ser Ile Lys Arg Arg Ile Gly Ile Lys Tyr Lys
             195                 200                 205

Tyr Gly Thr Phe Leu Tyr Val
 210                 215

(2) INFORMATION FOR SEQ ID NO:35:

(i) SEQUENCE CHARACTERISTICS:
        (A) LENGTH: 70 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:35:

Met Gly Ser Cys Val Ser Val Lys Ser Ile Ser Ile Ser Met Asp Thr
 1                5                  10                  15

Val Ser Ile Ser Ser Ile Asp Asp Glu Tyr Tyr Tyr Asn Ile Lys Asn
                 20                  25                  30

Lys Pro Ile Tyr Val Arg Arg Lys Asn Ser Cys Ser Ser Thr Leu Glu
             35                  40                  45

Ser Arg Tyr Ser Thr Tyr Ser Leu Glu Ser Arg Tyr Ser Thr Tyr Ser
 50                  55                  60

Ile Lys Ser Val Tyr Phe
 65                  70

(2) INFORMATION FOR SEQ ID NO:36:

(i) SEQUENCE CHARACTERISTICS:
        (A) LENGTH: 1323 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:36:

ATGAAAGAAA TTAATTCGTT AGAATGTCAG TGGGAGTCTA TCGATGATAA TAATGATACA      60

ACTATTCTCG GTGATGATAT ATATTTTGAT TATATAATTT CTCAGTTAGA TATACATCAA     120

AATTGGTCTC CTGATATCAG ACTAATAAGA TATTTTAGGA AGTTTAACAA AGAATCATTT     180
```

```
GATAAAATAT CAGATACGGA ATATATTAAC CCATCTTTTT TCCAACAAAG AGATAAACGA      240

TTTTATCCAC TTAATGATGA TTTCTATCAT ATATCAACAG GAGGTTATGG TATCGTATTT      300

AAAATGGATA AATACGTTGT TAAATTTGTT TATGAACCAA ATAAACAGTA TAGTCCCATT      360

GATACAACTG CCGAGTATAC AATACCTAAA TTTTTATATA ATAATCTTAA GGGAGATGAG      420

AAAAAACTTA TCGTTTGTGC ATGGGCAATG GGTTTAAATT ATAAATTAAC ATTTCTACAT      480

AGATTATATA AAAGAGTATT ATATATGTTA TTACTTATTA TTCAAACGAT AGATAATCAA      540

CGATTAAATA TTCATCATTT TTCTCATAAG TATTTTCTTA AGTCGTTCAA TGAAAAAAAG      600

AGCGATATAA AATTTGTAAA ATTATTATCA TATTTTTATC CTATTGTTGT TCAAAGTAAT      660

ATAAATGTAA TAAATTATTT TACACATATG TTTCATTTTT TCGAACATGA AAAAAGAGCT      720

AATTATTTAT ACGATAGAGG AAATATAATT ATATTCCCAT TAGCAAGATT TTCATCAGAT      780

AAAGTGACGG AACAGATGGC GATAGAACTT GGTTTTAAAT CTATAGTTCA ATATGTTAAG      840

TTTATTTTTT TACAAATATC ATTGTTATAT ATAAAAATAT ACGAACTTCC TTGTTGTGAT      900

AATTTTTTAC ACGTTGATTT AAAACCCGAT AATATTTTAA TATTTAATTC TGATTGTCCT      960

ATAACTATTA AATTTAAGAA ATATACATAC GTATTTAATG AACCGATTAA AGCGTGTCTT     1020

AACGATTTCG ATTTTTCACA GGTGGCTAAT ATATTAAATA AGAAAATTAA AAATAGTTTA     1080

AAAATAGAAC ACAATTGGTA TTATGATTTT CATTTTTTTA TACATACACT TCTACGAACT     1140

TATCCAGAAA TAGAATCTGA TAAAGAATTC AGCGATTCTT TAGAGGATTT TATAATGTGT     1200

TGTACAAAAA ATACATGTGA GAAATTTAGA TTAAAAGTAT CCATACTGCA TCCTATATCA     1260

TTTTTAGAAA ATTTGATTAC AAAAAACATT TTCTCAAATT GGATAAATGG AGAATCCTGT     1320

TAG                                                                  1323

(2) INFORMATION FOR SEQ ID NO:37:

(i) SEQUENCE CHARACTERISTICS:
        (A) LENGTH: 204 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:37:

ATGCACCTTA AAAATGAAGT AAATAATAAT ATGTTTGTTT TTACTTTATG TATTTTATTA       60

TACTCGTCTT TTTGTTATTT TTTTTATATT GAAAAAATAT TGCAACATAC AAAGCCAATA      120

TATACGAACT ATGGGCAGTT GTGTATCTGT AAAATCAATA AGTATAAGTA TGGATACAGT      180

GTCAATATCT TCTATAGACG ATGA                                            204

(2) INFORMATION FOR SEQ ID NO:38:

(i) SEQUENCE CHARACTERISTICS:
        (A) LENGTH: 222 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:38:

ATGAATAATC GTAAGTATTC AATAAATAAT GGTTTTATGT CATATTTACG AAAGAAATTT       60

ACTACATTTT TAAGAAAGAA ATCAACTTAT AGGATAAAAT CTAATACCGA CTATTACCAG      120
```

```
GAGAATGAAA AGTTGATACA TAAAAATAAC ATCAAAATAC CTTATAAAGT AAAAGTTATA      180

AGGAAACGTT GTAGTAGTAG CGATGATGAT GTTTTTATTT AG                         222
```

(2) INFORMATION FOR SEQ ID NO:39:

(i) SEQUENCE CHARACTERISTICS:
        (A) LENGTH: 261 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:39:

```
ATGAATACAA CAACTTCACA AATAATTATA GATAATGATA TGTCTAATGA AGTTGGAACA       60

ATAATGGTAA TTACATTATG TTTAGTTACT ATCGTGATAA CGTGTTATTT ACTACTACAA      120

TTAGTAAGAT GGTCGTTTAT AGTAGATATA TTTAGACAAA TAAGAACTAG ATGTTTACAA      180

TGGACATCGA AGAGAATT TTTACAATTA GATAATATGT ATTATACGAA CGATAGCAGC        240
```
*(ATGGACATCGA AGAGAATT TTTACAATTA GATAATATGT ATTATACGAA CGATAGCAGC 240)*
```
GTTGGTGTTA ATACCGAATA A                                                261
```

(2) INFORMATION FOR SEQ ID NO:40:

(i) SEQUENCE CHARACTERISTICS:
        (A) LENGTH: 825 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:40:

```
ATGGAGCCTA TTCTTCAAGA GTCTGATTCT AGGTTCGTTA TTTTCCCTAT TAAGTATCAT       60

GATATCTGGA AAATGTATAA ACAATCAGTG GCAAGTTTTT GGACCGTTGA AGAAGTAGAT      120

TTATCAAAAG ATTTAGATGA TTGGGATAAA TTAACTAAAG ACGAAAAATA CTTTATAAAA      180

CATATACTAG CATTTTTTGC ATCTAGTGAT GGTATTGTAA ATGAGAATTT AGCGGAAAGA      240

TTTTATGTGG ATGTACAGTG TTCAGAGGCA CGATGTTTCT ATGGATTTCA AATAGCTATG      300

GAAAATATTC ATTCAGAAAT GTATAGTTTA TTAATAGATA CATATGTAAG AGATAATATA      360

GAAAAAATGC ATTTATTTAA CGCTATAGAA ACAATGGAAT GCGTAAAAAA GAAAGCTGAT      420

TGGGCCAGAA AATGGATATC TAGCAACAAG GTATATGGAG AAAGAGTAGT AGCATTTGCA      480

GCTGTGGAGG GAATATTCTT TTCTGGTTCA TTTGCTGCTA TATTTGGAT AAAAAAACGA       540
```
*(GCTGTGGAGG GAATATTCTT TTCTGGTTCA TTTGCTGCTA TATTTTGGAT AAAAAAACGA 540)*
```
GGATTGATGC CCGGATTAAC ATTTTCTAAT GAACTAATAA GTAGAGACGA AGGTTTACAT      600

TGTGATTTTG CGTGTTTAAT GTTTAAACAT TTATTACATC CACCATCTAA GGAAGTTATA      660

ACGTCGATAA TCATTGATGC GGTTAATATA GAAAAGGAGT TTTTGACAGT TGCTATTCCG      720

GTGGATCTTA TAGGTATGAA TTGTTGTTTA ATGTCTCAGT ATATAGAATT CGTCGCAGAT      780

AGATTATTAA CAGAGTTAGG TTGTGAAAAG TCTCAATGTA TATAA                      825
```

(2) INFORMATION FOR SEQ ID NO:41:

(i) SEQUENCE CHARACTERISTICS:
        (A) LENGTH: 1503 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:41:

```
ATGTCTAAAC AAGAAACTTA CATTGATTAT AACTATATAG AAAGGTTAAA TGCTGTGAAT        60

CTAAACAGAA GTTATGATGA AGAGATAGTA TTTATTATGA CCGTTGGTGG TGTTGTTAAA       120

GTAAAAAAAG AATTACTTGT ATCTGTATCT AATTACTTTA AACTTATTAC AAAGAATCAG       180

AGTAATGAAA TAACGGTTTC ATTCCAGTAT GAATCTTTTC TTGATATAAT AAAATATATA       240

GAAACTGGAA TCGTTACTAT CGATTTAGAC AATGTAGAAA ATATTTTTTC CATATCTTGT       300

AGTAAAGCCA TAGATTTTTT AAAAAATTCA TGTATTGATT TTATGTCAAA ACATATAACG       360

GATTCTACAT GTGTTAAGAT TTACAAAATA GGTTTCTCGA ATGGATGTTT TGCGGTATAT       420

AATGATGCTA TAGCATATAT AAGGAAAAGA TTCACAAAAA TAGAAACAGA TATATTACTA       480

TCGTTATCCT TATTTGATTT GAGAATAATT CTAAAAAGTG GAGAATTAGA TGTATCATCA       540

GAAGATGATG TATTATTATT TATAATAAAA TGGTCTAGAC ATAAAAAATC CAACAGACGA       600

AAATCGTTTA CACTAGTAAC AGAGGTACTA AGATATAATT ATCTATCCAT ATATGGTAAG       660

TATAAATTAA CAAAATGGTT GGCACGATTC GGAAAAAATA ATAATGTAGA GTTAAATGAA       720

AATGAATTAC CTAGAATAAG TTATCAACAT AGATTTACAA ACAGAAGATA TACGATGGTT       780

ACACCATCTT CATTTAGTAT AAATATGCTA GGTAATGTAT CTGTTAAGAA TGAACTTAGT       840

ATAATCAATA GTATAGCTGA GAATCATAAT CCTTACTGTG GATCTGTACT TATGAATGAT       900

ATATTATATC TTATAGGTGG TATAAATAAA TCATTGGATC CTGTTAGTGA TATAACTAGC       960

GTAGACACTA GATCATTTAT AGAGTTGCAT ACACCACCAT TATTACATCC TAGAAAGTGT      1020

CCGGGTGTTG CTATTTTTAA AAATAGAATT TATGTGGTAG GTGGTATAGG ATACGATGGA      1080

CCATTAAAAA CAGTAGAAAG TTGGTCACCT GGAGAACAAC AATGGAGAGA AGAAGTACCA      1140

TTATTACAAC CCAGATTTAA TCCTTGCATA ATTGGAACAG ATAATGATTT ATATGTTGTT      1200

GGTGGTATTT CTGAAGATGA TAAAACTATT GAAATCTATT CTTATGAAGA AAACACTTGG      1260

TCTATTGGTA ATGCGATGAA TTATTCACAT TTTGGTGGAT GTATAGCATA TCACCATGGT      1320

TATATATATA TGATTGGTGG TTTATCTTTT ATAGATAATA TTCATGTATT TACTATGGTT      1380

GAGAAGTATA ACCCTCATTC GAATAAATGG ACTGTAGAAA AGTCTCTACC CTTTCCTCGA      1440

TTTAATTCAT CGCTTTGTAT TATAGAAGAC TCTATCGCTA ATAGGCTG GATATATTAT        1500

TAA                                                                    1503
```

(2) INFORMATION FOR SEQ ID NO:42:

(i) SEQUENCE CHARACTERISTICS:
        (A) LENGTH: 228 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:42:

```
ATGAATAAAT ATAATAATTA TAGAGCAATT TATTTTCTCT ATAAAGTCAT ATTACGAATA        60

CATAATACAG AATATATAAG TGGAACACTA CAAAGATCTA TACAGAATAT AACACCTACA       120

ACATCATCAT ATACGTATTG TGATAATTCA AAAAGACGCA GACATAGATT TAGAGATACG       180

GAAATCCTTA AAGCTATGGG TAGTAAAATG CGTAGAAAAC TTTTTTAG                    228
```

(2) INFORMATION FOR SEQ ID NO:43:

(i) SEQUENCE CHARACTERISTICS:

(A) LENGTH: 429 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:43:

ATGTCACTAT ATGTTAAATG TGTTAAGTTA TCTAATAATG CTATTATACC AAATAGATCA      60

ATGAGCGGAT CCGCTGGATA TGATCTGTAT AGTGCATATA GTTATACAGT TAAGCCGTAT     120

AATAGAATTT TAGTTAGAAC AGATATTTGT TTAATGATAC CAGATAAATG TTATGGACGC     180

ATATCGCCTA GATCGGGATT ATCGTTAAAT TATAATATAG ATATAGGAGG AGGCGTTATT     240

GATAGTGATT ACAGAGGGGA AATAGGTATC GTGTTTATAA AATGGATG TAGTGATTTT       300

AACATAAAGG TAGGTGATAG GATAGCACAA ATAATATTTG AAAGAGTAGA ATATCCTATA     360

ATGGAAGAAG TAAAATGTTT GGAAGATACA GAACGTGGAA ATAGTGGTTT TGGGTCAAGT    420

GGTATGTAA                                                             429

(2) INFORMATION FOR SEQ ID NO:44:

(i) SEQUENCE CHARACTERISTICS:
        (A) LENGTH: 504 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:44:

ATGTACAAGA AATATAACTC TAACGTATGC ATTAGGAATG TATTATATGT ATATCTAAAA      60

TATAATACTA TAAATAAACT TAGTAGATAT GAACGGATGA TATACACAAA GATAAAAAAT     120

CAATGTGAAG CGATAAAATA CAGATATTGT AATGATTTTA ATTCTGTTAC ATGTATTTTA     180

GAATACGATG AAAATAAGTA TATAGATAAC GTGCATAAAG AAGTTATTAG TATATTGTTA     240

TCAGATTCGC GACCTAGTAT CAAATTAGCT GCTATTTCGT TATTATCTAT AATAATAGAT     300

AAACTAATAT GTAGAAATAT TCGTATAGCT AAATATATAA TTGATGATAT AATAAATATT     360

ATATCAGAAG ACGGTATATA TATTATATTA TTTTTAGATG AATTTGATAA ATATACCGAT     420

ACCCGATGTA GGCGCCGTGG ATTAAGTATG ATGATAGCGA GCATTGTAAC TTACTACTGT     480

TTACGGTATG TATTAAAAAT ATAA                                            504

(2) INFORMATION FOR SEQ ID NO:45:

(i) SEQUENCE CHARACTERISTICS:
        (A) LENGTH: 405 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:45:

ATGAACCGTA ATATGTGGAT AGTGTTATCG TGTGTATTAT ATATGATTTA TATATGTAAC      60

GGACGAGATG TATTGTTATA TCCACCACAT AAGAAAACAA ATAAGGTTAT AGTAAAATGT    120

AACGGATATA CTAATTCTAC GTATAGTATC TTATATTGGA TGGTAGGTAA CAACAATACA    180

TTCGTAGAAC AACTAAATAG CGATCATTAT AAAGAGAAGA AATACAATAG TACTGAAAAA    240

AATGAGCATA TGTATAAGTT ACGTACCGAT CTTATTATAT ATAATATTAC GTCAGAAATG    300

```
GAGATGACAA AACTAACATG TGTATTATCA GATATATACA CACCTATCAA GGCATCTATA        360

ATATTAAATA ATTTATGGAG TTGTTTAAAT ACTACACAAG TATGA                        405

(2) INFORMATION FOR SEQ ID NO:46:

(i) SEQUENCE CHARACTERISTICS:
        (A) LENGTH: 261 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:46:

ATGTCAACTA TGAATACGTT GGCATTTTGT TATGGATTAC CTAACATAAA TGATATCACG         60

CAAGGTATAA TTTTTGTTAG AAATAACATA TTTTACTCAT ATTTAACAGA TTATGCAATG        120

GAAGCGTGTA TATTGAATTA TATAAATATT AGAGCCGATA AAATAGAAGA TCTAAAGAAA        180

TCATTAGTTG AAAAACTAT TAGCGTGAGA GTTATTAGAG TTGATGTATT AAAAGGATAT        240

ATAGATGTTT CAATTGTATA A                                                  261

(2) INFORMATION FOR SEQ ID NO:47:

(i) SEQUENCE CHARACTERISTICS:
        (A) LENGTH: 468 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:47:

ATGGATCCTG TTTGTTGGAT ATGTAAAGAT GACTACAGTA TTGAAAAGAA TTATTGTAAC         60

TGTAAAAACG AGTATAAAGT TGTACACGAT GAATGTATGA AAAAGTGGAT ACAATACTCA        120

AGGGAACGAT CTTGTAAATT ATGTAATAAA GAATATAACA TCATTAGTGT TAGAAAACCA        180

TTCTCACAGT GGGTATTCTC CATTAAAGAT TGCAAAAAGT CAGCAATTTT GTACGCTACT        240

CTATTCTTAT GTACGTTTAT TATATCGCTT GTTTTAACTA GAATTAATAT AACAAAAATA        300

ATAGATACAT CAAAAAATGA TGTTTCATTT AAGCTGGTTA CGATGATATT CTACTTATTA        360

CCATTTGTCA TAACTTGTAT ATCGTTCATA ACGCTGATAG TTTATCTATA TAAATATTGT        420

AAGATTTCCG CTAAAAACAA CACATACGAT ACGATTTATG AACTTTAA                     468

(2) INFORMATION FOR SEQ ID NO:48:

(i) SEQUENCE CHARACTERISTICS:
        (A) LENGTH: 825 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:48:

ATGCATTTCA TATTCATTAT ATTATCACTA TCATTTGTAG TAAATGCCGA TGTATTTCCA         60

TCGTCGGTTA CTTATCATC TAATGATTTT GATACAATAA TTAAATGGGA TAATAATGTA        120

ATATCATACG ATGTAGAATT AATGCAGTAC AGTCATGACG AATGGAGAAC CGTTTGTACT        180

AATTCTTTAG GATACTGTAA TTTAACAAAT TCTGATATCG ACAATGATGA TGAAACATGG        240

GTGAGGTTTA AATATGAAAA TAAGACATCT AATGAACATA ATATTGGCAG AGTATGTGAG        300
```

-continued

| ATTGTACAAA TAACTTCACC TATTGTTAAC ATGACAAGAG ATGGTTCAAT TATACTATTA | 360 |
| GATATACATC ATCCAATGAC ATACGATAAT CAGTATTATA TATATAATAA TATAACATTA | 420 |
| TGTGGATTTG AATTTATTTA CGAAGCTACA TTTATTATTA ATGATACAAT TATACCATAT | 480 |
| AGTATAGACA ATCAATATTG TGATGATGTT CATTGTTTAT TTTACTTTAT ATCACAAGAA | 540 |
| CCCGTTTGTG TGTATGTAAT GGGTATGGAA CAATATTATG AATTTGGTCC AAAAAAAACA | 600 |
| GATAATAGTA CTAGAGTGTG TGTAGATGGA TTAATTCCAA GAAAAATCGA TACATATTTT | 660 |
| ATTAAAGATT TCGATGATAT AGATAGAGTT AATAACAGAT TATATAGAGT TGTAAGTGAT | 720 |
| AAATATGAAT CCAATATATC GTCAAAGTTT ATGCACTTAT ATAATAATAT ATTATCTTCG | 780 |
| TTTAAACTAA TATTGCAAGA ACTTATGGTA AATACTGAAC AGTAA | 825 |

(2) INFORMATION FOR SEQ ID NO:49:

(i) SEQUENCE CHARACTERISTICS:
        (A) LENGTH: 711 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:49:

| ATGAATTCGT ATATTGTAAT AAAAAATTCA TTACGTGATT ATAGATCTGG AAGAATTATA | 60 |
| AGAAAATACA TAAGAAAATT AAATAAGGAT GAGTATAAGC ATTTTTGTGC TGTATTTAGA | 120 |
| TTAAATGTAG ATTTTTCTCA AGATGATAAA AATCCATCTA GAAAAGAAGT AATAAGAATA | 180 |
| ATAGATGAGG AATTCAATTT TTGTGATCTT AGACTATTTT ATGATATCAT GACCGTTGTA | 240 |
| CCTAATCATA TGAATGTGGC ATCTATTATT TATAGCGAAT ACGAATATCT TTTAAAAAAA | 300 |
| TCAAATTATA AAAATAAGAA GATAAATTAT ACTATATTAG ATAAGATTAA TAAATATCAT | 360 |
| AGTATAGATG ATATTATATT TATGTATCTT CATTGGAGAA AAAAATATAA CAACACATGC | 420 |
| GCATGTGGTA AGTTATTTAA GGAACTCATG AAATATGATA TATTAGCTAC AAAATATATA | 480 |
| TATAATGATA TTATAAATAC ATACAAAGAG GGAGATACTA TATCCATTAA CATACGTTTA | 540 |
| AAATGTAAAG ATGATATAAT TAAACATTGT AAGTCTTCTA TAGGTATGTT TGCTATATTA | 600 |
| TCATCGAAAA TAATCGACGT AGATTTTGAT GTTATATTCT TTTCACAAAT AAGTATAAGA | 660 |
| TATAGACTAA TATTCAAAAA ATATCTCATA CAATCATTAT ACTTACAATA A | 711 |

(2) INFORMATION FOR SEQ ID NO:50:

(i) SEQUENCE CHARACTERISTICS:
        (A) LENGTH: 1593 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:50:

| ATGAATTCAT TATTATTACG ATTACATGAT TTTTTTAAAC ATGGAATTAT GTGTGATATA | 60 |
| AAAATAGTAT CCATAGAGAA TAATAAAACC ATTAGCGCAC ATAGGTTAAT ATTATCTATG | 120 |
| TACTCTAAGT ACTTTTATAA TATATTTAAT TCAGATTTTA TTGATAAAAA TAATGATGAA | 180 |
| ATCTATATAT GCGCCGATTA TGATATATTG TATATTATAT GGAATTTAT GTACACCGGT | 240 |
| AATATAGTAC TAACAAAGGA TAATATAGAA TTAGTAATAC AAGTCTGTGA TTATCTATGT | 300 |
| ATAGATTCTT TAATAAAAAT ATGTGAAGAA TATATATGCG GTATAATAGA TGAAACAAAT | 360 |

-continued

```
TGTATACATC TCTTAAACTT TTCAGATACT TACAATCTAC AACGATTACG TGAAATGTCA      420

AAATGGTATT TACCAAAAAT AATAAATAAT AACAAACTGG TAGTAGAATT AGATATAGAT      480

GATATGATAT TAATTATAAA AGAAATTAAA TACATTGCAT GTGAATATAT AGTTAAAAAA      540

ATAATATTAA ATTGGATCGT TCATAAAGAT GAACGAATTA TTTATACTAA AAAATTAATG      600

AAACATATCA ATGATCAAGA CCATTATACA TCCTTATCGG ATATTGAATT GTACAATAAT      660

ATACGGGAAC GAATATATGA TAACAAAGAA CACGATGTAG ATATATCACA TAACTTTATA      720

ATAATGGTAG GAGGAAAAAA GATATTTAAT ATAACCGCAT TCAATCCGTT ATCGAATAAA      780

AAACATATTA TAGACAGATA CGATGATATG TTTGGTTGTA AAACTCATTT TAGTGTTGTA      840

TACTTAAATA GTATACTATA TATTATCGGT GGAAAGAAAC GAGGATATTT CACTAAAGAG      900

GTGTTGTCAT ATAATATAAA AAACAAATTA TGGTGTTACG AACCAGAATT AAATTATTTT      960

AGATACGATA CATCTGTATG TGTATCAAAT GGGATGATAT ATTCAATTGG TGGAAAAGAT     1020

ACAAATGGAT ATATGACAAA CATCGTAGAA TTTTGGAAAC CTGAATGGAA ATCATGGTAT     1080

GATGGTCAAC ATTTGTGTTA TCCTAGATGT TATATGTCGT TGGTAGACTA TAATAATGAA     1140

GTATATACAA TAGGTGGATT AAAAACATCA ATAACGGATG AATTTAATAT AGAAATGATT     1200

GTATCAGACG ATGCCGTAGA GAAACTGACC GATCATTCAT GGATGAAGTT AAAACAATTT     1260

CCCATAGCAA AGAGTGGTAT ATCATCCATA GTATATAACG ATTTTATATA CTGTATAGGT     1320

GGTCGTATAG ATACACCACA TATAAGTATA GAACACACTA ACGATGTTTA TATATATTCT     1380

TCAAGAGATG ATTGTTGGAA ATATTTATCA AATACAAATG TAAAAAGATC ATTTTGTCTA     1440

TCGTGTGTTT TTAATAATGA ATTATATATA ATAGGTGGAT ATAATACAAA CAGTGTAGAA     1500

AAGTACAATA AATTAAAAAA TACATGGAAG CGTTTAAACG ATATTCCTAA GTTTGAAGAA     1560

TGTGTTAATG AAGCATCGGC AATATATTTG TAG                                  1593
```

(2) INFORMATION FOR SEQ ID NO:51:

(i) SEQUENCE CHARACTERISTICS:
        (A) LENGTH: 810 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:51:

```
ATGTCAGATT GTATATTCGT ATTTCAGATT CCGTTCATTG TGTATAGTAA ACTCGATCAA       60

TGGATTTTTG GGAATATACT ATGTAAAATA ATGTCCGTAT TATACTACGT AGGATTCTTT      120

AGTAATATGT TTATAATAAC ACTTATGAGT ATAGATAGAT ATTTTGCGAT CGTTCATCCT      180

ATAAAGCGAC AACCGTATAG GACGAAACGT ATAGGTATCC TTATGTGCTG TTCCGCTTGG      240

TTATTATCCT TGATATTATC TAGTCCCGTA TCTAAACTAT ACGAGAATAT TCCTCATATG      300

TCTAAAGATA TATACCAATG TACTCTGACG AACGAGAATG ACTCCATAAT CGCATTCATA      360

AAAAGACTGA TGCAAATAGA GATCACTATA TTGGGATTCC TGATACCTAT AATCATATTC      420

GTATATTGCT ATTATAGAAT TTTTTCTACA GTGGTTAGAT TAAGAAATAG ACGAAAGTAT      480

AAATCTATAA AAATTGTATT AATGATTGTT GTATGTTCTC TAATATGTTG GATTCCGCTC      540

TATATCGTTC TAATGATAGC GACGATTGTT AGCTTATATA CATCTAATAT ATTTAGACAT      600

CTGTGCCTCT ATCTAAACCT GGCCTATGCG ATCACCTTTT CGGAGACTAT CTCGTTAGCG      660

CGTTGTTGTA TAAATCCAAT AATATATACA CTGATAGGTG AACATGTTCG ATCTCGTATA      720
```

```
TCTAGCATAT GTTCGTGTAT ATATAGAGAC AATAGGATTA GGAAAAAACT CTTTTCACGA        780

AAATCTTCTA GCAGTAGCAA TATTATTTAG                                         810
```

(2) INFORMATION FOR SEQ ID NO:52:

(i) SEQUENCE CHARACTERISTICS:
        (A) LENGTH: 279 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:52:

```
ATGCTATCGT ATATTATTAA TCCTTTGCTA AGTATTGTAT ACTTTATATT AGGAAATGTA         60

TCTAAGCTGC TTACATATAT ACTTATGAAA ATAATGATTT TTTTACTTCG TGCGGTGAAT        120

CCATACTCTC TGATATCTAA CAGAGGTTGG CTGTCGCTGG ATAGTATAAA TCCCTTTAAA        180

AAGGAAAAGC GTAGGGAGTC TTTTCTATCT AGTCTAAATC CGTTTAGAAA AGAGGAAACA        240

AAGAAAAAAG AAGGTTTCTT TTCTGGTTGG TTCGGATAA                              279
```

(2) INFORMATION FOR SEQ ID NO:53:

(i) SEQUENCE CHARACTERISTICS:
        (A) LENGTH: 1023 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:53:

```
ATGATTACTA AAGCGATTGT GATATTGTCT ATTATTACAG CATATGTAGA TGCTTCCGCA         60

TTCTTAGTAT ACAATTATAC ATATACTTTA CAAGATGATA ATCATCGATA TGACTTCGAA        120

GTCACCGATT ATTTTAATGA TATACTAATA AAACGTTTAA AACTAAATAG CGAGACAGGA        180

AGACCAGAAT TAAGAAATGA ACCACCAACA TGGTTTAATG AGACTAAGAT TAGATATTAT        240

CCGAAAAATA ATTATAATTT TATGTTCTGG CTAAATAGAA TGAGTGAAAC GCTAGATGAG        300

ATAAATAAAC TTCCAGAAAC GAGTAATCCT TACAAGACTA TGTCCTTGAC AATTGGATGT        360

ACTGATCTAA GACAACTTCA GTAAATTTTC GGTTATGTTA CTGTAGGTGG TAATATATGG        420

ACACGATTCG ACCCCAAGAA TAAACGCTTT AGTAAAGTTA GATCACGTAC ATTTCCAAAG        480

GTAGGAATGT TAACTGTTAA ATCACAACAC TGGGAACGTG TTATGAACA TCTTGGATCA        540

ATGGTAACAT TAACATGTCC GTTTACAGCG GATGATTATT ATAAAATTTC TAAGGGATAT        600

ATAGATAAGC CAGTTAAGCC TACTGTTACA GTTACAGGAA TTGAAAGAGG AGATAATACT        660

ACATTGATAT GCACATTTGA TAATCATTAT CCGTCGTCGG TCGCTGTTAA ATGGTATAAC        720

ATCGAGGACT TTGCTCCGGA CTATCGTTAT GATCCGTACG TAAATGAATT GCTTCCTGAT        780

ACGGACTATC TACCGGGTGA ACCAGGATAT CCGACTATAA CTAGGAGATT AGGTGATAAA        840

TATTTATTTA CATCATCACC TAGGGTTATG GTACCAACTA TCATGTCTAA TAGAATAGCA        900

TGTGTTGGAT TCATAGTAC GTTAGAACCA AGCATATATA GATGTGTAAA CTGCTCGGGA        960

CCTGAGCCTG TTTTACAATA CCAGGGAGAT AGAAGGAATG ACTTGGAGGA TGAGGAGGAT       1020

TAA                                                                     1023
```

(2) INFORMATION FOR SEQ ID NO:54:

(i) SEQUENCE CHARACTERISTICS:
    (A) LENGTH: 221 base pairs
    (B) TYPE: nucleic acid
    (C) STRANDEDNESS: double
    (D) TOPOLOGY: unknown (ii) MOLECULE TYPE: DNA (genomic)

(xi) SEQUENCE DESCRIPTION: SEQ ID NO:54:

```
ATGATGATTT CTATCATATA TCAACAGGAG GTTATGGTAT CGTATTTAAA ATGGATAAAT      60
ACGTTGTTAA ATTTGTTTAT GAACCAAATA AACAGTATAG TCCCATTGAT ACAACTGCCG     120
AGTATACAAT ACCTAAATTT TTATATAATA ATCTTAAGGG AGATGAGAAA AAACTTATCG     180
TTTGTGCATG GGCAATGGGT TTAAATTATA AATTAACATT T                         221
```

(2) INFORMATION FOR SEQ ID NO:55:

(i) SEQUENCE CHARACTERISTICS:
        (A) LENGTH: 675 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:55:

```
ATGGAGAATC CTGTTAGAAT AAATACATTA TATAACGTAT TCGTAGAAAG ATATATAGAG      60
AACTTATCAA TATATTCTAT ACCTATTAAT TCAACATGTG GTATACATAT AGGAGAAATC     120
AAAGGAACGT TCAAAAGATG TTTTTTGAAA ATACTCAATA TGTGTATAAA CGATAAAGAA     180
CTAAGTTTCA ATATTCTTAT AAAGACGCTT AAAGATGTAA CTAGTACGTT ATCTCAGAAA     240
GAGAAAGAGG AATTATCTAA AGAAATTGGA ATTGATATAT TAAACAATGA CCCTAAATAT     300
GTACCAGAAA TAATACGAAA CTGTTCATCA TCCGCAGATG TAACAAATAT TATTGATATT     360
CAAACATTAG ATGTTGGAAA ATGCATAGCT CCGTACGATA AACAGATTCT ATTACAGATT     420
GTTAATTCTG GTACTGCAGA AGCAAACTGT GTGATGAATT CTATCATGAA TTCTATGAAT     480
AGAAGATATA TTGACAATGC TAATATATAT AATTATTTGA ATTTAACAAA TAGACCATGG     540
TTTATATTTA GCATCATTAT TATTGCTATC ATATTTGTTA TAGGAATATG TTCTATAAAA     600
AGACGAATAG GAATTAAATA CAAATATGGT ACATTTTTAT ATGTCTAAAC CGGGTTAAAA     660
ATGAAACATA AATCA                                                      675
```

(2) INFORMATION FOR SEQ ID NO:56:

(i) SEQUENCE CHARACTERISTICS:
        (A) LENGTH: 260 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:56:

```
ATGGGCAGTT GTGTATCTGT AAAATCAATA AGTATAAGTA TGGATACAGT GTCAATATCT      60
TCTATAGACG ATGAATATTA TTATAATATA AAAAATAAGC CAATATATGT AAGAAGAAAA     120
AATAGTTGTA GTAGTACACT AGAATCGAGA TATTCTACAT ATAGTCTAGA ATCGAGATAT     180
TCCACATATA GTATTAAATC AGTATATTTC TAAATAAATA ATAATGAATA ATCGTAAGTA     240
TTCAATAAAT AATGGTTTTA                                                 260
```

(2) INFORMATION FOR SEQ ID NO:57:

(i) SEQUENCE CHARACTERISTICS:
  (A) LENGTH: 1104 base pairs
  (B) TYPE: nucleic acid
  (C) STRANDEDNESS: double
  (D) TOPOLOGY: unknown (ii) MOLECULE TYPE: DNA (genomic)

(ix) FEATURE:
  (A) NAME/KEY: CDS
  (B) LOCATION: 287..832

(xi) SEQUENCE DESCRIPTION: SEQ ID NO:57:

```
CTATTGGTTA TTTATACGAA CCATTATCCG AGGAGTATAG ACGTGTTATC GACTTTAGTG      60

ACATGAAGAA TTTACGATCT ATGTTTAACA AAATAACGAT CACGTATCTG ATAAATGCAT     120

ACAAGTTAAT AAAGGATATT TATCAGATTT TGTAACATCA TTAATACGAT TAAGCGATGT     180

GATATAAATA CCTATGATTC GTTTGATATT ACTTATATAG ATCCAAGAAG ACATATAACT     240

TGGAATAATA TTTTATCCAT ATTGAAGAAA ATAAATAAA CACTTT ATG TAT ATA         295
                                                   Met Tyr Ile
                                                     1

ATA ATG TCA TGT GGA TTT ATT CAT CTT ATA TTA GGA CCT ATG TTC TCT       343
Ile Met Ser Cys Gly Phe Ile His Leu Ile Leu Gly Pro Met Phe Ser
      5               10                  15

GGA AAG AGT ACA GAA TTA ATT AGG TTA GTA AAC CGG TAT CAA ATA GCC       391
Gly Lys Ser Thr Glu Leu Ile Arg Leu Val Asn Arg Tyr Gln Ile Ala
 20              25                  30                  35

ACG TAT AAT TGT AGA GTT ATA AAA TAT TCT AAA GAT AAT AGA TAT GGA       439
Thr Tyr Asn Cys Arg Val Ile Lys Tyr Ser Lys Asp Asn Arg Tyr Gly
             40                  45                  50

AAT GAT GCG GTA TAT ACA CAC GAT AAA TGT TAT ATA TCG GCT GTA TCT       487
Asn Asp Ala Val Tyr Thr His Asp Lys Cys Tyr Ile Ser Ala Val Ser
                 55                  60                  65

ACG GAT TCC TTA TTT GAT ATA AAA GAT ACA CTA GAT GAT GTA GAT ATT       535
Thr Asp Ser Leu Phe Asp Ile Lys Asp Thr Leu Asp Asp Val Asp Ile
             70                  75                  80

GTT GGA ATA GAC GAA GGA CAA TTC TTT AAT GAT ATT GTA GAG TTT TGT       583
Val Gly Ile Asp Glu Gly Gln Phe Phe Asn Asp Ile Val Glu Phe Cys
     85                  90                  95

GAA TAT ATA GCA AAT AAA GGA AAA ATT GTT ATC GTT GCT GCA TTA GAT       631
Glu Tyr Ile Ala Asn Lys Gly Lys Ile Val Ile Val Ala Ala Leu Asp
100             105                 110                 115

GGA ACA TAT GAA CGT AAA CCA TTT GGT AAT ATT CTT AAT CTT ATA CCA       679
Gly Thr Tyr Glu Arg Lys Pro Phe Gly Asn Ile Leu Asn Leu Ile Pro
                120                 125                 130

TTA TCG GAA AAA GTT ACT AAA TTA AAT GCT ATA TGC ATG ATA TGT CAT       727
Leu Ser Glu Lys Val Thr Lys Leu Asn Ala Ile Cys Met Ile Cys His
            135                 140                 145

CGT GAT GCA TCT TTT TCA AAG AGA TTA AGC GAC GAG AAA GAA ATA GAA       775
Arg Asp Ala Ser Phe Ser Lys Arg Leu Ser Asp Glu Lys Glu Ile Glu
                150                 155                 160

TTG ATA GGA GGA AAA GAA AAG TAT TTA TCG GTA TGT CGT TCA TGT TAC       823
Leu Ile Gly Gly Lys Glu Lys Tyr Leu Ser Val Cys Arg Ser Cys Tyr
165                 170                 175

TTA ACC TGAAATATTG AAAATATAAT TAATATCTTA GAGCTATTTA ATTTATAGTT        879
Leu Thr
180

ATTTACCATG GGTATTACAC ATGAATTAGA TATCTTTCTG GTTAGTGAAG ACATTGCTAT     939
```

| | |
|---|---|
| GAAACATGTC GAACTTCATA AAGGTAATAG TTATGGTTGT GTATTAAACA TTAAATCATC | 999 |
| TTGTAGGAAA CAAATGAAAT AATATTTGTG TTAAAGCCTG ATGGACCGAA ATAGATGCAT | 1059 |
| TAAACCATAT CAAATGGAAG CAGATCGAAT ATATATAGAC GTGAC | 1104 |

(2) INFORMATION FOR SEQ ID NO:58:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO:58:

```
Met Tyr Ile Ile Met Ser Cys Gly Phe Ile His Leu Ile Leu Gly Pro
 1               5                  10                  15
Met Phe Ser Gly Lys Ser Thr Glu Leu Ile Arg Leu Val Asn Arg Tyr
                20                  25                  30
Gln Ile Ala Thr Tyr Asn Cys Arg Val Ile Lys Tyr Ser Lys Asp Asn
            35                  40                  45
Arg Tyr Gly Asn Asp Ala Val Tyr Thr His Asp Lys Cys Tyr Ile Ser
        50                  55                  60
Ala Val Ser Thr Asp Ser Leu Phe Asp Ile Lys Asp Thr Leu Asp Asp
 65                  70                  75                  80
Val Asp Ile Val Gly Ile Asp Glu Gly Gln Phe Phe Asn Asp Ile Val
                85                  90                  95
Glu Phe Cys Glu Tyr Ile Ala Asn Lys Gly Lys Ile Val Ile Val Ala
               100                 105                 110
Ala Leu Asp Gly Thr Tyr Glu Arg Lys Pro Phe Gly Asn Ile Leu Asn
           115                 120                 125
Leu Ile Pro Leu Ser Glu Lys Val Thr Lys Leu Asn Ala Ile Cys Met
       130                 135                 140
Ile Cys His Arg Asp Ala Ser Phe Ser Lys Arg Leu Ser Asp Glu Lys
145                 150                 155                 160
Glu Ile Glu Leu Ile Gly Gly Lys Glu Lys Tyr Leu Ser Val Cys Arg
               165                 170                 175
Ser Cys Tyr Leu Thr
           180
```

(2) INFORMATION FOR SEQ ID NO:59:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:59:

| | |
|---|---|
| THGAYGARGG NCARTTYTT | 19 |

(2) INFORMATION FOR SEQ ID NO:60:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

-continued (xi) SEQUENCE DESCRIPTION: SEQ ID NO:60:

GGNCCNATGT TYAGYGGN                                                                 18

USE OF RECOMBINANT SWINE POXVIRUS AS A LIVE VACCINE VECTOR

CROSS-REFERENCE TO RELATED APPLICATION

This application is a continuation of U.S. patent Ser. No. 08/901,127, filed Jul. 28, 1997, now abandoned; which is a divisional of U.S. patent application Ser. No. 08/307,499, filed Sep. 14, 1994, now U.S. Pat. No. 5,651,972; which is a continuation of U.S. patent application Ser. No. 07/908,241, filed Jul. 2, 1992, now abandoned; which is a continuation-in-part of U.S. patent application Ser. No. 07/908,630, filed Jun. 29, 1992, now abandoned; which is a continuation of U.S. patent application Ser. No. 07/342,212, filed Apr. 21, 1989, now abandoned.

FIELD OF THE INVENTION

This invention relates generally to the field of recombinantly-produced proteins and vector systems, and specifically to novel, recombinant Swinepox sequences useful in vector molecules capable of expressing heterologous genes in transformed hosts and in making specialized vectors.

BACKGROUND OF THE INVENTION

Various attempts have been made to construct vaccine vectors from viruses. The use of viruses and virus proteins in eukaryotic host-vector systems has been the subject of a considerable amount of investigation and speculation. Many existing viral vector systems suffer from significant disadvantages and limitations which diminish their utility. For example, a number of eukaryotic viral vectors are either tumorigenic or oncogenic in mammalian systems, creating the potential for serious health and safety problems associated with resultant gene products and accidental infections. Further, in some eukaryotic host-viral vector systems, the gene product itself exhibits antiviral activity, thereby decreasing the yield of that protein.

In the case of simple viruses, the amount of exogenous DNA which can be packaged into a simple virus is limited. This limitation becomes a particularly acute problem when the genes used are eukaryotic. Because eukaryotic genes usually contain intervening sequences, they are too large to fit into simple viruses. In the case of complex viruses, size of exogenous DNA to be inserted is not a limiting factor. However, because they have many restriction sites, it is more difficult to insert exogenous DNA into complex viruses at specific locations.

Studies with vaccinia virus have demonstrated that poxviruses in general have several advantageous features as vaccine vectors. Poxviruses are taxonomically classified into the family Chordopoxvirinae, whose members infect vertebrate hosts, e.g., the Orthopoxvirus vaccinia. Vaccinia virus has recently been developed as a eukaryotic cloning and expression vector (Mackett, M. et al., [1985] *DNA Cloning*, Vol. II, ed. D. M. Glover, pp. 191–212, Oxford: IRL Press; Panicali, D. et al. [1982] *Proc. Natl. Acad. Sci. USA* 88:5364–5368). Numerous viral antigens have been expressed using vaccinia virus vectors (Paoletti, E. et al. [1986] *Proc. Natl. Acad. Sci. USA* 81:193–197; Piccine, A. et al. [1986] *BioEssays* 5:248–252) including, among others, HBsAg, rabies G protein and the gp120/gp41 of human immunodeficiency virus (HIV). Regulatory sequences from the spruce budworm EPV have been used previously with vaccinia (Yuen, L. et al. [1990] *Virology* 175:427–433).

The advantages of poxviruses as vaccine vectors include the ability of poxvirus-based vaccines to stimulate both cell-mediated and humoral immunity, minimal cost to mass produce vaccine and the stability of the lyophilized vaccine without refrigeration, ease of administration under non-sterile conditions, and the ability to insert at least 25,000 base pairs of foreign DNA into an infectious recombinant, thereby permitting the simultaneous expression of many antigens from one recombinant.

However, although recombinant vaccinia viruses have demonstrated great potential as vaccines, vaccinia has several drawbacks that have prevented its widespread use in both human and veterinary medicine. First, vaccinia virus has a wide host range that includes man and many domestic animals. This could permit the spread of a recombinant vaccinia vaccine to other animal populations not intended for vaccination. Secondly, although the vaccinia virus recombinants are attenuated by inactivation of the thymidine kinase gene, this virus still has the ability to cause potentially serious generalized vaccinal infections in immunocompromised individuals (i.e., patients with AIDS).

Another poxvirus, swinepox virus, the only known member of the genus Suipoxvirus, is naturally restricted to swine and occurs widely throughout the world. Swinepox virus produces a mild, self-limiting disease in swine. (Kasza et al. [1960] *Am. J. Vet. Res.* 21:269–272; Shope [1940] *Arch. Gesamte. Virustorsch* 1:457–467). This virus is characterized by a genome 175 kb in size which includes a thymidine kinase (TK) gene closely resembling the TK genes of other poxviruses (Feller et al. [1991] *Virol.* 183:578–585).

Pseudorabies is one of the most important diseases affecting the swine industries of the USA and several countries within Europe. Losses due to disease in the USA each year run into several million dollars. This disease is characterized in its reservoir host, swine, by central nervous system disorders in suckling pigs, respiratory disease in growing pigs, and fever and inappetence in adult swine. Cattle, dogs, cats, and other species are atypical hosts of pseudorabies, but develop an invariably fatal neurological disease similar to rabies. Highly pathogenic strains of pseudorabies have been detected in the USA and later in Europe since the 1960's (Gustafson, D. P. [1986] "Pseudorabies," in *Diseases of Swine*, pp. 274–289, 6th Edition, eds. Leman, A. D., Straw, B., Glock, R. D., Mengeling, W. I., Penny, R. H. C., and Scholl, E., Publ. ISU press, Ames, Iowa).

The control and the eradication of pseudorabies in the USA has proven to be difficult due to the existence of a large population of feral swine in the southern states which is known to be infected with pseudorabies virus.

There remains a need for a safer and effective vector system to create vaccines directed to diseases of humans and animals, including e.g., pseudorabies infections of swine.

BRIEF SUMMARY OF THE INVENTION

In one aspect, the present invention provides a recombinant swinepox virus vector which contains a heterologous gene or genes encoding a selected pathogenic immunogenic or antigenic protein under the control of a suitable regulatory sequence capable of directing the expression of said protein in a selected host cell. Preferably, the heterologous gene is inserted into the swinepox virus vector, either replacing or disrupting a naturally-occurring swinepox virus sequence or gene which is not essential to the replication of the recombinant swinepox virus vector in a selected host cell.

In one embodiment of such a vector, the heterologous gene is inserted into the thymidine kinase (TK) gene region of swinepox virus. TK is one of the proteins [SEQ ID NO: 58] encoded by a nucleic acid sequence [SEQ ID NO: 57] of the HindIII H fragment or a portion thereof, of the swinepox virus. In an illustrated embodiment, the foreign gene is a pseudorabies gene, most preferably the gp50 and/or gp63 gene. Additionally, other pseudorabies and non-pseudorabies genes are expected to be useful.

In a further aspect, the present invention provides the DNA sequences of the sense strand [SEQ ID NO: 1] and the anti-sense strand [SEQ ID NO: 14] of the approximately 14 kb HindIII C fragment of the swinepox virus. This DNA sequence contains fragments which encode about 27 swinepox virus proteins.

In a related aspect, the present invention provides the DNA sequences [SEQ ID NOS: 8–13 and 36–56], and putative amino acid sequences [SEQ ID NOS: 2–7 and 15–35] of the 27 proteins encoded by fragments from the 14 kb HindIII C fragment. Certain of these sequences from the fragment, like the TK gene, are expected to be non-essential and thus useful as locations for the insertion of, or replacement by, foreign genes for expression thereof.

In another aspect, the present invention provides the DNA sequence [SEQ ID NO: 57] of the SPV TK gene and the putative amino acid sequence [SEQ ID NO: 58] of TK.

In yet another aspect, the present invention provides a plasmid, p19SPB1, containing the full length SPV TK gene [SEQ ID NO: 57].

In a still further aspect, the present invention provides a therapeutic composition useful in treating a selected disease, which composition contains a swinepox virus vector capable of expressing a heterologous protein capable of alleviating the clinical symptoms of the selected disease.

Another aspect of the invention provides a method for treating an animal, which involves the step of administering to the animal an effective amount of a therapeutic composition as described above.

In yet a further aspect, the present invention provides a vaccine composition comprising a recombinant swinepox vector of this invention capable of expressing an antigen capable of eliciting a protective immune response to the causative agent of the disease for which prophylaxis is desired.

Another aspect of the invention provides a method of vaccinating an animal comprising administering to the animal an effective amount of a vaccine composition of the invention.

In yet another aspect, the present invention provides diagnostic reagents and methods useful for distinguishing between vaccinated and non-vaccinated animals by the use of a swinepox marker gene.

Other aspects and advantages of the present invention are described further in the following detailed description of the preferred embodiments thereof.

BRIEF DESCRIPTION OF THE FIGURES

FIG. 2 provides the DNA sequence [SEQ ID NO: 1] of the sense strand (5' to 3') of the HindIII C fragment of SPV and the putative amino acid sequences [SEQ ID NOS: 2–7] encoded thereby. Reading frame 1 encodes C24R and C23R. Reading frame 2 encodes C27R. Reading frame 3 encodes C26R, C25R and C22R.

FIG. 3 provides the DNA sequence [SEQ ID NO: 14] of the reverse complement strand (5°-3') of the 14,176 bp from the HindIII C fragment of SPV and the putative amino acid sequences [SEQ ID NOS: 17, 18, 23, 26, 28, 30, 31, 33, 34] encoded by reading frame 1.

FIG. 4 provides the DNA sequence [SEQ ID NO: 14] of the reverse complement strand (5' to 3') of the 14,176 bp from the HindIII C fragment of SPV and the amino acid sequences [SEQ ID NOS: 15, 20–22, 27, 32, 35] encoded by reading frame 2.

FIG. 5 provides the DNA sequence [SEQ ID NO: 14] of the reverse complement strand (5' to 3') of the 14,176 bp from the HindIII C fragment of SPV and the amino acid sequences [SEQ ID NOS: 16, 19, 24, 25, 29] encoded by reading frame 3.

FIG. 7 provides the DNA sequence [SEQ ID NO: 57], and putative amino acid sequence [SEQ ID NO: 58], of the SPV TK gene.

DETAILED DESCRIPTION OF THE INVENTION

The subject invention concerns a novel, efficient and safer means for vaccinating humans, swine, or other animals against various diseases. This procedure is carried out by the use of a modified recombinant swine poxvirus (SPV) as a vector into which heterologous antigenic sequences may be inserted. Because SPV is host-restricted to swine, the use of modified recombinant SPV as a live vaccine vector eliminates the risk of spreading infection with the virus to other animal populations not intended for vaccination.

The present invention thus provides novel swine poxvirus nucleotide sequences, which may be employed in the construction of the recombinant SPV vector useful for expressing heterologous proteins, preferably antigenic or immunogenic proteins, both in vivo as a vaccine, and in vitro for production of the selected protein. Such recombinant vectors are useful in therapeutic and vaccinal compositions. Such infectious agents of swine include pseudorabies virus, TGEV, African Swine Fever Virus, porcine parvovirus, swine influenza, hog cholera, and several bacterial pathogens.

Modification of the SPV involves the replacement of one or more SPV genes which are not essential to replication of the SPV, or portions thereof, with a foreign gene. Additionally, the foreign gene may be inserted within the selected SPV gene, thus disrupting the translation thereof into the SPV protein.

The SPV vector of this invention may be most desirably employed to express antigenic or immunogenic proteins from a variety of infectious agents which cause disease in animals and humans. It is anticipated that genes from any pathogen may be expressed in the SPV vector. For example, suitable genes include swine influenza hemagglutinin, the S gene from canine, bovine, feline, or porcine coronavirus, bovine herpesvirus glycoproteins, porcine parvivirus capsid gene, rabies G, HIV capsids gp120 and gag-pol, Lyme disease antigens, *Bordetella pertussis*, mycoplasma pneumonia, *Treponema hydystentry*, and human influenza genes. However, for purposes of illustration in this application, the foreign gene is selected from pseudorabies virus. Suitable pseudorabies genes include, for example, gII, gIII, and gp50.

Figure 6:
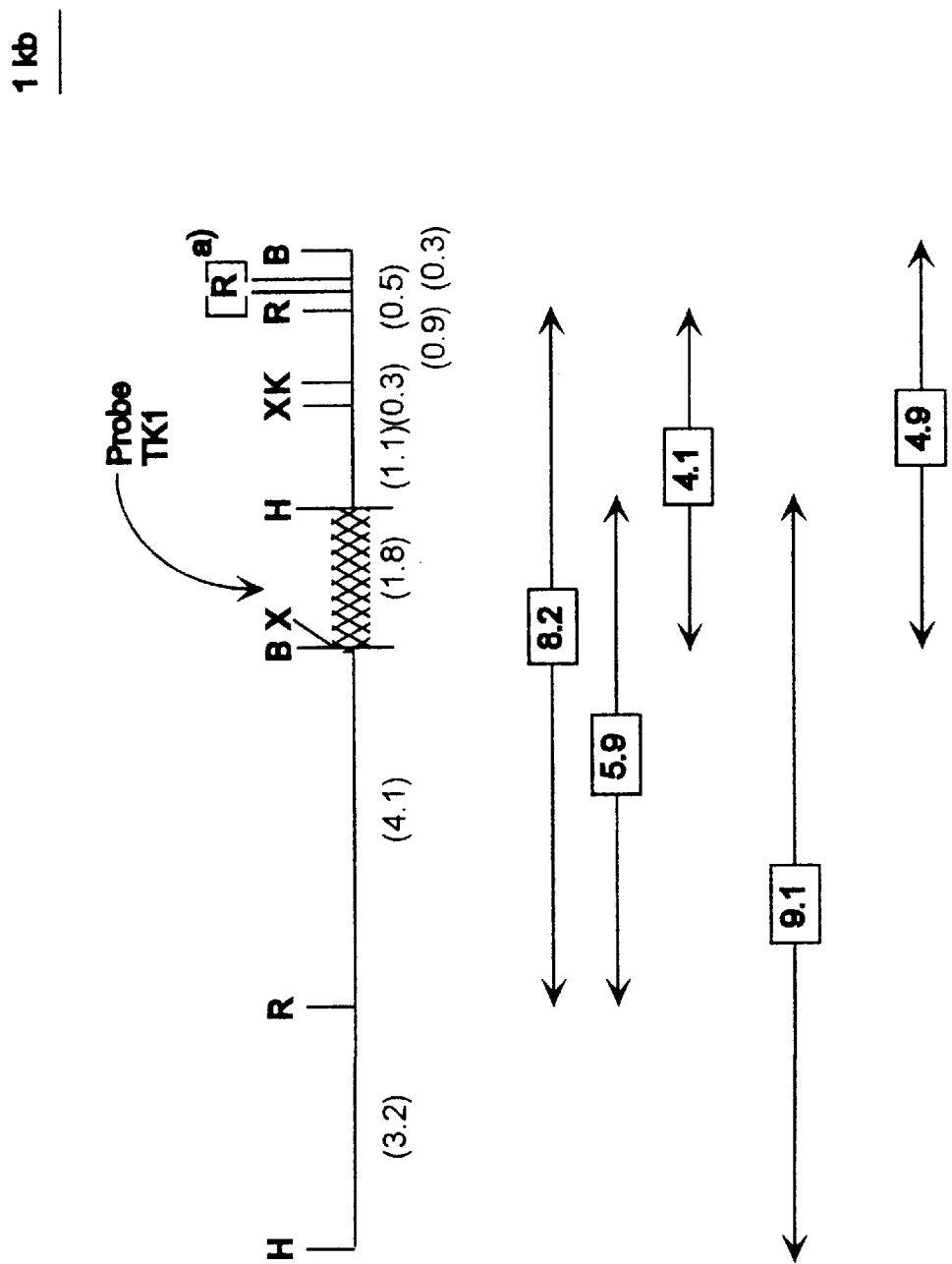
FIG. 6 is a map of the TK region of SPV DNA, corresponding to the G fragment of FIG. 1. Restriction endonuclease enzymes are indicated by letters: R for EcoRI, H for HindIII, B for BamHI, X for XbaI, and K for KpnI. Restriction fragment lengths in parentheses are inferred lengths. Lengths of the restriction fragments underlined are experimental results.

The SPV gene selected as a target site for insertion of, or replacement by, a foreign gene sequence depends upon its function as being non-essential to the replication of the SPV. Currently, the preferred target gene is the TK gene of SPV. The present invention provides the polynucleotide [SEQ ID NO: 57] and amino sequence [SEQ ID NO: 58] of the SPV TK gene. The isolation of this gene from the HindIII G fragment of SPV is described in Example 1, and its sequences are provided in FIG. 6. Because a drug resistance marker for TK is known, e.g., bromodeoxyuridine (BUdR) (selects for TK⁻; methotrexate (Aminopterin) selects for TK+), the insertion of a foreign gene which replaces or disrupts the TK gene may be detected in a successful recombinant SPV by conventional procedures.

It is expected that other SPV genes or portions thereof, will provide other non-essential gene sites as targets for insertion of the foreign gene in the recombinant vector. For example, C8L encodes the host range protein and C4L encodes the IFN-γ receptor. Expression or interruption of these gene sequences may impact upon the immunogenicity of the recombinant virus. The present invention provides the polynucleotide sequences, both sense [SEQ ID NO: 1] and anti-sense [SEQ ID NO: 14], of the HindIII C fragment of SPV, which is described in more detail in Example 2 below (FIG. 2 [SEQ ID NO: 1], FIG. 3 [SEQ ID NO: 14], FIG. 4 [SEQ ID NO: 14], and FIG. 5 [SEQ ID NO: 14]). Also provided are the putative amino acid sequences of 27 proteins encoded by these sequences (FIG. 2 [SEQ ID NOS: 2–7], FIG. 3 [SEQ ID NOS: 17, 18, 23, 26, 28, 30, 31, 33, 34], FIG. 4 [SEQ ID NOS: 15, 20–22, 27, 32, 35], and FIG. 5 [SEQ ID NOS: 16, 19, 24, 25, 29]).

In addition to the use of the amino acid sequences and corresponding nucleotide sequences of the specifically-recited embodiments of SPV proteins and genes of this invention which are described herein and in the Figures, the invention also encompasses the use of other DNA and amino acid sequences of the SPV proteins of this invention. For example, allelic variations (naturally-occurring base changes in the species population which may or may not result in an amino acid change) of the illustrated SPV DNA sequences encoding the various amino acid sequences are also included in the present invention, as well as analogs or derivatives thereof. Similarly, DNA sequences which code for protein sequences of the invention but which differ in codon sequence due to the degeneracies of the genetic code or variations in the DNA sequence encoding these proteins which are caused by point mutations or by induced modifications to enhance the activity, half-life or production of the peptide encoded thereby are also encompassed in the invention.

Variations in the amino acid sequences of the SPV proteins of this invention may typically include analogs that differ by only 1 to about 4 codon changes. Other examples of analogs include polypeptides with minor amino acid variations from the natural amino acid sequence of SPV gene proteins and/or the fusion partner; in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a significant effect on its activity, especially if the replacement does not involve an amino acid at an epitope of the polypeptides of this invention.

To construct modified recombinant SPV vectors of this invention, the modification technique of Turner and Moyer (1992) *J. Virol.* 66(4):2076–2085, incorporated herein by reference, may be used to insert the foreign gene or genes, whether they be markers, antigens, or another protein, to specific selected sequences of SPV. This method requires knowledge of the DNA sequence of the target gene, rather than the availability of a cloned copy.

Briefly, this method is performed as follows. The Ecogpt gene from *Escherichia coli* encodes a xanthine guanine phosphoribosyl transferase. When expressed in swinepox with the vaccinia $P_{7.5}$ promoter (Cochran, M. A., et al. [1985] *J. Virol.* 54:30–37), Ecogpt confers resistance to mycophenolic acid (MPA) in the presence of guanine and hypoxanthine, allowing the formation of virus plaques. By flanking $P_{7.5}$-Ecogpt (the gpt cassette) with the left and right arms of the target SPV gene, this selectable marker gene can be inserted into the desired protein by recombination following transfection.

The strategy described here involves the generation of these components by polymerase chain reaction (PCR) (Saiki, R. K. et al. [1988] *Science* 239:487–491), and their assembly by means of recombinant PCR (Higuchi, R. [1990] "Recombinant PCR," In *PCR Protocols: A Guide to Methods and Applications*, eds. M. A. Innis et al., Academic Press, Inc., New York, p. 177–183). PCR reactions are performed using standard parameters: 30 cycles of 94'C. for 1 minute, 45° C. for 1 minute, 72° C. for 2 minutes, followed by 72° C. for 8 minutes to complete extensions. Unrelated PCR products can be joined by this process following annealing, provided that the inside primers have an overlap. The resulting linear PCR products can be transfected directly into cells infected with wild-type virus, and $MPA^R$ virus recombinants selected. As an alternatively to this PCR technique, the heterologous gene may be cloned into a plasmid for recombination.

Thereafter the selected heterologous gene encoding an immunogenic or antigenic protein of interest from a selected pathogen is then inserted into the modified SPV by employing similar recombination processes. Briefly, a recombination plasmid, preferably an *E. coli* plasmid, is constructed in which the selected foreign gene, such as the pseudorabies gp50 and/or gp63 gene, is provided with a selected regulatory sequences, e.g, promoter regions. Preferably, when utilized in the vaccinia and fowlpox expression systems, the promoter is a vaccinia virus promoter. The construct formed by the foreign gene and the selected promoter or regulatory sequence may be inserted into the plasmid or assembled therein, to create a recombination vector.

However, other suitable plasmids and regulatory sequences capable of directing the replication and expression of the foreign gene product in a selected host cell are well known to those of skill in the art. Such promoters, for use in poxvirus, are poxvirus promoters including 7.5 k, 11 k, and ATI. Preferably, the plasmid is purified, using conventional techniques.

The recombination plasmid is then transfected by conventional techniques [See, e.g., Sambrook et al. [1989] *Molecular Cloning: A Laboratory Manual*, Cold Spring Harbor Laboratory, New York) into a suitable host and recombination occurs, placing the foreign gene and promoter system into the target gene region of SPV which contains the marker gene, thus destroying the functionality of that marker. In this manner, successful recombinants containing the foreign gene may be identified by the absence of the marker gene function. Alternatively, depending upon the gene inserted, one can select for a particular, rather than against, as described immediately above. Suitable markers for this include, for example, ecogpt+ and β-gal exp+.

Alternatively, as illustrated in Example 3, when the target gene is the SPV TK gene [SEQ ID NO: 57], conventional technologies for insertion of the foreign gene may be used. For example, following the construction of the recombination plasmid containing the desired foreign gene DNA as described above, the plasmid is transfected into cells infected with wild type SPV (TK$^+$). Within the infected cell the vector undergoes a homologous recombination event with the TK sequences of the wild type SPV DNA resulting in the generation of recombinant SPV with a TK negative (TK$^-$) genotype. The TK$^-$ progeny can then be selected by their ability to replicate in TK$^-$ swine host cells in the presence of 5-bromo-2-deoxyuridine (5-BUdr).

Recombinant SPV can be further selected by plaque hybridization using a probe derived from or complementary to the inserted foreign gene. The SPV recombinants can then be grown up in mass culture and analyzed for expression of the gene of interest. Alternatively, hybridization can be used to identify recombinant viruses when no marker exists.

Suitable hosts for use in production of the recombination plasmids include, for example, *E. coli*, Bacillus, Streptomyces, Saccharomyces, mammalian, such as Chinese Hamster ovary cells (CHO) or COS-1 cells, yeast, and insect cells. Suitable vectors therefor, which would be useful as recombination plasmids, are known and available from private and public laboratories and depositories and from commercial vendors. Currently, the most preferred host is *E. coli*. The selection of other suitable host cells and methods for transformation, culture, amplification, screening and product production and purification can be performed by one of skill in the art by reference to known techniques. See, e.g., Gething and Sambrook (1981) *Nature* 293:620–625).

The plasmid p19SPB1, which is currently being maintained in the laboratory of Dr. Richard Moyer of the University of Florida, contains a 1.8 kb HindIII to BamHI fragment containing the entire SPV TK gene. The plasmid can be obtained as described in Example 1 below and isolated and purified by use of standard procedures, for example, using cleared lysate-isopycnic density gradient procedures, and the like. This plasmid, which contains the SPV TK gene, thus provides a source of probes and selection for use in the methods described above.

Desirably, the recombinant SPV vectors of the invention can be formulated into therapeutic and vaccinal compositions, for use in treatment and prophylaxis of a desired disease. These formulations may contain appropriate, conventional, carriers or diluents, preservatives, pH adjusters or stabilizers.

For example, suitable carriers and diluents include sterile saline, lactose, sucrose, calcium phosphate, gelatin, dextrin, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

A therapeutic composition or vaccine composition of the invention may contain between about $10^1$ to about $10^8$ of the rSPV of the invention. These compositions of the invention contain suitable amounts of the active ingredient, the recombinant SPV vector containing the foreign gene, which can be determined by one of skill in the art based upon the level of immune response desired. In general, however, the therapeutic or vaccine composition contains between about $1 \times 10^5$ to about $1 \times 10^7$ plaque forming units (PFU) per mL, and more preferably between $1 \times 10^6$ and $3 \times 10^6$ PFU/mL.

The therapeutic or vaccine composition of the invention may contain one or more rSPV of the invention, each of which may contain different antigens directed to the same or different pathogens.

Such a therapeutic composition may be administered 1–2 times per day over about a 6 week period. However, suitable dosage adjustments may be made by the attending veterinarian depending upon the age, sex, weight and general health of the patient or animal.

Optionally, this composition may also contain therapeutic agents useful in treating pseudorabies, or other conditions related to the infection being treated. For example, the recombinant SPV vector may be useful in delivery of a growth hormone, growth hormone releasing factor, or cytokine, such as IL-2, IL-5 and IL-3.

A vaccine composition of the invention may also contain a suitable adjuvant. The adjuvant is used as a non-specific irritant to attract leukocytes or enhance an immune response. Such adjuvants include, among others, mineral oil and water, aluminum hydroxide, Amphigen, Avridine, L121/squalene, D-lactide-polylactide/glycoside, pluronic plyois, muramyl dipeptide, killed Bordetella, saponins, as Quil A.

Suitable doses of the vaccine composition of the invention can be readily determined by one of skill in the art. Generally, a suitable dose is between 1 to 5 mL of the vaccine composition. Further, the quantity to be administered depends on the size of the host to be treated, the capacity of the host's immune system to synthesize antibodies, the degree of protection desired, and may be adjusted by one of skill in the art. However, suitable dose ranges are of the order of about several hundred micrograms of active ingredient per host.

The therapeutic or vaccine compositions are administered in a manner compatible with the dosage formulation, and such amount as will be therapeutically effective and immunogenic. Typically, the composition can be administered by intradermal scarification using a bifurcated needle analogous to that used for smallpox vaccines in humans. However, any suitable route is acceptable. Preferably, this route is intradermal, intramuscular, subcutaneously or oral. It is anticipated that a suitable regime for administration is a single treatment.

Further, the present recombinant swinepox vectors of the invention are useful as diagnostic reagents and in methods for diagnosing or distinguishing between vaccinated and non-vaccinated animals. As with any antigenic protein or peptide, antibodies may be developed against a selected protein of the invention using conventional techniques. These antibodies may be polyclonal, recombinant, or, preferably monoclonal, and may optionally be associated with a detectable label. Further, using known techniques, probes may be developed from the swinepox proteins of the invention and used to detect antibodies directed thereto in a fluid sample, preferably serum. Alternatively, known sandwich assay techniques may be used, and may, preferably, be adapted into a kit for use by clinical or veterinary laboratories.

The examples below, specifically Examples 5 through 7, illustrate the utility of SPV as a vaccine vector using the pseudorabies gene coding for the gp50 and gp63 glycoproteins as an indicator gene. Such recombinant viruses avoid the possibility and consequences of reversion to virulence or recombination (Butler, R. M. et al. [1985] *Nature* 317:813–815; Joklik, W. K. et al. [1988] *Vaccine* 6:123–128), can easily be differentiated from natural infection, and allow the simultaneous inclusion of other gene inserts or the use of a "cocktail" of recombinants for vaccination against additional diseases.

In Examples 5 through 7 below, following demonstration of pseudorabies virus (PRV) serum neutralizing antibodies in pigs vaccinated with a swinepox-pseudorabies gp50/63 recombinant virus (SP-PRV) by scarification or intramuscular (IM) injection, two efficacy trials were conducted. In the first efficacy trial, which was designed to investigate parenteral vaccination, 30 pigs were challenged with virulent PRV three weeks after the administration of SP-PRV by scarification (n=10) of IM injection (n=10). The recombinant virus conferred partial protection by either route when the response to challenge in vaccinates was compared to that in unvaccinated controls (n=10). Pigs vaccinated by IM injection developed the highest PRV serum neutralizing (SN) antibody titers, exhibited less severe clinical signs, maintained positive weight gains and shed PRV for fewer days after challenge.

In the second efficacy trial, which was designed to investigate oral vaccination, 34 pigs were challenged with virulent PRV three weeks after the oral administration of swinepox virus (SPV) with an intact thymidine kinase (TK) gene (SPV TK$^+$) (n=6), SPV negative for the TK gene (SPV TK$^-$) (n=6) or SP-PRV (n=10). Although there was no evidence of a PRV SN antibody response in pigs vaccinated with SP-PRV, they exhibited less severe clinical signs, maintained their weight and shed PRV for fewer days after challenge when compared to the response in unvaccinated controls (n=10). When evaluating the same parameters, SPV TK$^+$ vaccinates responded almost as well, suggesting the presence of non-specific immunity. The SPV TK$^-$ vaccinates and controls, in turn, responded poorly to challenge.

No transmission of recombinant virus to in-contact controls was detected during the 3-week observation after vaccination in either efficacy trial. The antibody response elicited in pigs vaccinated with SP-PRV by scarification or IM injection, and the evidence of subsequent protection upon challenge with virulent PRV, demonstrates that SPV may be a potential vaccine vector. Since SPV is host restricted and there appears to be no transmission of SP-PRV to in-contact controls, this virus is an ideal vaccine vector candidate when used parenterally. Although SP-PRV failed to induce a PRV SN antibody response by the oral route, the data suggests the presence of some immunity (cell-mediated immunity was not evaluated).

The following examples illustrate the preferred methods for preparing the vector and compositions of the invention, as well as the trials described above. These examples are illustrative only and do not limit the scope of the invention.

EXAMPLE 1

Obtaining SPV TK Gene

SPV DNA is large and similar in size to the 180 kb genome of vaccinia. Many strains of SPV are available from conventional depositories, such as the American Type Culture Collection or from the Centers for Disease Control. SPV DNA was digested with the restriction enzymes HindIII, BamHI, EcoRI, SalI, and doubly digested with the following combinations of enzymes: HindIII+EcoRI, BamHI+EcoRI, and SalI+EcoRI. The restriction enzymes disclosed can be purchased from Bethesda Research Laboratories, Gaithersburg, Md., or New England Biolabs, Beverly, Mass. The enzymes are used according to the instructions provided by the supplier.

The digestion products were separated by agarose gel electrophoresis, the resolved fragments transferred to either nitrocellulose or nylon membranes and hybridized at 45° C. with a radiolabeled oligonucleotide probe of the following sequence:

T(TCA)GA(TC)GA(AG)GGXCA(AG)TT(TC)TT [SEQ ID NO: 59].

The oligonucleotide probes are degenerate, i.e., the probes are really mixtures of oligos with a selected set of sequences. In the above sequence, X=N=any nucleotide (A, C, T, or G) at that position. The () indicate that at that position, only those nucleotides indicated within the parentheses were used during synthesis. The probes were synthesized using conventional phosphoramidite methodology and an Applied Biosystems machine.

Hybridization to DNA fragments of the following molecular weights, depending on the particular digest, was observed: HindIII=9.1 kb; EcoRI=9.2 kb; SalI and EcoRI=8.2 kb (i.e., no SalI site within the EcoRI fragment); BamHI=4.9 kb; HindIII and EcoRI=5.9 kb; BamHI and EcoRI=4.1 kb. Construction of a map based on this data correctly predicted that upon HindIII and EcoRI digestion, the probe should hybridize with a 1.8 kb fragment (see FIGS. 1 and 7).

In order to clone the gene, SPV DNA was digested with BamHI, and the total mixture of fragments was cloned into pUC19 (available from United States Biochemical Corporation, Cleveland, Ohio 44122). Transformant bacterial colonies were replica lifted onto nitrocellulose filters and hybridized to the radiolabeled oligonucleotide probe described above.

From one of the positive colonies, a plasmid was isolated which contained a BamHI fragment of the expected size which upon rehybridization to the probe remained positive. The likelihood that the fragment of a cloned SPV contained the TK gene was confirmed by hybridization with a second degenerate oligonucleotide probe prepared from conserved sequences derived from a different conserved region of previously sequenced TK genes. The sequence of this second probe was as follows with the X and () as described above:

GGXCCXATGTT(CT)AG(CT)GGX [SEQ ID NO: 60].

Figure 8:
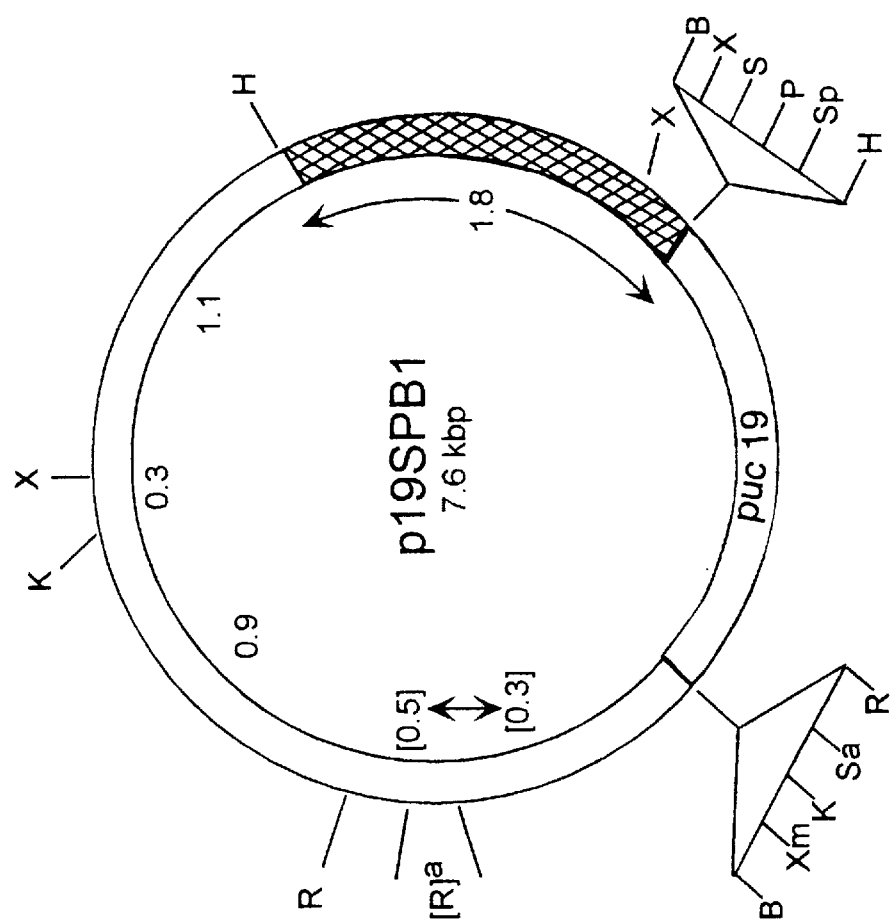
FIG. 8 is a restriction map of clone p19SPB1. Restriction enzymes are indicated by letters as described in FIG. 6 and also including S for SalI, P for PstI, Xm for XmaI and Sp for SphI. The symbol (a) indicates an alternate restriction enzyme position. The thick solid line indicates the smallest fragment hybridizing with $TK_1$ or $TK_2$. The XbaI site in this region was not seen before sequencing.

Restriction mapping of this plasmid, designated p19SPB1, separation of the resulting fragments and hybridization of the resulting fragments with the probes described thus far allowed preparation of the map shown in FIG. 8 and further localization of the TK gene to a 1.8 kb HindIII/BamHI fragment bordering the cloning site of the plasmid.

Sequencing of 1.8 kb HindIII/BamHI fragment yielded an open reading frame of 543 nucleotides with an upstream sequence typical of early vaccinia promoters. The sequence of the TK gene [SEQ ID NO: 57] is shown in FIG. 7, wherein the coding portion is shown by the designation of amino acids [SEQ ID NO: 58].

EXAMPLE 2

Analysis of SPV HindIII C Fragment Sequence

Figure 1:
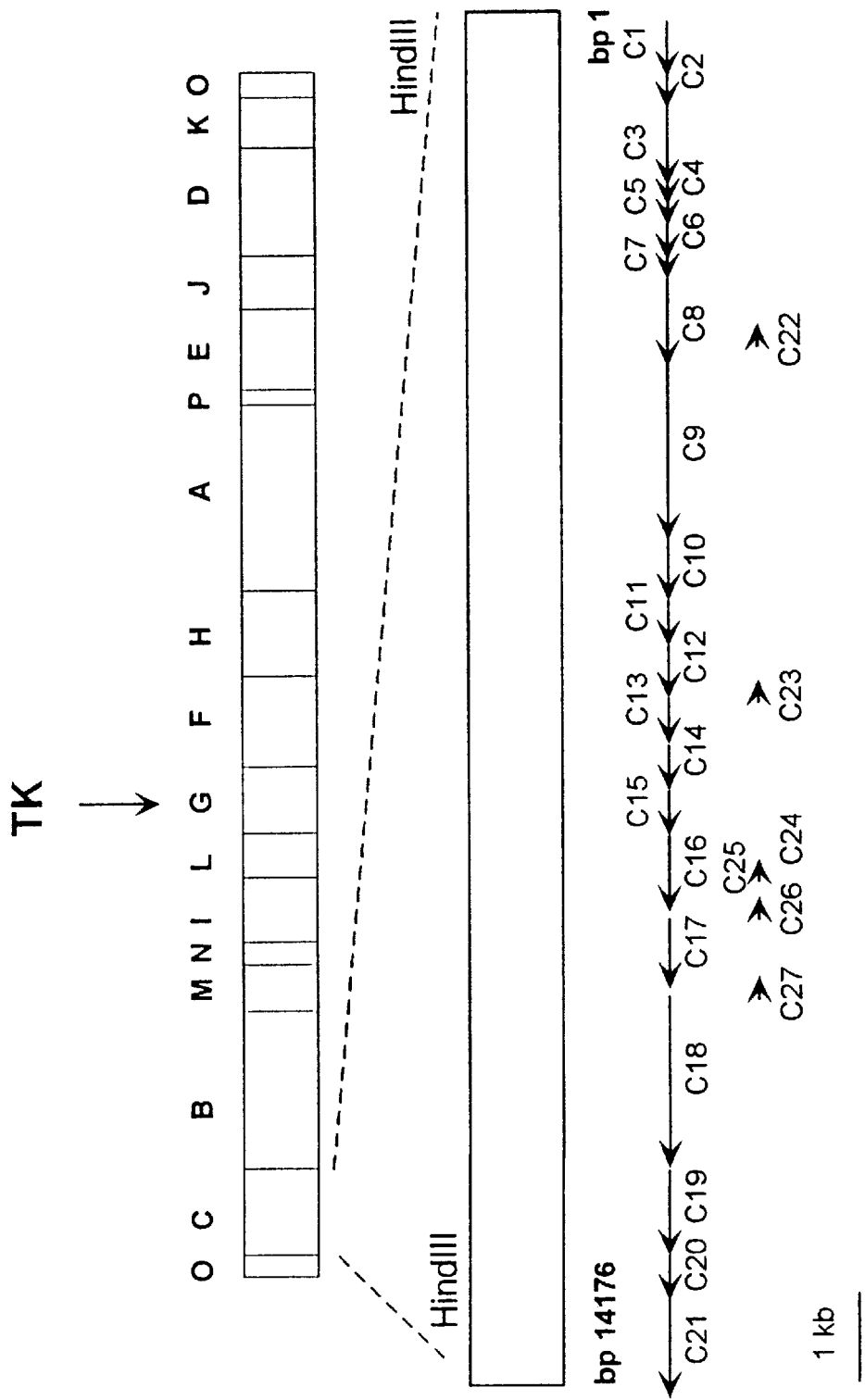
FIG. 1 is a DNA map showing the localized map of SPV DNA based upon probe hybridizations to SPV DNA after restriction enzyme digestion. The approximately 14 kb HindIII C fragment is expanded in the lower portion of the figure to indicate the relative locations and reading frame directions of identified genes, which are labeled by C followed by a number.

Digestion of SPV with HindIII, as described above in Example 1, resulted in the identification of 17 fragments, designated A to O, in order of decreasing size. The map of these HindIII fragments is illustrated in FIG. 1 above. As described above, the TK gene is found in the HindIII G fragment.

Analysis of the HindIII C fragment, revealed 27 open reading frames, 6 on the sense strand [SEQ ID NO: 1] and 21 on the reverse complementary strand [SEQ ID NO: 14] (FIGS. 3, 4, and 5). FIG. 3 illustrates the DNA sequence [SEQ ID NO: 14] of the reverse complementary strand, 5'-3', and the proteins encoded by reading frame 1 of that strand. These proteins are designated C20L [SEQ ID NO: 31], C19L [SEQ ID NO: 30], C17L [SEQ ID NO: 28], C15L [SEQ ID NO: 26], C12L [SEQ ID NO: 23], C7L [SEQ ID NO: 18], C6L [SEQ ID NO: 17], C3L [SEQ ID NO: 34] and C2L [SEQ ID NO: 33] because in the virus genome, the nucleotides encoding these proteins are translated from right to left. FIG. 4 also illustrates the DNA sequence [SEQ ID NO: 14] of the reverse complementary strand, 5' to 3', and the proteins encoded by reading frame 2 (C21L [SEQ ID NO: 32], C16L [SEQ ID NO: 27], C11L [SEQ ID NO: 22], C10L [SEQ ID NO: 21], C9L [SEQ ID NO: 20], C5L [SEQ ID NO: 35] and C1L [SEQ ID NO: 15]). FIG. 5 illustrates the DNA sequence [SEQ ID NO: 14] of this same strand, and the proteins encoded by reading frame 3 (C18L [SEQ ID NO: 29], C14L [SEQ ID NO: 25], C13L [SEQ ID NO: 24], C8L [SEQ ID NO: 19] and C4L [SEQ ID NO: 16]). FIG. 2 illustrates the DNA sequence of the sense strand [SEQ ID NO: 1] of the HindIII C fragment, and the proteins encoded thereby. These proteins, designated C27R to C22R [SEQ ID NOS: 2–7], are encoded on nucleotides which are translated from left to right. Proteins C26R [SEQ ID NO: 3] and C25R [SEQ ID NO: 4] are on reading frame 1; protein C22R [SEQ ID NO: 7] is on reading frame 2; and proteins C27R [SEQ ID NO: 2], C24R [SEQ ID NO: 5] and C23R [SEQ ID NO: 6] are on reading frame 3.

Table 1 below provides a tabular summary of characteristics of these deduced proteins of the open reading frames (ORF).

TABLE 1

| Protein | Amino Acid Length | Molecular Weight[a] | N-glycosylation sites[b] | Charge[c] | Homology |
|---|---|---|---|---|---|
| C2L [SEQ ID NO: 33] | 340 | 39.6 | 4 | −4 | Yes |
| C1L [SEQ ID NO: 5] | 92 | 10.8 | 1 | +8 | None |
| C3L [SEQ ID NO: 34] | 269 | 31.5 | 1 | +20 | Yes |
| C4L [SEQ ID NO: 16] | 530 | 62.6 | 3 | −10 | Yes |
| C5L [SEQ ID NO: 33] | 236 | 28.5 | 4 | −4 | Yes |
| C6L [SEQ ID NO: 33] | 274 | 32.2 | 4 | −4 | Yes |
| C7L [SEQ ID NO: 33] | 155 | 18.5 | 4 | −4 | Yes |
| C8L [SEQ ID NO: 33] | 86 | 9.8 | 4 | −4 | Yes |
| C9L [SEQ ID NO: 33] | 134 | 15.8 | 4 | −4 | Yes |
| C10L [SEQ ID NO: 33] | 167 | 19.9 | 4 | −4 | Yes |
| C11L [SEQ ID NO: 33] | 142 | 15.7 | 4 | −4 | Yes |
| C12L [SEQ ID NO: 33] | 75 | 9.2 | 4 | −4 | Yes |
| C13L [SEQ ID NO: 33] | 500 | 57.5 | 4 | −4 | Yes |
| C14L [SEQ ID NO: 33] | 274 | 31.8 | 4 | −4 | Yes |
| C15L [SEQ ID NO: 33] | 86 | 10.1 | 4 | −4 | Yes |
| C16L [SEQ ID NO: 33] | 73 | 8.9 | 4 | −4 | Yes |
| C17L [SEQ ID NO: 33] | 70 | 8.1 | 4 | −4 | Yes |
| C18L [SEQ ID NO: 33] | 67 | 8.3 | 4 | −4 | Yes |
| C19L [SEQ ID NO: 33] | 215 | 24.6 | 4 | −4 | Yes |
| C20L [SEQ ID NO: 33] | 440 | 52.9 | 4 | −4 | Yes |
| C21L [SEQ ID NO: 33] | 67 | 8.1 | 4 | −4 | Yes |
| C22L [SEQ ID NO: 33] | 124 | 14.8 | 4 | −4 | Yes |
| C23L [SEQ ID NO: 33] | 100 | 11.5 | 4 | −4 | Yes |
| C24L [SEQ ID NO: 33] | 59 | 6.6 | 4 | −4 | Yes |
| C25L [SEQ ID NO: 33] | 50 | 6.0 | 4 | −4 | Yes |
| C26L [SEQ ID NO: 33] | 114 | 13.0 | 4 | −4 | Yes |
| C27L [SEQ ID NO: 33] | 121 | 13.2 | 4 | −4 | Yes |

[a]Expressed in kD; calculated by GCG PeptideSort.
[b]Potential sites predicted by GCG PeptideStructure.
[c]Charge of polypeptide at pH 7.0; calculated by GCG PeptideSort.
Charges >0 represent basic proteins while charges <0 would be acidic proteins.

Using the GCG programs, the complete nucleotide sequence of the HindIII C fragment was searched for homology against the GenBank and EMBL databases. The sequence was also searched for any open reading frames. An arbitrary designation of proteins of >50 amino acids was chosen for consideration. The individual polypeptides of the ORFs were searched for homology against the SwissProt (Release 20.0) database using the Fasta program (Devereux et al. 1984).

As can be seen in the table above, several of the proteins were found to have homology to known sequences. Sequences were considered to be homologous under the arbitrarily defined parameters of either a 20% or greater homology or an amino acid overlap greater than approximately 50 aa. C2L [SEQ ID NO: 33] has a 20% identity with mouse Ig epsilon chain (75 amino acid overlap) and an 18% identity with Berne virus peplomer glycoprotein (162 amino acid overlap). C3L [SEQ ID NO: 34] has a 26% identity with rabbit RMLP receptor (217 amino acid overlap), 23% identity with dog RDCL receptor (263 amino acid overlap), 25% identity with human CSA receptor (246 amino acid overlap), and 22% identity with human FMLP receptor (250 amino acid overlap). C4L [SEQ ID NO: 16] has a 30% identity with myxomal virus MT-9 protein (440 amino acid overlap), 33% identity with myxoma virus MT-8 protein (250 amino acid overlap), 29% identity with vaccinia A55 protein (532 amino acid overlap), and a 22% identity with vaccinia C2 protein (467 amino acid overlap). C5L [SEQ ID NO: 35] has a 35% identity with vaccinia K7 protein (79 amino acid overlap) and a 20% identity with fowlpox DNA polymerase (247 amino acid overlap). C6L [SEQ ID NO: 17] has a 25% identity with the human γ interferon receptor (206 amino acid overlap). C8L [SEQ ID NO: 19] has a 44% identity with vaccinia K4 protein (79 amino acid overlap), a 30% identity with cowpox host range protein, (27 amino acid overlap), and a 26% identity with vaccinia host range protein (27 amino acid overlap). C10L [SEQ ID NO: 21] has a 20% identity with yeast SEC 59 membrane protein (161 amino acid overlap). C11L [SEQ ID NO: 22] has 56% identity with vaccinia protease-like protein (146 amino acid overlap), 53% identity with ORF virus pseudoprotease (137 amino acid overlap), and 34% identity with FIV protease (133 amino acid overlap). C13L [SEQ ID NO: 24] has a 25% identity with vaccinia F3 protein (490 amino acid overlap), 21% identity with vaccinia C2 protein (250 amino acid overlap), 24% identity with vaccinia A55 protein (95 amino acid overlap), and 26% identity with myxoma virus MT-9 protein (203 amino acid overlap). C14L [SEQ ID NO: 25] has 78% identity with vaccinia ribonucleoside diphosphate reductase small chain protein (270 amino acid overlap), and with the same gene in *Spisula solidissma* 74% identity (247 amino acid overlap), yeast 58% identity (285 amino acid overlap), mouse 74% identity (270 amino acid overlap), varicella zoster virus 26% identity (271 amino acid overlap), HSV 26% identity (260 amino acid overlap), *E. coli* 27% identity (123 amino acid overlap), and epstein barr 29% identity (239 amino acid overlap). C19L [SEQ ID NO: 30] has 46% identity with vaccinia F9 protein (215 amino acid overlap), 25% identity with fowlpox FP2 protein (169 amino acid overlap), and 43% identity with cowpox ATI inclusion protein (21 amino acid overlap). C20L [SEQ ID NO: 31] has 72% identity with a vaccinia possible protein kinase gene (432 amino acid overlap) and 20% identity with yeast clathrin heavy chain protein (54 amino acid overlap). C21L [SEQ ID NO: 32] has a 35% identity with Dicstylstelium D5 protein (51 amino acid overlap). C26R [SEQ ID NO: 3] has 20% identity with EBV GP85 precursor protein (104 amino acid overlap). C27R [SEQ ID NO: 2] has 74% identity with vaccinia 8.3 kD protein (F ORF B) (73 amino acid overlap) and 22% identity with rhinovirus coat proteins (88 amino acid overlap).

Only C2L [SEQ ID NO: 33], C7L [SEQ ID NO: 18], C9L [SEQ ID NO: 20], C12L [SEQ ID NO: 23], C15L [SEQ ID NO: 26], C16L [SEQ ID NO: 27], C17L [SEQ ID NO: 28], C18L [SEQ ID NO: 29], C22R [SEQ ID NO: 7], C23R [SEQ ID NO: 6], C24R [SEQ ID NO: 5], and C25R [SEQ ID NO: 4] were found to have no apparent homologies under the given search parameters.

EXAMPLE 3

Construction of Recombinant Virus

A PRV gp50/63 gene was isolated from Indiana-Funkhauser strain of PRV and was cloned into the Moss vector pGS20 (Dr. Bernard Moss, NIH) behind the 7.5 k vaccinia promoter as described in detail in Kost, T. A. et al (1989) *Virol.* 171:365–376. The gene and promoter fragment was then recombined back into the TK region of SPV (strain Kasza; ATCC #VR-363) by transfection, destroying the functionality of the SPV TK gene. Transfection was performed using Lipofectin reagent (Gibco BRL) according to manufacturer's directions (see, Feller, J. A. et al. [1991] *Virol.* 183:578–585). Thymidine kinase negative strains of SPV were selected for by growth in a TK$^-$ pig kidney cell line (PK-15 cells; ATCC CCL 33) using selective media containing 100 μg/ml 5-bromodeoxyuridine (BUdR) (Boyle et al. [1985] *Gene* 65:123–128; Weir, J. P. et al. [1982] *Proc. Natl. Acad. Sci. USA* 79:1210–1214; Wigler, M. et al. [1977] *Cell* 11:223–232).

The insertion and orientation of the inserted gene was confirmed and expression was evaluated in vitro using standard methods. Following confirmation of adequate expression and gp50/63 synthesis in vitro the recombinant swinepox-pseudorabies virus (SP-PRV) was expanded, concentrated and titered in PK-15 TK$^-$ cells. All trials were conducted within 3 passages of a SP-PRV stock (SP-PRV #10) prepared in PK-15 cells using basal medium Eagle's (BME) supplemented with 0.1 M L-glutamine and 10 per cent fetal bovine serum.

EXAMPLE 4

Virus Isolation

In the following examples, virus isolation was performed as follows. Shedding of SP-PRV in feces were assayed 12 well plates seed with $2 \times 10^5$ PK-15 cells per well using plates using BME supplemented with 5 per cent fetal bovine serum, 0.1 M L-glutamine, 300,000 IU penicillin G sodium, 300,000 μg streptomycin sulphate and 750 μg amphotericin B (Gibco). Fecal swabs were thawed at 37° C., vortexed and spun at 3,600 revolutions per minute for 30 minutes before inoculating serial ten-fold dilutions of the supernatant into the wells. After 6 days incubation at 37° C. in a humid, 5% $CO_2$ incubator the media were discarded, plates were washed and fixed in 80% cold acetone. One ml (1:1000 dilution) of a monoclonal antibody specific to PRV gp50 (Mellencamp, M. W. et al. [1989] *J. Clin. Microbiol.* 27(10) :2208–2213) was added to each well and the plates were incubated at 37° C. for 30 minutes. Substrate was discarded and plates were washed. One ml FITC-labeled goat anti-mouse conjugate (Kirkegaard and Perry Laboratories, Gaithersburg, Md. 20879) diluted 1:200 in phosphate buffered saline was added to each well and plates were again incubated at 37° C. for 30 minutes. Excess conjugate was discarded, plates were washed and examined for fluorescence.

Shedding for SP-PRV in pharyngeal swabs was evaluated by the method as described for fecal swabs except that samples were not centrifuged, and 96 well plates containing $3 \times 10^4$ cells per well were used. Serum (1:50 dilution) from a pig that had been hyperimmunized with swinepox virus was used in place of the monoclonal antibody. Following incubation with the SPV hyperimmune serum, the plates were incubated with FITC-labeled goat anti-swine IgG conjugate at 1:200 (Kirkegaard and Perry Laboratories).

Levels of SP-PRV present in the scarification site lesions were assayed as follows. Serial 10-fold dilutions of the nasal swab media (0.1 mL in tissue culture media) were inoculated into 96 well plates containing $3 \times 10^4$ PK-15 cells (ATCC) per well. The plates were incubated at 37° C. in 5% $CO_2$ for 7 days and then examined for cytopathic effect.

Nasal shedding of PRV was assayed from nasal swabs as follows. Serial 10-fold dilutions of the nasal swab media (0.1 mL in tissue culture media) were inoculated into 96 well plates containing $3\times10^4$ ST-56 cells (SmithKline Beecham) per well. The plates were incubated at 37° C. in 5% $CO_2$, and examined for cytopathic effect at 72 and 96 hours. Tonsil tissue suspensions, prepared using 2 ml DMEM, were assayed for PRV by inoculation of 2 mL of the tissue suspension in 6 well plates seeded $9\times10^5$ ST-56 cells per well. Plates were incubated at 37° C. in a humid, 5% $CO_2$ incubator and were observed daily for cytopathic effect. At the first sign of cytopathic effect or after 5 days incubation the monolayer was scraped off; the cell suspension was frozen at −70° C. The presence of PRV was subsequently confirmed by inoculation of the suspension onto 2-well chamber slides seeded with $3\times10^5$ PK-15 cells per chamber. Slides were incubated at 37° C. in a humid, 5% $CO_2$ incubator and were observed daily for cytopathic effect. At the first sign of cytopathic effect or after 5 days the media were discarded, slides were rinsed and fixed in 80 percent cold acetone. One ml of FITC-labeled anti-PRV swine sera (1:100 dilution) was added to each well and incubated at 37° C. for 30 minutes. Conjugate was discarded, slides were washed and examined for fluorescence.

The data were analyzed by analysis of variance of Fisher's Exact test using a proprietary software program (SAS); significance level was set at $p\leq0.05$.

EXAMPLE 5

Seroconversion and Response to Revaccination
(Trial 1)

Ten 4-week-old pigs (8 males and 2 females) from a PRV negative source were used. Two were purebred Durocs, whereas the others were out of a Duroc×Hampshire× Yorkshire dam sired by a Hampshire boar. One Duroc and 2 crossbreeds (1 with a Hampshire-like phenotype and 1 with a Yorkshire-like phenotype) were assigned to each of groups 1 and 2 (all males). Two crossbreeds (1 male and 1 female) were assigned to each of groups 3 and 4.

Groups 1 and 2 were housed in one room to facilitate containment of the recombinant virus, and groups 3 and 4 in another. Each room was subdivided into 2 pens by a solid wall two feet high and one foot wide. Pigs were fed a commercial ration and had ad lib access to water.

Group 1 pigs were scarified at 2 sites in the inguinal area with 0.2 ml of SP-PRV per site ($1.2\times10^6$ PFU per pig). Group 2 pigs were injected intramuscularly (IM) with 0.8 ml of PS-PRV in the left ham ($2.5\times10^6$ PFU per pig). Group 3 pigs were scarified at two sites with 0.2 ml of SPV TK⁻ per site ($2.0\times10^6$ PFU per pig) and group 4 pigs were scarified at two sites with 0.2 ml of BME per site. Groups 3 and 4 were removed from the study and groups 1 and 2 were transferred to separate rooms at 29 days post vaccination (dpv). Group 1 and 2 pigs were revaccinated by the original route used at 150 dpv. Groups 1 pigs were scarified in the relatively hairless area behind the left ear with 0.2 ml ($10^{5.4}$ PFU per pig) and group 2 pigs were injected IM in the ham with 1.0 ml ($10^{6.1}$ PFU per pig).

Pigs were observed daily. Body temperatures were recorded daily for 10 days post-vaccination. The scarification sites were almost healed at 6 dpv (groups 1, 3 and 4) when localized lesions typical of swinepox appeared at the sites of scarification in groups 1 and 3. The nature of these lesions was confirmed by histopathology. No swinepox lesions were evident in groups 2 (Sp-PRV IM) or 4 (BME scarified) at this time. At 15 dpv it was noted that pig #403 in group 1 (SP-PRV scarified) had developed lesions extending beyond the sites of scarification. In group 2 (SP-PRV IM), pig #406 had developed several abdominal lesions. All lesions healed spontaneously by 30 dpv. There was no evidence of lesions following revaccination in either group.

Blood samples were collected at approximately weekly intervals starting at −1 days post-vaccination and continuing through 150 days post-vaccination. After revaccination, blood samples were collected at 16 and 36 days when the trial was terminated. Sera were stored at −20° C.

Sera were assayed by serum neutralization (SN) and latex agglutination for the presence of PRV-specific antibodies after the first vaccination. After revaccination (trial 1) and for the subsequent trials sera were assayed by SN only. Pseudorabies virus SN antibody titers were determined in 96-well ST-56 cell-coated plates using standard methods (Hill et al. [1977] *American Assoc. Vet. Lab. Diagnosticians, 20th Annual Proceedings*, pp. 375–377). The Bucharest PRV strain (SmithKline Beecham Animal Health) was used as test virus at a range of 50 to 300 $TCID_{50}$. Multiple dilutions (two-fold or four-fold) were assayed and results were read after 3 to 5 days incubation at 37° C. in a humid, 5% $CO_2$ incubator. Neutralization titers were calculated as fifty per cent endpoints using the Spearman-Karber formula (Schmidt and Emmons [1989] In *Diagnostic Procedures for Viral, Rickettsial, and Chlamydial Infections*, 6th ed., American Public Health Association, Inc., Washington, D.C., pp. 18–21). Titers $\geq 1:2$ were regarded as positive.

Latex agglutination (LA) was performed on samples diluted 1:4 (Viral Antigens, Inc.). Wells were examined for agglutination at 5, 10 and 15 minutes. Positive and negative controls were assayed.

The following table illustrates the effect of breed and phenotype on pseudorabies virus serum neutralizing antibody titers after initial vaccination with a recombinant swinepox-pseudorabies virus.

TABLE 2

| Group | Pig | Breed | Phenotype | Route of Vaccine | SN titer at 35 days post-vaccine |
|---|---|---|---|---|---|
| 1 | 401 | Duroc | Duroc | Scarified | 1:8 |
|   | 402 | Crossbreed | Hampshire | Scarified | 1:8 |
|   | 403 | Crossbreed | Yorkshire | Scarified | 1:16 |
| 2 | 404 | Duroc | Duroc | Intramuscular | 1:6 |
|   | 405 | Crossbreed | Hampshire | Intramuscular | 1:45 |
|   | 406 | Crossbreed | Yorkshire | Intramuscular | 1:128 |

All pigs vaccinated with SP-PRV were positive by PRV SN as of 15 dpv and remained positive for the duration of the trial. Pig #403 (with secondary abdominal lesions) and pig #406 (with primary abdominal lesions) had the highest peak SN titers in groups 1 (SP-PRV scarified) and 2 (SP-PRV IM), respectively (Table 2). The Durocs maintained the lowest SN titers over the course of the first 71 days. Pigs scarified with SP-PRV generally had lower SN titers than IM injected pigs. Control pigs remained negative by SN through 29 dpv when they were removed from the trial. Following revaccination, both groups responded with an anamnestic response.

All crossbreds vaccinated with SP-PRV were positive to LA from 15 dpv. The Durocs, however, remained negative for the duration of the trial. Latex agglutination test results were generally assessed as weak positives with agglutination taking up to 15 min to develop. Samples with SN titers ≧1:64 agglutinated rapidly. Control pigs remained negative by LA through 29 dpv.

EXAMPLE 6

Efficacy Following Vaccination by Scarification or Intramuscular Injection (Trial 2)

Thirty-four 4-week-old crossbred pigs were supplied by a PRV negative source, the pigs were out of Duroc sows sired by York×Landrace boars. Breeding stock were vaccinated against leptospirosis and parvovirus only. Pigs were grouped after weaning, ear-tagged at random and assigned as scarified vaccinates (group 1, n=10), intramuscular vaccinated (n=10), controls (group 3, n=10) or in-contact controls (n=4). The pigs were randomized across the two treatment groups by weight, sex and phenotype.

Vaccinates and in-contact controls were housed in plastic bins (Polydome) in a single room. Controls, previously kept separated, were introduced on the day of challenge. Each group was housed in 2 plastic bins; groups 1 and 2 had 6 pigs per bin (5 vaccinates plus 1 in-contact control), whereas group 3 had 5 pigs per bin. Pigs were fed a commercial ration containing 100 grams per ton of chlortetracycline, 0.011 per cent of sulfamethazine and 50 grams per ton of procaine penicillin and had ad libitum access to water.

Group 1 pigs were scarified in the relatively hairless area immediately behind the left ear with 0.25 ml of SP-PRV ($10^{5.4}$ PFU per pig), group 2 pigs were injected IM in the neck on the left-hand side with 1.0 ml SP-PRV ($10^{6.1}$ PFU per pig), whereas controls (group 3) and in-contact controls remained untreated.

All pigs were challenged 21 days post-vaccination by the intranasal administration of virulent pseudorabies virus (PRV) (strain ISU 4892-5) (National Veterinary Services Laboratories, Ames, Iowa). Each pig received 1 ml per nostril of 2 ml total ($10^{7.3}$ $TCID_{50}$ per pig), the administration being timed to coincide with inspiration.

Body temperatures were measured daily (vaccinates) or weekly (controls) before challenge and daily thereafter. Blood samples were collected prior to vaccination and weekly thereafter. Sera were stored at −20° C. Body weights were measured weekly, at the time of death or at termination of the trial. The clinical signs after vaccination were as follows. There were no obvious adverse effects noted after vaccination. Several group 1 and 2 pigs experienced an episode of diarrhea between 3 and 8 dpv which is commonly seen after weaning and is associated with dietary changes. Scarification site lesions typical of swinepox appeared at 5 dpv in group 1 pigs. These were most evident at 7 dpv and healed spontaneously by 13 dpv. There was no extension of scarification site lesions and no lesions developed in IM vaccinated pigs.

A comparison of mean body temperatures by group showed mildly elevated mean body temperatures from 12 through 15 dpv with the group 2 (IM) mean being consistently higher over this period. The group 3 (control) mean body temperature could not be used for comparison since they were housed under different environmental conditions before challenge.

From 7 to 14 dpv, group 2 (IM) pigs had the lowest mean body weight gain. Gains from 1 to 7 dpv and from 14 to 21 dpv in this group and gains from 0 to 21 dpv in the other groups were unremarkable.

Following challenge, several pigs showed clinical signs typical of pseudorabies, characterized by central nervous system (CNS) signs (ataxia, circling, posterior paresis, convulsions) and/or respiratory signs (sneezing, coughing, dyspnea). The incidence of clinical disease for the 10-day period after challenge is shown in Table 3.

TABLE 3

|  | CNS system signs | Resp. signs | CNS system and/or resp. signs | Survival rate |
|---|---|---|---|---|
| Scarified | 33 | 33 | 40 | 90 |
| Intramuscular | 20 | 20 | 33 | 90 |
| Control | 70 | 50 | 90 | 80 |

Slightly fewer group 2 (IM) pigs showed clinical signs than group 1 (scarified) pigs (33 versus 40 per cent). In contrast, 90 per cent of the controls showed clinical signs typical of pseudorabies. One group 2 (IM) pig died of respiratory disease 5 days post challenge (dpc). At 5 dpc a group 1 (scarified) and a control pig with severe CNS signs were euthanized and a control pig died after showing CNS signs; there were no further deaths. Pigs that developed clinical disease generally showed the same extent and severity of clinical signs irrespective of their group.

After challenge, the mean body temperature of groups 1 (scarified) and 2 (IM) peaked at 3 dpc after which it steadily decreased to reach approximately normal levels of 7 dpc. The mean body temperature of group 3 (control) plateaued at a similar temperature from 3 through 5 dpc when it decreased; the mean body temperature of this group remained consistently highest after challenge.

The effect of challenge on mean body weight by group is illustrated in Table 4. Specifically, the following table provides data representing the growth performance of pigs vaccinated with a recombinant swinepox-pseudorabies virus by scarification or intramuscular injection for the seven day period after challenge with virulent pseudorabies virus.

TABLE 4

| Parameter | Scarified | I.M. | Control |
|---|---|---|---|
| Gain[1] | −0.05 | 0.32 | −0.68 |
| Average daily gain[2] | −0.01 | 0.04 | −0.10 |
| Percentage gain[3] | 0.39 | 3.31 | −5.55 |
| Percentage average daily gain[4] | 0.00 | 0.41 | −0.84 |
| % of pigs that maintained or lost weight | 40 | 20 | 100 |

[1](weight at end of period − weight at beginning of period)
[2](weight at end of period − weight at beginning of period)/number days in period
[3](weight at end of period − weight at beginning of period)/weight at beginning of period * 100
[4](weight at end of period − weight at beginning of period)/weight at beginning of period * 100/number of days in period During the first 7 dpc group 1 (scarified) maintained its mean body weight, the group 2 (IM) mean increased, whereas the group 3 (control) mean decreased. During this period, 40, 20 and 100 percent, respectively of pigs in groups 1 (scarified), 2 (IM) and 3 (controls) lost or maintained their body weight (Table 4). During the second 7-day period after challenge all surviving pigs showed similar weight gains. Controls, however, never made up for the weight loss during the first 7-day period after challenge.

After vaccination, the serology tests showed a PRV SN antibody response in 70 and 90 percent of group 1 (scarified) pigs at 14 dpv (range—1:2 to 1:8) and 21 dpv (range—1:2 to 1:16), respectively and in 90 and 100 percent of group 2 (IM) pigs at 14 dpv (range—1:2 to 1:8) and 21 dpv (range—1:2 to 1:128), respectively. Group 2 (IM) pigs had the higher geometric mean titer at either sampling (Table 4). All pigs were negative before vaccination; group 3 (control) pigs and in-contact controls remained negative through 21 dpv.

TABLE 5

| Group | Days post vaccination | | | | | |
| --- | --- | --- | --- | --- | --- | --- |
| | 0 | 7 | 14 | 21[1] | 28 | 35 |
| Scarified (10) | <1:2 | <1:2 | 1:2 | 1:5 | ≧1:1756(9) | >1:5161(9) |
| IM (10) | <1:2 | <1:2 | 1:4 | 1:18 | ≧1:2048(9) | >1:5161(9) |
| Control (10) | <1:2 | <1:2 | <1:2 | <1:2 | 1:7(8) | >1:152(8) |

[1]Day of challenge
Sample size in parentheses.

TABLE 6

Isolation of recombinant swinepox-pseudorabies virus from skin scrapings taken at the site of scarification.

| Pig | Phenotype | Days post vaccination | | | |
| --- | --- | --- | --- | --- | --- |
| | | 5 | 7[1] | 10 | 13 |
| 58 | White | 2.8 | ≦1.8 | <1.5 | <1.5 |
| 59 | Red/white | 3.5 | ≦1.8 | <1.5 | <1.5 |
| 75 | White | 3.5 | 2.8 | <1.5 | <1.5 |
| 80 | Red | 4.0 | 3.3 | <1.8 | <1.5 |

[1]Swinepox-like lesions most evident (prior to scab formation).

Titer of SP-PRV at the site of scarification was highest when lesions become noticeable at 5 dpv. SP-PRV was not detected in skin scrapings taken at 13 DPV (Table 6). There was no detectable fecal shedding of SP-PRV in group 1 (IM) pigs. Although toxicity was experienced during the evaluation of faecal swabs, 50 per cent of the swabs collected from group 2 (IM) pigs at 3 dpv could be evaluated for cytopathic effect; all were negative. Further evaluation of fecal swabs were not pursued.

TABLE 7

Isolation rates of pseudorabies virus from pigs vaccinated with a recombinant swinepox-pseudorabies virus by scarification or intramuscular injection and challenged 21 days later with virulent pseudorabies virus

| Group | Days post challenge | | | | | | | | | | | | | Mean |
| --- | --- | --- | --- | --- | --- | --- | --- | --- | --- | --- | --- | --- | --- | --- |
| | 0 | 1 | 2 | 3 | 4 | 5 | 6 | 7 | 8 | 9 | 10 | 11 | 12 | days[1] |
| IM | 0 | 60 | 100 | 100 | 80 | 67 | 0 | 0 | 0 | 0 | 0 | 0 | 0 | 4.0 |
| Scarified | 0 | 80 | 100 | 100 | 100 | 80 | 0 | 0 | 0 | 0 | 0 | 0 | 0 | 4.6 |
| Control | 0 | 100 | 100 | 100 | 100 | 100 | 100 | 63 | 50 | 38 | 25 | 25 | 13 | 8.5 |

[1]Mean number of days that pseudorabies virus was shed by pigs surviving challenge.

After challenge Group 1 (scarified) and 2 (IM) pigs responded by 7 dpc with a marked increase in the geometric mean PRV SN titer (anamnestic response) (Table 6). Controls showed a response typically seen in naive pigs. None of the in-contact controls showed evidence of an anamnestic response.

Fecal swabs were collected for SP-PRV isolation in 2 ml Dulbecco's MEM (DMEM) from all vaccinates at 0, 3, 6, 9 and 12 dpv and stored at −70° C. The DMEM was supplemented with 0.1 M L-glutamine, 300,000 IU penicillin G sodium, 300,000 μg streptomycin sulphate and 750 μg amphotericin B. Skin scrapings were collected for SP-PRV isolation in 2 ml supplemented DMEM from 4 scarified pigs on the day that scarification site lesions appeared and every 3 days thereafter until 21 dpv and stored at −70° C. Nasal swabs were collected for PRV isolation in 2 ml supplemented DMEM on the day of challenge and daily thereafter; both nostrils were probed with a single cotton-tipped swab. Tonsil tissue samples were collected from all pigs that died, and from two pigs per group at termination of the trial, and stored at −70° C.

Following challenge, the geometric mean virus titer of PRV shed in nasal swabs collected daily was determined. Group 1 (scarified) and 2 (IM) pigs showed a similar pattern, shedding lower levels of PRV over a shorter period of time compared to controls. Group 1 (scarified), 2 (IM) and 3 (controls) shed PRV for an average of 4.6, 4.0 and 8.5 days, respectively (Table 7). Although groups 1 and 2 showed a similar shedding pattern, isolation rates show that fewer group 2 (IM) pigs were shedding PRV than group 1 (scarified) pigs.

Pseudorabies virus was isolated from the tonsil tissue of all pigs, vaccinated with a recombinant swinepox-pseudorabies virus by scarification or intramuscular injection and challenged 21 days later with virulent pseudorabies virus, that died or were euthanized due to pseudorabies and from the two controls sampled at termination of the trial (Table 8). None of the vaccinates sampled at termination of the trial (two pigs per group) were positive.

TABLE 8

| Group | Pig | Cause of death | Result |
|---|---|---|---|
| Scarified | 65 | Euthanized due to disease | + |
| | 60 | Euthanized at termination | − |
| | 77 | Euthanized at termination | − |
| IM | 68 | Died due to disease | + |
| | 57 | Euthanized at termination | − |
| | 71 | Euthanized at termination | − |
| Control | 88 | Euthanized due to disease | + |
| | 91 | Died due to disease | + |
| | 84 | Euthanized at termination | + |
| | 92 | Euthanized at termination | + |

Table 9 below provides results of the isolation of pseudorabies virus from tonsil tissue of pigs vaccinated with a recombinant swinepox-pseudorabies virus by scarification or intramuscular injection and challenged 21 days later with virulent pseudorabies virus.

TABLE 9

| Group | Pig | Cause of death | Result |
|---|---|---|---|
| SPV TK+ | No tag | Died due to disease | + |
| | 89 | Euthanized at termination | − |
| | 107 | Euthanized at termination | + |
| SPV TK− | 85 | Euthanized due to disease | + |
| | 95 | Euthanized due to disease | + |
| | 118 | Euthanized due to disease | + |
| | 102 | Euthanized at termination | + |
| | 107 | Euthanized at termination | + |
| SP-PRV | 93 | Euthanized at termination | + |
| | 101 | Euthanized at termination | + |
| Control | 81 | Died due to disease | + |
| | 83 | Died due to disease | + |
| | 100 | Euthanized due to disease | + |
| | 116 | Died due to disease | + |
| | 90 | Euthanized at termination | − |
| | 99 | Euthanized at termination | − |

EXAMPLE 7

Efficacy Following Oral Vaccination (Trial 3)

Thirty-nine 3-week-old crossbred pigs were supplied by the same as for trial 2 (Example 6). Pigs were assigned as SPV TK+ vaccinated (group 1, n=6), SPV TK− vaccinates (group 2, n=6), SP-PRV vaccinated (group 3, n=10), controls (group 4, n=10) or in-contact controls (n=2). Grappa pigs were randomized across the three treatment groups by weight, sex and phenotype.

Pigs were housed in plastic bins (Polydome) in a single room. The control group was introduced on the day of challenge. Groups 1 and 2 were housed in separate bins (6 pigs per bin). Groups 3 and 4 were each housed in two bins. Group 3 had 5 vaccinates plus 1 in-contact control per bin before challenge. The in-contact controls were removed immediately before challenge. Group 4 (control) had 6 pigs per bin before challenge and 5 pigs per bin post challenge. Pigs were fed a commercial pig ration containing 100 grams per ton of chlortetracycline, 0.011 per cent of sulfamethazine and 50 grams per ton of procaine penicillin and had ad lib access to water.

Group 1 pigs received one ml of SPV TK+ ($10^{6.7}$ PFU per pig), group 2 pigs received one ml of SPV TK− ($10^{6.3}$ PFU per pig) and group 3 pigs received one ml of SP-PRV ($10^{6.1}$ PFU per pig) squirted into the oral cavity with a syringe. Controls and in-contact controls remained untreated. Three pigs housed in a separate bin were scarified behind the left ear on the day of vaccination; each pig received one of the three inocula.

All pigs were challenged 21 dpv by the intranasal administration of virulent PRV (strain ISU 4892-5) [National Veterinary Services Laboratories, Ames, Iowa]. Each pig received 1 ml per nostril or 2 ml total ($10^{7.1}$ TCID$_{50}$ per pig), the administration being timed to coincide with inspiration.

Body temperatures were measured daily (vaccinates) or weekly (controls) before challenge and daily thereafter. There were no obvious adverse effects noted after vaccination. Pigs in all groups experienced episodes of diarrhea between 1 and 3 dpv, which is commonly seen post-weaning and is associated with dietary changes, and again between 10 and 17 dpv. Group 1 (SPV TK+) pigs were most affected between 10 and 17 dpv. Since several pigs had weeping lesions on the ears from fighting, and were still fighting at the time of oral vaccination, there was a concern that pigs could effectively scarify one another. However, no lesions developed on the ears, or elsewhere on the body, of pigs in any of the vaccinated groups.

Mildly elevated mean body temperatures were observed from 8 through 21 dpv for the vaccinated groups. The group 3 (control) pigs were housed under similar environmental conditions, but were only monitored weekly before challenge.

From 7 to 21 dpv, group 1 (SPV TK+) pigs had the lowest mean body weight gain. Mean body weight gain for this group from 0 to 7 dpv and for the other groups from 0 to 21 were unremarkable.

Following challenge, several pigs showed clinical signs typical of pseudorabies, characterized by central nervous system (CNS) signs (ataxia, circling, posterior paresis, convulsions) and/or respiratory signs (sneezing, coughing, dyspnea). The incidence of clinical disease for the 10-day period after challenge is shown in Table 10. Table 10 shows the results of pseudorabies disease incidence and survival rates of pigs vaccinated orally with a recombinant swinepox-pseudorabies virus and challenged 21 days later with virulent pseudorabies virus.

TABLE 10

| Group | CNS System signs | Respiratory signs | CNS system and/or resp. signs | Survival rate |
|---|---|---|---|---|
| SPV TK+ | 67 | 33 | 67 | 83 |
| SPV TK− | 100 | 33 | 100 | 33 |
| SP-PRV | 50 | 50 | 60 | 100 |
| Control | 100 | 30 | 100 | 50 |

Slightly fewer group 2 (SP-PRV) pigs shows clinical signs than group 1 (SPV TK+) pigs (60 versus 67 per cent). In contract, 100 per cent of group 2 (SPV TK−) pigs and controls showed clinical signs typical of pseudorabies. Three group 4 (control) pigs showing severe CNS signs died at 6 dpc, two group 2 (SPV TK−) pigs showing severe CNS signs were euthanized as well as a group 4 pig showing both severe respiratory and CNS signs. At 7 dpc a group 1 (SPV TK+) and group 4 (control) pig died after both showed severe respiratory and CNS signs, a group 2 (SPV TK−) pig died after showing CNS signs and another was euthanized after showing severe CNS signs; there were no further deaths. Pigs that developed clinical disease in groups 2 (SPV TK−) and 4 (control) soon after challenge showed more severe clinical signs. However, although all group 3 (SP-PRV) pigs survived and only one group 1 (SPV TK+) pig died, pigs with clinical signs in either of these groups still showed clinical signs after the majority of surviving pigs in groups 2 (SPV TK−) and 4 (control) pigs had recovered. In addition, 2 pigs in group 3 (SP-PRV) developed severe ocular lesions (one pig was blind, the other semi-blind). Similar, but milder, lesions which healed were observed in one pig in each of groups (SPV TK$^+$), 2 (SPV TK$^-$) and 4 (control). Pseudorabies virus was isolated from ocular swabs taken from one of the group 3 (SP-PRV) pigs at termination of the trial (titer=3.8 $\log_{10}$ TCID$_{50}$).

The mean body temperatures of groups 1 (SPV TK$^+$) and 3 (SP-PRV) plateaued from 2 through 6 dpc after which they gradually decreased to reach approximately normal levels at 12 dpc. The mean body temperatures of groups 2 (SPV TK$^-$) and 4 (controls) peaked at a higher temperature at 2 dpc after which they steadily decreased to approximately normal levels at 7 dpc. Prior to 5 dpc groups 2 (SPV TK$^-$) and 4 (control) had the highest mean body temperature, from 5 through 12 dpc groups 1 (SPV TK$^+$) and 3 (SP-PRV) generally had the highest mean body temperatures. Table 11 shows the results of growth performance of pigs vaccinated orally with a recombinant swinepox-pseudorabies virus for the seven day period after challenge with virulent pseudorabies virus.

TABLE 11

| Parameter | SPV TK$^+$ | SPV TK$^-$ | SP-PRV | Control | Unchall.[5] |
|---|---|---|---|---|---|
| Gain[1] | 0.11 | −1.17 | −0.36 | −1.80 | 4.66 |
| Avg daily gain[2] | 0.02 | −0.18 | −0.05 | −0.27 | 0.67 |
| % gain[3] | 2.04 | −9.73 | −2.53 | −11.48 | 31.25 |
| % average daily gain[4] | 0.29 | −1.49 | −0.36 | −1.74 | 4.46 |
| % of pigs that maintained or lost weight | 50 | 83 | 70 | 90 | 0 |

[1](weight at end of period − weight at beginning of period)
[2](weight at end of period − weight at beginning of period)/number days in period
[3](weight at end of period − weight at beginning of period)/weight at beginning of period * 100
[4](weight at end of period − weight at beginning of period)/weight at beginning of period * 100/number of days in period
[5]Two pigs from the same farrowing group were housed with the control group prior to challenge with pseudorabies virus; these were not transferred to the room containing the vaccinates and were not challenged with pseudorabies virus.

During the first 7 dpc group 1 (SPV TK$^+$) maintained its weight, the group 3 (SP-PRV) mean showed a slight decrease, whereas the groups 2 (SPV TK$^-$) and 3 (control) means decreased sharply. During this period, 50, 83, 70 and 90 per cent respectively, of pigs in groups 1 (SPV TK$^+$), 2 (SPV TK$^-$), 3 (SP-PRV) and 4 (controls) lost or maintained their body weight (Table 11). During the second 7-day period post challenge all surviving pigs showed similar weight gains, except for the 2 remaining pigs in group 2 (SPV TK$^-$) which barely gained weight.

Blood samples were collected prior to vaccination and weekly thereafter; sera were stored at −20° C. Body weights were measured weekly, at the time of death or at termination of the trial. A PRV SN antibody response was not evident in group 3 (SP-PRV) pigs at 14 or 21 dpv. All pigs were negative prior to vaccination; group 1 (SPV TK$^+$), 2 (SPV TK$^-$), 4 (control) pigs and in-contact controls remained negative through 21 dpv.

All groups responded to challenge showing a response typically associated with naive pigs (Table 12). None of the in-contact controls showed evidence of an anamnestic response. Table 12 shows the results of pseudorabies virus serum neutralizing antibody titers (geometric means) of pigs vaccinated orally with a recombinant swinepox-pseudorabies virus and challenged 21 days later with virulent pseudorabies virus.

TABLE 12

| | Days post vaccination | | | | | |
|---|---|---|---|---|---|---|
| Group | 0 | 7 | 14 | 21[1] | 28 | 35 |
| SPV TK$^+$ (6) | <1:2 | — | — | <1:2 | 1:7(5) | 1:111(5) |
| SPV TK$^-$ (6) | <1:2 | — | — | <1:2 | 1:11(2) | 1:181(2) |
| SP-PRV (10) | <1:2 | <1:2 | <1:2 | <1:2 | 1:13(10) | 1:128(10) |
| Control (10) | <1:2 | — | — | <1:2 | 1:9(5) | 1:128(5) |

[1]Day of challenge.
Sample size in parentheses.
— Not tested

Fecal swabs for SP-PRV isolation and pharyngeal swabs for SP-PRV and SPV isolation were collected in 2 ml supplemented DMEM from all vaccinates at 0, 3, 6, 9 and 12 dpv and frozen at −70° C. Since the toxicity associated with the fecal samples as described in trial 2 could not be resolved, the group 3 (SP-PRV) fecal samples were not assayed for the presence of SP-PRV. Nasal swabs and tonsillar tissue samples were collected as described for trial 2. Evaluation of pharyngeal swabs showed only one SPV TK$^+$ vaccinate with a positive swab at 3 dpv. No virus was detected in any other pigs at this or later samplings.

After challenge, all groups showed a similar pattern of shedding although groups 1 (SPV TK$^+$) and 3 (SP-PRV) peaked at a lower level. Group 1 (SPV TK$^+$), 2 (SPV TK$^-$), 3 (SP-PRV) and 4 (control) shed PRV for an average of 8.4, 9.0, 6.9 and 7.2 days, respectively (Table 13). From the isolation rates it appears that shedding was delayed in group 3 (SP-PRV). This group also consistently had the lowest geometric mean titer as of 5 dpc.

TABLE 13

Isolation rates of pseudorabies virus from pigs vaccinated orally with a recombinant swinepox-pseudorabies virus and challenged 21 days later with virulent pseudorabies virus

| | Days post challenge | | | | | | | | | | | | | Mean |
|---|---|---|---|---|---|---|---|---|---|---|---|---|---|---|
| Group | 0 | 1 | 2 | 3 | 4 | 5 | 6 | 7 | 8 | 9 | 10 | 11 | 12 | days[1] |
| SP-PRV | 0 | 50 | 70 | 100 | 100 | 100 | 100 | 80 | 40 | 30 | 10 | 10 | 0 | 6.9 |
| SPV TK$^+$ | 0 | 20 | 100 | 100 | 100 | 100 | 100 | 80 | 60 | 80 | 40 | 20 | 20 | 8.4 |
| SPV TK$^-$ | 0 | 80 | 100 | 100 | 100 | 100 | 100 | 100 | 100 | 100 | 50 | 0 | 0 | 9.0 |
| Control | 0 | 70 | 100 | 100 | 100 | 100 | 100 | 80 | 40 | 40 | 20 | 0 | 0 | 7.2 |

[1]Mean number of days that pseudorabies virus was shed by pigs surviving challenge.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A recombinant vector comprising a swinepox virus comprising a heterologous nucleotide sequence encoding a protein from a selected pathogen inserted into, or replacing, all or a portion of a swinepox virus gene, which gene is not essential to replication of the virus in a host cell.

2. The recombinant vector according to claim 1 wherein said non-essential gene is the TK gene.

3. The recombinant vector according to claim 2 wherein said non-essential gene is the TK gene SEQ ID NO: 57.

4. The vector according to claim 1 wherein said pathogen is pseudorabies.

5. The vector according to claim 4 wherein said nucleotide sequence encodes the pseudorabies gp50 and gp63 protein.

6. A vaccine capable of protecting against infection with a selected pathogen comprising a recombinant vector comprising a swinepox virus comprising a heterologous nucleotide sequence encoding a protein from a selected pathogen inserted into, or replacing, all or a portion of a swinepox virus gene, which gene is not essential to replication of the virus in a host cell.

7. The vaccine according to claim 6 wherein said non-essential gene is the SPV TK gene or a portion of the HindIII C fragment.

8. The vaccine according to claim 7 wherein said SPV TK gene has the sequence of SEQ ID NO: 57 and said HindIII C fragment has the sequence of SEQ ID NO: 1 and 14.

9. A therapeutic composition useful in treating animals infected with a selected pathogen comprising a recombinant vector comprising a swinepox virus comprising a heterologous nucleotide sequence encoding a protein from a selected pathogen inserted into, or replacing, all or a portion of a swinepox virus gene, which gene is not essential to replication of the virus in a host cell.

10. The composition according to claim 9 wherein said non-essential gene is the SPV TK gene or a portion of the HindIII C fragment, and wherein said heterologous sequence encodes a protein capable of alleviating the clinical symptoms of said infection.

11. The composition according to claim 10, wherein said SPV TK gene has the sequence of SEQ ID NO: 57 and said HindIII C fragment has the sequence of SEQ ID NO: 1 and 14.

12. A method of vaccinating an animal against infection with a selected pathogen comprising administering to said animal a vaccine comprising a recombinant vector comprising a swinepox virus comprising a heterologous nucleotide sequence encoding a protein from a selected pathogen inserted into, or replacing, all or a portion of a swinepox virus gene, which gene is not essential to replication of the virus in a host cell.

13. The method according to claim 12 wherein said non-essential gene is swinepox virus TK gene or a portion of the HindIII C fragment.

14. The method according to claim 13 wherein said swinepox virus TK gene has the sequence of SEQ ID NO: 57 and said HindIII C fragment has the sequence of SEQ ID NO: 1 and 14.

15. A method of treating an animal infected with a selected pathogen comprising administering to said animal a therapeutic composition comprising a recombinant swinepox virus comprising a heterologous nucleotide sequence encoding a protein from a selected pathogen inserted into, or replacing, all or a portion of a swinepox virus gene, which gene is not essential to replication of the virus in a host cell.

16. The method according to claim 15 wherein said non-essential gene is the swinepox virus TK gene or a portion of the HindIII C fragment, and wherein said heterologous protein is capable of alleviating the clinical symptoms of said infection.

17. The method according to claim 16 wherein said swinepox virus TK gene has the sequence of SEQ ID NO: 57 and said HindIII C fragment has the sequence of SEQ ID NO: 1 and 14.

* * * * *

UNITED STATES PATENT AND TRADEMARK OFFICE
CERTIFICATE OF CORRECTION

PATENT NO. : 6,217,882 B1
DATED : April 17, 2001
INVENTOR(S) : Moyer et al.

It is certified that error appears in the above-identified patent and that said Letters Patent is hereby corrected as shown below:

Column 11,
Line 61, "[SEQ ID NO: 5]" should read -- [SEQ ID NO: 15] --.

Column 12,
Line 67, "CSA" should read -- C5A --.

Column 20,
Line 14, "<1.8" should read -- $\leq 1.8$ --.

Signed and Sealed this

Twelfth Day of March, 2002

JAMES E. ROGAN
Director of the United States Patent and Trademark Office

*Attest:*

*Attesting Officer*